(12) United States Patent
Borzilleri et al.

(10) Patent No.: US 7,459,562 B2
(45) Date of Patent: Dec. 2, 2008

(54) MONOCYCLIC HETEROCYCLES AS KINASE INHIBITORS

(75) Inventors: Robert M. Borzilleri, New Hope, PA (US); Lyndon A. M. Cornelius, Jackson, NJ (US); Robert J. Schmidt, Hainesport, NJ (US); Gretchen M. Schroeder, Ewing, NJ (US); Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 391 days.

(21) Appl. No.: 11/111,144

(22) Filed: Apr. 21, 2005

(65) Prior Publication Data

US 2005/0245530 A1 Nov. 3, 2005

Related U.S. Application Data

(60) Provisional application No. 60/564,842, filed on Apr. 23, 2004, provisional application No. 60/639,178, filed on Dec. 23, 2004.

(51) Int. Cl.
C07D 211/72 (2006.01)
A61N 43/40 (2006.01)

(52) U.S. Cl. ...................................... 546/300; 514/335

(58) Field of Classification Search ................. 546/290, 546/292, 295, 297, 336, 314, 266, 271; 514/277, 514/341, 349
See application file for complete search history.

(56) References Cited

U.S. PATENT DOCUMENTS

| | | | |
|---|---|---|---|
| 3,646,202 A | 2/1972 | Mrozik | |
| 4,602,912 A | 7/1986 | de Sousa et al. | |
| 4,663,341 A | 5/1987 | Jacobson | |
| 4,753,940 A | 6/1988 | Sturm et al. | |
| 4,845,093 A | 7/1989 | Haga et al. | |
| 4,908,056 A | 3/1990 | Tseng | |
| 5,132,314 A | 7/1992 | Maienfisch et al. | |
| 5,135,949 A | 8/1992 | von der Saal et al. | |
| 5,496,846 A * | 3/1996 | Wilson et al. | 514/449 |
| 5,646,176 A | 7/1997 | Golik et al. | |
| 6,022,884 A | 2/2000 | Mantlo et al. | |
| 6,143,743 A | 11/2000 | Wilde et al. | |
| 6,143,764 A | 11/2000 | Kubo et al. | |
| 6,214,344 B1 | 4/2001 | Schwall et al. | |
| 6,232,320 B1 | 5/2001 | Stewart et al. | |
| 6,262,094 B1 | 7/2001 | Hoefle et al. | |
| 6,355,660 B1 * | 3/2002 | Ricks et al. | 514/357 |
| 6,380,386 B2 | 4/2002 | Seitz et al. | |
| 6,429,213 B1 | 8/2002 | Xue et al. | |
| 6,521,622 B1 | 2/2003 | Ricks et al. | |
| 6,559,341 B2 | 5/2003 | Tohnishi et al. | |
| 6,603,044 B1 | 8/2003 | Tohnishi et al. | |
| 6,620,827 B2 | 9/2003 | De la Brouse-Elwood et al. | |
| 6,696,487 B2 | 2/2004 | Gerusz et al. | |
| 6,706,740 B2 | 3/2004 | Ricks et al. | |
| 6,750,246 B1 | 6/2004 | Kadow et al. | |
| 6,858,626 B2 | 2/2005 | Xue et al. | |
| 6,869,952 B2 | 3/2005 | Bhide et al. | |
| 6,900,208 B2 | 5/2005 | Salvati et al. | |
| 6,906,067 B2 | 6/2005 | Moriarty et al. | |
| 6,982,265 B1 | 1/2006 | Hunt et al. | |
| 7,030,112 B2 | 4/2006 | Salvati et al. | |
| 2001/0041673 A1 | 11/2001 | Fossa | |
| 2002/0065270 A1 | 5/2002 | Moriarty et al. | |
| 2003/0082631 A1 | 5/2003 | Gustavsson et al. | |
| 2003/0139435 A1 | 7/2003 | Ahmed et al. | |
| 2003/0232765 A1 | 12/2003 | Carter et al. | |
| 2003/0232831 A1 | 12/2003 | Dyckman et al. | |
| 2004/0044203 A1 | 3/2004 | Wittman et al. | |
| 2004/0048891 A1 | 3/2004 | Kato et al. | |
| 2004/0053908 A1 | 3/2004 | Funahashi et al. | |

(Continued)

FOREIGN PATENT DOCUMENTS

AU 200195986 4/2002

(Continued)

OTHER PUBLICATIONS

Atwell et al J Med Chem 1973, 16, 673-678.*

(Continued)

*Primary Examiner*—Rita Desai
*Assistant Examiner*—John Mabry
(74) *Attorney, Agent, or Firm*—Gary D. Greenblatt; Maureen S. Gibbons

(57) ABSTRACT

The present invention is directed to compounds having the formula

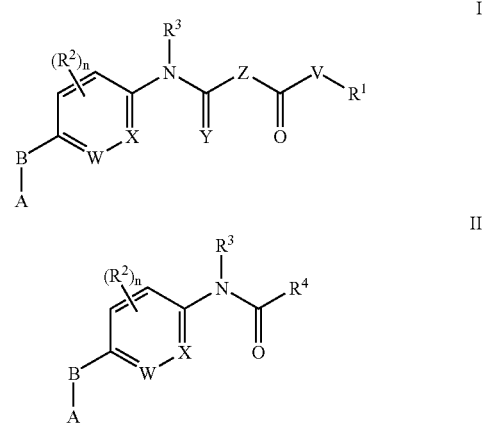

and methods for using them for the treatment of cancer.

17 Claims, No Drawings

U.S. PATENT DOCUMENTS

| | | | |
|---|---|---|---|
| 2004/0072832 | A1 | 4/2004 | Bhide et al. |
| 2004/0082582 | A1 | 4/2004 | Dyckman et al. |
| 2004/0209886 | A1 | 10/2004 | Salvati et al. |
| 2004/0242603 | A1 | 12/2004 | Fujiwara et al. |
| 2005/0038035 | A1 | 2/2005 | Takasugi et al. |
| 2005/0043306 | A1 | 2/2005 | Leftheris et al. |
| 2005/0143398 | A1 | 6/2005 | Das et al. |
| 2005/0239820 | A1 | 10/2005 | Borzilleri et al. |
| 2005/0288289 | A1 | 12/2005 | Crispino et al. |
| 2005/0288290 | A1 | 12/2005 | Borzilleri et al. |
| 2006/0004006 | A1 | 1/2006 | Borzilleri et al. |
| 2006/0084650 | A1 | 4/2006 | Dong et al. |
| 2007/0117802 | A1 * | 5/2007 | Borzilleri et al. ............ 514/243 |

FOREIGN PATENT DOCUMENTS

| | | | |
|---|---|---|---|
| DE | 31 39 457 | | 4/1983 |
| DE | 197 10 609 | | 9/1998 |
| EP | 0 151 962 | | 8/1985 |
| EP | 0 119 774 | | 6/1987 |
| EP | 0 152 910 | | 7/1989 |
| EP | 0 919 542 | | 6/1999 |
| EP | 1 243 582 | | 9/2002 |
| EP | 1 411 046 | | 4/2004 |
| GB | 2 106 500 | | 4/1983 |
| JP | 54-115384 | | 9/1979 |
| JP | 57-51835 | | 3/1982 |
| JP | 62-62 | | 1/1987 |
| JP | 62-5959 | | 1/1987 |
| JP | 62-5960 | | 1/1987 |
| JP | 62-135463 | | 6/1987 |
| JP | 2003-321472 | | 11/2003 |
| SU | 1761753 | | 9/1992 |
| WO | WO 97/17329 | | 5/1997 |
| WO | WO 98/41513 | | 9/1998 |
| WO | WO 99/01454 | | 1/1999 |
| WO | WO 99/02514 | | 1/1999 |
| WO | WO 99/24404 | | 5/1999 |
| WO | WO 00/43366 | | 7/2000 |
| WO | WO 00/50405 | | 8/2000 |
| WO | WO 00/56738 | | 9/2000 |
| WO | WO 00/71129 | | 11/2000 |
| WO | WO 00/75145 | | 12/2000 |
| WO | WO 01/21576 | | 3/2001 |
| WO | WO 01/21596 | | 3/2001 |
| WO | WO 01/27089 | | 4/2001 |
| WO | WO 01/42243 | | 6/2001 |
| WO | WO 01/47890 | | 7/2001 |
| WO | WO 01/47897 | | 7/2001 |
| WO | WO 01/94353 | | 12/2001 |
| WO | WO 02/28835 | A1 * | 4/2002 |
| WO | WO 02/32872 | | 4/2002 |
| WO | WO 02/40486 | | 5/2002 |
| WO | WO 02/44156 | | 6/2002 |
| WO | WO 02/051397 | | 7/2002 |
| WO | WO 02/085859 | | 10/2002 |
| WO | WO 03/000194 | | 1/2003 |
| WO | WO 03/000660 | | 1/2003 |
| WO | WO 03/011028 | | 2/2003 |
| WO | WO 03/033472 | | 4/2003 |
| WO | WO 03/042172 | | 5/2003 |
| WO | WO 03/082208 | | 10/2003 |
| WO | WO 03/099286 | | 12/2003 |
| WO | WO 2004/001059 | | 12/2003 |
| WO | WO 2004/002410 | | 1/2004 |
| WO | WO 2004/032846 | | 4/2004 |
| WO | WO 2004/043950 | A1 * | 5/2004 |
| WO | WO 2004/048386 | | 6/2004 |
| WO | WO 2004/054514 | | 7/2004 |
| WO | WO 2004/058144 | | 7/2004 |
| WO | WO 2004/060305 | | 7/2004 |
| WO | WO 2005/004863 | A1 * | 1/2005 |
| WO | WO2005/005389 | | 1/2005 |
| WO | WO 2005/005389 | | 1/2005 |
| WO | WO 2005/021554 | | 3/2005 |
| WO | WO 2005/026124 | | 3/2005 |
| WO | WO 2005/030140 | | 4/2005 |
| WO | WO 2005/042537 | | 5/2005 |
| WO | WO 2005/058891 | | 6/2005 |
| WO | WO 2005/082854 | | 9/2005 |
| WO | WO 2005/082855 | | 9/2005 |
| WO | WO 2005/097790 | | 10/2005 |

OTHER PUBLICATIONS

Cain et al J Med Chem 1969, 12, 199-206.*
Cain et al J Med Chem 1968, 11, 963-966.*
Atwell et al J Med Chem 1974, 17, 930-934.*
Abramovitch et al J Chem Soc Chem Comm 1979, 21, 956-957.*
Doll et al J Med Chem 1976, 19, 1079-1088.*
Abramovitch et al J Chem Soc Chem Comm 1981, 11, 561-562.*
F. Z. Dorwald Side Reactions in Organic Synthesis: A Guide to Successful Synthesis Design 2005, Wiley-VCH Verlag GmbH and Co. KGaA, Wienheim.*
Kempter, G. et al., "Synthesis of potential plant protective agents and pesticides from substituted anilines", Wissenschaftliche Zeitschrift, vol. 27, No. 1, pp. 101-120 (1983) (with English abstract).
Search Report "A", dated Dec. 16, 2004.
Kurogi, Y. et al., "Discovery of Novel Mesangial Cell Proliferation Inhibitors Using a Three-Dimensional Database Searching Method", J. Med. Chem., vol. 44, No. 14, pp. 2304-2307 (2001).
Okada, H. et al., "Synthesis and Antitumor Activities of Novel Benzoylphenylurea Derivatives", Chem. Pharm. Bull., vol. 39, No. 9, pp. 2308-2315 (1991).
U.S. Appl. No. 11/113,838, filed Apr. 25, 2005, Borzilleri et al.
U.S. Appl. No. 11/165,875, filed Jun. 24, 2005, Crispino et al.
U.S. Appl. No. 11/167,043, filed Jun. 24, 2005, Borzilleri et al.
U.S. Appl. No. 11/167,049, filed Jun. 24, 2005, Borzilleri et al.
Search Report "A", dated Jul. 2, 2003.
Dumas, J. et al., "Synthesis and Structure Activity Relationships of Novel Small Molecule Cathepsin D Inhibitors", Bioorganic & Medicinal Chemistry Letters, vol. 9, pp. 2531-2536 (1999).
Hunt, J.T. et al., "Discovery of the Pyrrolo[2,1-*f*][1,2,4]triazine Nucleus as a New Kinase Inhibitor Template", J. Med. Chem., vol. 47, No. 16, pp. 4054-4059 (2004).
Xue, C.-B. et al., "Rational Desing, Synthesis and Structure-Activity Relationships of a Cyclic Succinate Series of TNF-α Converting Enzyme Inhibitors. Part 2: Lead Optimization", Bioorganic & Medicinal Chemistry Letters, vol. 13, pp. 4299-4304 (2003).
Bardelli, A. et al., "Concomitant activation of pathways downstream of Grb2 and PI 3-kinase is required for *MET*-mediated metastasis", Oncogene, vol. 18, pp. 1139-1146 (1999).
Bottaro, D.P. et al., "Identification of the Hepatocyte Growth Factor Receptor as the c-*met* Proto-Oncogene Product", Science, vol. 251, pp. 802-804 (1991).
Bryant, R.D. et al., "A Large Scale Synthesis of 3-Chloro-5-methoxypyridazine", J. Heterocyclic Chem., vol. 32, pp. 1473-1476 (1995).
Burckhalter, J.H. et al., "Aminoalkylphenols as Antimalarials. II. (Heterocyclic-amino)-α-amino-*o*-cresols. The Synthesis of Camoquin", J. Am. Chem. Soc., vol. 70, pp. 1363-1373 (1948).
Bussolino, F. et al., "Hepatocyte Growth Factor Is a Potent Angiogenic Factor Which Stimulates Endothelial Cell Motility and Growth", The Journal of Cell Biology, vol. 119, No. 3, pp. 629-641 (1992).
Camp, R.L. et al., "*Met* Expression Is Associated with Poor Outcome in Patients with Axillary Lymph Node Negative Breast Carcinoma", Cancer, vol. 86, No. 11, pp. 2259-2265 (1999).
Cañibano, V. et al., "Mild Regioselective Halogenation of Activated Pyridines with *N*-Bromosuccinimide", Synthesis, vol. 14, pp. 2175-2179 (2001).
Christensen, J.G. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).

Chung, H.-A. et al., "Direct Functionalization of 4,5-Dichloropyridazin-6-one", J. Heterocyclic Chem., vol. 36, pp. 905-910 (1999).

Cooper, C.S. et al., "Amplification and overexpression of the *met* gene in spontaneously transformed NIH3T3 mouse fibroblasts", The EMBO Journal, vol. 5, No. 10, pp. 2623-2628 (1986).

Di Renzo, M.F. et al., "Overexpression and Amplification of the Met/HGF Receptor Gene during the Progression of Colorectal Cancer", Clinical Cancer Research, vol. 1, pp. 147-154 (1995).

Frey, L.F. et al., "Practical routes toward the synthesis of 2-halo- and 2-alkylamino-4-pyridinecarboxaldehydes", Tetrahedron Letters, vol. 42, pp. 6815-6818 (2001).

Furge, K.A. et al., "Met receptor tyrosine kinase: enhanced signaling through adapter proteins", Oncogene, vol. 19, pp. 5582-5589 (2000).

Gemma, S. et al., "Polycondensed heterocycles. Part 12: An approach to the synthesis of 2-acetyl-1'-methyl-1,2,3,4-tetrahydrospiro-[isoquinoline-1,4'-pyrrolidine]-2'-one", Tetrahedron, vol. 58, pp. 3689-3692 (2002).

Gero, T.W. et al., "Halogenation of 2-Hydroxynicotinic Acid", Synthetic Communications, vol. 19, Nos. 3&4, pp. 553-559 (1989).

Greene, T.W. et al., Protective Groups in Organic Synthesis, 2nd Ed., John Wiley & Sons, Inc., publ., pp. ix-x (table of contents) (1991).

Gual, P. et al., "Sustained recruitment of phospholipase C-γ to Gab1 is required for HGF-induced branching tubulogenesis", Oncogene, vol. 19, pp. 1509-1518 (2000).

Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Kirk, K.L., "Synthesis of Ring-Fluorinated Serotonins and Melatonins", J. Heterocyclic Chem., vol. 13, pp. 1253-1256 (1976).

Lai, J.-F. et al., "Involvement of Focal Adhesion Kinase in Hepatocyte Growth Factor-induced Scatter of Madin-Darby Canine Kidney Cells", The Journal of Biological Chemistry, vol. 275, No. 11, pp. 7474-7480 (2000).

Lee, J.-H. et al., "A novel germ line juxtamembrane *Met* mutation in human gastric cancer", Oncogene, vol. 19, pp. 4947-4953 (2000).

Lubensky, I.A. et al., "Hereditary and Sporadic Papillary Renal Carcinomas with c-*met* Mutations Share a Distinct Morphological Phenotype", American Journal of Pathology, vol. 155, No. 2, pp. 517-526 (1999).

Masuya, D. et al., "The tumour-stromal interaction between intratumoral c-Met and stromal hepatocyte growth factor associated with tumour growth and prognosis in non-small-cell lung cancer patients", British Journal of Cancer, vol. 90, pp. 1555-1562 (2004).

Matsumoto, K. et al., "Hepatocyte Growth Factor: Molecular Structure, Roles in Liver Regeneration, and Other Biological Functions", Critical Reviews in Oncogenesis, vol. 3, Nos. 1,2, pp. 27-54 (1992).

Montesano, R. et al., "Indentification of a Fibroblast-Derived Epithelial Morphogen as Hepatocyte Growth Factor", Cell, vol. 67, pp. 901-908 (1991).

Nicolaou, I. et al., "[1-(3,5-Difluoro-4-hydroxyphenyl)-1*H*-pyrrol-3-yl]phenylmethanone as a Bioisostere of a Carboxylic Acid Aldose Reductase Inhibitor", J. Med. Chem., vol. 47, No. 10, pp. 2706-2709 (2004).

Park, M. et al., "Sequence of *MET* protooncogene cDNA has features characteristic of the tyrosine kinase family of growth-factor receptors", Proc. Natl. Acad. Sci. USA, vol. 84, pp. 6379-6383 (1987).

Quintela, J.M. et al., "A Ready One-pot Preparation for Pyrrolo [2,1-*f*][1,2,4]triazine and Pyrazolo[5,1-*c*]pyrimido[4,5-*e*]triazine Derviatives", Tetrahedron, vol. 52, No. 8, pp. 3037-3048 (1996).

Rong, S. et al., "Met Expression and Sarcoma Tumorigenicity", Cancer Research, vol. 53, pp. 5355-5360 (1993).

Rong, S. et al., "Met Proto-oncogene Product Is Overexpressed in Tumors of p53-deficient Mice and Tumors of Li-Fraumeni Patients", Cancer Research, vol. 55, pp. 1963-1970 (1995).

Sachs, M. et al., "Essential Role of Gab1 for Signaling by the c-Met Receptor In Vivo", The Journal of Cell Biology, vol. 150, No. 6, pp. 1375-1384 (2000).

Scarpino, S. et al., "Hepatocyte Growth Factor (HGF) Stimulates Tumour Invasiveness in Papillary Carcinoma of the Thyroid", Journal of Pathology, vol. 189, pp. 570-575 (1999).

Schaeper, U. et al., "Coupling of Gab1 to c-Met, Grb2, and Shp2 Mediates Biological Responses", The Journal of Cell Biology, vol. 149, No. 7, pp. 1419-1432 (2000).

Schaus, J.M. et al., "Synthesis and Structure-Activity Relationships of Potent and Orally Active 5-HT$_4$ Receptor Antagonists: Indazole and Benzimidazolone Derivatives", J. Med. Chem., vol. 41, No. 11, pp. 1943-1955 (1998).

Soman, N.R. et al., "The *TPR-MET* oncogenic rearrangement is present and expressed in human gastric carcinoma and precursor lesions", Proc. Natl. Acad. Sci. USA, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The Journal of Cell Biology, vol. 123, No. 1, pp. 223-235 (1993).

Stabile, L.P. et al., "Inhibition of human non-small cell lung tumors by a c-Met antisense/U6 expression plasmid strategy", Gene Therapy, vol. 11, pp. 325-335 (2004).

Stella, M.C. et al., "HGF: a multifunctional growth factor controlling cell scattering", The International Journal of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K.A. et al., "Hepatocyte growth factor/scatter factor-induced intracellular signalling", International Journal of Experimental Pathology, vol. 81, pp. 17-30 (2000).

Tabanella, S. et al., "Preparation of enantiomerically pure pyridyl amino acids from serine", Org. Biomol. Chem., vol. 1, pp. 4254-4261 (2003).

Takayama, H. et al., "Diverse tumorigenesis associated with aberrant development in mice overexpressing hepatocyte growth factor/scatter factor", Proc. Natl. Acad. Sci. USA, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Traxler, P.M., "Protein tyrosine kinase inhibitors in cancer treatment", Exp. Opin. Ther. Patents, vol. 7, No. 6, pp. 571-588 (1997).

Barker, J.M. et al., "Thienopyridines. Part 7. Some Electrophilic Substitution Reactions of Thieno[2,3-*b*]- and -[3,2-*b*]pyridine Isosteres of 4-Oxygenated and 2,4-Dioxygenated Quinolines", J. Chem. Research (S), pp. 122-123 (1986).

Cheng, C.-C. et al., "Comprehensive Studies on Dual Excitation Behavior of Double Proton versus Charge Transfer in 4-(*N*-Substituted amino)-1H-pyrrolo[2,3-*b*]pyridines", J. Phys. Chem. A, vol. 107, No. 10, pp. 1459-1471 (2003).

Cheng, C.C. et al., "Potential Purine Antagonists. XII. Synthesis of 1-Alkyl(aryl)-4,6-disubstituted Pyrazolo[3,4-*d*]pyrimidines", J. Org. Chem., vol. 23, pp. 852-861 (1958).

Chi, S.-M. et al., "Palladium-catalyzed functionalization of 5- and 7-azaindoles", Tetrahedron Letters, vol. 41, pp. 919-922 (2000).

Dorn, H. et al., "Unambiguous Synthesis of 4,7-Dihydro-4-oxo-1H-pyrazolo[3,4-b]pyridine—Further Comments on the '(N-C)-Rearrangement' of (2-Alkoxycarbonyl-vinyl-amino)pyrazols", J. Prakt. Chem., vol. 324, No. 4, pp. 557-562 (1982).

Girgis, N.S. et al., "The Synthesis of 5-Azaindoles by Substitution-Rearrangement of 7-Azaindoles upon Treatment with Certain Primary Amines", J. Heterocyclic Chem., vol. 26, pp. 317-325 (1989).

Hamdouchi, C. et al., "Imidazo[1,2-*b*]pyridazines, Novel Nucleus with Potent and Broad Spectrum Activity against Human Picornaviruses: Design, Synthesis, and Biological Evaluation", J. Med. Chem., vol. 46, No. 20, pp. 4333-4341 (2003).

Itoh, T. et al., "Studies on the Chemical Synthesis of Potential Antimetabolites. 30. Regioselective Introduction of a Chlorine Atom into the Imidazo[4,5-*b*]pyridine Nucleus", J. Heterocyclic Chem., vol. 19, pp. 513-517 (1982).

Kitamura, C. et al., "Synthesis and reactions of 3,3'-dibromodihydrodipyrrins", J. Chem. Soc. Perkin Trans. 1, pp. 1443-1447 (1997).

Koch, V. et al., "Chemistry of 3-Hydroxpyridine Part 2: Synthesis of 5,6-Dihalo-3-hydroxypyridines", Synthesis, pp. 499-501 (1990).

Morril, C. et al., "Synthesis of Functionalized Vinyl Boronates via Ruthenium-Catalyzed Olefin Cross-Metathesis and Subsequent Conversion to Vinyl Halides", J. Org. Chem., vol. 68, No. 15, pp. 6031-6034 (2003).

Sanghvi, Y.S. et al., "Synthesis and Biological Evaluation of Certain C-4 Substituted Pyrazolo[3,4-*b*]pyridine Nucleosides", J. Med. Chem., vol. 32, No. 5, pp. 945-951 (1989).

Tedder, M.E. et al., "Structure-based design, synthesis, and antimicrobial activity of purine derived SAH/MTA nucleosidase inhibitors", Bioorganic & Medicinal Chemistry Letters, vol. 14, pp. 3165-3168 (2004).

Temple, Jr., C. et al., "Preparation and Properties of Some Isomeric *v*-Triazolopyridines. 1- and 3-Deaza-8-azapurines", J. Org. Chem., vol. 37, No. 23, pp. 3601-3604 (1972).

Thibault, C. et al., "Concise and Efficient Synthesis of 4-Fluoro-1*H*-pyrrolo[2,3-*b*]pyridine", Organic Letters, vol. 5, No. 26, pp. 5023-5025 (2003).

Zhang, Z. et al., "A General Method for the Preparation of 4- and 6-Azaindoles", J. Org. Chem., vol. 67, pp. 2345-2347 (2002).

Database Crossfire Beilstein Beilstein Institut Zur Foerderung Der Chemischen Wissenschaft, Frankfurt Am Main, DE; XP002362294 Database accession No. BRN 667921.

Database Crossfire Beilstein Beilstein Institut Zur Foerderung Der Chemischen Wissenschaft, Frankfurt Am Main, DE; XP002362295 Database accession No. BRN 413351.

Database Crossfire Beilstein Beilstein Institut Zur Foerderung Der Chemischen Wissenschaft, Frankfurt Am Main, DE; XP002362296 Database accession No. BRN 450834.

Database Crossfire Beilstein Beilstein Institut Zur Foerderung Der Chemischen Wissenschaft, Frankfurt Am Main, DE; XP002362297 Database accession No. BRN 448780.

U.S. Appl. No. 11/292,358, filed Dec. 1, 2005, Borzilleri et al.

"Hepatocyte growth factor/scatter factor, Met and cancer references", Van Andel Institute, http://www.vai.org/vari/metandcancer/ (as revised Oct. 4, 2005).

U.S. Appl. No. 11/406,795, filed Apr. 19, 2006, Borzilleri et al.

U.S. Appl. No. 60/819,171, filed Jul. 07, 2006, Bristol-Myers Squibb Company.

U.S. Appl. No. 60/619,302, filed Oct. 15, 2004, Takeda San Diego, Inc.

U.S. Appl. No. 60/679,690, filed May 11, 2005, Takeda San Diego, Inc.

* cited by examiner

MONOCYCLIC HETEROCYCLES AS KINASE INHIBITORS

RELATED APPLICATIONS

This application claims priority benefit under Title 35 § 119(e) of U.S. Provisional Applications Nos. 60/564,842, filed Apr. 23, 2004, and 60/639,178, filed Dec. 23, 2004, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54,1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65,1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology,* 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.,* 63:7345-55, 2003; Lee et al., *Oncogene,* 19:4947-53, 2000 and Direnzo et al., *Clin. Cancer Res.,* 1: 147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer,* 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701-6, 1997) and an amplified/overexpressed Met spontaneously transforms NIH-3T3 cells (Cooper et al., *EMBO J.,* 5:2623-8, 1986).

Biological agents, such as ribozymes, antibodies and antisense RNA targeting either HGF or Met have been shown to inhibit tumorogenesis (Stabile et al., *Gene Therapy,* 11:325-35, 2004, Jiang et al., *Clin. Cancer Res,* 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases.

SUMMARY OF THE INVENTION

The present invention is directed to compounds having Formulas I and II as described below that are useful in the treatment of cancer.

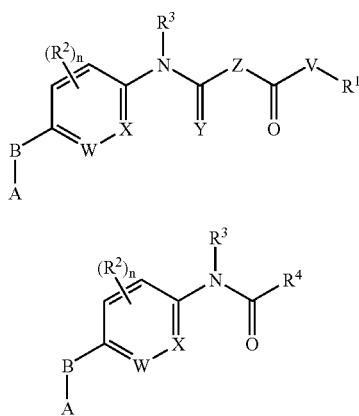

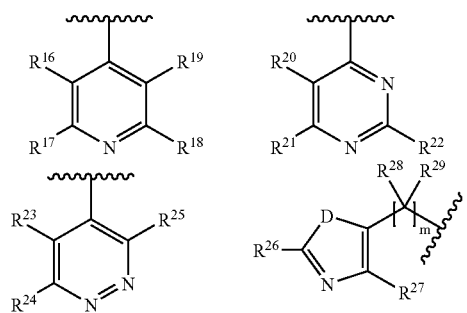

or an enantiomer, diastereomer, hydrate, solvate or pharmaceutically acceptable salt thereof wherein:

$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;

each $R^2$ is independently H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, arylalkyl, substituted arylalkyl, heterocycloalkyl, or substituted heterocycloalkyl;

B is O, $NR^8$, $NR^8CH_2$, S, SO, $SO_2$, or $CR^9R^{10}$;

V is $NR^{11}$ or —$(CR^{37}R^{38})_p$— provided that when $VR^{11}$ is N, $R^1$ is an alkyl or cycloalkyl;

W and X are each independently C or N;

Y is selected from O, S, and $NR^{12}$;

Z is —$CR^{13}R^{14}$—, or —$(CR^{13}R^{14})_l NR^{15}$—;

l is 0 to 2;

n is 0 to 4 if W and X are both C, 0 to 3 if one of X or W is N, and 0 to 2 if X and W are both N;

p is 1 to 4;

$R^3$, $R^5$, $R^6$, $R^7$, $R^8$, $R^{11}$ and $R^{15}$ are independently selected from H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo;

$R^4$ is selected from aryl, substituted aryl, heteroaryl, substituted heteroaryl, heterocycloalkyl, and substituted heterocycloalkyl, provided that (a) if $R^4$ is phenyl
  (i) $R^4$ is not substituted with both hydroxy and amido; and
  (ii) $R^4$ is not substituted with —$NRSO_2R$— wherein R is alkyl or aryl;

(b) if $R^4$ is pyridyl, $R^4$ is not substituted with both hydroxy and methoxy; and (c) if $R^4$ is pyrimidinyl, it is not substituted with =O;

$R^9$ and $R^{10}$ are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{12}$ is selected from H, alkyl, substituted alkyl, alkenyl, substituted alkenyl, alkynyl, substituted alkynyl, CN, $NO_2$ or $SO_2NH_2$;

$R^{13}$ and $R^{14}$ are independently selected from H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;

A is selected from one of the following:

wherein
D is S or O;
m is 0 to 6;
$R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are independently selected from H, halogen, $NR^{30}R^{31}$, $OR^{32}$, $CO_2R^{33}$, $CONR^{34}R^{35}$, $SO_2R^{36}$, alkyl, substituted alkyl, cycloalkyl, substituted cycloalkyl, alkenyl, substituted alkenyl, alkynyl, substituted alkynyl, —CN, aryl, substituted aryl, heteroaryl, substituted heteroaryl, heterocycloalkyl, or substituted heterocycloalkyl;

$R^{28}$ and $R^{29}$ are independently selected from H, alkyl, substituted alkyl, cycloalkyl, substituted cycloalkyl, aryl, substituted aryl, or taken together to form a carbocyclic or heterocyclic ring of 3 to 8 atoms;

$R^{30}$, $R^{31}$, $R^{33}$, $R^{32}$, $R^{34}$, $R^{35}$, and $R^{36}$ are independently selected from H, alkyl, substituted alkyl, alkenyl, substituted alkenyl, alkynyl, substituted alkynyl, cycloalkyl, substituted cycloalkyl, alkoxycarbonyl, aryl, substituted aryl, heteroaryl, substituted heteroaryl, heterocyclo, substituted heterocyclo, heterocycloalkyl, or substituted heterocycloalkyl; and $R^{37}$ and $R^{38}$ are each independently H, halogen, or alkyl.

DESCRIPTION OF THE INVENTION

The present invention provides for compounds of Formulas I and II defined above, pharmaceutical compositions employing such compounds, and methods of using such compounds in the treatment of cancer.

The term "alkyl" herein alone or as part of another group refers to a monovalent alkane (hydrocarbon) derived radical containing from 1 to 12 carbon atoms unless otherwise defined. Preferred alkyl groups are lower alkyl groups having from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, cycloalkyl, heterocycloalkyl, —CN, aryl, heteroaryl, halo (such as F, Cl, Br, I), haloalkyl (such as $CCl_3$ or $CF_3$), hydroxyl, alkoxy, alkylthio, alkylamino, —COOH, —COOR, —C(O)R, —OCOR, amino, carbamoyl (—NHCOOR— or —OCONHR—), urea (—NHCONHR—) or thiol (—SH).

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkynyl groups include those listed above for alkyl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "cycloalkyl" herein alone or as part of another group is a species of alkyl containing from 3 to 15 carbon atoms, without alternating or resonating double bonds between carbon atoms. It may contain from 1 to 4 rings. Exemplary groups include cyclopropyl, cyclobutyl, cyclopentyl, cyclohexyl, adamantyl, etc. Cycloalkyl groups may be substituted at any available point of attachment. Exemplary substituents include one or more of the following groups: halogen, such as F, Br, or Cl, hydroxyl, alkyl, alkoxy, amino, nitro, cyano, thiol, alkylthio, and any of the substituents described above for alkyl groups.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group.

The term "alkylcarbonyloxy" herein alone or as part of another group denotes an alkylcarbonyl group bonded through an oxygen linkage.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "arylalkyl" or "aralkyl" herein alone or as part of another group denotes an aryl group as described above bonded through an alkyl group, as described above. And example of an aralkyl group is a benzyl group.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, =O, —$CO_2H$, —C(=O)H, —$CO_2$-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' or R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocyclic ring" herein alone or as part of another group refers to a stable, saturated, or partially unsaturated monocyclic ring system containing 5 to 7 ring members of carbon atoms and other atoms selected from nitrogen, sulfur and/or oxygen. Preferably, a heterocyclic ring is a 5 or 6-membered monocyclic ring and contains one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably rifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

Suitable examples of salts of the compounds according to the invention with inorganic or organic acids are hydrochloride, hydrobromide, sulfate, methanesulfonate, maleate, fumarate, and phosphate. Salts which are unsuitable for pharmaceutical uses but which can be employed, for example, for the isolation or purification of free compounds I or II, their pharmaceutically acceptable salts, are also included.

In general, the instant invention comprises compounds having Formula I or II:

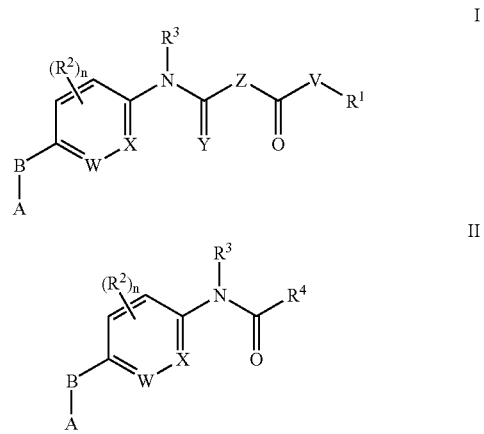

or an enantiomer, diastereomer, hydrate, solvate or pharmaceutically acceptable salt thereof wherein:

$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;

each $R^2$ is independently H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, arylalkyl, substituted arylalkyl, heterocycloalkyl, or substituted heterocycloalkyl;

B is O, $NR^8$, $NR^8CH_2$, S, SO, $SO_2$, or $CR^9R^{10}$;

V is $NR^{11}$ or $—(CR^{37}R^{38})_p—$ provided that when V is N, $R^1$ is an alkyl or cycloalkyl;

W and X are each independently C or N;

Y is selected from O, S, and $NR^{12}$;

Z is $—CR^{13}R^{14}—$, or $—(CR^{13}R^{14})_1NR^{15}—$;

1 is 0 to 2;

n is 0 to 4 if W and X are both C, 0 to 3 if one of X or W is N, and 0 to 2 if X and W are both N;

p is 1 to 4;

$R^3$, $R^5$, $R^6$, $R^7$, $R^8$, $R^{11}$ and $R^{15}$ are independently selected from H, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo;

$R^4$ is selected from aryl, substituted aryl, heteroaryl, substituted heteroaryl, heterocycloalkyl, and substituted heterocycloalkyl, provided that (a) if $R^4$ is phenyl
  (i) $R^4$ is not substituted with both hydroxy and amido; and
  (ii) $R^4$ is not substituted with $—NRSO_2R—$ wherein R is alkyl or aryl;
(b) if $R^4$ is pyridyl, $R^4$ is not substituted with both hydroxy and methoxy; and
(c) if $R^4$ is pyrimidinyl, it is not substituted with $=O$;

$R^9$ and $R^{10}$ are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{12}$ is selected from H, alkyl, substituted alkyl, alkenyl, substituted alkenyl, alkynyl, substituted alkynyl, CN, $NO_2$ or $SO_2NH_2$;

$R^{13}$ and $R^{14}$ are independently selected from H, halogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;

A is selected from one of the following:

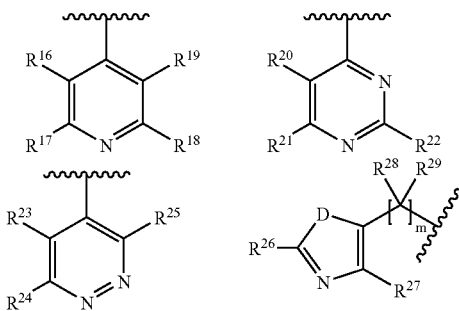

wherein

D is S or O;

m is 0 to 6;

$R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are independently selected from H, halogen, $NR^{30}R^{31}$, $OR^{32}$, $CO_2R^{33}$, $CONR^{34}R^{35}$, $SO_2R^{36}$, alkyl, substituted alkyl, cycloalkyl, substituted cycloalkyl, alkenyl, substituted alkenyl, alkynyl, substituted alkynyl, —CN, aryl, substituted aryl, heteroaryl, substituted heteroaryl, heterocycloalkyl, or substituted heterocycloalkyl;

$R^{28}$ and $R^{29}$ are independently selected from H, alkyl, substituted alkyl, cycloalkyl, substituted cycloalkyl, aryl, substituted aryl, or taken together to form a carbocyclic or heterocyclic ring of 3 to 8 atoms;

$R^{30}$, $R^{31}$, $R^{32}$, $R^{33}$, $R^{34}$, $R^{35}$, and $R^{36}$ are independently selected from H, alkyl, substituted alkyl, alkenyl, substituted alkenyl, alkynyl, substituted alkynyl, cycloalkyl, substituted cycloalkyl, alkoxycarbonyl, aryl, substituted aryl, heteroaryl, substituted heteroaryl, heterocyclo, substituted heterocyclo, heterocycloalkyl, or substituted heterocycloalkyl; and $R^{37}$ and $R^{38}$ are each independently H, halogen, or alkyl.

In some embodiments of the present invention, $R^1$ is a substituted or unsubstituted phenyl, such as fluorophenyl, a substituted or unsubstituted $C_1$ to $C_4$ alkyl, such as methyl, or a substituted or unsubstituted $C_3$ to $C_8$ cycloalkyl, such as cyclohexyl or cyclopentyl.

In some embodiments of the present invention, $R^2$ is $C_1$ to $C_4$ alkyl, halogen, or haloalkyl.

In some embodiments of the present invention, $R^4$ is optionally substituted phenyl, or a 5 or 6 membered nitrogen containing heteraryl group such as pyridyl, pyridinone, pyrazolyl, or pyrrolidyl.

According to one embodiment of the present invention, B is O, $NHCH_2$, $CH_2$ or CH(OH); Y is O or S and Z is —$CR^{13}R^{14}$ or —$NR^{15}$ wherein $R^{13}$, $R^{14}$, and $R^{15}$ are each H.

In some embodiments of the present invention, A is an optionally substituted pyridine or pyrimidine, wherein the substituent is alkyl, alkenyl, alkynyl, halogen, cycloalkyl, heterocycloalkyl, —$NR^{39}COR^{40}$, —$NR^{39}C(O)_2R^{40}$, —$NR^{41}R^{42}$, or —$C(O)NR^{43}R^{44}$, wherein $R^{39}$, $R^{40}$, $R^{41}$, $R^{42}$, $R^{43}$, and $R^{44}$ are independently H, lower alkyl, substituted lower alkyl, hydroxyalkyl, aminoalkyl, cycloalkyl, substituted cycloalkyl, heterocycloalkyl, substituted heterocycloalkyl, cycloalkenyl, substituted cycloalkenyl, aryl, substituted aryl, heteroaryl, substituted heteroaryl, or —$NR^{43}R^{44}$ form a heterocycloalkyl.

According to some embodiments of the present invention, A is a pyridine substituted with —$NR^{41}R^{42}$, —$NR^{39}COR^{40}$, —$C(O)NR^{43}R^{44}$, halogen, $C_1$ to $C_4$ alkyl, optionally substituted with hydroxy, hydroxyalkylamino, alkylamino, aminoalkylamino, or heteroarylalkyl; or —C≡C—$R^{45}$, —C≡C—$R^{46}$, wherein $R^{45}$ and $R^{46}$ are alkyl, hydroxyalkyl, aminoalkyl, cycloalkyl, heterocycloalkyl, —$C(O)R^{47}$, —$NR^{39}COR^{40}$, aryl, or heteroaryl; or the pyridine is substituted with aryl, such as phenyl, which may be further substituted with $CONH_2$, methyl, aminoethyl, hydroxyethyl, —$CONHCH_2CH_2NHCH_3$, or $CH_2CONH_2$; the pyridines may also be substituted with pyridyl or piperidyl groups.

According to some embodiments of the present invention, A is an optionally substituted pyrimidine. Preferred substituents include —$NR^{41}R^{42}$, or —$NR^{39}CO_2R^{40}$, wherein $R^{41'}$ and $R^2$ are preferably H or methyl and $R^{39}$ and $R^{40}$ are preferably, H or alkyl.

In one embodiment of the present invention, compounds have the following formula III:

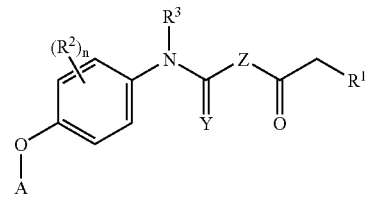

III wherein $R^1$ is optionally substituted phenyl or alkyl; Z is NH or $NCH_3$; $R^2$ is F, Cl, $CH_3$ or $CF_3$; $R^3$ is H; and Y is O or S. In some embodiments, $R^1$ is $C_3$ to $C_7$ cycloalkyl, substituted or unsubstituted phenyl, or —$CH_2)_n$—$R^{50}$ wherein n is 1 to 3, $R^{50}$ is H, substituted or unsubstituted phenyl, amino, amido, CN, —$C(O)_2H$, or —$C(O)_2CH_3$.

In some embodiments of the present invention, compounds have the following formula Formula IV:

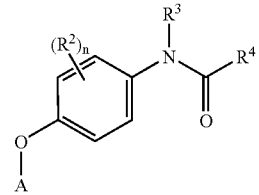

IV wherein $R^2$ is halo or H; $R^3$ is H; $R^4$ is optionally substituted phenyl, optionally substituted pyrazole, or optionally substituted pyridyl, pyridinone, or pyridine-N-oxide.

In one embodiment of the present invention, compounds are of the following formula V:

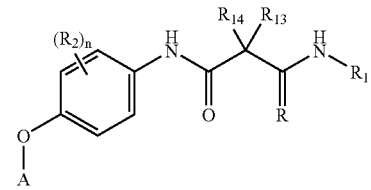

V wherein $R^1$ is optionally alkyl or cycloalkyl; A is optionally substituted pyrimidine or pyridine; and $R_2$ is halo or H; and $R^{13}$ and $R^{14}$ are either H or together with the carbon to which they are attached form a cycloalkyl, such as cyclopropyl.

The invention also provides methods for treating a proliferative disease, such as cancer by administering to a mammalian species in need of such treatment an effective amount of a compound of formulas I or II, as defined above. In another embodiment, the invention provides a method for treating a proliferative disease via modulation of Met kinase by administering to a mammalian species in need of such treatment an effective amount of a compound of formulas I or II, as defined above, in combination (simultaneously or sequentially) with at least one other anti-cancer agent. In a preferred embodiment, the proliferative disease is cancer.

Certain compounds of Formulas I and II may generally be prepared according to the following Schemes 1-14. The compounds are synthesized readily using synthetic methods known to one skilled in the art. Solvates (e.g., hydrates) of the compounds of Formulas I and II are also within the scope of the present invention. Methods of solvation are generally known in the art. Accordingly, the compounds of the instant invention may be in the free or hydrate form, and may be obtained by methods exemplified by the following schemes below.

General routes to the pyridine and pyrimidine analogues described in the invention are illustrated in Scheme 1. An appropriately substituted pyridine or pyrimidine 1 can be treated with functionalized phenols 2, 4, and 8 in the presence of a base, such as sodium hydride, sodium hydroxide, or potassium carbonate, to furnish the desired ethers 3, 5, and 9, respectively. Removal of the acetamide protecting group of compound 3 with aqueous HCl in methanol provides the key intermediate 5. Alternatively, aniline 5 can be obtained from compound 9 via reduction of the nitro group with either zinc dust and ammonium chloride or Adams' catalyst (platinum (IV) oxide) under hydrogenation conditions. Analogues 6 and 7 can then be prepared by acylation of aniline 5 with, for example isocyanates, acid chlorides or by treatment with a carboxylic acid and a coupling reagent, such as: benzotriazol-1-yloxytris(trimethylamino)phosphonium hexafluorophosphate (BOP reagent), bromotripyrrolidinophosphonium hexafluorophosphate (PyBroP), O-(1H-benzotriazol-1-yl)-N,N,N',N'-tetramethyluronium tetrafluoroborate (TBTU). Formation of the acylthiourea of 6 (Y=S, Z=NH) can be accomplished by treating aniline 5 with an appropriately substituted isothiocyanate.

SCHEME 1

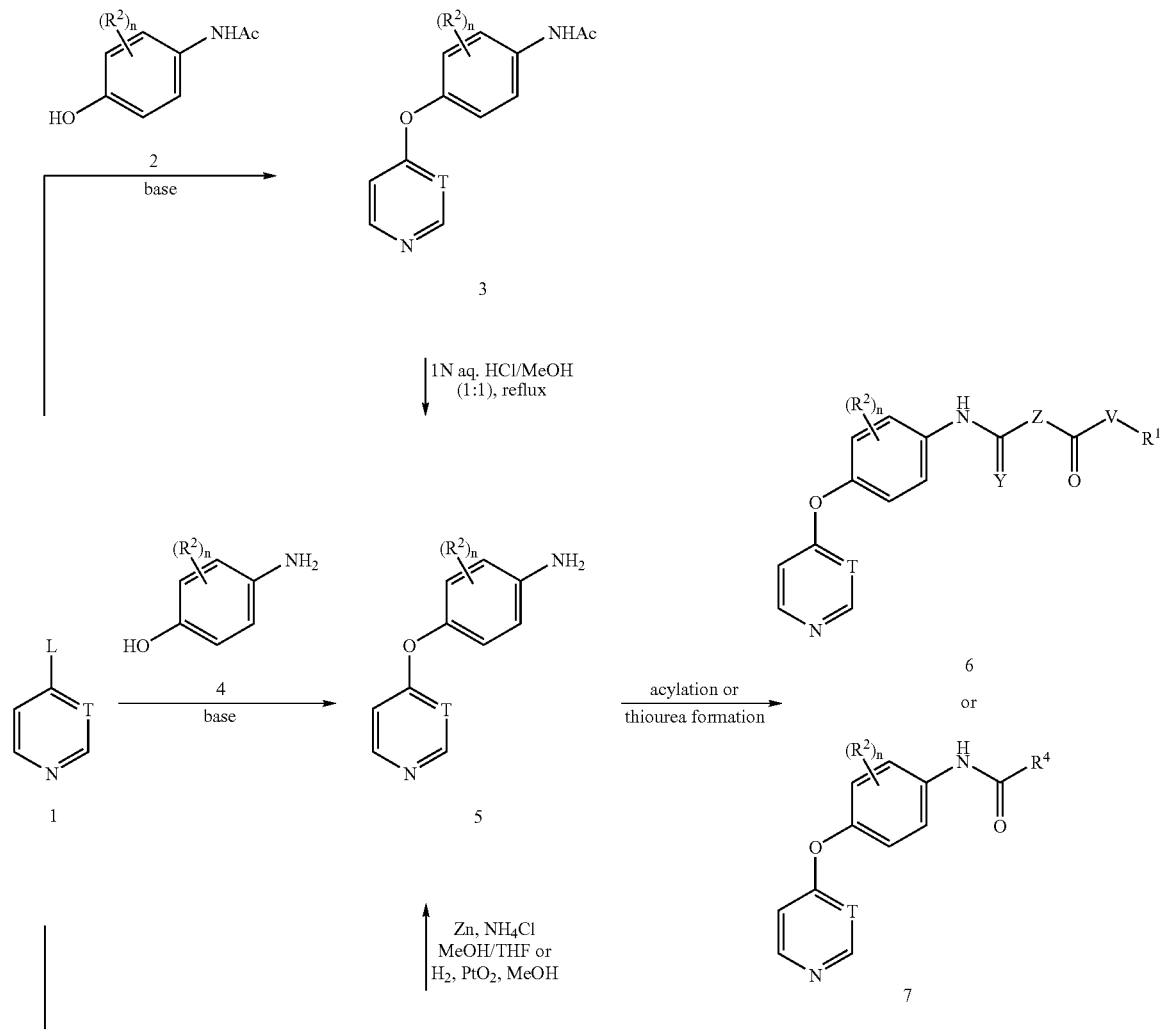

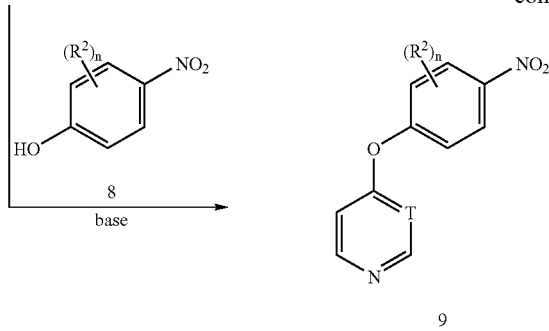

T = CR$^{19}$ or N
L = leaving group, such as a halogen or NO$_2$

The two different regioisomeric aminopyrimidine analogues 14 and 19 can be prepared using the synthetic routes outlined in Schemes 2 and 3. PMB-protected aminopyrimidine 11, derived from commercially available 2,4-dichloropyrimidine (10, Aldrich), can be converted to ether 13 via aniline 12 using the same chemistry outlined in Scheme 1. Removal of the PMB group of 13 can be accomplished with trifluoroacetic acid and anisole to generate compound 14.

SCHEME 2

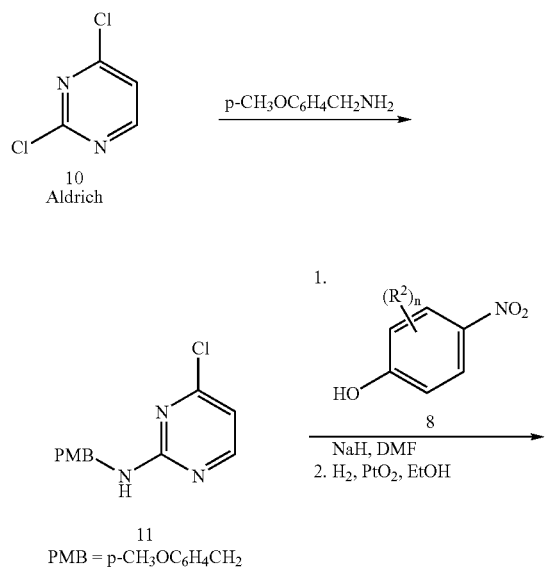

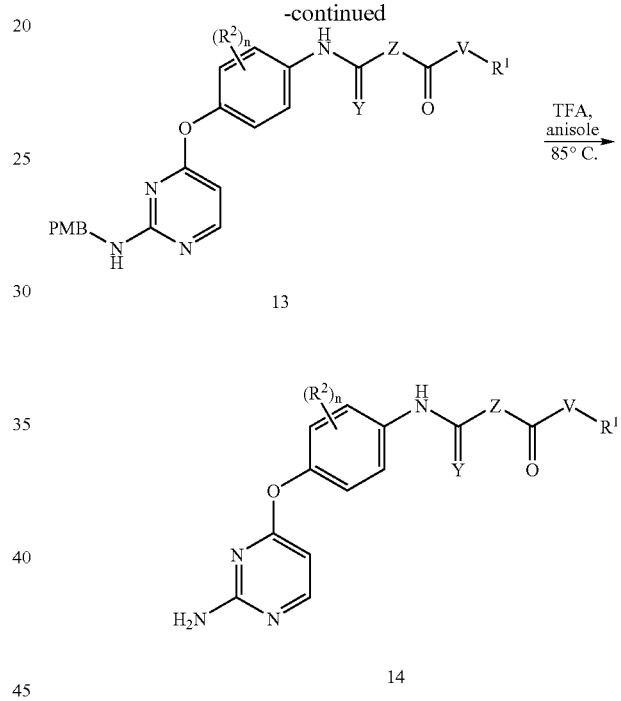

Similarly, PMB-protected aminopyrimidine 16, derived from commercially available 4,6-dichloropyrimidine (15, TCI America), can be converted to ether 17 following the PMB deprotection step (Scheme 3). Bis-Boc (t-butyloxycarbonyl) protection of the amine of 17 with excess di-tert-butyl dicarbonate followed by hydrogenation with Adams' catalyst provides aniline 18. Amine 19 can be obtained from compound 18 following an acylation or thiourea formation step and removal of the Boc protecting groups under acidic conditions.

SCHEME 3

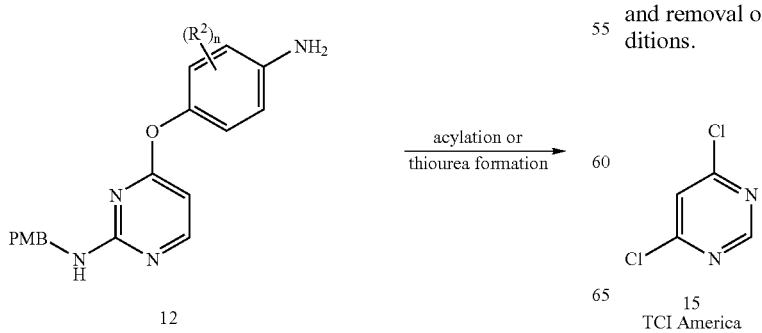

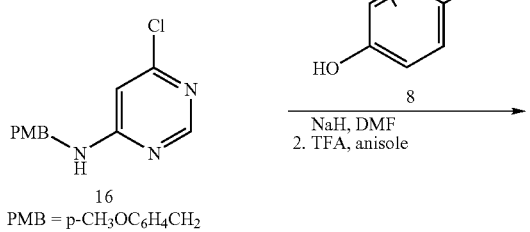
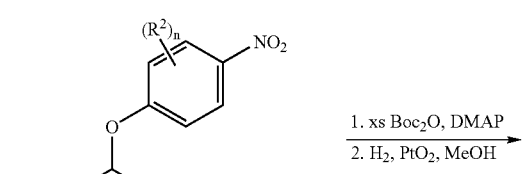
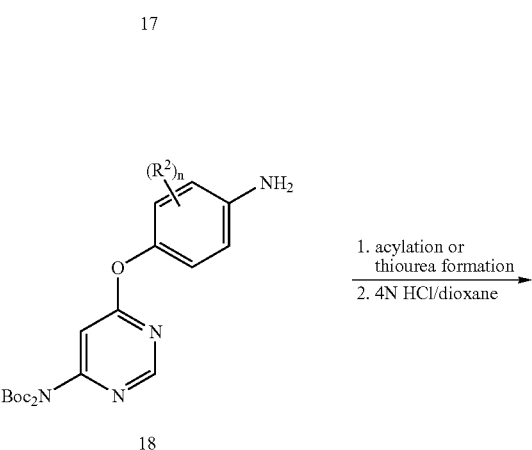
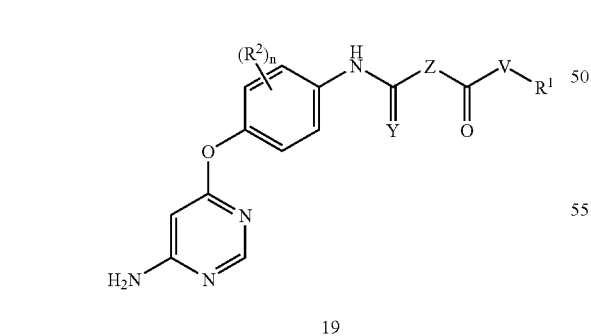

Aminopyridazine derivative 26 may be prepared using the synthetic route outlined in Scheme 4 which is based on similar chemistry cited in the following references: Chung, H.-A. et al. *J. Heterocyclic Chem.* 1999, 36, 905-910 and Bryant R. D. et al. *J. Heterocyclic Chem.* 1995, 32, 1473-1476, the disclosures of which are herein incorporated by reference.

4,5-Dichloropyridazin-3(2H)-one (20, Aldrich) can be protected with, for example a tetrahydropyran (THP) group to give intermediate 21. Treatment of compound 21 with an appropriately substituted phenol and a base (i.e., sodium hydride) followed by reduction of the nitro containing intermediate under catalytic hydrogenation conditions can provide aniline 22. Protection of the aniline group of 22 as a bis-benzyl carbamate (Cbz) followed by removal of the THP group under acidic conditions may furnish compound 23. Treatment of compound 23 with either trifluoroacetic anhydride (TFAA), phosphorous oxychloride or phosphorous oxybromide in the presence of a base, such as triethylamine or diisopropylethylamine may introduce the necessary leaving group at the 3-position of compound 24. Displacement of the leaving group X of compound 24 with an appropriately substituted amine, followed by removal of the Cbz groups can generate intermediate 25. Aniline 25 may be converted to the desired 3-aminopyridazine analogue 26 using chemistry previously described in Schemes 1-3.

SCHEME 4

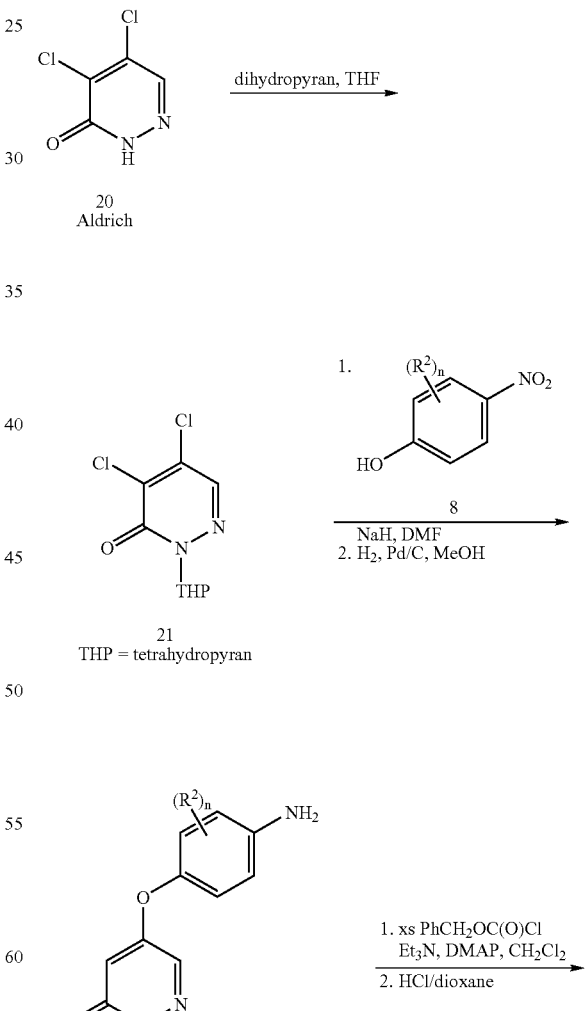

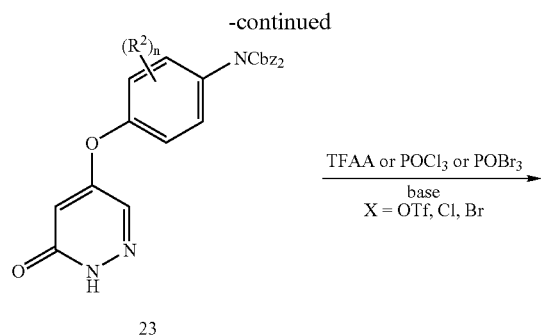

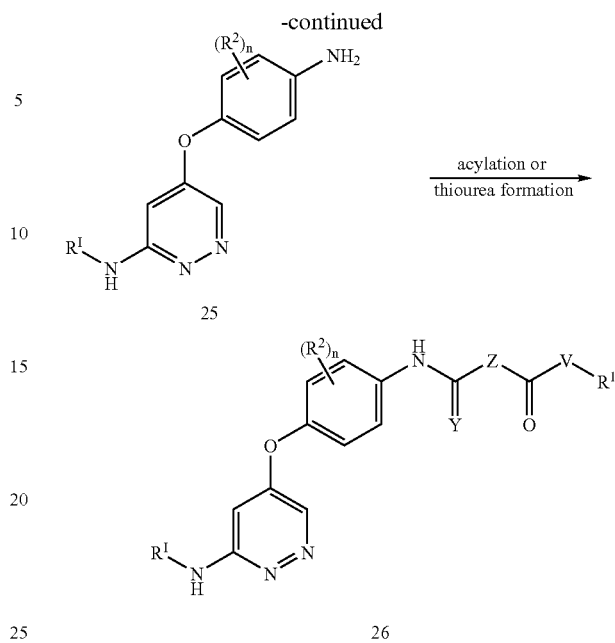

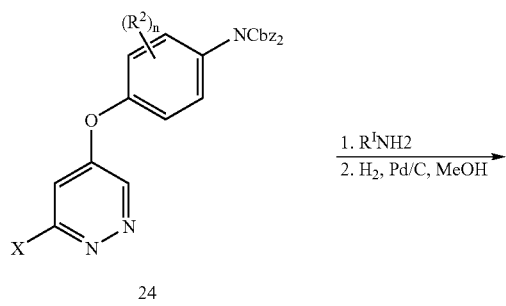

2-Aminopyridine derivatives may be prepared using the synthetic routes outlined in Schemes 5 and 6. Aniline 27, derived from chemistry described in Scheme 1 may be converted to intermediate 28 upon heating with Cu powder and potassium carbonate in benzylamine (Scheme 5). Removal of the benzyl protecting group of compound 28 under catalytic hydrogenation conditions with palladium on carbon provides aminopyridine 29. Intermediates 28 or 29 can be treated with isothiocyanates 30, isocyanates 32, and carboxylic acids 34 in the presence of a coupling reagent to afford acylthiourea 31, acylurea 33, and amide 35, respectively.

SCHEME 5

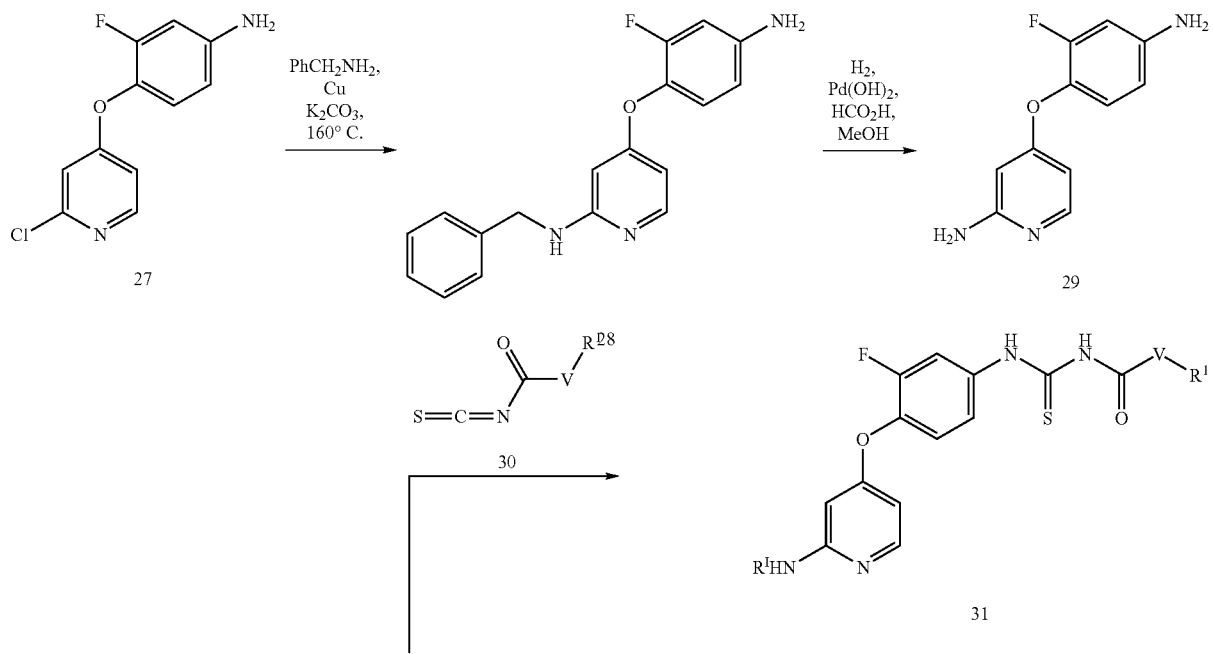

-continued

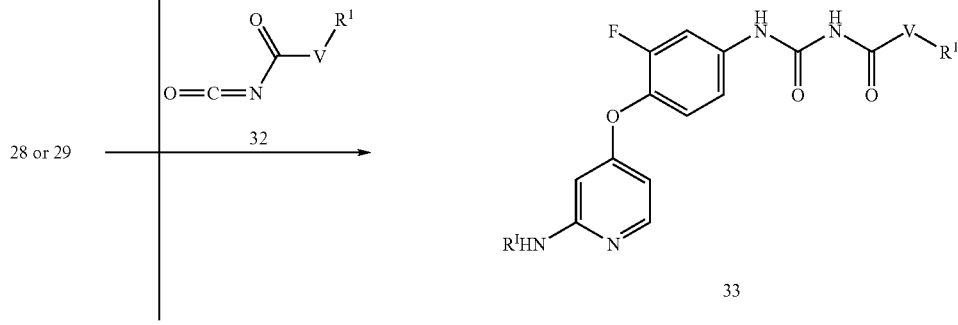

28 or 29 → 32 → 33

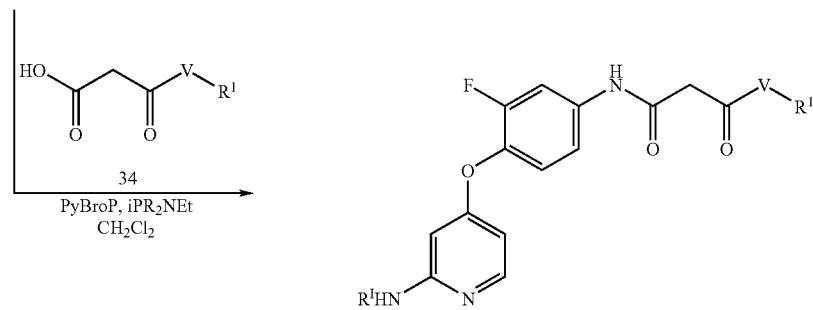

34
PyBroP, iPR$_2$NEt
CH$_2$Cl$_2$

35

R$^1$ = H or PhCH$_2$

In a related approach, 2-chloropyridine intermediate 36, obtained using chemistry described in Scheme 1 can be converted to the N-oxide 37 using 3-chloroperoxybenzoic acid (m-CPBA) in chloroform (see, WO2004/002410) (Scheme 6). Treatment of compound 37 with an appropriately substituted amine can afford intermediate 38. Reduction of the N-oxide of compound 38 with, for example triphenylphosphine, followed by removal of the acetamide protecting group under acidic conditions can provide aniline 39. Conversion of aniline 39 to the desired analogue 40 can be accomplished using chemistry previously described in Schemes 1-5.

SCHEME 6

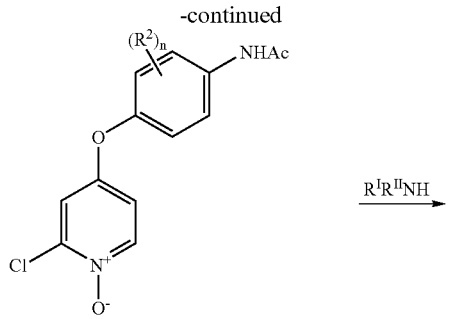

36 m-CPBA / CHCl$_3$ →

-continued

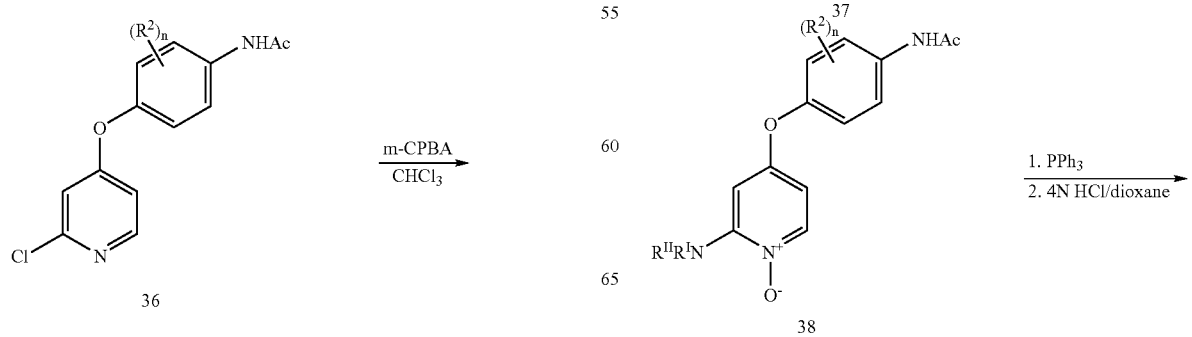

37

R$^I$R$^{II}$NH →

38

1. PPh$_3$
2. 4N HCl/dioxane →

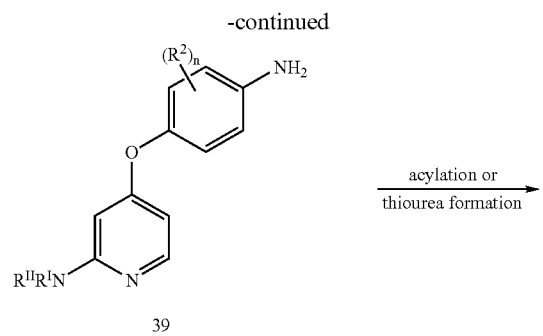

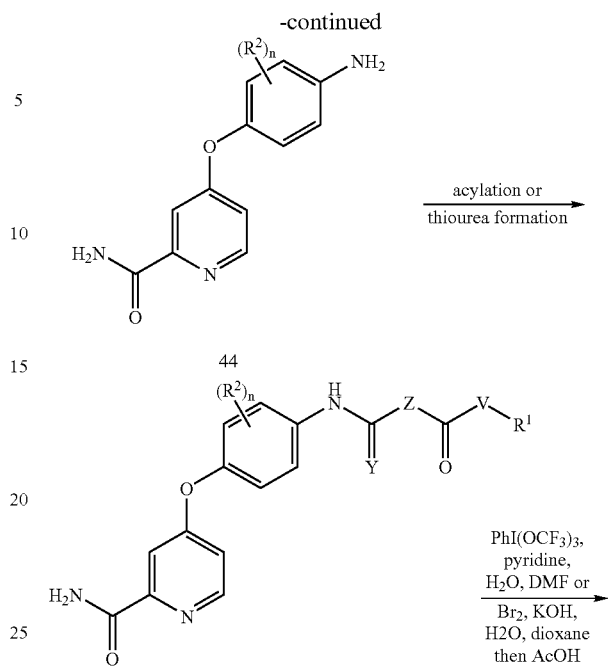

In an alternative approach to compounds related to 40, the 2-aminopyridine derivatives 47 and 48 may be prepared according to the synthetic sequence illustrated in Scheme 7. To this end, 4-chloropicolinic acid (41, TCI America) can be converted to 4-chloropicolinamide (42) using a two step procedure involving thionylchloride followed by ammonia in methanol. Coupling of intermediate 42 with 4-aminophenol derivative 43, in the the presence of a base, such as potassium t-butoxide can afford the picolinamide derivative 44. Acylation or acylurea formation of intermediate 44 can provide intermediates such as 45 and 46. Treatment of the picolinamide derivatives 45 and 46 with either bis-(trifluoroacetoxy)-iodobenzene, pyridine and water in DMF or bromine, potassium hydroxide in water promotes a Hofmann rearrangement to generate the desired 2-aminopyridine derivatives 47 and 48.

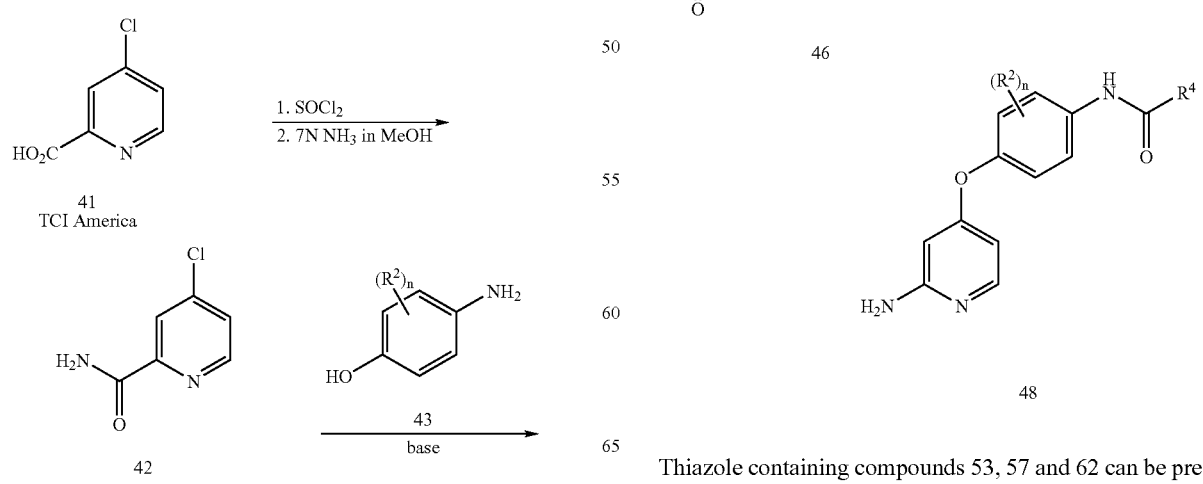

Thiazole containing compounds 53, 57 and 62 can be prepared using the synthetic routes described in Schemes 8-10.

Displacement of the leaving groups of 49 (Scheme 8) or 54 (Scheme 9) with an aniline/phenol 50 can provide intermediates 51 and 55, respectively. Reduction of the nitro substituents of 51 and 55 with zinc dust and ammonium chloride in a THF-MeOH mixture should generate anilines 52 and 56, respectively. Conversion of anilines 52 and 56 to the desired compounds 53 and 57 can be accomplished using chemistry previously described (vide supra).

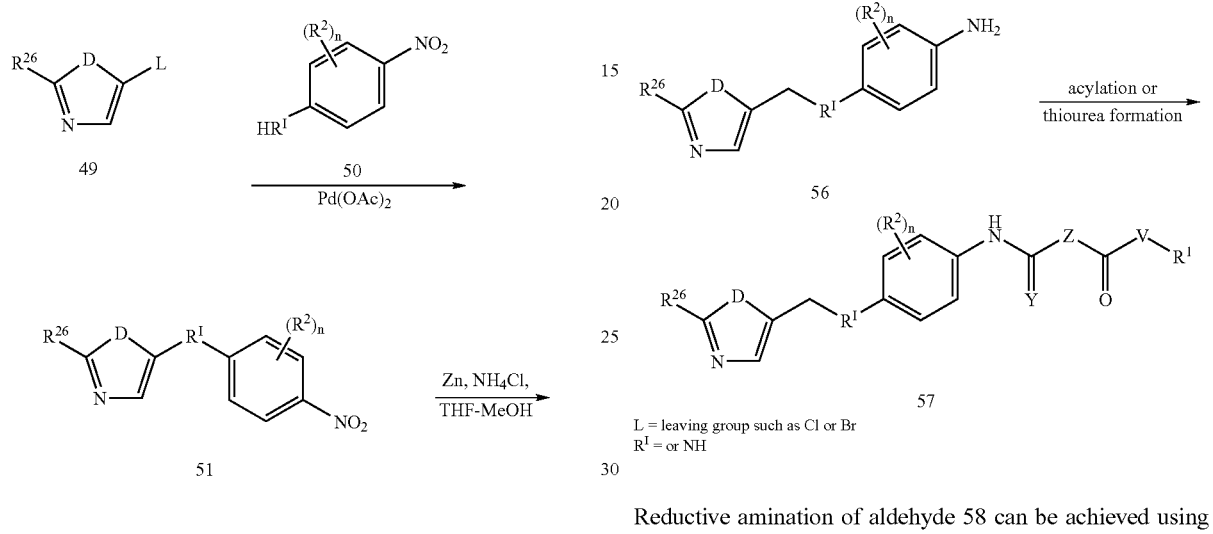

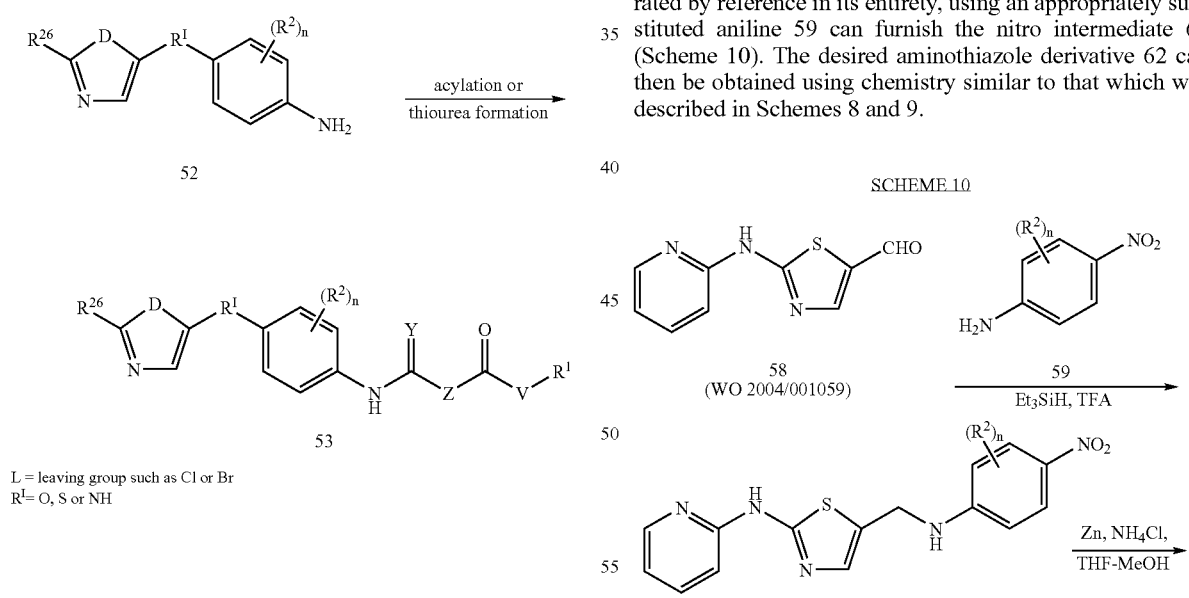

L = leaving group such as Cl or Br
R$^I$ = or NH

Reductive amination of aldehyde 58 can be achieved using the methods described in WO 2004/001059, herein incorporated by reference in its entirety, using an appropriately substituted aniline 59 can furnish the nitro intermediate 60 (Scheme 10). The desired aminothiazole derivative 62 can then be obtained using chemistry similar to that which was described in Schemes 8 and 9.

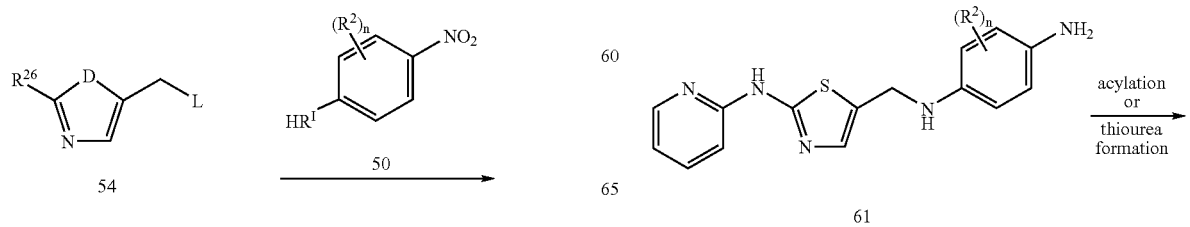

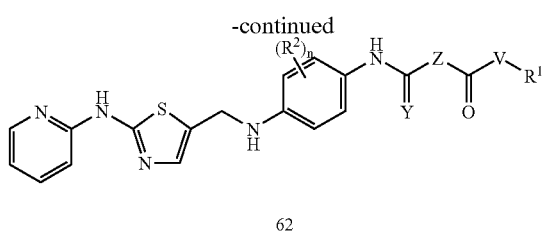

62

Incorporation of various substituents at the 3-position of the pyridine nucleus can be accomplished using the chemistry outlined in Scheme 11. To this end, 4-chloro-3-iodopyridine (63, Tabanella, S. et al. *Org. Biomol. Chem.* 2003, 1, 4254-4261.) can be coupled with the 4-nitrophenol derivative 8 in the presence of a base, such as diisopropylethylamine (Hunig's base) to afford the desired iodide intermediate 64. A variety of organometallic mediated coupling reactions can then be carried out with the iodide derivative 64, examples of which are illustrated in Scheme 11. The iodide 64 can be treated with amines (R"R'NH), substituted alkynes 66, arylboronates 67, vinylstannanes, and α,β-unsaturated esters in the presence of a palladium or copper catalyst to afford the intermediates 65, 68-71, respectively. The nitro moiety of compounds 65 and 68-71 can be reduced with, for example zinc dust and ammonium chloride in a THF-MeOH mixture, and the resulting aniline intermediates can be acylated using chemistry previously described in Schemes 1-5.

Intermediate 71 can then be converted to the α,β-unsaturated amides 73 (Scheme 12). Compound 72, derived from acid promoted hydrolysis of ester 71, can be coupled with various amines (R"R'NH) in the presence of a coupling reagent such as, but not limited to EDCI, TBTU, DCC, to furnish the desired amide intermediate 73. Reduciton of the nitro moiety of 73 and subsequent acylation of the requisite aniline intermediate can be accomplished using chemistry previously described in Schemes 1-5.

SCHEME 11

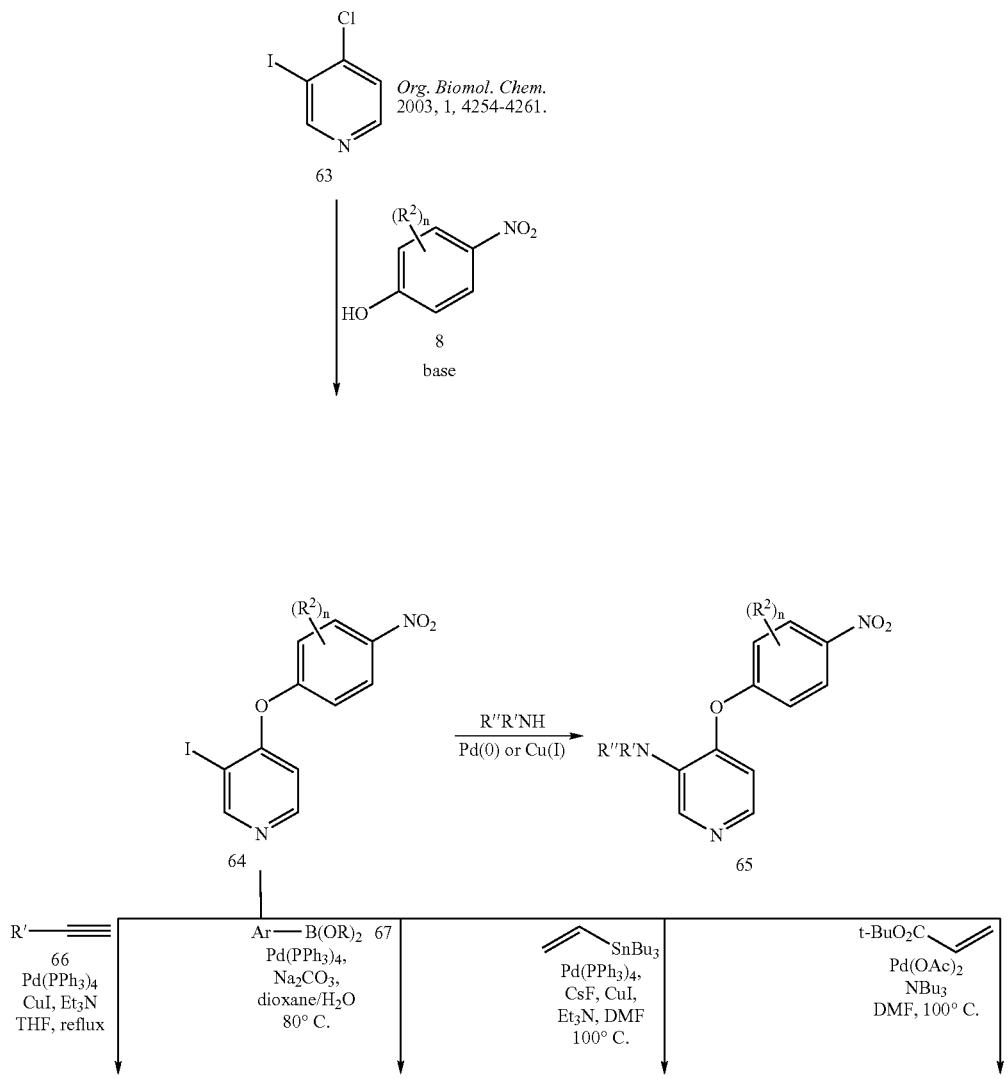

-continued

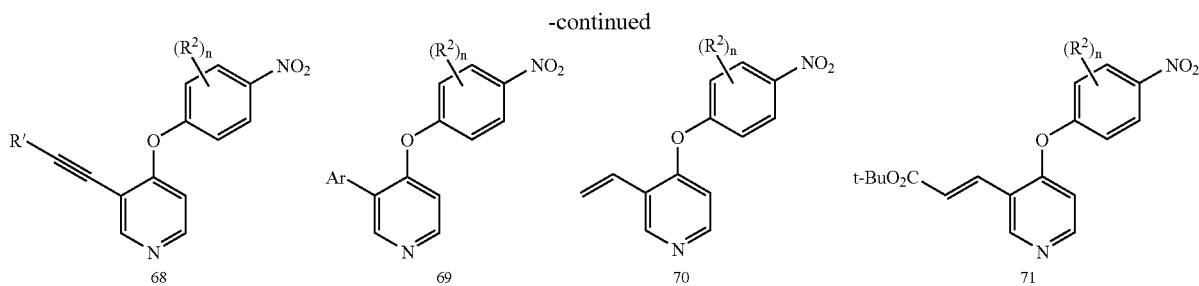

SCHEME 12

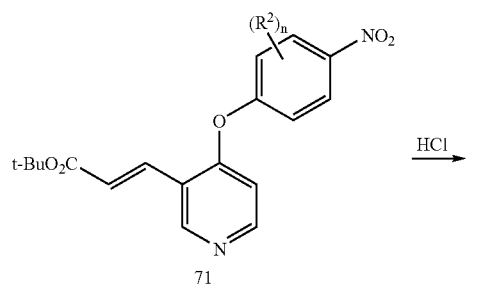

SCHEME 13

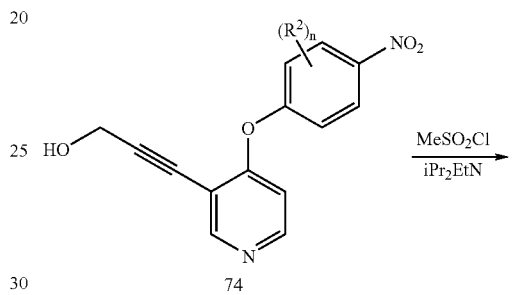

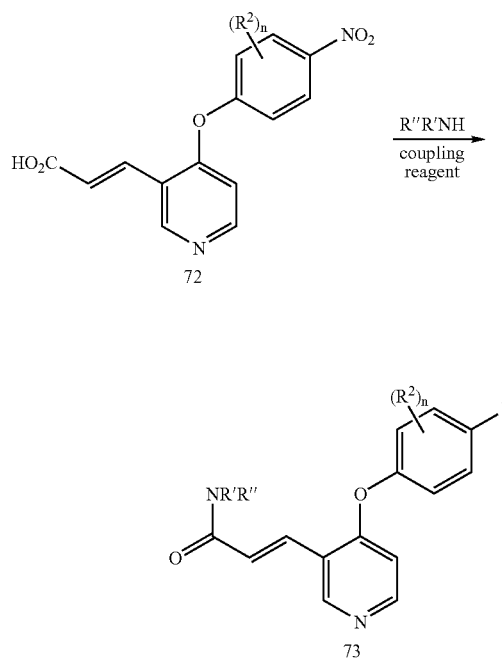

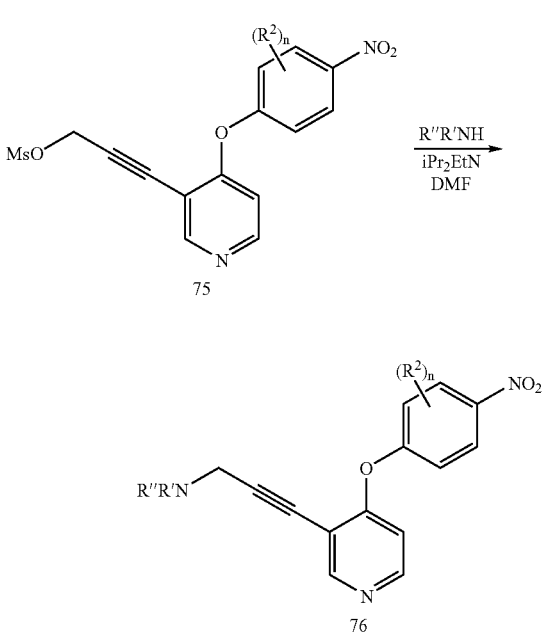

Intermediate 74 can also be further modified to prepare propargylic amines 76 (Scheme 13). Mesylation of the propargylic alcohol 74, can be accomplished with methanesulfonyl chloride in the presence of a base, such as diisopropylethylamine (Hunig's base) to provide the mesylate 75. Displacement of the mesylate group of compound 75 with various amines (R"R'NH) can provide the propargylic amines 76. Reduction of the nitro moiety of 76 and subsequent acylation of the requisite aniline intermediate can be accomplished using chemistry previously described in Schemes 1-5.

The 3-aminopyridine derivatives 79 and 80 can be prepared according to the synthetic route described in Scheme 14. To this end, 4-chloro-3-nitropyridine (77, Lancaster Synthesis Ltd.) can be coupled with 4-aminophenol in the presence of a base, such as sodium hydride in DMF to afford the nitro intermediate 78. Chemistry previously described above can be used to convert intermediate 78 to the desired compounds 79 and 80. The amino substituent of 79 and 80 can also be further modified, for example via alkylation, acylation, arylation or sulfonylation.

SCHEME 14

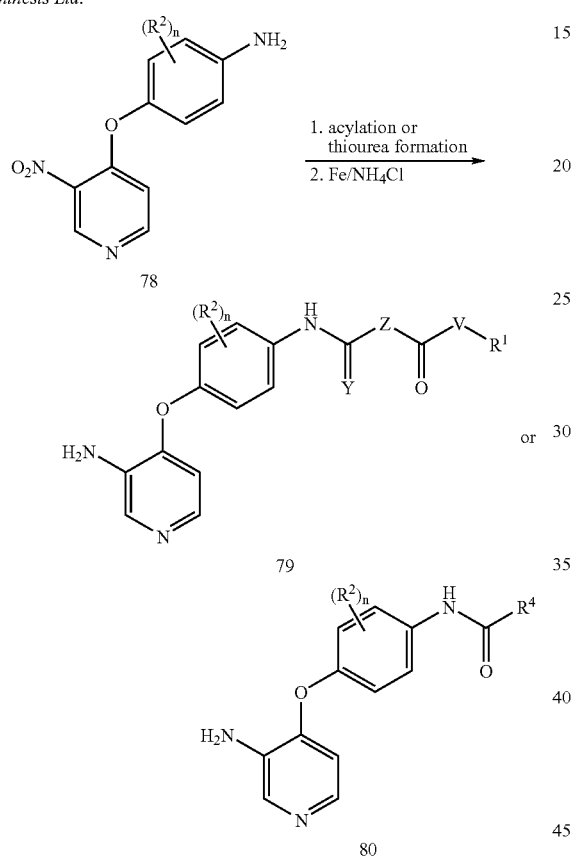

SCHEME 15

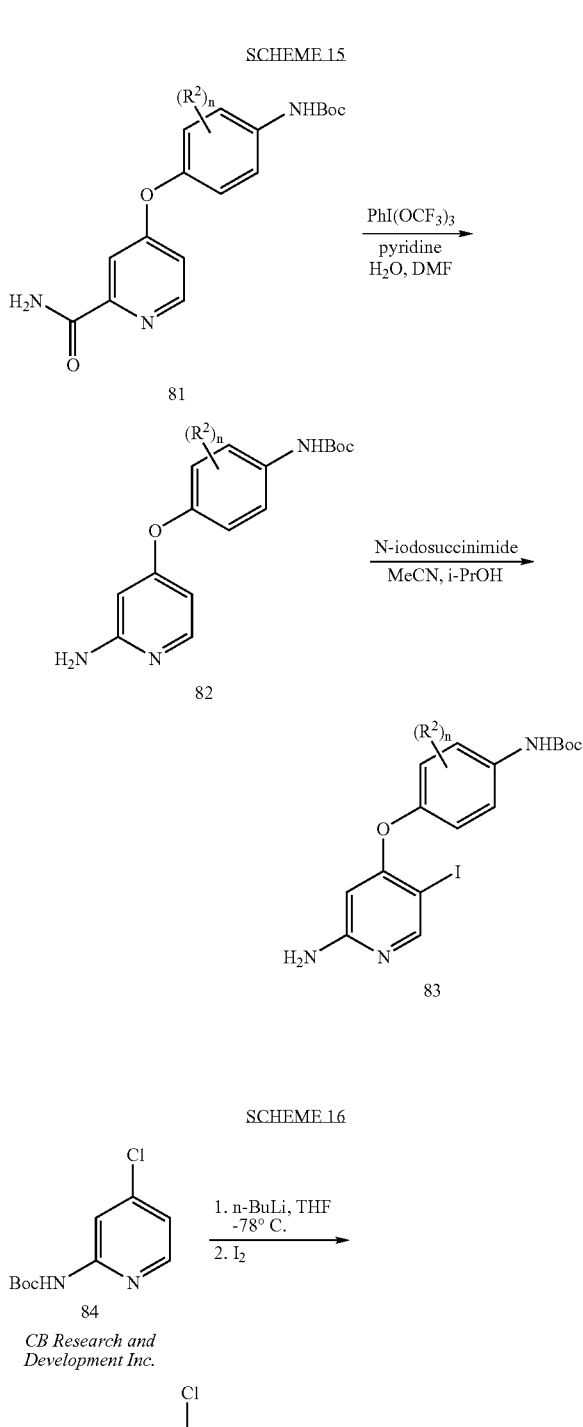

mediate 86. The iodide intermediates 83 and 86 can be further processed using chemistry similar to that previously described in Scheme 11.

Incorporation of subsituents on either the 5- or 3-position of the 2-aminopyridine ring can be accomplished using the iodide intermediates 83 and 86, respectively (Schemes 15 and 16). The 2-carboxamide derivative 81 can be converted to the 2-aminopyridine derivative 82 using the Hofmann rearrangement protocol previously described in Scheme 7. Iodination of the 5-position of compound 82 can be achieved with N-iodosuccinimide in an acetonitrile-isopropanol mixture to afford the desired iodide intermediate 83. Alternatively, t-butyl 4-chloropyridin-2-ylcarbamate (84, CB Research and Development Inc.) can be converted to t-butyl 4-chloro-3-iodopyridin-2-ylcarbamate (85) via a two step process involving n-butyllithium in THF at low temperature followed by the addition of iodine. Removal of the N-Boc (t-butylcarbamate) protecting group of 85 with refluxing aqueous hydrogen bromide followed by coupling of the chloride intermediate with the 4-nitrophenol derivative 8 in the presence diisopropylamine (Hunig's base) in N-methylpyrrolidinone (NMP) at elevated temperature can provide the iodide inter-

SCHEME 16

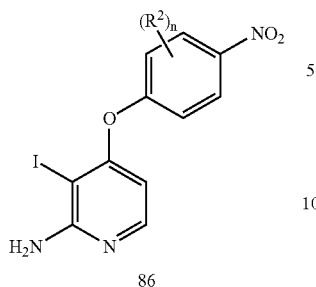

86

The methylene linked (B=CH$_2$) analogues 93 and 94 can be prepared according to the synthetic sequence outlined in Scheme 17. Compound 88, derived from N-Boc protection of the 4-bromoaniline derivative 87, can be treated with methylmagnesium bromide followed by tert-butyllithium and 2-chloroisonicotinaldehyde (Frey, L. F. et al. *Tetrahedron Lett.* 2001, 42, 6815-6818) at low temperature to provide intermediate 90. Oxidation of the pyridine ring of 90 with 3-chloroperoxybenzoic acid (m-CPBA), followed by displacement of the chloro substituent with an amine (R'NH$_2$) and subsequent reduction of the N-oxide intermediate with zinc and ammonium formate in methanol can provide intermediate 91. When allylamine is used as the nucleophilic amine (R'NH$_2$), the allyl group can be removed from the amine of 91 using a rhodium catalyst in an ethanol-water mixture. Removal of the hydroxyl group of 91 can be accomplished by two different methods. For example, hydrogenolysis of compound 91 in the presence of a palladium catalyst, followed by deprotection of the N-Boc group on the aniline under acidic conditions (HCl in methanol) can afford compound 92. Alternatively, compound 92 can be obtained by acylation of the alcohol of 91 and subsequent hydrogenolysis of the intermediate in the presence of a palladium catalyst and removal of the N-Boc protecting group under acidic conditions (trifluoroacetic acid in methylene chloride). Intermediate 92 can then be acylated to furnish the desired compounds 93 and 94 using chemistry previously described in Schemes 1-5.

SCHEME 17

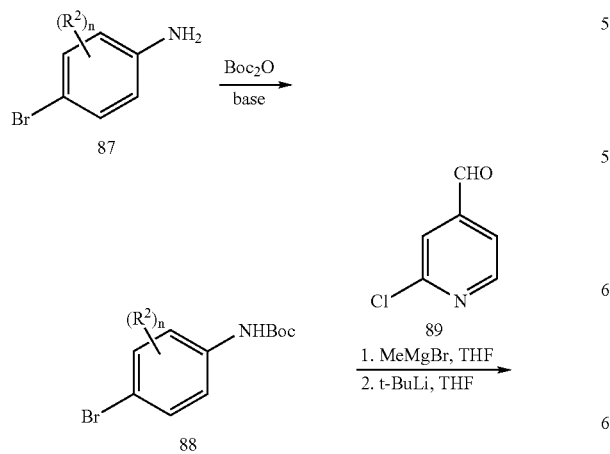

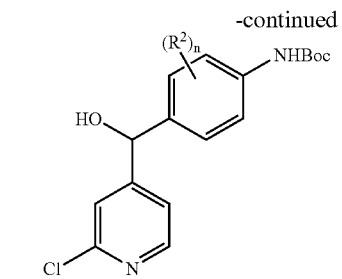

90

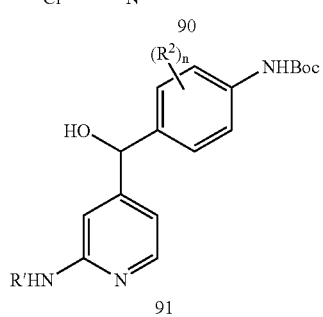

91

R' = allyl, 3-dimethylaminopropyl

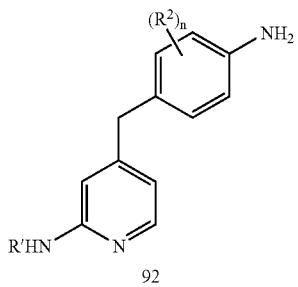

92

R' = H, 3-dimethylaminopropyl

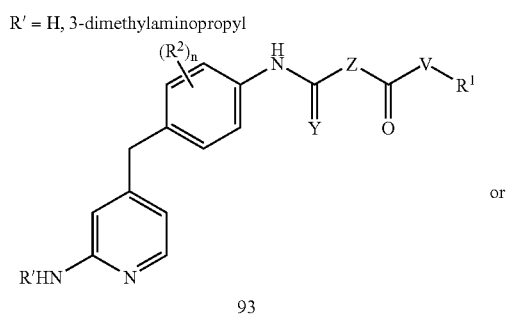

93

R' = H, 3-dimethylaminopropyl

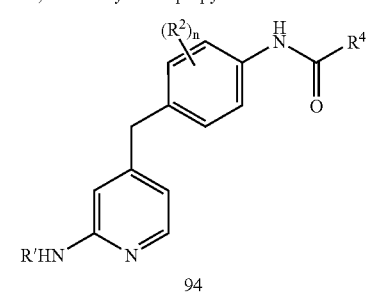

94

The heterocyclic amide derivatives 100 and 105 can be prepared according to the synthetic routes described in Schemes 18 and 19. To this end, methyl 2-oxo-1-phenyl-1,2-dihydropyridine-3-carboxylate (97) can be obtained in a two step process beginning with commercially available (E)-dimethyl 2-(3-methoxyallylidene)malonate (95) (Scheme 18). Thus, treatment of compound 95 with aniline at room temperature can provide intermediate 96, which can then cyclized in the presence of a base, such as sodium hydride in dimethylsulfoxide to generate 97. Hydrolysis of intermediate 97 under basic conditions can provide 2-oxo-1-phenyl-1,2-dihydropyridine-3-carboxylic acid (98). The carboxylic acid 98 can then be coupled with the aniline derivative 99 in the presence of a coupling reagent, such as 1-(dimethylaminopropyl)-3-ethylcarbodiimide hydrochloride (EDCI) and hydroxybenzotriazole (HOBt) in DMF to furnish the desired compound 100.

SCHEME 18

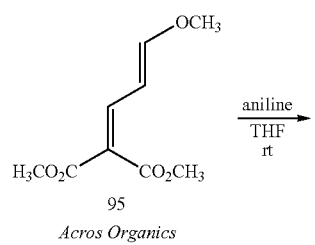

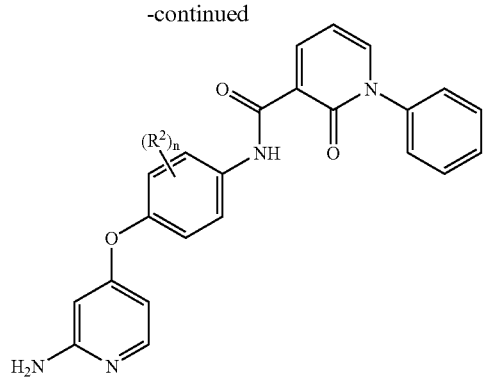

The pyridyl N-oxide intermediate 104 (Scheme 19) can be obtained by a two step process in which the commercially available 6-bromopicolinic acid (101) is coupled with the phenyl-1,3,2-dioxaborinane 102 (Aldrich) in the presence of a palladium(0) catalyst and sodium carbonate, followed by oxidation of the requisite intermediate 103 at elevated temperature. Coupling of intermediate 104 with the aniline derivative 99 can furnish the desired compound 105.

SCHEME 19

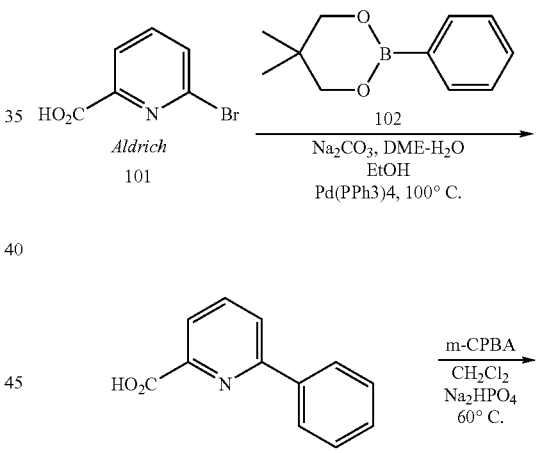

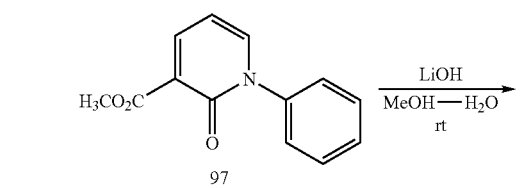

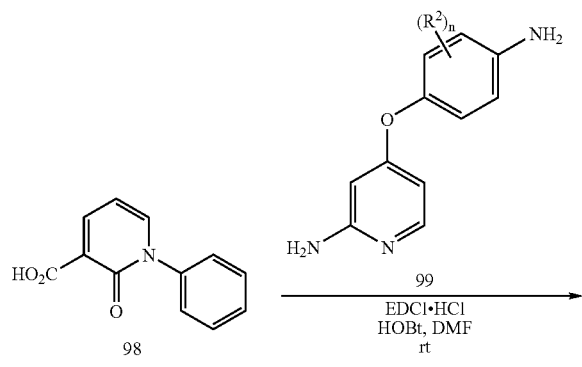

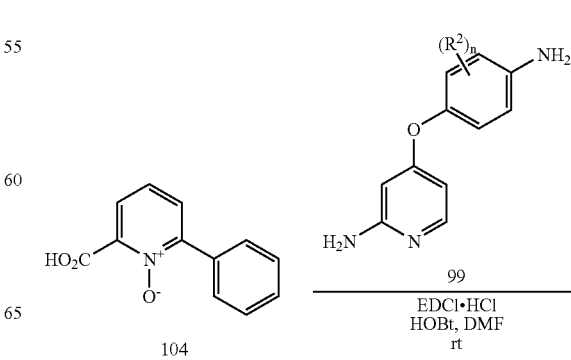

-continued

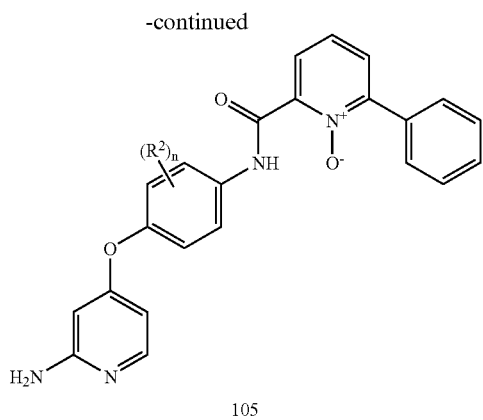

105

The compounds of Formulas I and II are useful in the treatment of a variety of cancers, including, but not limited to, the following:
 (a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
 (b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
 (c) hematopoietic tumors of myeloid lineage, including acute and chronic myelogenous leukemias, myelodysplastic syndrome and promyelocytic leukemia;
 (d) tumors of mesenchymal origin, including fibrosarcoma and rhabdomyosarcoma;
 (e) tumors of the central and peripheral nervous system, including astrocytoma, neuroblastoma, glioma and schwannomas; and
 (f) other tumors, including melanoma, seminoma, teratocarcinoma, osteosarcoma, xenoderoma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulo-nephritis, restenosis following angioplasty or vascular surgery, hypertrophic scar formation, inflammatory bowel disease, transplantation rejection, endotoxic shock, and fungal infections.

Compounds of Formulas I and II as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I and II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulas I and II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I and II may also be useful in inhibiting tumor angiogenesis and metastasis.

The term "anticancer" agent includes any known agent that is useful for the treatment of cancer including 17α-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, VEGF inhibitors, including as anti-VEGF antibodies such as Avastin, and small molecules such as ZD6474 and SU6668, vatalanib, BAY-43-9006, SU11248, CP-547632, and CEP-7055 are also included. Anti-Her2 antibodies from Genentech (such as Herceptin) may also be utilized. Suitable EGFR inhibitors include gefitinib, erlotinib, and cetuximab. Pan Her inhibitors include canertinib, EKB-569, and GW-572016. Also included are Src inhibitors as well as Casodex® (bicalutamide, Astra Zeneca), Tamoxifen, MEK-1 kinase inhibitors, MAPK kinase inhibitors, PI3 inhibitors, and PDGF inhibitors, such as imatinib. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kinases, and inhibitors of integrin signaling. Additional anticancer agents include microtubule-stabilizing agents such as paclitaxel (also known as Taxol®), docetaxel (also known as Taxotere®), 7-O-methylthiomethylpaclitaxel (disclosed in U.S. Pat. No. 5,646, 176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in WO 99/02514), [1S-[1R*,3R* (E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formulas I and II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formulas I and II may also be administered sequentially with known anticancer or cytotoxic agents when a combination formulation is inappropriate. The invention is not limited in the sequence of administration; compounds of Formulas I and II may be administered either prior to or after administration of the known anticancer or cytotoxic agent(s).

Assays

The pharmacological properties of the compounds of this invention may be confirmed by a number of pharmacological assays. The exemplified pharmacological assays which follow have been carried out with the compounds according to the invention and salts thereof.

| Met Kinase assay | |
|---|---|
| Reagents | Substrate Mix Final Concentration |
| Stock Solution | |
| Tris-HCl, (1 M, pH 7.4) | 20 mM |
| MnCl$_2$ (1 M) | 1 mM |
| DTT(1 M) | 1 mM |

| -continued | |
|---|---|
| Met Kinase assay | |
| Reagents | Substrate Mix Final Concentration |
| BSA (100 mg/ml) | 0.1 mg/ml |
| polyGlu$_4$/tyr (10 mg/ml) | 0.1 mg/mL |
| ATP (1 mM) | 1 µM |
| γ-ATP (10 µCi/µl) | 0.2 µCi/ml |

| Buffer | Enzyme mix |
|---|---|
| 20 ul 1 M DTT | 4 ul GST/Met enzyme(3.2 mg/ml) = 10 ng/rxn |
| 200 ul 1 M Tris-HCL, pH 7.4 | qs 12 ml Buffer |
| 20 ul 100 mg/ml BSA | |
| qs 20 ml H$_2$0 | |

Incubation mixtures employed for the Met kinase assay contain the synthetic substrate polyGlu:Tyr, (4:1), ATP, ATP-γ-$^{33}$P and buffer containing Mn$^{++}$ and/or Mg$^{++}$, DTT, BSA, and Tris buffer. Reactions were incubated for 60 minutes at 27° C. and stopped by the addition of cold trichloroacetic acid (TCA) to a final concentration 4%. TCA precipitates were collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves were generated to determine the concentration required to inhibit 50% of kinase activity (IC$_{50}$). Compounds were dissolved at 10 mM in dimethyl sulfoxide (DMSO) and evaluated at six concentrations, each in quadruplicate. The final concentration of DMSO in the assay is 1%. IC$_{50}$ values were derived by non-linear regression analysis and had a coefficient of variance (SD/mean, n=6)=16%.

Preferred compounds of the invention inhibit Met kinase with IC$_{50}$ values between 0.01 to 100 µM. The most preferred compounds have IC$_{50}$ values of less than 0.5 µM.

Further subject matter of the invention also includes pharmaceuticals for use as described above including controlling cancer, inflammation and arthritis, which contain at least one compounds of Formulas I and II as defined above or at least one of its pharmacologically acceptable acid addition salts, and the use of a compound of the Formulas I and II as defined above for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be other embodiments which fall within the spirit and scope of the invention as defined by the claims appended hereto.

EXAMPLES

The invention will now be further described by the following working examples, which are preferred embodiments of the invention. All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using 10% methanol, 90% water, 0.1% TFA (solvent A) and 90% methanol, 10% water, 0.1% TFA (solvent B) and detection at 220 nm on one of the following columns: A—Shimadzu S5 ODS-VP 20×100 mm column with a flow rate of 20 mL/min; B—YMC S5 ODS 30×100 mm column with a flow rate of 20 mL/min; C—Phenomonex 30×250 mm column with a flow rate of 10 mL/min; D—YMC S5 ODS 20×250 mm column with a flow rate of 10 mL/min; E—YMC S10 ODS 50×500 mm column with a flow rate of 50 mL/min; or F—YMC S10 ODS 30×500 mm column with a flow rate of 20 mL/min.

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; TEA: triethylamine; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT or rt: room temperature; $t_R$: retention time; h: hour(s); min: minute(s); PyBroP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt or HOBT: hydroxybenzotriazole; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether; DCM: dichloromethane or methylene chloride; m-CPBA: 4-chloroperoxybenzoic acid.

Example 1

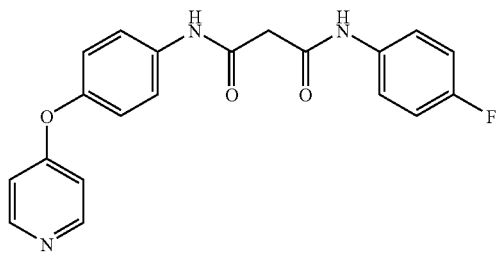

N-(4-Fluorophenyl)-N-(4-(pyridin-4-yloxy)phenyl) malonamide

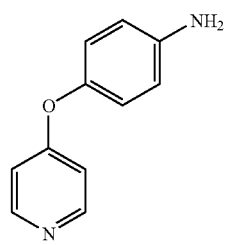

A) 4-(4-Aminophenoxy)pyridine

A solution of 4-chloropyridine hydrochloride (Aldrich, 3.0 g, 20.0 mmol) in dimethyl sulfoxide (40 mL) was treated with 4-aminophenol (Aldrich, 2.1 g, 20.0 mmol) and sodium hydroxide pellets (2.0 g, 50.0 mmol) and the mixture was heated at 100° C. for 18 h. The mixture was cooled to room temperature, poured onto a mixture of ice-water (300 g) and extracted with Et$_2$O (3×150 mL). The combined extracts were washed with brine, dried (MgSO$_4$) and concentrated to give the 4-(4-aminophenoxy)aniline as a pale yellow solid (3.5 g, 94%). $^1$H NMR (DMSO-d$_6$) δ 8.38 (dd, 2H, J=5.5, 1.5 Hz), 6.83-6.79 (m, 4H), 6.63-6.59 (m, 2H), 5.13 (br s, 2H); MS(ESI$^+$) m/z 187.2 (M+H)$^+$.

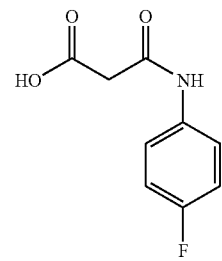

B) 3-(4-Fluorophenylamino)-3-oxopropanoic acid

To a solution of ethyl 3-chloro-3-oxopropanoate (Aldrich, 5.0 mL, 40 mmol) in methylene chloride (100 mL) at 0° C. was added diisopropylethylamine (8.4 mL, 48 mmol) followed by 4-fluoroaniline (Aldrich, 3.6 mL, 38 mmol). The reaction mixture was stirred at room temperature overnight and was then quenched with 100 mL of saturated NaHCO$_3$ solution. The aqueous layer was extracted with chloroform (3×100 mL). The combined organic extracts were dried over anhydrous Na$_2$SO$_4$ and concentrated in vacuo to give the crude product as a yellow oil that solidified upon standing (10 g). $^1$H NMR (CDCl$_3$) δ 9.30 (br s, 1H), 7.55 (m, 2H), 7.05 (t, 2H, J=8.8 Hz), 4.28 (q, 2H, J=7.2 Hz), 3.49 (s, 2H), 1.35 (t, 3H, J=7.1 Hz); MS(ESI$^+$) m/z 226.11 (M+H)$^+$.

The above ester was dissolved in 100 mL of ethanol and cooled to 0° C. 1 N aq. NaOH solution (100 mL) was added and the reaction was stirred at 0° C. for 1 h. The reaction was concentrated in vacuo to remove ethanol. The aqueous solution was extracted with EtOAc (50 mL) and was then made acidic with 1N aq HCl solution. The aqueous solution was extracted with EtOAc (5×100 mL). The combined organic extracts were dried over anhydrous Na$_2$SO$_4$ and concentrated in vacuo to give the crude product as a yellow solid (6.31 g, 84%) which was used without further purification. $^1$H NMR (DMSO-d$_6$) δ 12.9 (br s, 1H), 10.3 (br s, 1H), 7.59 (m, 2H), 7.16 (t, 2H, J=8.9 Hz), 3.34 (s, 2H); MS(ESI$^+$) m/z 198.43 (M+H)$^+$.

C) N-(4-Fluorophenyl)-N-(4-(pyridin-4-yloxy)phenyl)malonamide

A solution of 4-(4-aminophenoxy)pyridine (93 mg, 0.50 mmol) in DMF was treated with 3-(4-fluorophenylamino)-3-oxopropanoic acid (99 mg, 0.50 mmol), DIPEA (113 μL, 0.65 mmol) and TBTU (209 mg, 0.65 mmol) and the mixture was stirred at RT for 2 h. The mixture was concentrated to remove the DMF and the residue partitioned between EtOAc and saturated sodium bicarbonate solution. The EtOAc phase was washed with saturated sodium bicarbonate solution, brine, dried (MgSO$_4$) and concentrated to give the title compound as an off-white foam (140 mg, 76%). $^1$H NMR (DMSO-d$_6$) δ 10.30 (s, 1H), 10.24 (s, 1H), 8.43 (dd, 2H, J=5.5, 1.5 Hz), 7.70 (d, 2H, J=9.1 Hz), 7.63-7.60 (m, 2H), 7.17-7.14 (m, 4H), 6.89 (dd, 2H, J=5.5, 1.5 Hz), 3.46 (s, 2H); MS(ESI$^+$) m/z 365.9 (M+H)$^+$.

Example 2

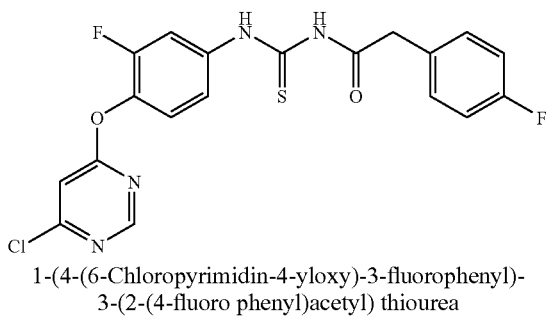

1-(4-(6-Chloropyrimidin-4-yloxy)-3-fluorophenyl)-3-(2-(4-fluoro phenyl)acetyl) thiourea

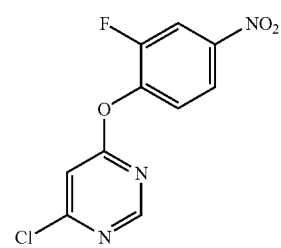

A) 4-Chloro-6-(2-fluoro-4-nitrophenoxy)pyrimidine

A mixture of 4,6-dichloropyrimidine (Aldrich, 0.74 g, 5.0 mmol), 2-fluoro-4-nitrophenol (Aldrich, 0.79 g, 5.0 mmol) and DMF (10 ml) was treated with potassium carbonate (0.72 g, 5.2 mmol) and heated at 80° C. for 3 h. The mixture was cooled, diluted with water and extracted with ethyl acetate. The ethyl acetate extract was washed with brine, dried (MgSO$_4$), and concentrated to give the crude product as a yellow solid. The crude product was triturated with isopropyl ether to give 4-chloro-6-(2-fluoro-4-nitrophenoxy)pyrimidine as a yellow solid (1.3 g, 94%). $^1$H NMR (DMSO-d$_6$) δ 8.80 (s, 1H), 8.51 (dd, 1H, J=8.6, 2.5 Hz), 8.31 (d, 1H, J=9.1 Hz), 7.87 (d, 1H, J=9.1 Hz), 7.84 (s, 1H).

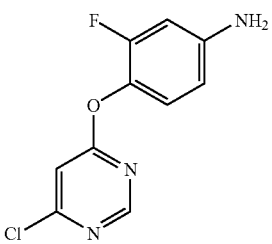

B) 4-Chloro-6-(2-amino-2-fluorophenoxy)pyrimidine

A solution of 4-chloro-6-(2-fluoro-4-nitrophenoxy)pyrimidine (1.3 g, 4.8 mmol) in methanol (120 mL) was treated with Raney nickel (1.5 g, aqueous slurry) and the reaction mixture was stirred under a blanket of hydrogen (from a latex balloon) at RT for 3 h. The catalyst was filtered off, the filtrate concentrated, and the residue partitioned between CH$_2$Cl$_2$ and water. The methylene chloride phase was separated, dried (MgSO$_4$) and concentrated. The crude product was purified by flash chromatography on silica gel using 1-2% MeOH in CH$_2$Cl$_2$ as the eluent to give 4-chloro-6-(2-amino-2-fluorophenoxy)pyrimidine as a white solid (600 mg, 52%). $^1$H NMR (DMSO-d$_6$) δ 8.64 (s, 1H), 7.39 (s, 1H), 6.97 (dd, 1H, J=8.8, 8.8 Hz), 6.46 (dd, 1H, J=13.1, 2.5 Hz), 6.38 (dd, 1H, J=8.6, 2.5 Hz), 5.44 (br s, 2H); MS(ESI$^+$) m/z 240.04 (M+H)$^+$.

C) 1-(4-(6-Chloropyrimidin-4-yloxy)-3-fluorophenyl)-3-(2-(4-fluorophenyl)acetyl)thiourea 4-Fluorophenylacetyl chloride (Lancaster, 0.52 g, 3.0 mmol) was added to a mixture of NaSCN (0.27 g, 3.3 mmol) and EtOAc (12 mL) and the resulting mixture stirred at RT for 30 min. This mixture was added to a solution of 4-chloro-6-(2-amino-2-fluorophenoxy)pyrimidine in 1:1 EtOAc/CH$_2$Cl$_2$ (5 ml) and the resulting mixture stirred at RT overnight. The mixture was concentrated and the residue partitioned between EtOAc/H$_2$O. The EtOAc phase was separated, washed with brine, dried (MgSO$_4$) and concentrated. The product was purified by flash chromatography using 10-35% EtOAc/hexanes as the eluent to give the title compound as a yellow crystalline solid (0.85 g, 65%). $^1$H NMR (DMSO-d$_6$) δ 12.40 (s, 1H), 11.81 (s, 1H), 8.67 (s, 1H), 7.90 (dd, 1H, J=12.1, 2.0 Hz), 7.62 (s, 1H), 7.47-7.41 (m, 2H), 7.38-7.35 (m, 2H), 7.17 (t, 2H, J=8.8 Hz), 3.81 (s, 2H); MS(ESI$^+$) m/z 434.98 (M+H)$^+$.

Example 3

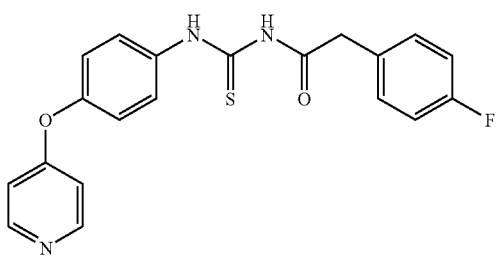

1-(2-(4-Fluorophenyl)acetyl)-3-(4-(pyridin-4-yloxy)phenyl)thiourea

The title compound was prepared using 4-(4-aminophenoxy)pyridine (Compound A of Example 1) and a similar procedure outlined for the preparation of Compound C of Example 2. Yield: 10%. $^1$H NMR (CDCl$_3$) δ 12.3 (s, 1H), 8.63 (s, 1H), 8.49, (d, 2H, J=6.2 Hz), 7.71 (d, 2H, J=8.9 Hz), 7.31-7.27 (m, 2H), 7.14-7.09 (m, 4H), 6.90 (dd, 2H, J=4.8, 1.4 Hz), 3.73 (s, 2H); MS(ESI$^+$) m/z 382.2 (M+H)$^+$.

Example 4

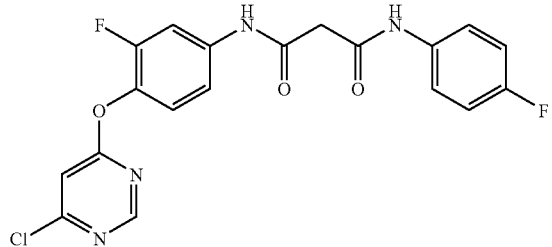

N$^1$-(4-(6-Chloropyrimidin-4-yloxy)-3-fluorophenyl)-N$^3$-(4-fluorophenyl)malonamide A solution of 4-chloro-6-(2-amino-2-fluorophenoxy)pyrimidine (29 mg, 0.12 mmol, Compound B of Example 2), 3-(4-fluorophenylamino)-3-oxopropanoic acid (26 mg, 0.13 mmol, Compound B of Example 1) in DMF (1.5 mL) was treated with DIPEA (24 µl, 0.14 mmol) and TBTU (46 mg, 0.14 mmol). The reaction mixture was stirred at RT overnight, diluted with EtOAc (25 mL), and the organic phase was washed with brine (3×20 mL), dried (MgSO$_4$) and concentrated. The product was purified by flash chromatography using 1-3% MeOH in CH$_2$Cl$_2$ as the eluent to give the title compound as a white solid (35 mg, 78%). $^1$H NMR (DMSO-d$_6$) δ 10.49 (s, 1H), 10.25 (s, 1H), 8.65 (s, 1H), 7.78 (d, 1H, J=12.1 Hz), 7.63-7.57 (m, 3H), 7.40-7.34 (m, 2H), 7.16 (t, 2H, J=8.8 Hz), 3.48 (s, 2H); MS(ESI$^+$) m/z 419.21 (M+H)$^+$.

Example 5

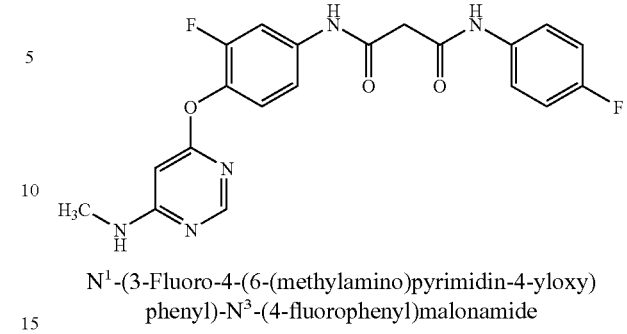

N$^1$-(3-Fluoro-4-(6-(methylamino)pyrimidin-4-yloxy)phenyl)-N$^3$-(4-fluorophenyl)malonamide A solution of N$^1$-(4-(6-chloropyrimidin-4-yloxy)-3-fluorophenyl)-N$^3$-(4-fluorophenyl)malonamide (100 mg, 0.42 mmol, Example 4) in n-BuOH (3 mL) was treated with 2 M methylamine/THF (0.2 mL) and heated in a screw cap vial at 80° C. for 12 h. The mixture was concentrated and the residue purified by preparative HPLC using a gradient of MeOH—H$_2$O containing 0.1% TFA. The fraction containing the product was lyophilized to give the title compound as a pale yellow solid (60 mg, 34%). $^1$H NMR (DMSO-d$_6$) δ 10.58 (s, 1H), 10.36 (br s, 2H), 8.19 (br s, 1H), 7.76 (d, 1H, J=12.1 Hz), 7.64-7.62 (m, 2H), 7.36-7.27 (m, 2H), 7.15 (dd, 2H, J=8.8, 8.8 Hz), 5.95 (br s, 1H), 3.49 (s, 2H), 2.80 (s, 3H); MS(ESI$^+$) m/z 414.16 (M+H)$^+$.

Example 6

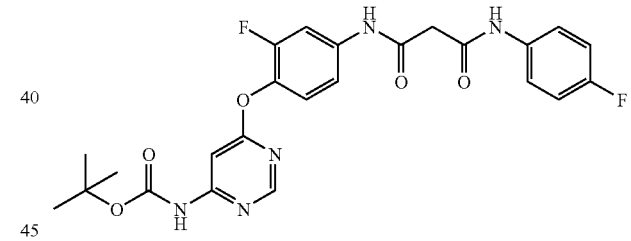

tert-Butyl 6-(2-fluoro-4-(3-(4-fluorophenylamino)-3-oxopropanamido)phenoxy)pyrimidin-4-ylcarbamate

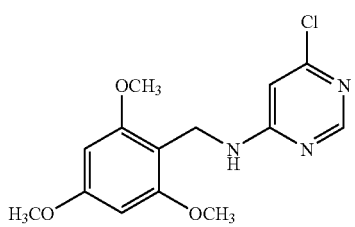

A) N-(2,4,6-Trimethoxybenzyl)-6-chloropyrimidin-4-amine

A mixture of 4,6-dichloropyrimidine (Aldrich, 1.48 g, 10.0 mmol), 2,4,6-trimethoxybenzylamine hydrochloride (2.33 g, 10.0 mmol), DIPEA (4.8 mL, 27.7 mmol), and n-BuOH (50 mL) was heated at 100° C. for 2 h. The mixture was cooled, diluted with water (200 mL) and the precipitated product was collected by vacuum filtration on a Büchner funnel. The product was washed with cold water, ether, and vacuum dried to give an off-white solid (2.8 g, 90%). $^1$H NMR (DMSO-d$_6$) δ 8.28 (s, 1H), 7.38 (s, 1H), 6.49 (s, 1H), 6.25 (s, 2H), 4.34 (s, 2H), 3.77 (s, 9H).

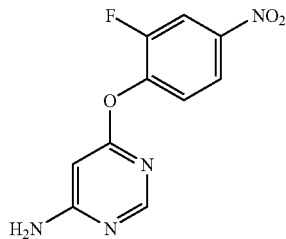

B) 6-(2-Fluoro-4-nitrophenoxy)pyrimidin-4-amine

A mixture of N-(2,4,6-trimethoxybenzyl)-6-chloropyrimidin-4-amine (2.2 g, 7.11 mmol), 2-fluoro-4-nitrophenol (1.1 g, 7.0 mmol), and 2-methoxyethyl ether (50 mL) was heated at 160° C. for 60 h. The reaction mixture was cooled to RT and poured into H$_2$O (200 mL). The solid was collected, washed with 2 M aqueous Na$_2$CO$_3$ and H$_2$O, and then vacuum dried on a Büchner funnel. The crude product was treated with TFA (20 mL) in dioxane (40 mL) and stirred at RT for 4 h. The reaction mixture was concentrated, the residue partitioned between EtOAc and saturated NaHCO$_3$ solution. The EtOAc phase was separated, dried (MgSO$_4$), concentrated and the crude product purified by flash chromatography using 1-2% MeOH in CH$_2$Cl$_2$ as the eluent to give 6-(2-fluoro-4-nitrophenoxy)pyrimidin-4-amine (440 mg, 31%). $^1$H NMR (DMSO-d$_6$) δ 8.31 (dd, 1H, J=10.4, 2.5 Hz), 8.14 (dd, 1H, J=9.8, 2.0 Hz), 8.04 (s, 1H), 7.61 (dd, 1H, J=8.3, 8.3 Hz), 7.07 (s, 2H), 6.02 (s, 1H); MS(ESI$^+$) m/z 251.15 (M+H)$^+$.

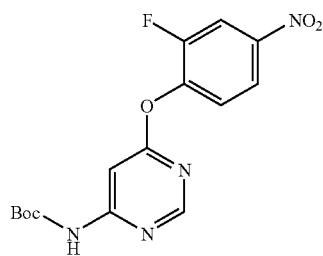

C) tert-Butyl 6-(2-fluoro-4-nitrophenoxy)pyrimidin-4-ylcarbamate

A mixture of 6-(2-fluoro-4-nitrophenoxy)pyrimidin-4-amine (439 mg, 1.2 mmol), BOC$_{20}$ (261 mg, 1.2 mmol), DMAP (10 mg), and THF (10 mL) was stirred at RT for 1 h then concentrated in vacuo to give the crude product. The product was purified by flash chromatography using 1-2% MeOH in CH$_2$Cl$_2$ as the eluent to give tert-butyl 6-(2-fluoro-4-nitrophenoxy)pyrimidin-4-ylcarbamate as a white solid (110 mg, 26%). $^1$H NMR (DMSO-d$_6$) δ 10.59 (s, 1H), 8.39 (dd, 1H, J=8.8, 1.1 Hz), 8.32 (dd, 1H, J=10.3, 2.4 Hz), 8.15 (ddd, 1H, J=9.1, 2.5, 1.0 Hz), 7.67 (dd, 1H, J=8.8, 8.8 Hz), 7.45 (s, 1H), 1.44 (s, 9H); MS(ESI$^-$) m/z 349.08 (M−H).

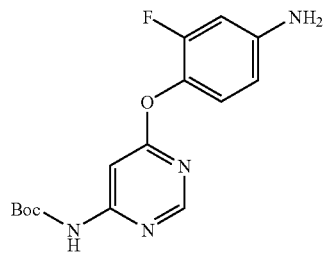

D) tert-Butyl 6-(4-amino-2-fluorophenoxy)pyrimidin-4-ylcarbamate

A solution of tert-butyl 6-(2-fluoro-4-nitrophenoxy)pyrimidin-4-ylcarbamate (11 mg, 0.031 mmol) in MeOH (2 mL) was treated with PtO$_2$ and the reaction mixture was stirred under a blanket of hydrogen (from a latex balloon) for 2 h. The catalyst was filtered off and the filtrate concentrated to give tert-butyl 6-(4-amino-2-fluorophenoxy)pyrimidin-4-ylcarbamate (8 mg, 81%). $^1$H NMR (DMSO-d$_6$) δ 10.62 (s, 1H), 8.43 (d, 1H, J=2.5 Hz), 8.36 (dd, 1H, J=9.8, 2.5 Hz), 8.36 (dd, 1H, J=9.8, 2.5 Hz), 8.20-8.17 (m, 1H), 7.71 (dd, 1H, J=8.8, 8.8 Hz), 7.49 (s, 1H), 1.48 (s, 9H).

E) tert-Butyl 6-(2-fluoro-4-(3-(4-fluorophenylamino)-3-oxopropanamido)phenoxy)pyrimidin-4-ylcarbamate The title compound was prepared from tert-butyl 6-(4-amino-2-fluorophenoxy)pyrimidin-4-ylcarbamate (8 mg, 0.025 mmol) and (4-fluorophenylamino)-3-oxopropanoic acid (6 mg, 0.031 mmol, Compound B of Example 1), TBTU (11 mg, 0.034 mmol), and DIPEA (6 μL, 0.030 mmol) using a similar procedure described for the preparation of Compound C, Example 1. Flash chromatography using 1-1.5% MeOH in CH$_2$Cl$_2$ as the eluent gave the title compound as a white solid (10 mg, 80%). $^1$H NMR (DMSO-d$_6$) δ 10.48 (s, 1H), 10.46 (s, 1H), 10.25 (s, 1H), 8.39 (s, 1H), 7.74-7.77 (m, 1H), 7.62 (d, 1H, J=5.5 Hz), 7.61 (d, 1H, J=4.9 Hz), 7.36-7.30 (m, 2H), 7.17-7.13 (m, 2H), 3.48 (s, 2H), 1.46 (s, 9H); MS(ESI$^+$) m/z 500.12 (M+H)$^+$.

Example 7

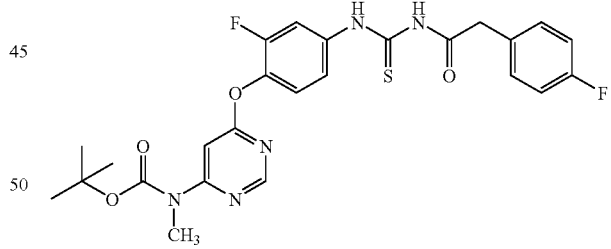

tert-Butyl 6-(2-fluoro-4-(3-(4-fluorophenylamino)-3-oxopropanamido)phenoxy)pyrimidin-4-yl(methyl) carbamate

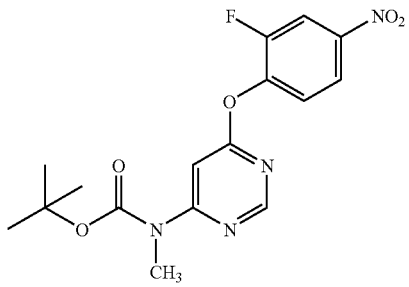

A) tert-Butyl 6-(2-fluoro-4-nitrophenoxy)pyrimidin-4-yl(methyl)carbamate

A solution of tert-butyl 6-(2-fluoro-4-nitrophenoxy)pyrimidin-4-ylcarbamate (Compound C of Example 6, 44 mg, 0.13 mmol) in anhydrous DMF (1 mL) was cooled in an ice bath and treated with 60% NaH (44 mg, 0.16 mmol) and stirred at the same temperature for 30 minutes. The reaction mixture was treated with iodomethane (10 µL, 0.15 mmol) and stirred at 0-5° C. for 10 min. The reaction mixture was allowed to warm to room temperature and stirred for 30 min. The mixture was diluted with $H_2O$ (10 mL) and extracted with EtOAc (2×10 mL). The combined extracts were dried ($MgSO_4$) and concentrated in vacuo to give the product (35 mg, 74%) as a pale yellow solid. $^1H$ NMR (DMSO-$d_6$) δ 8.57 (d, 1H, J=1.1 Hz), 8.37 (dd, 1H, J=9.8, 3.0 Hz), 8.19 (ddd, 1H, J=9.1, 2.5, 1.0 Hz), 7.71 (dd, 1H, J=8.8, 8.8 Hz), 7.66 (s, 1H), 3.38 (s, 3H), 1.51 (s, 9H).

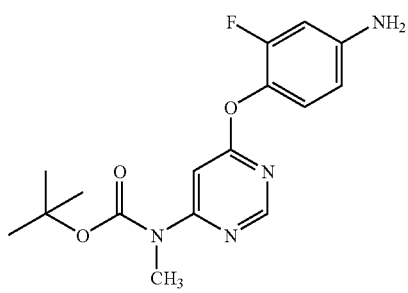

B) tert-Butyl 6-(4-amino-2-fluorophenoxy)pyrimidin-4-yl(methyl)carbamate

A mixture of tert-butyl 6-(2-fluoro-4-nitrophenoxy)pyrimidin-4-yl(methyl)carbamate in 1:1 EtOH/MeOH (2 mL) was treated with $PtO_2$ (10 mg) and the reaction mixture was stirred under a blanket of $H_2$ (from a latex balloon) for 2 h. The reaction mixture was filtered and concentrated to give the desired product (30 mg, 75%) as a light brown solid. MS(ESI$^+$) m/z 365.13 (M+H)$^+$.

C) tert-Butyl 6-(2-fluoro-4-(3-(4-fluorophenylamino)-3-oxopropanamido)phenoxy)pyrimidin-4-yl(methyl)carbamate The title compound was prepared from tert-butyl 6-(4-amino-2-fluorophenoxy)pyrimidin-4-yl(methyl)carbamate (30 mg, 0.068 mmol), 4-fluorophenylacetyl chloride (Lancaster, 15 mg, 0.088 mmol) and NaSCN (9 mg, 0.11 mmol) in EtOAc/$CH_2Cl_2$ using a similar procedure described for the preparation of Compound C of Example 2. Flash chromatography on $SiO_2$ using 1-40% EtOAc in hexanes as the eluent gave the title compound (30 mg, 83%) as a white solid. $^1H$ NMR (DMSO-$d_6$) δ 12.40 (s, 1H), 11.79 (s, 1H), 8.55 (s, 1H), 7.86 (dd, 1H, J=12.1, 2.5 Hz), 7.54 (d, 1H, J=1.1 Hz), 7.45-7.35 (m, 4H), 7.20-7.14 (ddd, 2H, J=8.8, 8.8, 2.1 Hz), 3.81 (s, 2H), 3.36 (s, 3H), 1.49 (s, 9H); MS(ESI$^+$) m/z 530.09 (M+H)$^+$.

Example 8

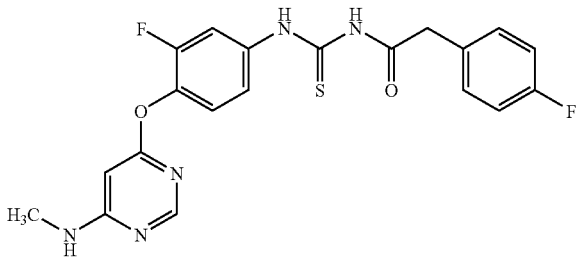

1-(3-Fluoro-4-(6-(methylamino)pyrimidin-4-yloxy)phenyl)-3-(2-(4-fluorophenyl)acetyl)thiourea tert-Butyl 6-(2-fluoro-4-(3-(4-fluorophenylamino)-3-oxopropanamido)phenoxy)pyrimidin-4-yl(methyl)carbamate (Example 7, 25 mg, 0.047 mmol) was treated with 4 M HCl in 1,4-dioxane (3 mL), stirred at RT for 4 h and concentrated in vacuo. The residue was partitioned between saturated aq. NaHCO$_3$ solution and EtOAc. The EtOAc phase was separated, dried (MgSO$_4$) and concentrated in vacuo. Flash chromatography on SiO$_2$ using 1% MeOH in CH$_2$Cl$_2$ as the eluent gave the title compound (10 mg, 50%) as a white solid. $^1H$ NMR (DMSO-$d_6$) δ 12.37 (s, 1H), 11.77 (s, 1H), 8.09 (s, 1H), 7.82 (d, 1H, J=11.6 Hz), 7.41-7.35 (m, 5H), 7.32-7.28 (m, 1H), 7.19-7.14 (m, 2H), 3.81 (s, 2H), 2.78 (s, 3H); MS(ESI$^+$) m/z 430.07 (M+H)$^+$.

Example 9

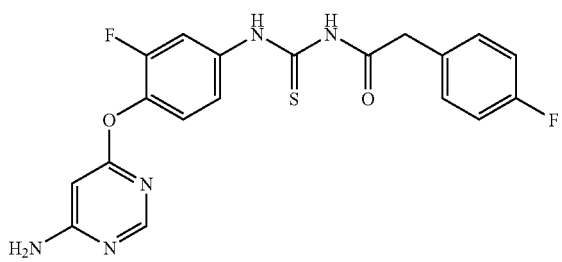

1-(4-(6-Aminopyrimidin-4-yloxy)-3-fluorophenyl)-3-(2-(4-fluorophenyl)acetyl)thiourea

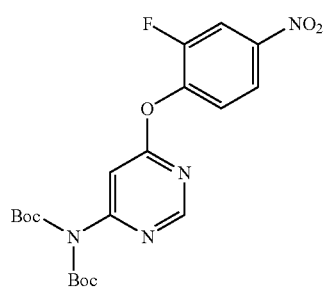

A) 6-(N,N-di-tert-Butyloxycarbonyl)amino-4-(2-fluoro-4-nitrophenoxy)pyrimidine A mixture of 6-(2-fluoro-4-nitrophenoxy)pyrimidin-4-amine (Compound B of Example 6, 150 mg, 0.60 mmol), BOC$_2$O (275 mg, 1.26 mmol), DMAP (5 mg), and THF (20 mL) was stirred at RT for 2.5 h. The reaction mixture was concentrated in vacuo to give the crude product. Flash chromatography on SiO$_2$ using 5-15% EtOAc in hexanes as the eluent gave the title compound (180 mg, 67%) as white solid. $^1$H NMR (DMSO-d$_6$) δ 8.62 (d, 1H, J=1.0 Hz), 8.42-8.39 (m, 1H), 8.21 (ddd, 1H, J=9.1, 2.5, 1.0 Hz), 7.77 (dd, 1H, J=8.8, 8.8 Hz), 7.49 (d, 1H, J=1.1 Hz), 1.49 (s, 18H); MS(ESI$^+$) m/z 451.12 (M+H)$^+$.

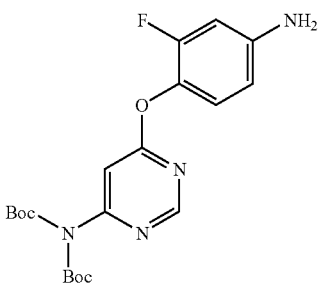

B) 6-(N,N-di-tert-Butyloxycarbonyl)amino-4-(4-amino-2-fluorophenoxy)pyrimidine A mixture of the 6-(N,N-di-tert-butyloxycarbonyl)amino-4-(2-fluoro-4-nitrophenoxy)pyrimidine (175 mg, 0.38 mmol) in toluene (5 mL) and MeOH (3 mL) was treated with PtO$_2$ (35 mg) and the reaction mixture was stirred under a blanket of H$_2$ (from a latex balloon) for 15 h. The catalyst was filtered off, the filtrate concentrated in vacuo and the residue was purified by flash chromatography on SiO$_2$ using 1-10% MeOH in CH$_2$Cl$_2$ as the eluent to give the product (110 mg, 68%) as a white solid. $^1$H NMR (DMSO-d$_6$) δ 8.56 (s, 1H), 7.17 (s, 1H), 6.97 (dd, 1H, J=8.8, 8.8 Hz), 6.46 (dd, 1H, J=12.6, 2.5 Hz), 6.38 (dd, 1H, J=8.8, 2.5 Hz), 5.40 (s, 2H), 1.89 (s, 18H).

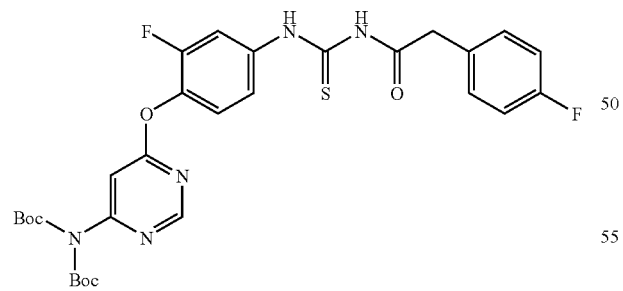

C) 1-(4-(N,N-di-tert-Butyloxycarbonyl 6-aminopyrimidin-4-yloxy)-3-fluorophenyl)-3-(2-(4-fluorophenyl)acetyl)thiourea The title compound was prepared from 6-(N,N-di-tert-butyloxycarbonyl)amino-4-(4-amino-2-fluorophenoxy)pyrimidine (20 mg, 0.048 mmol), 4-fluorophenylacetyl chloride (Lancaster, 10 mg, 0.062 mmol), and NaSCN (95 mg, 0.062 mmol) in EtOAc/CH$_2$Cl$_2$ using a similar procedure described for the preparation of Compound C of Example 2. Flash chromatography on SiO$_2$ using 10-20% EtOAc in hexanes as the eluent gave the title compound (23 mg, 77%) as a white solid. $^1$H NMR (DMSO-d$_6$) δ 12.40 (s, 1H), 11.79 (s, 1H), 8.59 (s, 1H), 7.88 (dd, 1H, J=12.5, 1.8 Hz), 7.46-7.41 (m, 2H), 7.38-7.35 (m, 3H), 7.17 (dd, 2H, J=8.8, 8.8 Hz), 3.81 (s, 2H), 1.47 (s, 18H); MS(ESI$^+$) m/z 616.12 (M+H)$^+$.

D) 1-(4-(6-Aminopyrimidin-4-yloxy)-3-fluorophenyl)-3-(2-(4-fluorophenyl)acetyl)thiourea A mixture of 1-(4-(N,N-di-tert-butylcarbonyl 6-aminopyrimidin-4-yloxy)-3-fluorophenyl)-3-(2-(4-fluorophenyl)acetyl)thiourea (18 mg, 0.029 mmol) and 4 M HCl in dioxane (1.5 mL) was stirred at RT for 18 h and then concentrated to give the crude product. The crude product was partitioned between EtOAc and saturated aq. NaHCO$_3$ solution. The EtOAc phase separated, dried (MgSO$_4$), concentrated in vacuo and the residue was purified by flash chromatography on SiO$_2$ using 1-2% MeOH in CH$_2$Cl$_2$ to give the title compound (12 mg, 99%) as a white solid. $^1$H NMR (DMSO-d$_6$) δ 12.38 (s, 1H), 11.77 (s, 1H), 8.05 (s, 1H), 7.83 (dd, 1H, J=12.3, 1.8 Hz), 7.41-7.35 (m, 3H), 7.31 (dd, 2H, J=8.8, 8.8 Hz), 7.17 (t, 1H, J=8.8 Hz), 7.02 (s, 2H), 5.89 (s, 1H), 3.81 (s, 2H); MS(ESI$^+$) m/z 416.06 (M+H)$^+$.

Example 10

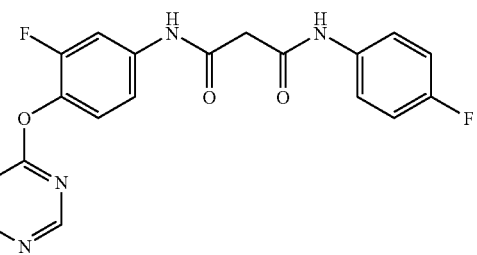

N$^1$-1-(4-(6-Aminopyrimidin-4-yloxy)-3-fluorophenyl)-N$^3$-(4-fluorophenyl)malonamide

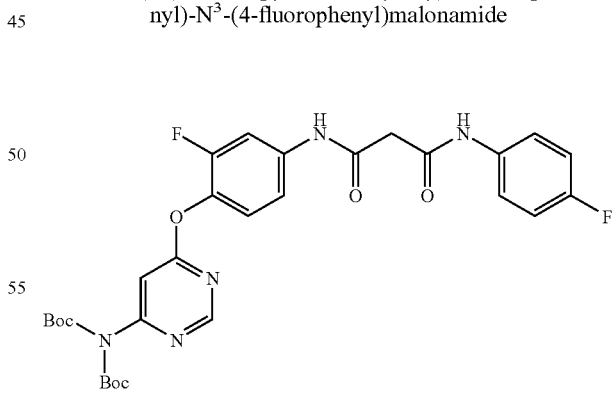

A) N$^1$-(4-(N,N-di-tert-Butylcarbonyl 6-aminopyrimidin-4-yloxy)-3-fluorophenyl)-N$^3$-(4-fluorophenyl)malonamide The title compound was prepared from a mixture of 6-(N,N-di-tert-butyloxycarbonyl)amino-4-(4-amino-2-fluorophenoxy)pyrimidine (Compound B of Example 9, 20 mg, 0.048 mmol), 3-(4-fluorophenylamino)-3-oxopropanoic (Compound B of Example 1, 14 mg, 0.072 nmol), DIPEA (12 µL, 0.069 mmol) in DMF using a similar procedure described for the preparation of Compound C of Example 1. Flash chromatography on SiO$_2$ using 15-50% EtOAc in hexanes as the eluent gave the title compound (23 mg, 80%) as a white solid. $^1$H NMR (DMSO-d$_6$) δ 10.47 (s, 1H), 10.24 (s, 1H), 8.58 (d, 1H, J=1 Hz), 7.77 (dd, 1H, J=12.9, 1.8 Hz), 7.63-7.60 (m, 2H), 7.37-7.36 (m, 2H), 7.32 (s, 1H), 7.15 (t, 2H, J=8.8 Hz), 1.47 (s, 18H); MS(ESI$^+$) m/z 600.17 (M+H)$^+$.

B) N$^1$-(4-(6-Aminopyrimidin-4-yloxy)-3-fluorophenyl)-N$^3$-(4-fluorophenyl)malonamide The title compound was prepared from N-1-(4-(N,N-di-tert-butylcarbonyl 6-aminopyrimidin-4-yloxy)-3-fluorophenyl)-N$^3$-(4-fluorophenyl)malonamide (20 mg, 0.032 mmol) using a similar procedure described for the preparation of Compound D of Example 9 to give the title compound (13 mg, 98%) as a white solid. $^1$H NMR (DMSO-d$_6$) δ 10.42 (s, 1H), 10.24 (s, 1H), 8.03 (s, 1H), 7.73 (d, 1H, J=11.0 Hz), 7.61 (dd, 2H, J=9.2, 4.9 Hz), 7.33-7.30 (m, 1H), 7.28-7.23 (m, 1H), 7.18-7.13 (m, 2H), 6.89 (s, 2H), 5.80 (s, 1H), 3.47 (s, 2H); MS(ESI$^+$) m/z 400.09 (M+H)$^+$.

Example 11

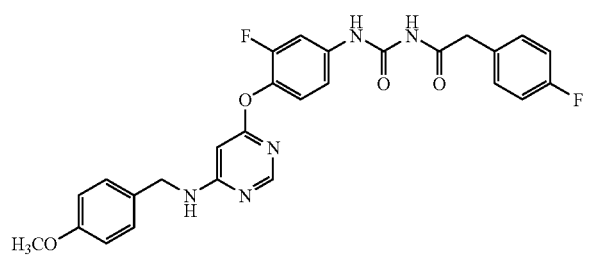

1-(4-(6-(4-Methoxybenzylamino)pyrimidin-4-yloxy)-3-fluorophenyl)-3-(2-(4-fluorophenyl)acetyl)urea

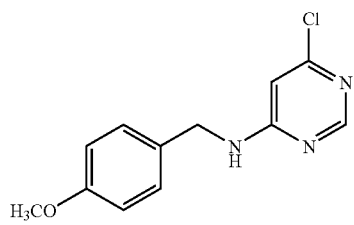

A)
N-(4-Methoxybenzyl)-6-chloropyrimidin-4-amine

A mixture of 4,6-dichloropyrimidine (Aldrich, 3.6 g, 24.2 mmol), 4-methoxybenzylamine (2.7 g, 19.7 mmol), DIPEA (5 ml, 28.8 mmol), and n-BuOH was heated at reflux for 3 h. The mixture was concentrated and the residue treated with H$_2$O (150 mL) and EtOAc (175 mL). The EtOAc phase was separated, washed with saturated aq. NaHCO$_3$ solution and brine, dried (MgSO$_4$), and concentrated to give the title compound (4.5 g) which was used without further purification. $^1$H NMR (DMSO-d$_6$) δ 8.29 (s, 1H), 8.13 (br s, 1H), 7.25 (d, 2H, J=8.2 Hz), 6.90 (d, 2H, J=8.2 Hz), 6.56 (s, 1H), 4.48 (s, 2H), 3.75 (s, 3H).

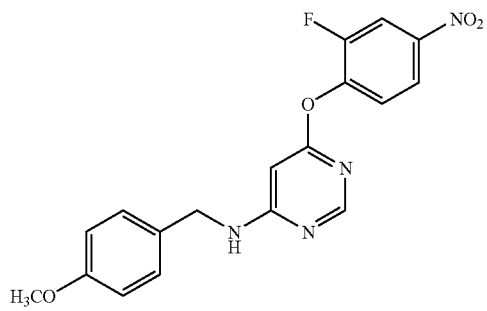

B) N-(4-Methoxybenzyl)-6-(2-fluoro-4-nitrophenoxy)pyrimidin-4-amine

A mixture of N-(4-methoxybenzyl)-6-chloropyrimidin-4-amine (2.3 g, 9.2 mmol), 2-fluoro-4-nitrophenol (1.45 g, 9.2 mmol), DIPEA (15 mL), and 2-methoxyethyl ether (75 mL) was heated at 160° C. in a sealed pressure bottle for 50 h. The mixture was cooled, poured onto crushed ice (200 g), treated with EtOAc (200 mL). After vigorously stirring for 10 min, the insoluble material was filtered off. The EtOAc phase was washed with saturated aq. Na$_2$CO$_3$ solution (100 mL), brine (3×100 mL), dried (MgSO$_4$) and concentrated in vacuo. The gummy solid obtained was triturated with isopropyl ether to give the title compound (1.75 g, 76%) as a brown solid. $^1$H NMR (DMSO-d$_6$) δ 8.32 (dd, 1H, J=10.2, 2.0 Hz), 8.15 (d, 2H, J=9.2 Hz), 8.05 (br s, 1H), 7.61 (dd, 1H, J=8.4, 8.4 Hz), 7.26 (d, 2H, J=8.5 Hz), 6.91 (d, 2H, J=8.5 Hz), 6.14 (br s, 1H), 4.48 (br s, 2H), 3.74 (s, 3H).

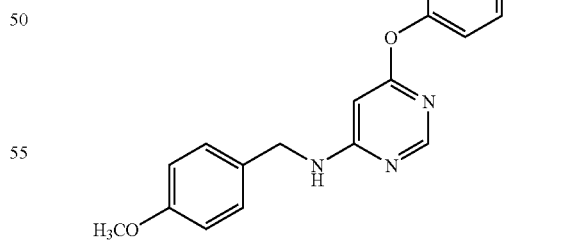

C) N-(4-Methoxybenzyl)-6-(4-amino-2-fluorophenoxy)pyrimidin-4-amine

A solution of N-(4-methoxybenzyl)-6-(2-fluoro-4-nitrophenoxy)pyrimidin-4-amine (150 mg, 0.41 mmol) in 1:1 MeOH/THF (20 mL) was treated with ammonium chloride (0.22 g, 4.1 mmol), and zinc dust (<20 microns, 0.27 g, 4.2 mmol). The reaction mixture was stirred at RT for 1 h. An additional portion of zinc dust (150 mg) was added to the mixture and the reaction mixture was stirred at RT for 1 h and heated at 70° C. for 20 min. The mixture was filtered to remove the inorganic solids, concentrated in vacuo, and the residue partitioned between EtOAc and brine. The EtOAc phase was separated, washed with brine, dried (MgSO$_4$) and concentrated in vacuo to give the title compound (145 mg, 99%). $^1$H NMR (DMSO-d$_6$) δ 8.10 (br s, 1H), 7.76 (br s, 1H), 7.21 (d, 2H, J=8.6 Hz), 6.88 (d, 3H, J=8.6 Hz), 6.44 (dd, 1H, J=12.7, 2.0 Hz), 6.36 (dd, 1H, J=8.3, 2.3 Hz), 5.79 (s, 1H), 4.41 (br s, 2H), 3.73 (s, 3H); MS(ESI$^+$) m/z 341.18 (M+H)$^+$.

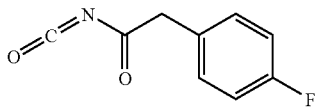

D) 2-(4-Fluorophenyl)acetyl isocyanate

Silver cyanate (0.912 g, 6.08 mmol, 1.05 eq) was added to a solution of 4-fluorophenylacetyl chloride (Lancaster, 0.794 ml, 5.79 mmol, 1.0 eq) in toluene (16 ml) at room temperature. The reaction mixture was shielded from light and heated to reflux. After 60 minutes, the mixture was cooled to room temperature and filtered (Acrodisc, PTFE 0.2 μM) to give a 0.36 M solution of 2-(4-fluorophenyl)acetyl isocyanate in toluene, which was used without further purification.

E) 1-(4-(6-(4-Methoxybenzylamino)pyrimidin-4-yloxy)-3-fluorophenyl)-3-(2-(4-fluorophenyl)acetyl)urea A solution of N-(4-methoxybenzyl)-6-(4-amino-2-fluorophenoxy)pyrimidin-4-amine (88 mg, 0.26 mmol) in THF (2 mL) was treated with 0.36 M 2-(4-fluorophenyl)acetyl isocyanate in toluene (0.72 mL, 0.26 mmol) and the reaction mixture was stirred at RT for 1 h. The mixture was concentrated in vacuo and the solid obtained was triturated with isopropyl ether to give the title compound (125 mg, 93%) as an off-white solid. $^1$H NMR (DMSO-d$_6$) δ 11.00 (s, 1H), 10.50 (s, 1H), 8.09 (s, 1H), 7.85 (br s, 0.5H), 7.66 (d, 1H, J=12.6 Hz), 7.36-7.15 (m, 9.5H), 6.88 (d, 1H, J=8.1 Hz), 5.91 (s, 1H), 4.42 (br s, 2H), 3.72 (s, 2H), 3.71 (s, 3H); MS(ESI$^+$) m/z 520.14 (M+H)$^+$.

Example 12

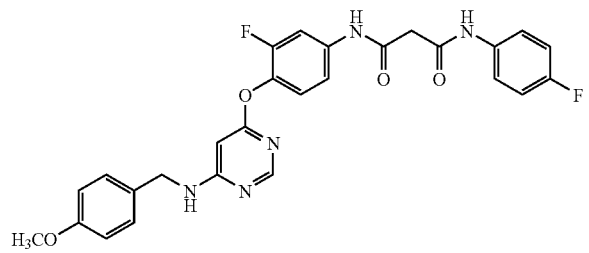

N$^1$-(4-(6-(4-Methoxybenzylamino)pyrimidin-4-yloxy)-3-fluorophenyl)-N$^3$-(4-fluorophenyl)malonamide The title compound was prepared from N-(4-methoxybenzyl)-6-(4-amino-2-fluorophenoxy)pyrimidin-4-amine. (Compound C of Example 11, 200 mg, 0.59 mmol), 3-(4-fluorophenylamino)-3-oxopropanoic acid (Compound B of Example 1, 128 mg, 0.65 mmol), TBTU (228 mg, 0.71 mmol), and DIPEA (123 μL, 0.71 mmol) in DMF using a similar procedure described for the preparation of Compound C of Example 1. The crude product was purified by trituration with isopropyl ether to give the title compound (250 mg, 82%) as an off-white solid. $^1$H NMR (DMSO-d$_6$) δ 10.43 (s, 1H), 10.25 (s, 1H), 8.09 (s, 1H), 7.85 (s, 1H), 7.72 (dd, 1H, J=9.1, 5.0 Hz), 7.62 (dd, 2H, J=8.8, 5.0 Hz), 7.31-7.21 (m, 4H), 7.15 (dd, 2H, J=8.8, 8.8 Hz), 6.88 (m, 2H), 5.90 (s, 1H), 4.42 (br s, 2H), 3.71 (s, 3H), 3.46 (s, 2H); MS(ESI$^+$) m/z 520.14 (M+H)$^+$.

Example 13

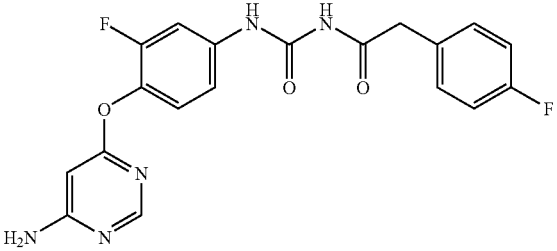

1-(4-(6-Aminopyrimidin-4-yloxy)-3-fluorophenyl)-3-(2-(4-fluorophenyl)acetyl)urea

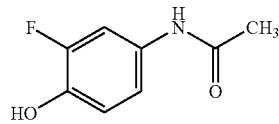

A) N-(3-Fluoro-4-hydroxyphenyl)acetamide

The title compound was prepared from the commercially available 2-fluoro-4-nitrophenol according the procedure of Burckhalter, J. H. et al. (J. Am. Chem. Soc. 1948, 70, 1363). Nitrophenol (5.73 g, 36.5 mmol) and acetic anhydride (3.72 g, 36.5 mmol) were dissolved in acetic acid (20 mL) and PtO$_2$ (150 mg) was then added. The reaction mixture was shaken under H$_2$ atmosphere (50 psi) at RT for 24 h. The precipitate which formed was collected by vacuum filtration and the filter paper was washed with acetic acid (25 mL). The combined filtrate and washing was concentrated in vacuo to give the title compound (2.0 g). The solid that remained on the filter paper was treated with MeOH to dissolve the product and the Pt$_2$O filtered off. The filtrate was concentrated in vacuo and the solid obtained was triturated with 1:1 EtOAc/hexanes (200 mL) to give a second crop of the title compound (1.8 g, 62% overall). $^1$H NMR (DMSO-d$_6$) δ 9.83 (s, 1H), 9.51 (s, 1H), 7.50 (dd, 1H, J=13.6, 2.5 Hz), 7.03 (d, 1H, J=8.5 Hz), 6.84 (dd, 1H, J=9.3, 9.3 Hz), 1.98 (s, 3H); MS(ESI⁺) m/z 170.23 (M+H)⁺.

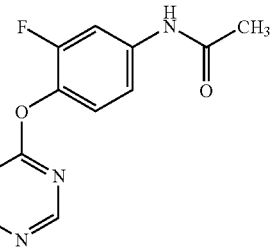

B) N-(4-(6-Chloropyrimidin-4-yloxy)-3-fluorophenyl)acetamide

A mixture of 4,6-dichloropyrimidine (1.50 g, 10.0 mmol), N-(3-fluoro-4-hydroxyphenyl)acetamide (1.70 g, 10.0 mmol), K₂CO₃ (1.8 g, 13.0 mmol), and DMF (15 mL) was heated at 70° C. for 1.5 h. The mixture was concentrated to half its original volume and cooled in an ice bath. The mixture was treated with H₂O (100 mL) to precipitate the product which was collected by vacuum filtration. The product was washed with H₂O and vacuum dried on the funnel overnight to give the title compound (2.0 g, 71%) as a gray solid. ¹H NMR (DMSO-d₆) δ 10.26 (s, 1H), 8.67 (s, 1H), 7.78 (dd, 1H, J=12.6, 2.0 Hz), 7.56 (s, 1H), 7.37-7.30 (m, 2H), 2.08 (s, 3H); MS(ESI⁺) m/z 282.10 (M+H)⁺.

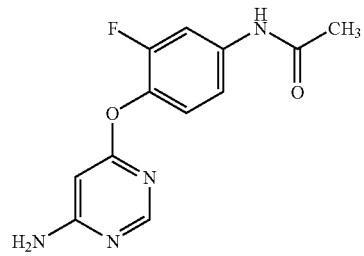

C) N-(4-(6-Aminopyrimidin-4-yloxy)-3-fluorophenyl)acetamide

A mixture of N-(4-(6-aminopyrimidin-4-yloxy)-3-fluorophenyl)acetamide (1.0 g, 3.5 mmol) and ca. 7 M NH₃ in MeOH (5 mL) was heated at 100° C. in a sealed pressure bottle for 2 h. The mixture was concentrated in vacuo and the residue partitioned between EtOAc and saturated aq. NaHCO₃ solution. The EtOAc phase was separated, washed with brine, dried (MgSO₄) and concentrated. Flash chromatography on SiO₂ using first 50% EtOAc in hexanes then 5% MeOH in CH₂Cl₂ as eluents gave the title compound (175 mg, 20%) as a brown solid. ¹H NMR (DMSO-d₆) δ 10.17 (s, 1H), 8.02 (s, 1H), 7.70 (dd, 1H, J=13.2, 2.2 Hz), 7.26 (dd, 1H, J=8.8, 2.2 Hz), 7.22 (dd, 1H, J=8.8, 8.8 Hz), 6.89 (br s, 2H), 2.05 (s, 3H); MS(ESI⁺) m/z 263.15 (M+H)⁺.

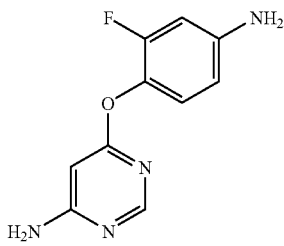

D) 6-(4-Amino-2-fluorophenoxy)pyrimidin-4-amine

A mixture of N-(4-(6-aminopyrimidin-4-yloxy)-3-fluorophenyl)acetamide (175 mg, 0.67 mmol), 1 M HCl (6 mL), and MeOH (2 mL) was heated at reflux for 3 h. The reaction mixture was cooled, made basic (pH 8) with aqueous Na₂CO₃ solution and extracted with EtOAc (2×25 mL). The combined extracts were dried (MgSO₄) and concentrated in vacuo to give the title compound (140 mg, 96%) as a brown solid. ¹H NMR (DMSO-d₆) δ 8.02 (s, 1H), 6.89 (dd, 1H, J=9.0, 9.0 Hz), 6.80 (br s, 2H), 6.43 (dd, 1H, J=12.7, 2.8 Hz), 6.35 (dd, 1H, J=8.8, 2.2 Hz), 5.67 (s, 1H), 5.34 (br s, 2H).

E) 1-(4-(6-Aminopyrimidin-4-yloxy)-3-fluorophenyl)-3-(2-(4-fluorophenyl)acetyl)urea The title compound was prepared from 6-(4-amino-2-fluorophenoxy)pyrimidin-4-amine (92 mg, 0.42 mmol) and 0.36 M 2-(4-fluorophenyl)acetyl isocyanate in toluene (Compound D of Example 11, 1.3 mL, 0.45 mmol) in THF as described above for Example 11. The crude product was purified by trituration using 1:1 EtOH/H₂O followed by absolute EtOH. The product was vacuum dried to give the title compound (100 mg, 60%). A second, slightly less pure crop of the product (45 mg, 27%) was obtained by extracting the combined filtrates and washing with EtOAc. ¹H NMR (DMSO-d₆) δ 10.99 (s, 1H), 10.50 (s, 1H), 8.01 (s, 1H), 7.65 (dd, 1H, J=12.6, 2.1 Hz), 7.33 (dd, 2H, J=8.1, 6.0 Hz), 7.28 (dd, 1H, J=8.6, 2.0 Hz), 7.22 (dd, 1H, J=8.8, 8.8 Hz), 7.17-7.12 (m, 2H), 6.89 (br s, 2H), 5.80 (s, 1H), 3.71 (s, 2H); MS(ESI⁺) m/z 400.09 (M+H)⁺.

Example 14

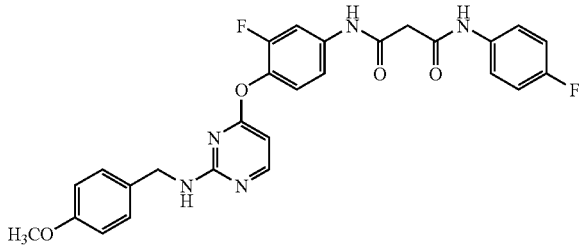

N¹-(4-(2-(4-Methoxybenzylamino)pyrimidin-4-yloxy)-3-fluorophenyl)-N³-(4-fluorophenyl)malonamide

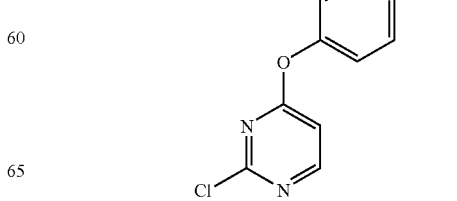

A) 2-Chloro-4-(2-fluoro-4-nitrophenoxy)pyrimidine

A mixture of 2,4-dichloropyrimidine (Aldrich, 0.74 g, 5.0 mmol), 2-fluoro-4-nitrophenol (Avacado, 0.79 g, 5.0 mmol), $K_2CO_3$ (0.76 g, 5.5 mmol), and DMF (50 mL) was heated at 100° C. for 2 h. The mixture was cooled and diluted with saturated $NaHCO_3$ solution (100 mL) and extracted with EtOAc. The EtOAc extract was washed with brine, dried ($MgSO_4$) and concentrated in vacuo to give a mixture of the 2-phenoxy- and 4-phenoxypyrimidine regioisomers as a yellow solid. The regioisomers were separated by flash chromatography using 10-40% EtOAc in hexanes as the eluent to give the title compound (0.71 g, 53%) as a white solid. $^1$H NMR (DMSO-$d_6$) δ 8.76 (dd, 1H, J=6.0, 1.6 Hz), 8.43 (dt, 1H, J=9.8, 2.2 Hz), 8.23 (dd, 1H, J=8.8, 1.6 Hz), 7.80 (dt, 1H, J=9.8, 2.2 Hz), 7.48 (dd, 1H, J=6.0, 2.2 Hz).

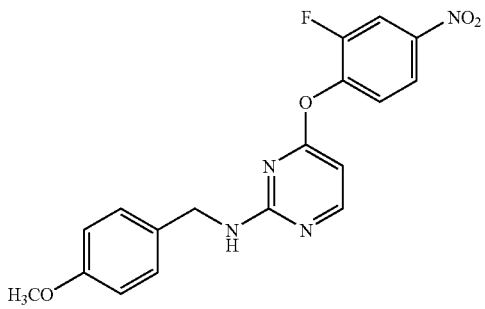

B) N-(4-Methoxybenzyl)-4-(2-fluoro-4-nitrophenoxy)pyrimidin-2-amine

A mixture of 2-chloro-4-(2-fluoro-4-nitrophenoxy)pyrimidine (0.66 g, 2.44 mmol), 4-methoxybenzylamine (0.34 g, 3.45 mmol), $K_2CO_3$ (0.37 g, 2.66 mmol), and DMF (15 mL) was heated at 100° C. for 1 h. The mixture was cooled, diluted with $H_2O$ (100 mL) and extracted with EtOAc (100 mL). The organic phase was washed twice each with saturated $NaHCO_3$ solution and brine. The organics were dried ($MgSO_4$) and concentrated to give the crude product. Flash chromatography on $SiO_2$ using 1-3% MeOH in $CH_2Cl_2$ as the eluent gave the title compound (275 mg, 29%) as a pale yellow solid. $^1$H NMR (DMSO-$d_6$) δ 8.40-8.21 (m, 2H), 8.16 (dd, 1H, J=8.8, 1.7 Hz), 7.98 (br s, 0.5H), 7.73-7.55 (m, 1.5H), 7.16 (br s, 1H), 6.85-6.71 (m, 3H), 6.37 (s, 1H), 4.43 (br s, 1H), 3.95 (br s, 1H), 3.69 (s, 3H).

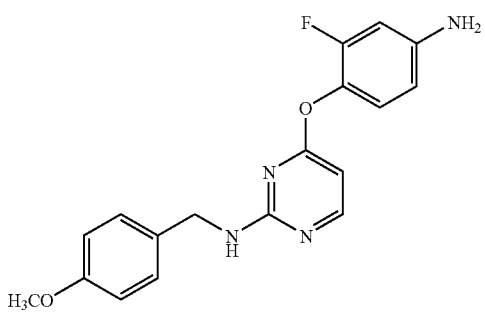

C) N-(4-Methoxybenzyl)-4-(4-amino-2-fluorophenoxy)pyrimidin-2-amine

The title compound was obtained by the reduction of N-(4-methoxybenzyl)-4-(2-fluoro-4-nitrophenoxy)pyrimidin-2-amine (270 mg, 0.73 mmol) with zinc dust (475 mg, 7.3 mmol) and $NH_4Cl$ (387 mg, 7.3 mmol) in 1:1 THF/MeOH (20 mL) using a similar procedure described for Compound C of Example 11. Flash chromatography on $SiO_2$ using 1-3% MeOH in $CH_2Cl_2$ as the eluent gave the title compound (235 mg, 95%) as a brown film. $^1$H NMR (DMSO-$d_6$) δ 8.01 (s, 1H), 7.65 (br s, 0.5H), 7.49 (br s, 0.5H), 7.08 (br s, 1H), 6.83 (br s, 2H), 6.81 (m, 1H), 6.69 (br s, 2H), 6.39 (br s, 0.5H), 6.31 (br s, 0.5H), 6.01 (m, 1H), 5.26 (br s, 2H), 4.24 (br s, 1H), 3.95 (br s, 1H), 3.61 (s, 3H); MS(ESI$^+$) m/z 341.16 (M+H)$^+$.

D) $N^1$-(4-(2-(4-Methoxybenzylamino)pyrimidin-4-yloxy)-3-fluorophenyl)-$N^3$-(4-fluorophenyl)malonamide The title compound was obtained from N-(4-methoxybenzyl)-4-(4-amino-2-fluorophenoxy)pyrimidin-2-amine (34 mg, 0.10 mmol), 3-(4-fluorophenylamino)-3-oxopropanoic acid (Compound B of Example 1, 22 mg, 0.11 mmol), TBTU (39 mg, 0.12 mmol) and DIPEA (23 mL, 0.17 mmol) using a similar procedure described for the preparation of Compound C of Example 1. The crude product was triturated with 3:1 isopropyl ether/EtOAc to give the title compound (35 mg, 61%) as an off-white solid. $^1$H NMR (DMSO-$d_6$) δ 10.47 (br s, 1H), 10.26 (s, 1H), 8.15 (s, 1H), 7.77 (m, 3H), 7.61 (m, 2H), 7.35-7.25 (m, 2H), 7.15 (dd, 2H, J=8.8, 8.8 Hz), 6.81-6.73 (m, 2H), 6.24 (s, 1H), 4.32 (br s, 1H), 3.96 (br s, 1H), 3.68 (s, 1H), 3.48 (s, 2H); MS(ESI$^+$) m/z 520.14 (M+H)$^+$.

Example 15

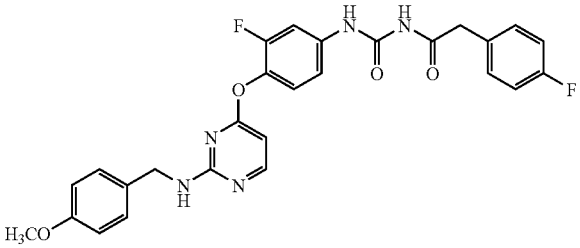

1-(4-(2-(4-Methoxybenzylamino)pyrimidin-4-yloxy)-3-fluorophenyl)-3-(2-(4-fluorophenyl)acetyl)urea A solution of N-(4-methoxybenzyl)-4-(4-amino-2-fluorophenoxy)pyrimidin-2-amine (Compound C of Example 14, 34 mg, 0.10 mmol) in THF (1 ml) was treated with 0.36 M 2-(4-fluorophenyl)acetyl isocyanate in toluene (Compound D of Example 11, 0.31 mL, 0.11 mmol) and the mixture stirred at RT for 1 h. The mixture was concentrated in vacuo and the solid obtained was triturated first with 3:1 isopropyl ether/EtOAc and then $CH_2Cl_2$ to give the title compound (32 mg, 62%) as an off-white solid. $^1$H NMR (DMSO-$d_6$) δ 10.47 (s, 1H), 10.26 (s, 1H), 8.15 (s, 1H), 7.76 (d, 1H, J=12.6 Hz), 7.61 (dd, 3H, J=9.1, 5.0 Hz), 7.29 (s, 2H), 7.31-7.21 (m, 3H), 6.81 (s, 3H), 6.24 (s, 1H), 4.32 (s, 1H), 3.96 (s, 1H), 3.68 (s, 3H), 3.48 (s, 2H); MS(ESI$^+$) m/z 520.14 (M+H)$^+$.

Example 16

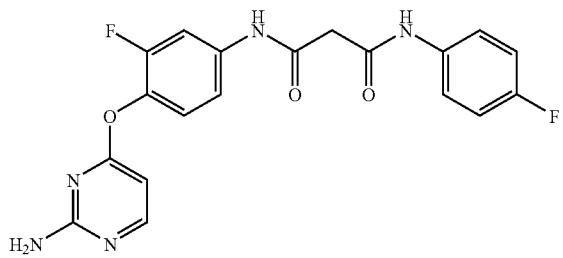

N[1]-(4-(2-Aminopyrimidin-4-yloxy)-3-fluorophenyl)-N[3]-(4-fluorophenyl)malonamide A mixture of N[1]-(4-(2-(4-methoxybenzylamino)pyrimidin-4-yloxy)-3-fluorophenyl)-N[3]-(4-fluorophenyl)malonamide (Example 14, 25 mg, 0.048 mmol), anisole (52 mg, 0.48 mmol) in TFA (1 mL) was heated at 85° C. for 6 h. The TFA was removed under vacuum and the residue partitioned between EtOAc and saturated aq. NaHCO$_3$ solution. The EtOAc phase was washed with brine, dried (MgSO$_4$), and concentrated in vacuo. Flash chromatography on SiO$_2$ using EtOAc then 1-2% MeOH in CH$_2$Cl$_2$ as eluents gave the title compound (12 mg, 63%) as an off-white solid. $^1$H NMR (DMSO-d$_6$) δ 11.00 (s, 1H), 10.51 (s, 1H), 8.02 (s, 1H), 7.66 (dd, 1H, J=12.6, 2.0 Hz), 7.42-7.31 (m, 2H), 7.32-7.27 (m, 1H), 7.23 (t, 2H, J=8.6 Hz), 7.16 (t, 2H, J=9.1 Hz), 6.91 (s, 2H), 3.73 (s, 2H); MS(ESI$^+$) m/z 400.11 (M+H)$^+$.

Example 17

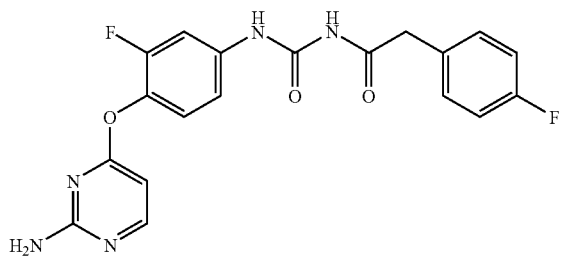

1-(4-(2-Aminopyrimidin-4-yloxy)-3-fluorophenyl)-3-(2-(4-fluorophenyl)acetyl)urea The title compound was prepared from 1-(4-(2-(4-methoxybenzylamino)pyrimidin-4-yloxy)-3-fluorophenyl)-3-(2-(4-fluorophenyl)acetyl)urea (Example 15, 20 mg, 0.039 mmol) using a similar procedure described for Example 16. Flash chromatography on SiO$_2$ using EtOAc then 1-2% MeOH in CH$_2$Cl$_2$ as eluents gave the title compound (10 mg, 62%) as an off-white solid. $^1$H NMR (DMSO-d$_6$) δ 11.01 (s, 1H), 10.52 (s, 1H), 8.20 (d, 1H, J=6.0 Hz), 7.70 (dd, 1H, J=12.1, 2.0 Hz), 7.36-7.30 (m, 6H), 7.16 (dd, 2H, J=8.8, 8.8 Hz), 6.45 (d, 1H, J=6.1 Hz), 3.73 (s, 2H); MS(ESI$^+$) m/z 400.09 (M+H)$^+$.

Example 18

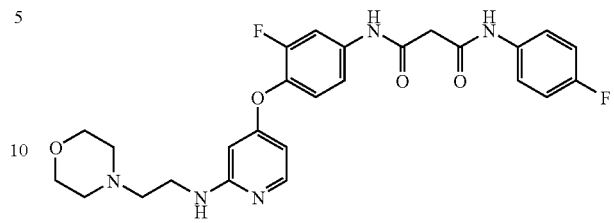

N[1]-(3-Fluoro-4-(2-(2-morpholinoethylamino)pyridin-4-yloxy)phenyl)-N[3]-(4-fluorophenyl)malonamide, hydrochloride salt

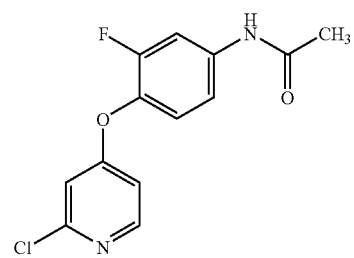

A) N-(4-(2-Chloropyridin-4-yloxy)-3-fluorophenyl) acetamide

A mixture of N-(3-fluoro-4-hydroxyphenyl)acetamide (Compound A of Example 13, 1.33 g, 7.87 mmol), 2-chloro-4-nitropyridine (Aldrich, 1.24 g, 7.87 mmol), K$_2$CO$_3$ (1.6 g, 11.8 mmol), and DMF (25 mL) was heated at 100° C. for 9 h. The reaction mixture was concentrated in vacuo and the residue partitioned between EtOAc and saturated NaHCO$_3$ solution. The EtOAc phase was washed with brine, dried (MgSO$_4$), and concentrated. Flash chromatography using 30-80% EtOAc in hexanes as the eluent gave the title compound (1.6 g, 73%) as a pale yellow solid. $^1$H NMR (DMSO-d$_6$) δ 10.24 (s, 1H), 8.65 (s, 1H), 7.89-7.64 (m, 1H), 7.56 (s, 1H), 7.46-7.19 (m, 2H), 2.06 (s, 3H); MS(ESI$^+$) m/z 281.16 (M+H)$^+$.

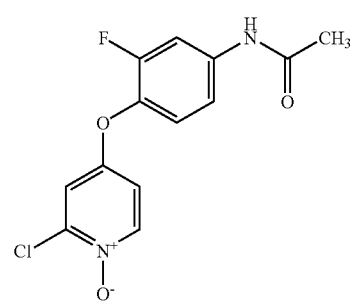

B) N-(4-(2-Chloropyridin-4-yloxy-1-oxide)-3-fluorophenyl)acetamide

A mixture of N-(4-(2-chloropyridin-4-yloxy)-3-fluorophenyl)acetamide (0.98 g, 3.5 mmol), m-chloroperoxybenzoic acid (>90%, 1.3 g, 7.6 mmol), and CHCl$_3$ (50 mL) was stirred at RT for 60 h. The mixture was concentrated and the residue triturated with Et$_2$O (2×100 mL) to give the title compound (0.89 g, 87%) as a pale yellow solid. $^1$H NMR (DMSO-d$_6$) δ 10.25 (s, 1H), 8.34 (d, 1H, J=7.1 Hz), 7.80 (d, 1H, J=13.2 Hz), 7.49 (d, 1H, J=3.3 Hz), 7.33 (d, 2H, J=4.9 Hz), 7.02 (dd, 1H, J=7.1, 3.3 Hz), 2.06 (s, 3H); MS(ESI$^-$) m/z 295.04 (M−H).

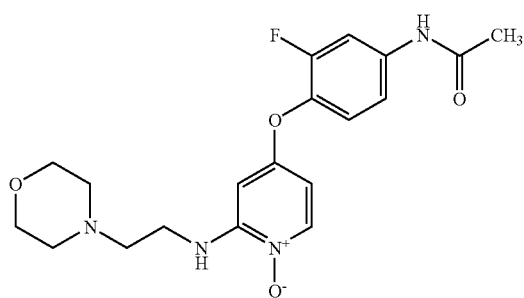

C) N-(3-Fluoro-4-(2-(2-morpholinoethylamino)pyridin-4-yloxy-1-oxide)phenyl)acetamide A mixture of N-(4-(2-chloropyridin-4-yloxy-1-oxide)-3-fluorophenyl)acetamide (205 mg, 0.62 mmol), 4-(2-aminoethyl)morpholine (Aldrich, 169 mg, 1.30 mmol), and absolute EtOH was heated at reflux 16 h. The reaction mixture was concentrated in vacuo, the residue treated with H$_2$O (3 mL) and applied to a 10 g Varian C-18 cartridge. The cartridge was eluted first with H$_2$O then with 30% MeOH in H$_2$O. The fractions which contained the desired product were pooled, concentrated to 5 mL volume, and extracted 3 times with EtOAc. The combined extracts were washed with brine, dried (MgSO$_4$) and concentrated to give the title compound (100 mg, 40%). $^1$H NMR (DMSO-d$_6$) δ 10.22 (s, 1H), 7.84 (d, 1H, J=6.1 Hz), 7.77 (dd, 1H, J=13.2, 2.2 Hz), 7.31 (dd, 1H, J=8.8, 2.2 Hz), 7.24 (t, 1H, J=8.8 Hz), 6.41 (m, 1H), 6.13 (dd, 1H, J=5.5, 2.2 Hz), 5.81 (d, 1H, J=2.2 Hz), 3.60-3.52 (m, 4H), 3.31-3.28 (m, 2H), 2.38 (t, 2H, J=7.1 Hz), 2.34 (m, 4H), 2.06 (s, 3H); MS(ESI$^+$) m/z 405.22 (M+H)$^+$.

D) N-(3-Fluoro-4-(2-(2-morpholinoethylamino)pyridin-4-yloxy)phenyl)acetamide, trifluoroacetic acid salt A mixture of N-(3-fluoro-4-(2-(2-morpholinoethylamino)pyridin-4-yloxy-1-oxide)phenyl)acetamide (100 mg, 0.26 mmol), and triphenylphosphine polymer supported (1.4-2.0 mmol/g) on polystyrene (500 mg) and DMF (2 mL) was stirred at 135° C. for 15 h. The mixture was filtered to remove the resin and the resin washed with DMF and EtOAc. The filtrate and washings were combined and concentrated. The crude product was purified by preparative HPLC (Shimadzu S5 VP-ODS 20×100 mm) to give the title compound (45 mg, 46%) as a white solid. $^1$H NMR (DMSO-d$_6$) δ 10.33 (s, 1H), 8.02 (d, 1H, J=6.6 Hz) 7.84 (dd, 1H, J=13.2, 2.0 Hz), 7.39-7.31 (m, 2H), 6.52 (s, 1H), 6.10 (s, 1H), 3.83 (br s, 4H), 3.64 (m, 2H), 3.28 (m, 6H), 2.08 (s, 3H); MS(ESI$^+$) m/z 375.12 (M+H)$^+$.

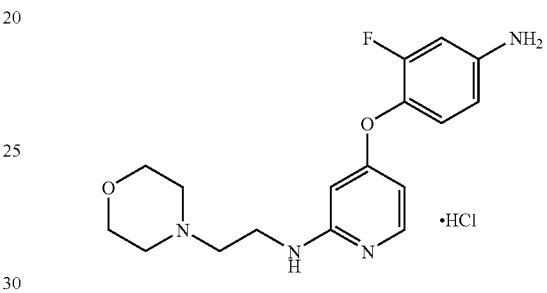

E) 4-(4-Amino-2-fluorophenoxy)-N-(2-morpholinoethyl)pyridin-2-amine, hydrochloride salt A mixture of N-(3-fluoro-4-(2-(2-morpholinoethylamino)pyridin-4-yloxy)phenyl)acetamide trifluoroacetate (40 mg), MeOH (1 mL), and 6 M HCl (0.2 mL) was heated at reflux for 3 h. The reaction mixture was concentrated on a rotary evaporator and the residue lyophilized to give the title compound (30 mg, 76%) as a white solid. $^1$H NMR (DMSO-d$_6$) δ 11.12 (br s, 1H), 8.85 (br s, 1H), 7.95 (d, 1H, J=7.2 Hz), 7.08 (dd, 1H, J=8.8, 8.8 Hz), 6.65-6.63 (m, 2H), 6.54 (d, 1H, J=8.3 Hz), 6.31 (br s, 1H), 3.85 (m, 6H), 3.33 (m, 6H); MS(ESI$^-$) m/z 373.14 (M−H).

F) N$^1$-(3-Fluoro-4-(2-(2-morpholinoethylamino)pyridin-4-yloxy)phenyl)-N$^3$-(4-fluorophenyl)malonamide The title compound was prepared from a mixture of 4-(4-amino-2-fluorophenoxy)-N-(2-morpholinoethyl)pyridin-2-amine, hydrochloride salt (15 mg, 0.043 mmol), 3-(4-fluorophenylamino)-3-oxopropanoic acid (Compound B of Example 1, 10 mg, 0.052 mmol), TBTU (17 mg, 0.052 mmol), DIPEA (30 μL), and DMF (1 mL) using a similar procedure described for the preparation of Compound C of Example 1. The crude product was purified by preparative HPLC (Shimadzu S5 VP-ODS 20×100 mm). The product obtained from HPLC purification was treated with 1 M HCl and lyophilized to give the title compound (10 mg, 40%) as a white solid. $^1$H NMR (DMSO-d$_6$) δ 10.37 (s, 1H), 10.05 (s, 1H), 9.90 (br s, 1H), 7.90 (d, 1H, J=6.1 Hz), 7.75 (d, 1H, J=13.2 Hz), 7.58-7.55 (m, 2H), 7.53-7.50 (m, 1H), 7.40 (d, 1H, J=8.8 Hz), 7.24 (t, 1H, J=8.8 Hz), 7.08-7.03 (m, 3H), 6.39 (d, 1H, J=6.1 Hz), 6.11 (s, 1H), 3.80-3.81 (m, 4H), 3.67-3.65 (m, 2H), 3.47 (br s, 2H), 3.20 (br s, 4H); MS(ESI$^+$) m/z 512.12 (M+H)$^+$.

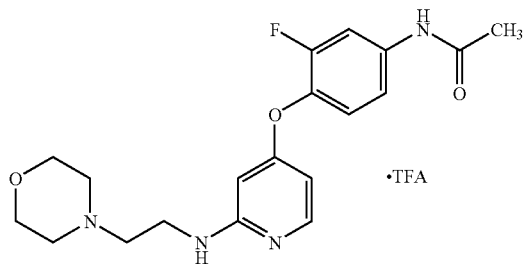

Example 19

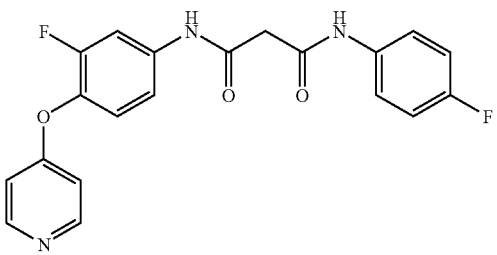

$N^1$-(3-Fluoro-4-(pyridin-4-yloxy)phenyl)-$N^3$-(4-fluorophenyl)malonamide

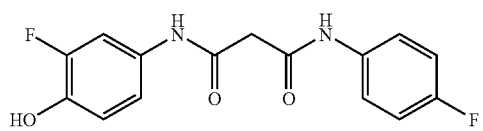

A) $N^1$-(3-Fluoro-4-hydroxyphenyl)-$N^3$-(4-fluorophenyl)malonamide

To a solution of 2-fluoro-4-nitrophenol (Avacado, 1.00 g, 6.37 mmol) in 4 mL of tetrahydrofuran and 6 mL of methanol at 0° C. was added zinc dust (2.08 g, 31.8 mmol, <10 micron) followed by ammonium chloride (1.70 g, 31.8 mmol). The mixture was stirred at room temperature overnight. The heterogeneous mixture was filtered through a thin pad of Celite® with methanol and the filtrate was concentrated in vacuo to give 4-amino-2-fluorophenol as a brown solid which was used without further purification (656 mg, 81%).

3-(4-Fluorophenylamino)-3-oxopropanoic acid (Compound B of Example 1, 197 mg, 1.00 mmol) was dissolved in dimethylformamide (4 mL). Triethylamine (140 μL, 1.00 mmol) was added and the solution was cooled to 0° C. 4-Amino-2-fluorophenol (Step A of Example 19, 127 mg, 1.00 mmol) was added followed by benzotriazol-1-yloxytris(dimethylamino)phosphonium hexafluorophosphate (BOP reagent, 442 mg, 1.00 mmol). The reaction was allowed to warm to room temperature and was then stirred at room temperature for 3 h. The reaction mixture was concentrated to remove methylene chloride and water was added to precipitate the product. Filtration and trituration with water gave the title compound (211 mg, 69%) as a white solid. $^1$H NMR (CD$_3$OD) δ 7.61-7.57 (m, 2H), 7.51 (dd, 1H, J=13, 2.5 Hz), 7.08-6.99 (m, 3H), 6.88 (t, 1H, J=9.4 Hz), 3.51 (s, 2H); MS(ESI$^+$) m/z 307.44 (M+H)$^+$.

B) $N^1$-(3-Fluoro-4-(pyridin-4-yloxy)phenyl)-$N^3$-(4-fluorophenyl)malonamide $N^1$-(3-Fluoro-4-hydroxyphenyl)-$N^3$-(4-fluorophenyl)malonamide (31 mg, 0.10 mmol), copper(II) acetate (27 mg, 0.15 mmol), pyridin-4-ylboronic acid (25 mg, 0.20 mmol), and pyridine (16 μL, 0.20 mmol) were placed in a pressure tube in that order. The tube was charged with methylene chloride (0.5 mL) and sealed. The reaction was stirred at 120° C. for 5 h. The reaction mixture was filtered through silica gel using 5% methanol/ethyl acetate. After concentration, the crude product was purified by prep HPLC. The appropriate fraction was concentrated to remove methanol and the resulting aqueous solution was made basic with saturated NaHCO$_3$ solution (5 mL). The aqueous solution was extracted with EtOAc (3×10 mL) and the combined organic extracts were dried over anhydrous Na$_2$SO$_4$ and concentrated in vacuo. The product was treated with 4N HCl in dioxane and concentrated. Lyophilization with water gave the title compound (8 mg, 21%) as a yellow solid. $^1$H NMR (CD$_3$OD) δ 8.31 (d, 2H, J=6.1 Hz), 7.72 (dd, 1H, J=12.7, 2.4 Hz), 7.49-7.46 (m, 2H), 7.27-7.25 (m, 1H), 7.15 (t, 1H, J=8.8 Hz), 6.97 (t, 2H, J=8.7 Hz), 6.85 (dd, 2H, J=5.1, 1.2 Hz), 3.46 (s, 2H); MS(ESI$^+$) m/z 384.21 (M+H)$^+$.

Example 20

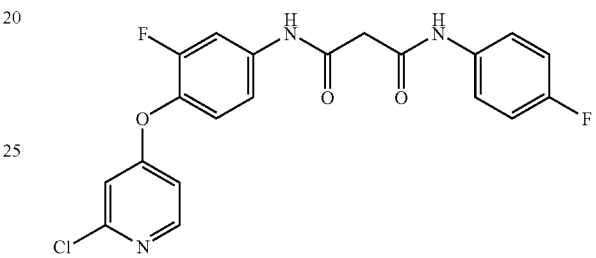

$N^1$-(4-(2-Chloropyridin-4-yloxy)-3-fluorophenyl)-$N^3$-(4-fluorophenyl)malonamide

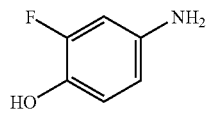

A) 2-Fluoro-4-aminophenol

A mixture of platinum oxide (0.010 g) and 2-fluoro-4-nitrophenol (Aldrich, 1.24 g, 7.78 mmol, 1.0 eq) in MeOH (100 ml) were stirred under a H$_2$ atmosphere at 50 psi at room temperature. The reaction mixture was filtered through celite and the filtrate concentrated in vacuo to afford the title compound (1.00 g, 100%), as a solid which was used without further purification. $^1$H NMR (DMSO-d$_6$) δ 8.57 (s, 1H), 6.46-6.47 (m, 1H), 6.33-6.46 (m, 1H), 6.19-6.21 (m, 1H), 4.79 (s, 2H); MS(ESI$^+$) m/z 128 (M+H)$^+$.

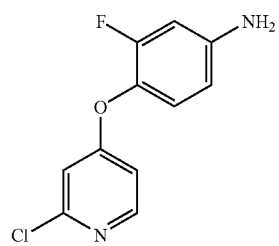

B)
4-(2-Chloropyridin-4-yloxy)-3-fluorobenzenamine

Sodium hydride (60%, 0.104 g, 2.60 mmol, 1.1 eq) was added to a solution of 2-fluoro-4-aminophenol (0.30 g, 2.36 mmol, 1.0 eq) in DMF (6.5 mL) at room temperature and the reaction mixture was stirred for 30 minutes. 2-Chloro-4-nitropyridine (Aldrich, 0.374 g, 2.36 mmol, 1.0 eq) was added and the reaction mixture was heated to 90° C. for 12 h. The reaction mixture was cooled to room temperature, quenched with saturated aqueous NaCl solution and extracted with ethyl acetate (3×70 mL). The combined organic extracts were washed with 10% aq. LiCl solution (3×70 mL), dried over $Na_2SO_4$, filtered and the filtrate concentrated in vacuo to afford the title compound (0.430 g, 76%) which was used without further purification. $^1$H NMR (DMSO-$d_6$) δ 8.27 (d, 1H, J=5.7 Hz), 6.90-7.04 (m, 3H), 6.42-6.54 (m, 2H), 5.54 (s, 2H); MS(ESI$^+$) m/z 239 (M+H)$^+$; HRMS(ESI$^+$) calcd.: 239.0387, found: 239.0391.

C) $N^1$-(4-(2-Chloropyridin-4-yloxy)-3-fluorophenyl)-$N^3$-(4-fluorophenylmalonamide Diisopropylethylamine (0.091 mL, 0.525 mmol, 2.5 eq) was added to a solution of 4-(2-chloropyridin-4-yloxy)-3-fluorobenzenamine (0.050 g, 0.21 mmol, 1.0 eq), 3-(4-fluorophenylamino)-3-oxopropanoic acid (Compound B of Example 1, 0.041 g, 0.21 mmol, 1.0 eq), and PyBroP (0.117 g, 0.252 mmol, 1.2 eq) in $CH_2Cl_2$ (1.0 mL) at 0° C. The reaction mixture was warmed to room temperature and stirred for 12 h. The reaction mixture was quenched with saturated aqueous NaCl solution, and the mixture was extracted with $CH_2Cl_2$ (3×20 mL). The combined organic extracts were dried over $Na_2SO_4$, filtered and the filtrate concentrated in vacuo. The residue was purified by silica gel flash chromatography (Merck, 40-63 μM, 230-240 mesh, eluting 3/1 ethyl acetate/hexane) to afford the title compound (0.056 g, 64%) as a solid. $^1$H NMR (DMSO-$d_6$) δ 10.61 (s, 1H), 10.34 (s, 1H), 8.36-8.38 (m, 1H), 7.91-7.93 (m, 1H), 7.67-7.71 (m, 2H), 7.46-7.48 (m, 2H), 7.04-7.26 (m, 4H), 3.56 (s, 2H); MS(ESI$^+$) m/z 418 (M+H)$^+$; HRMS(ESI$^+$) calcd.: 418.0770, found: 418.0767.

Example 21

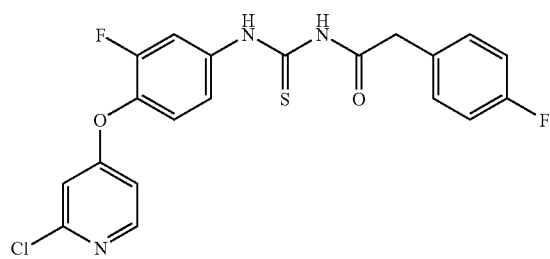

1-(4-(2-Chloropyridin-4-yloxy)-3-fluorophenyl)-3-(2-(4-fluorophenyl)acetyl)thiourea 4-Fluorophenylacetylchloride (Aldrich, 0.072 mL, 0.525 mmol, 2.5 eq) was added to a solution of sodium thiocyanate (0.056 g, 0.695 mmol, 3.3 eq) in ethyl acetate (2.0 mL) at room temperature and the reaction mixture was stirred for 1.5 h to afford a solution of 2-(4-fluorophenyl)ethanoyl isothiocyanate (0.263 M). A solution of 4-(2-chloropyridin-4-yloxy)-3-fluorobenzenamine (0.050 g, 0.21 mmol, 1.0 eq) in $CH_2Cl_2$ (1.0 mL) was added dropwise to the 2-(4-fluorophenyl)ethanoyl isothiocyanate solution and the reaction mixture was stirred at room temperature for 12 h. The reaction mixture was concentrated in vacuo and the resulting residue was purified by silica gel flash chromatography (Merck, 40-63 μM, 230-240 mesh, eluting 3/1 hexane/ethyl acetate) to afford the title compound (0.058 g, 64%) as a solid. $^1$H NMR (DMSO-$d_6$) δ 12.46 (s, 1H), 11.84 (s, 1H), 8.35-8.33 (m, 1H), 8.02-8.33 (m, 1H), 6.99-7.52 (m, 8H), 3.84 (s, 2H); MS(ESI$^+$) m/z 434 (M+H)$^+$; HRMS(ESI$^+$) calcd.: 434.0542, found: 434.0547.

Example 22

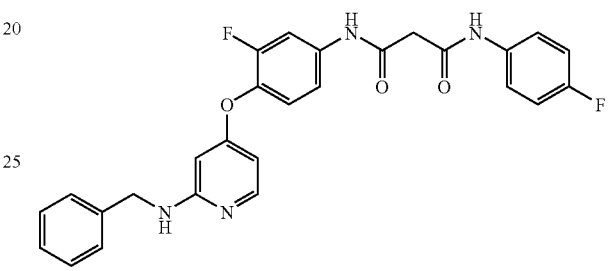

$N^1$-(4-(2-(Benzylamino)pyridin-4-yloxy)-3-fluorophenyl)-$N^3$-(4-fluorophenyl) malonamide

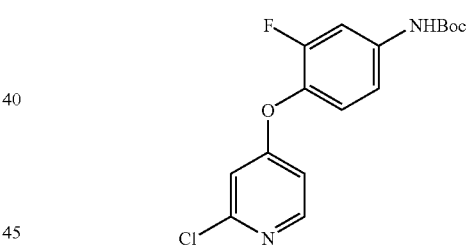

A) tert-Butyl 4-(2-chloropyridin-4-yloxy)-3-fluorophenylcarbamate

Di-tert-butyl dicarbonate (0.920 g, 4.22 mmol, 4.5 eq) was added to a solution of 4-(2-chloropyridin-4-yloxy)-3-fluorobenzenamine (Compound B of Example 20, 0.224 g, 0.939 mmol, 1.0 eq) and triethylamine (0.391 mL, 3.00 mmol, 3.0 eq) in THF (10 mL) and the reaction mixture was heated at 55° C. for 14 h. The reaction mixture was cooled to room temperature and quenched with 1N HCl. The solution was extracted with $CH_2Cl_2$ (3×70 mL), the combined organic extracts washed with 1N NaOH (100 mL), dried ($Na_2SO_4$), filtered and concentrated in vacuo. The residue was purified by silica gel flash chromatography (Merck, 40-63 μM, 230-240 mesh, eluting 4:1 hexane/ethyl acetate) to afford the title compound (0.270 g, 85%). $^1$H NMR (DMSO-$d_6$) δ 8.35-8.36 (m, 1H), 7.55-7.57 (m, 1H), 7.45-7.46 (m, 1H), 7.21-7.24 (m, 1H), 6.96-6.97 (m, 2H), 1.40 (s, 9H); MS(ESI$^+$) m/z 339 (M+H)$^+$; HRMS(ESI$^+$) calcd.: 339.0912, found: 339.0915.

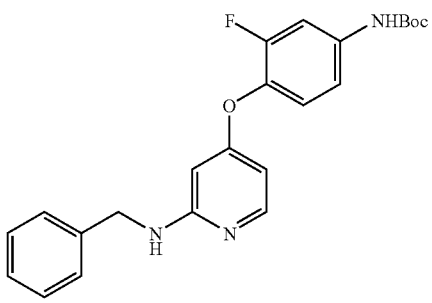

B) tert-Butyl-4-(2-(benzylamino)pyridin-4-yloxy)-3-fluorophenylcarbamate tert-Butyl 4-(2-chloropyridin-4-yloxy)-3-fluorophenylcarbamate (0.100 g, 0.295 mmol, 1.0 eq) was added to a degassed solution of dppf.PdCl$_2$ (Matrix Scientific, 0.011 g, 0.0148 mmol, 0.05 eq), dppf (0.012 g, 0.022 mmol, 0.075 eq), and NaOt-Bu (0.040 g, 0.414 mmol, 1.4 eq) in toluene at room temperature. Benzylamine (0.045 mL, 0.414 mmol, 1.4 eq) was added to the reaction mixture and the resulting solution was stirred at 80° C. for 4 h. The reaction mixture was cooled to room temperature, quenched with 1N HCl and the solution extracted with CHCl$_3$ (3×50 mL). The combined organic extracts were washed with 1 N NaOH (70 mL), dried (Na$_2$SO$_4$), filtered and concentrated in vacuo. The residue was purified by silica gel flash chromatography (Merck, 40-63 μM, 230-240 mesh, eluting 2:1 hexane/ethyl acetate) to afford the title compound (0.020 g, 17%). $^1$H NMR (CDCl$_3$) δ 7.80-7.90 (m, 1H), 7.35-7.45 (m, 1H), 7.19-7.24 (m, 3H), 6.91-6.93 (m, 2H), 6.59 (br m, 1H), 6.10-6.20 (m, 1H), 5.75 (br m, 1H), 5.30-5.40 (m, 1H), 4.34 (s, 2H), 1.46 (s, 9H); MS(ESI$^+$) m/z 410 (M+H)$^+$; HRMS(ESI$^+$) calcd.: 410.1880, found: 410.1884.

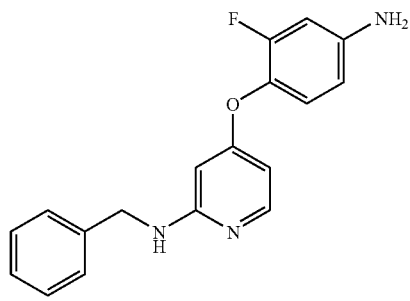

C) 4-(4-Amino-2-fluorophenoxy)-N-benzylpyridin-2-amine, hydrochloride salt

Anhydrous HCl in dioxane (4N, 2.00 mL, 8.00 mmol, 165 eq) was added to tert-butyl 4-(2-(benzylamino)pyridin-4-yloxy)-3-fluorophenylcarbamate (0.020 g, 0.0489 mmol, 1.0 eq) and the reaction mixture was stirred at room temperature for 12 h. The reaction mixture was concentrated in vacuo to afford the title compound (0.017 g, 100%) a solid that was used without further purification. MS(ESI$^+$) m/z 310 (M+H)$^+$; HRMS(ESI$^+$) calcd.: 310.1356, found: 310.1364.

D) N$^1$-(4-(2-(Benzylamino)pyridin-4-yloxy)-3-fluorophenyl)-N$^3$-(4-fluorophenyl)malonamide Diisopropylethylamine (0.014 mL, 0.081 mmol, 3.5 eq) was added to a solution of 4-(4-amino-2-fluorophenoxy)-N-benzylpyridin-2-amine, hydrochloride salt (0.008 g, 0.023 mmol, 1.0 eq), 3-(4-fluorophenylamino)-3-oxopropanoic acid (Compound B of Example 1, 0.005 g, 0.023 mmol, 1.0 eq), and PyBroP (0.013 g, 0.028 mmol, 1.2 eq) in CH$_2$Cl$_2$ (1.0 mL) at 0° C. The reaction mixture was warmed to room temperature and stirred for 16 h. The reaction mixture was concentrated in vacuo and the residue was purified by reverse phase HPLC chromatography (YMC-ODS-A, C-18, S10, 30×500 mm, eluting 20-90% aqueous MeOH with 0.1% TFA, 30 min. gradient). The appropriate fractions were concentrated in vacuo, neutralized with sat. aqueous NaHCO$_3$ solution and the mixture extracted with CHCl$_3$ (3×10 mL). The combined organic extracts were dried (Na$_2$SO$_4$), filtered and concentrated in vacuo to afford the title compound (0.0025 g, 45%) as a solid. MS(ESI$^+$) m/z 489 (M+H)$^+$; HRMS(ESI$^+$) calcd.: 489.1738, found: 489.1743.

Example 23

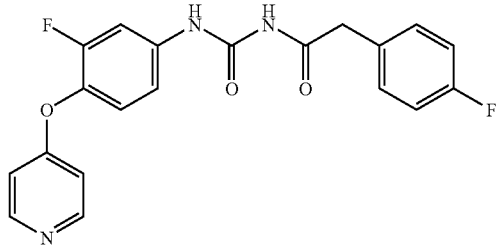

1-(3-Fluoro-4-(pyridin-4-yloxy)phenyl)-3-(2-(4-fluorophenyl)acetyl)urea

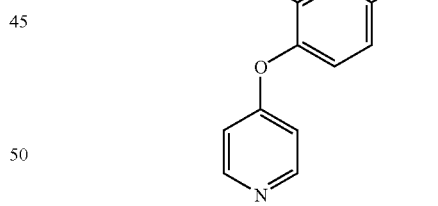

A) 3-Fluoro-4-(pyridin-4-yloxy)benzenamine

Potassium hydride (30%, 0.520 g, 3.90 mmol, 3.0 eq) was added to a solution of 2-fluoro-4-aminophenol (Compound A of Example 20, 0.254 g, 2.00 mmol, 1.5 eq) in DMF (5.0 mL) at room temperature and the reaction mixture was stirred for 15 minutes. 4-Chloro-pyridine (Aldrich, 0.200 g, 1.30 mmol, 1.0 eq) was added and the reaction mixture was heated to 150° C. for 2 h. The reaction mixture was cooled to room temperature, quenched with 1N NaOH and the solution extracted with ethyl acetate (3×50 mL). The combined organic extracts were washed with 1N aqueous NaOH (2×30 mL) followed by 10% aqueous LiCl (3×50 mL). The combined organic extracts were dried (Na$_2$SO$_4$), filtered and concentrated in vacuo to afford the title compound as a solid. $^1$H NMR (DMSO-d$_6$) δ 8.44-8.46 (m, 2H), 6.89-7.03 (m, 1H), 6.87-6.88 (m, 2H), 6.44-6.56 (m, 2H), 5.51 (s, 2H); MS(ESI$^+$) m/z 205 (M+H)$^+$; HRMS(ESI$^+$) calcd.: 205.0777, found: 205.0775.

B) 1-(3-Fluoro-4-(pyridin-4-yloxy)phenyl)-3-(2-(4-fluorophenyl)acetyl)urea

Silver cyanate (0.912 g, 6.08 mmol, 1.05 eq) was added to a solution of 4-fluorophenylacetyl chloride (Aldrich, 0.794 mL, 5.79 mmol, 1.0 eq) in toluene (16 mL) at room temperature shielded from light. The reaction mixture was heated to reflux for 60 minutes and then cooled to room temperature. The reaction mixture was filtered (Acrodisc, PTFE 0.2 μM) and the resultant 2-(4-fluorophenyl)acetyl isocyanate solution (0.36 M, 0.75 mL, 0.27 mmol, 1.1 eq) was added to a solution of 3-fluoro-4-(pyridin-4-yloxy)benzenamine (0.050 g, 0.245 mmol, 1.0 eq) in CH$_2$Cl$_2$ (2.0 mL) at room temperature. The reaction mixture was stirred at room temperature for 1 h, quenched with saturated aqueous NaCl solution and the mixture was extracted with CH$_2$Cl$_2$ (3×30 mL). The combined organic extracts were dried (Na$_2$SO$_4$), filtered and concentrated in vacuo. The residue was purified by silica gel flash chromatography (Merck, 40-63 μM, 230-240 mesh, eluting 0-5% MeOH in CHCl$_3$) to afford the title compound (0.043 g, 46%) as a solid. $^1$H NMR (DMSO-d$_6$) δ 11.06 (s, 1H), 10.60 (s, 1H), 8.47 (s, 2H), 7.77-7.80 (m, 1H), 6.92-7.48 (m, 8H), 3.75 (s, 2H); MS(ESI$^+$) m/z 384 (M+H)$^+$; HRMS(ESI$^+$) calcd.: 384.1160, found: 384.1147.

Example 24

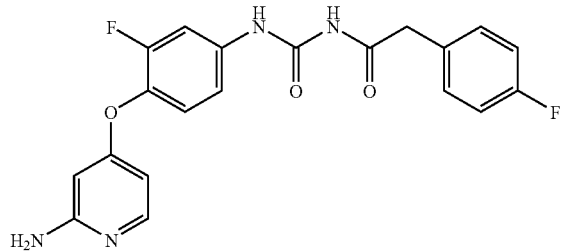

1-(4-(2-Aminopyridin-4-yloxy)-3-fluorophenyl)-3-(2-(4-fluorophenyl)acetyl)urea

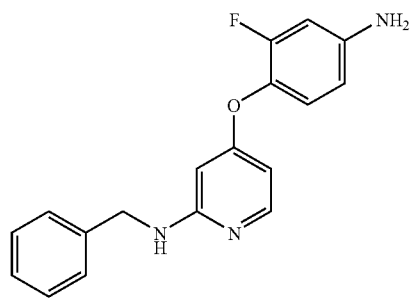

A) 4-(4-Amino-2-fluorophenoxy)-N-benzylpyridin-2-amine

Benzylamine (9.1 mL, 83.8 mmol, 20 eq) was added to 4-(2-chloropyridin-4-yloxy)-3-fluorobenzenamine (Compound B of Example 20, 1.0 g, 4.19 mmol, 1.0 eq), copper powder (0.266 g, 4.19 mmol, 1.0 eq) and K$_2$CO$_3$ (0.578 g, 4.19 mmol, 1.0 eq) in a sealed tube and the reaction mixture was heated to 160° C. for 12 h. The reaction mixture was cooled to room temperature and quenched with saturated aqueous NaCl solution. The solution was extracted with ethyl acetate (3×100 mL), the combined organic extracts dried (Na$_2$SO$_4$), filtered and concentrated in vacuo. The residue was purified by preparative reverse phase HPLC (YMC C-18 ODS-A S10 50×500 mm, eluting 10-90% aqueous MeOH with 0.1% TFA, 30 minute gradient) and the appropriate fractions were concentrated in vacuo. The concentrate was neutralized with saturated aqueous NaHCO$_3$ solution and extracted with CH$_2$Cl$_2$ (3×100 mL). The combined organic extracts were dried (Na$_2$SO$_4$), filtered and concentrated in vacuo to afford the title compound (0.675 g, 52%) as a solid. $^1$H NMR (CD$_3$OD) δ 7.78-7.80 (m, 1H), 7.28-7.30 (m, 5H), 6.80-6.90 (m, 1H), 6.52-6.55 (m, 2H), 6.18-6.20 (m, 1H), 5.87-5.88 (m, 1H), 4.40 (s, 2H); MS(ESI$^+$) m/z 310 (M+H)$^+$; HRMS(ESI$^+$) calcd.: 310.1356, found: 310.1360.

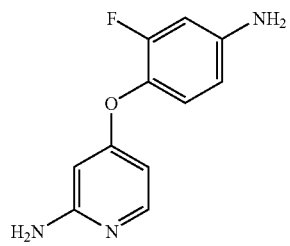

B) 4-(4-Amino-2-fluorophenoxy)pyridin-2-amine

Palladium hydroxide on carbon (10%, 0.050 g) was added to a solution of 4-(4-amino-2-fluorophenoxy)-N-benzylpyridin-2-amine (0.245 g, 0.790 mmol, 1.0 eq) in 5% HCO$_2$H-MeOH (10 mL) under a blanket of hydrogen (from a balloon) at room temperature. The reaction mixture was stirred at room temperature for 12 h, filtered through Celite® and the filtrate concentrated in vacuo. The residue was purified by reverse phase preparative HPLC (YMC ODS-A S10 30×500 mm., 10-90% aqueous MeOH with 0.1% TFA, 30 minute gradient) and the appropriate fractions were concentrated in vacuo. The concentrate was neutralized with saturated aqueous NaHCO$_3$ solution and the mixture was extracted with CHCl$_3$ (3×35 mL). The combined organic extracts were dried (Na$_2$SO$_4$), filtered and concentrated in vacuo to afford the title compound (0.045 g, 26%) as a solid. $^1$H NMR (CD$_3$OD) δ 7.62-7.63 (m, 1H), 6.77-6.82 (m, 1H), 6.38-6.47 (m, 2H), 6.09-6.11 (m, 1H), 5.83-5.84 (m, 1H); MS(ESI$^+$) m/z 220 (M+H)$^+$; HRMS(ESI$^+$) calcd.: 220.0886, found: 220.0877.

C) 1-(4-(2-Aminopyridin-4-yloxy)-3-fluorophenyl)-3-(2-(4-fluorophenyl)acetyl)urea 2-(4-Fluorophenyl)acetyl isocyanate (Compound D of Example 11, 0.362 M, 0.351 mL, 0.127 mmol, 1.3 eq) was added to a solution of 4-(4-amino-2-fluorophenoxy)pyridin-2-amine (0.022 g, 0.100 mmol, 1.0 eq) in CH$_2$Cl$_2$ (2.0 mL) at room temperature. The reaction mixture was stirred for 13 h at room temperature and then concentrated in vacuo. The residue was purified by silica gel flash chromatography (Merck gel 40-63 μM, 230-240 mesh, 1:1 ethyl acetate/hexane) to afford the title compound (0.025 g, 64%) as a solid. $^1$H NMR (CD$_3$OD) δ 7.62-7.67 (m, 2H), 7.23-7.29 (m, 2H), 7.07-7.12 (m, 2H), 6.95-6.99 (m, 2H), 6.12-6.14 (m, 1H), 5.86-5.87 (m, 1H), 3.61 (s, 2H); MS(ESI$^+$) m/z 399 (M+H)$^+$; HRMS(ESI$^+$) calcd.: 399.1269, found: 399.1269.

Alternatively, Example 24 was prepared in the following manner:

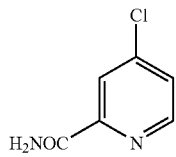

A') 4-Chloropicolinamide

A heterogeneous mixture of 4-chloropicolinic acid (TCI America, 5.4 g, 34.2 mmol, 1.0 eq) and thionyl chloride (30 mL) were heated at 80° C. for 2 h. The reaction mixture was cooled to room temperature and concentrated in vacuo. The residue was treated with an ammonia in MeOH solution (7N, 45 mL) in an ice bath and the reaction mixture was stirred for 15 minutes. The ice bath was then removed and the reaction was warmed to room temperature and then stirred for 3 h. The reaction mixture was concentrated in vacuo and the residue purified by recrystallization from EtOAc to afford the product (5.14 g, 96%) as a solid. $^1$H NMR (DMSO-d$_6$) δ 8.61-8.63 (m, 1H), 8.21 (m, 1H), 8.03-8.04 (m, 1H), 7.76-7.83 (m, 2H); MS(ESI$^+$) m/z 157 (M+H)$^+$.

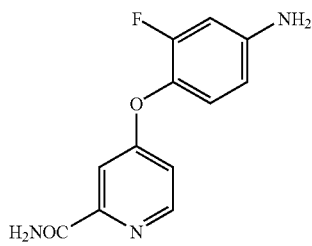

B') 4-(4-Amino-2-fluorophenoxy)picolinamide

A solution of 4-amino-2-fluorophenol (Compound A of Example 20, 0.81 g, 6.4 mmol, 1.0 eq) in DMF (6.5 mL) was treated with potassium tert-butoxide (0.79 g, 7.1 mmol, 1.1 eq) at room temperature and the reaction mixture was stirred for 1 h. 4-Chloropicolinamide (1.0 g, 6.4 mmol, 1.0 eq) was added and the reaction mixture was heated to 110° C. for 8 h. The reaction was cooled to room temperature and the reaction mixture quenched with water. The resulting heterogeneous solution was filtered and the solid material was washed with water. The solid was triturated with a small amount of MeOH followed by Et$_2$O. The solid was filtered and dried in vacuo to afford the product (1.3 g, 82%) as a solid. $^1$H NMR (DMSO-d$_6$) δ 8.49-8.50 (m, 1H), 8.12 (br s, 1H), 7.71 (br s, 1H), 7.35-7.36 (m, 1H), 7.14-7.16 (m, 1H), 7.01-7.06 (m, 1H), 6.44-6.47 (m, 2H), 5.53 (s, 2H); MS(ESI$^+$) m/z 248 (M+H)$^+$.

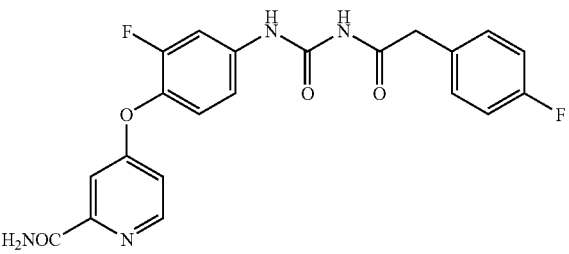

C') 1-(4-(2-Carbamoylpyridin-4-yloxy)-3-fluorophenyl)-3-(2-(4-fluorophenyl)acetyl)urea A solution of 2-(4-fluorophenyl)acetyl isocyanate (Compound D of Example 11, 0.29 M in toluene, 54.9 mL, 15.9 mmol, 2.1 eq) was added to 4-(4-amino-2-fluorophenoxy)picolinamide (1.86 g, 7.53 mmol, 1.0 eq) in 10/3 DCM/DMF (65 mL) at room temperature and the reaction mixture was stirred for 17 h. The reaction mixture was concentrated in vacuo and the residue redissolved in CHCl$_3$. The organic layer was washed with saturated aqueous NaCl, the organic fraction separated, dried (Na$_2$SO$_4$), filtered and concentrated in vacuo. The residue was purified by silica gel chromatography (eluting ⅓ hexane/EtOAc, then to elute product 5% MeOH in CHCl$_3$), and the appropriate fractions concentrated in vacuo to afford the product (2.2 g, 69%) as a solid. $^1$H NMR (DMSO-d$_6$) δ 11.07 (s, 1H), 10.62 (s, 1H), 8.54 (d, 1H, J=5.60 Hz), 8.16-8.19 (m, 1H), 7.76-7.84 (m, 2H), 7.35-7.49 (m, 5H), 7.16-7.23 (m, 3H), 3.76 (s, 2H); MS(ESI$^+$) m/z 427 (M+H)$^+$. HRMS (ESI$^+$) calcd.: 427.1218, found: 427.1214.

D') 1-(4-(2-Aminopyridin-4-yloxy)-3-fluorophenyl)-3-(2-(4-fluorophenyl)acetyl)urea, hydrochloride salt Bis-(trifluoroacetoxy)-iodobenzene (Aldrich, 3.09 g, 7.20 mmol, 1.4 eq) was added to a solution of 1-(4-(2-carbamoylpyridin-4-yloxy)-3-fluorophenyl)-3-(2-(4-fluorophenyl)acetyl)urea (2.19 g, 5.14 mmol, 1.0 eq), water (0.241 mL, 13.4 mmol, 2.6 eq) and pyridine (1.62 mL, 20 mmol, 3.9 eq) in DMF (20 mL) at room temperature and the reaction mixture was stirred for 5 h. The reaction mixture was quenched with 1 N HCl and the aqueous solution extracted with Et$_2$O, discarding the organic layer. The aqueous layer was neutralized with 1 N NaOH and extracted with EtOAc. The combined organic layers were washed with 10% aq LiCl, dried (Na$_2$SO$_4$), filtered and concentrated in vacuo. The residue was purified by silica gel chromatography (eluting with 0-5% MeOH in CHCl$_3$) and the appropriate fractions were concentrated in vacuo. The residue was dissolved in THF (50 mL) cooled to 0° C. and treated with anhydrous HCl (4N, 10 mL, 40 mmol, 7.8 eq). The reaction mixture was allowed to warm to room temperature and stirred for 2 h resulting in a heterogeneous solution. The solution was filtered and the solid washed with Et$_2$O and dried in vacuo to afford the title compound (1.38 g, 63%) as a solid. $^1$H NMR (DMSO-d$_6$) δ 11.09 (s, 1H), 10.65 (s, 1H), 7.97-8.00 (m, 1H), 7.83-7.90 (m, 3H), 7.35-7.48 (m, 4H), 7.15-7.21 (m, 2H), 6.70-6.72 (m, 1H), 6.16-6.17 (m, 1H), 3.77 (s, 2H); MS(ESI$^+$) m/z 399 (M+H)$^+$. HRMS(ESI$^+$) calcd.: 399.1269; found: 399.1258. Elem analysis for C$_{20}$H$_{16}$N$_4$O$_3$F$_2$ 1.0 HCl.0.22H$_2$O Calcd.: C, 54.75; H, 4.01, N, 12.77, Cl; 8.08. Found: C, 54.75; H, 4.35, N, 4.35, Cl; 8.06.

Example 25

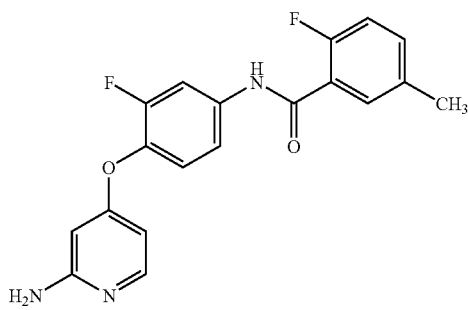

N-(4-(2-Aminopyridin-4-yloxy)-3-fluorophenyl)-2-fluoro-5-methylbenzamide

Diisopropylethylamine (0.035 mL, 0.200 mmol, 2.0 eq) was added to a solution of 4-(4-amino-2-fluorophenoxy)pyridin-2-amine (Compound B of Example 24, 0.022 g, 0.100 mmol, 1.0 eq), 2-fluoro-5-methyl benzoic acid (Aldrich, 0.015 g, 0.100 mmol, 1.0 eq), EDCI (0.021 g, 0.11 mmol, 1.1 eq) and HOBT (0.014 g, 0.100 mmol, 1.0 eq) in DMF (0.700 mL) at room temperature. The reaction mixture was stirred at room temperature for 8 h, quenched with saturated aqueous NaHCO$_3$ solution and extracted with CHCl$_3$ (3×10 mL). The combined organic extracts were dried (Na$_2$SO$_4$), filtered and concentrated in vacuo. The residue was purified by reverse phase preparative HPLC (YMC ODS-A S10 30×500 mm, 30-90% aqueous MeOH with 0.1% TFA, 30 minute gradient) and the appropriate fractions were concentrated in vacuo. The concentrate was neutralized with saturated aqueous NaHCO$_3$ solution and the mixture extracted with CHCl$_3$ (3×30 mL). The combined organics were dried (Na$_2$SO$_4$), filtered and concentrated in vacuo to afford the title compound (0.014 g, 40%) as a solid. $^1$H NMR (CD$_3$OD) δ 7.67-7.80 (m, 2H), 7.36-7.45 (m, 3H), 7.03-7.14 (m, 2H), 6.14-6.16 (m, 1H), 5.89-5.90 (m, 1H), 2.29 (s, 3H); MS(ESI$^+$) m/z 356 (M+H)$^+$; HRMS(ESI$^+$) calcd.: 356.1211, found: 356.1203.

Example 26

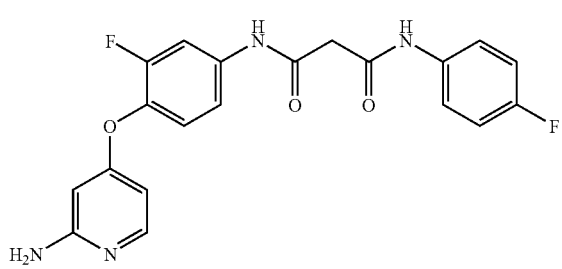

N$^1$-(4-(2-Aminopyridin-4-yloxy)-3-fluorophenyl)-N$^3$-(4-fluorophenylmalonamide Diisopropylethylamine (0.105 mL, 0.604 mmol, 3.3 eq) was added to a solution of 4-(4-amino-2-fluorophenoxy)pyridin-2-amine (Compound B of Example 24, 0.040 g, 0.183 mmol, 1.0 eq), 3-(4-fluorophenylamino)-3-oxopropanoic acid (Compound B of Example 1, 0.054 g, 0.274 mmol, 1.5 eq), and PyBroP (0.139 g, 0.298 mmol, 1.6 eq) in CH$_2$Cl$_2$ (2.0 mL) at 0° C. The reaction mixture was warmed to room temperature and stirred for 18 h. The reaction mixture was quenched with saturated aqueous NaHCO$_3$ and the solution extracted with CHCl$_3$ (3×10 mL). The combined organic extracts were dried (Na$_2$SO$_4$), filtered and concentrated in vacuo. The residue was purified by silica gel flash chromatography (Merck 40-63 μM, 230-240 mesh, eluting 0-6% MeOH in CHCl$_3$ to afford the title compound (0.056 g, 77%) as a solid. $^1$H NMR (CD$_3$OD) δ 7.67-7.68 (m, 2H), 7.48-7.52 (m, 2H), 7.13-7.25 (m, 1H), 7.10-7.12 (m, 1H), 6.94-6.99 (m, 2H), 6.16-6.17 (m, 1H), 5.88-5.89 (m, 1H), 3.30 (s, 2H); MS(ESI) m/z 399 (M−H+); HRMS(ESI$^+$) calcd.: 399.1269, found: 399.1261.

Example 27

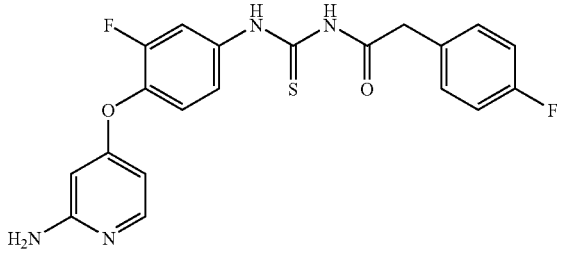

1-(4-(2-Aminopyridin-4-yloxy)-3-fluorophenyl)-3-(2-(4-fluorophenyl)acetyl)thiourea 4-Fluorophenylacetylchloride (Aldrich, 0.017 mL, 0.126 mmol, 2.5 eq) was added to a solution of sodium thiocyanate (0.014 g, 0.176 mmol, 3.5 eq) in ethyl acetate (1.0 mL) at room temperature and the reaction mixture was stirred for 1.5 h to afford a 2-(4-fluorophenyl)ethanoyl isothiocyanate solution (0.126 M). 4-(4-Amino-2-fluorophenoxy)pyridin-2-amine (Compound B of Example 24, 0.011 g, 0.050 mmol, 1.0 eq) was dissolved in CH$_2$Cl$_2$ (1.0 mL) and 2-(4-fluorophenyl)ethanoyl isothiocyanate (0.126 M, 0.50 mL, 0.063 mmol, 1.3 eq) was added and the reaction mixture was stirred at room temperature for 20 h. The reaction mixture was concentrated in vacuo and the resulting residue was purified by silica gel flash chromatography (Merck, 40-63 μM, 230-240 mesh, eluting 0-6% MeOH in CHCl$_3$) to afford the title compound (0.008 g, 38%) as a solid. $^1$H NMR (CD$_3$OD) δ 7.85-7.95 (m, 1H), 7.67-7.69 (m, 1H), 7.13-7.28 (m, 4H), 6.95-7.00 (m, 2H), 6.05-6.15 (m, 1H), 5.90-5.91 (m, 1H), 3.65 (s, 2H); MS(ESI$^+$) m/z 415 (M+H)$^+$; HRMS(ESI$^+$) calculated: 415.1040, found: 415.1041.

Example 28

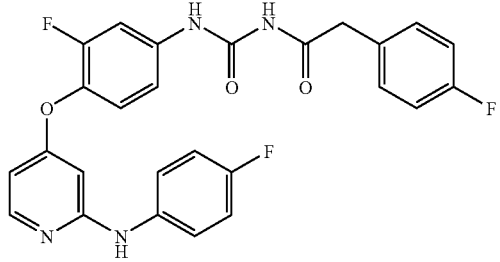

1-(3-Fluoro-4-(2-(4-fluorophenylamino)pyridin-4-yloxy)phenyl)-3-(2-(4-fluorophenyl)acetyl)urea

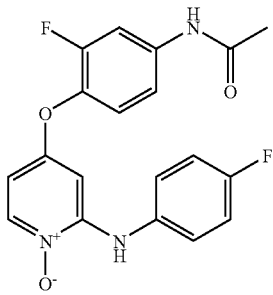

A) N-(3-Fluoro-4-(2-(4-fluorophenylamino)pyridin-4-yloxy-1-oxide)phenyl)acetamide A mixture N-(4-(2-chloropyridin-4-yloxy-1-oxide)-3-fluorophenyl)acetamide (Compound B of Example 18, 62 mg, 0.21 mmol), 4-fluoroaniline (47 mg, 0.42 mmol), and 2-methoxyethyl ether (91 mL) was heated at 140° C. for 15 min. The mixture was cooled to RT, diluted with EtOAc (20 mL), washed with saturated NaHCO$_3$ solution and brine (several times), dried (MgSO$_4$), and concentrated in vacuo to give a 4:1 mixture of the title compound and the parent pyridine as a light brown oil (45 mg, 58%). The product was used in the subsequent step without any further purification. MS(ESI$^+$) m/z 372.1 (M+H)$^+$.

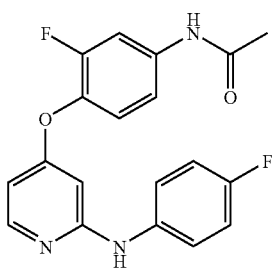

B) N-(3-Fluoro-4-(2-(4-fluorophenylamino)pyridin-4-yloxy)phenyl)acetamide

A mixture of N-(3-fluoro-4-(2-(4-fluorophenylamino)pyridin-4-yloxy-1-oxide)phenyl)acetamide (45 mg), triphenylphosphine polymer supported (~3 mmol/g) on polystyrene (200 mg, Fluka) and DMF (3 mL) was heated at 135° C. for 48 h. The resin was filtered off, washed with DMF and EtOAc. The filtrate and washings were combined and concentrated in vacuo. The crude product was purified by flash chromatography using 30-80% EtOAc in hexanes as the eluent to give the title compound (22 mg, 51%) as a pink solid. $^1$H NMR (DMSO-d$_6$) δ 10.24 (s, 1H), 8.99 (s, 1H), 8.03 (d, 1H, J=6.3 Hz), 7.80 (dd, 1H, J=13.0, 2.1 Hz), 7.63-7.60 (m, 2H), 7.36-7.29 (m, 2H), 7.05 (dd, 1H, J=9.1, 8.6 Hz), 6.44 (dd, 1H, J=5.5, 2.2 Hz), 6.09 (d, 1H, J-2 Hz), 2.07 (s, 3H); MS(ESI$^+$) m/z 356.7 (M+H)$^+$.

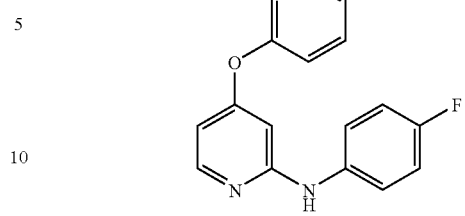

C) 4-(4-Amino-2-fluorophenoxy)-N-(4-fluorophenyl)pyridin-2-amine

A mixture of N-(3-fluoro-4-(2-(4-fluorophenylamino)pyridin-4-yloxy)phenyl)acetamide (18 mg, 0.051 mmol), 6 M HCl (0.1 mL, 0.60 mmol) and MeOH (1.5 mL) was heated at reflux for 2 h. The mixture was concentrated in vacuo and the residue made basic with saturated aq. NaHCO$_3$ solution then extracted with EtOAc. The extract was dried (MgSO$_4$) and concentrated in vacuo to give the title compound (14 mg, 88%) as a red gum. $^1$H NMR (DMSO-d$_6$) δ 8.97 (s, 1H), 7.98 (d, 1H, J=5.8 Hz), 7.64-7.60 (m, 2H), 7.05 (dd, 2H, J=9.1, 8.8 Hz), 6.97 (dd, 1H, J=9.4, 8.8 Hz), 6.51 (dd, 1H, J=13.3, 2.6 Hz), 6.40 (ddd, 2H, J=9.0, 6.2, 2.1 Hz), 6.08 (d, 1H, J=2.0 Hz), 5.44 (br s, 2H); MS(ESI$^+$) m/z 314.17 (M+H)$^+$.

D) 1-(3-Fluoro-4-(2-(4-fluorophenylamino)pyridin-4-yloxy)phenyl)-3-(2-(4-fluorophenyl)acetyl)urea A solution 4-(4-amino-2-fluorophenoxy)-N-(4-fluorophenyl)pyridin-2-amine (11 mg, 0.035 mmol) in THF (1 mL) was cooled in an ice bath and treated with a solution of 2-(4-fluorophenyl)acetyl isocyanate in toluene (Compound D of Example 11, 250 µL, 0.070 mmol) and stirred at RT for 2 h. The mixture was concentrated in vacuo and the residue triturated with isopropyl ether to give the title compound (11 mg, 65%) as a white solid. $^1$H NMR (DMSO-d$_6$) δ 11.04 (s, 1H), 10.56 (s, 1H), 9.01 (s, 1H), 8.03 (d, 1H, J=5.6 Hz), 7.77 (dd, 1H, J=13.3, 2.0 Hz), 7.63-7.60 (m, 2H), 7.41-7.31 (m, 5H), 7.19-7.14 (m, 2H), 7.05 (dd, 1H, J=9.1, 8.5 Hz), 6.43 (dd, 1H, J=6.2, 2.1 Hz), 6.10 (d, 1H, J=2.1 Hz), 3.74 (s, 2H); MS(ESI$^+$) m/z 493.2 (M+H)$^+$.

Example 29

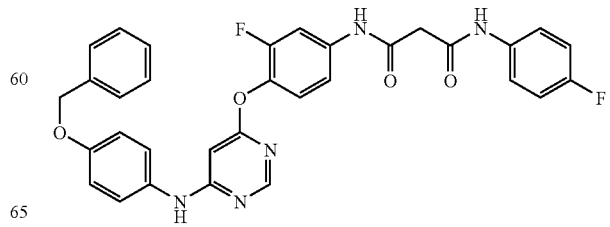

N$^1$-(4-(6-(4-(Benzyloxy)phenylamino)pyrimidin-4-yloxy)-3-fluorophenyl)-N$^3$-(4-fluorophenyl)malonamide

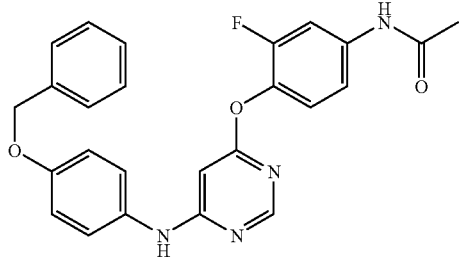

A) N-(4-(6-(4-(Benzyloxy)phenylamino)pyrimidin-4-yloxy)-3-fluorophenyl)acetamide A mixture of N-(4-(6-chloropyrimidin-4-yloxy)-3-fluorophenyl)acetamide (Compound B of Example 13, 281 mg, 1.00 mmol), 4-benzyloxyaniline (Aldrich, 398 mg, 2.00 mmol), and 2-methoxyethyl ether (2 mL) was heated at 160° C. for 45 min. The cooled mixture was treated with H$_2$O (50 mL) and extracted with EtOAc (100 mL). The EtOAc extract was washed with brine (3×25 mL), dried (MgSO$_4$) and concentrated in vacuo to give the title compound (200 mg, 22%) as a purple solid. $^1$H NMR (400 MHz, DMSO-d$_6$) δ 10.19 (s, 1H), 9.43 (s, 1H), 8.23 (s, 1H), 7.72 (dd, 1H, J=12.5, 2.0 Hz), 7.44-7.42 (m, 4H), 7.38 (dd, 2H, J=8.0, 6.9 Hz), 7.33-7.23 (m, 3H), 6.98 (d, 2H, J=9.0 Hz), 6.07 (s, 1H), 5.07 (s, 2H), 2.05 (s, 3H); MS(ESI$^+$) m/z 445.13 (M+H)$^+$.

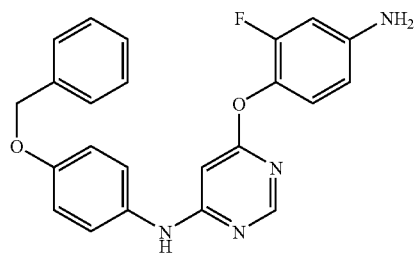

B) 6-(4-Amino-2-fluorophenoxy)-N-(4-(benzyloxy)phenyl)pyrimidin-4-amine

A mixture of N-(4-(6-(4-(benzyloxy)phenylamino)pyrimidin-4-yloxy)-3-fluorophenyl)acetamide (150 mg, 0.34 mmol), 6 M HCl (0.5 mL) and MeOH (3 mL) was heated at reflux for 2 h. The mixture was concentrated to remove the MeOH and the residue treated with saturated NaHCO$_3$ solution and extracted with EtOAc. The organic phase was dried (MgSO$_4$) and concentrated in vacuo to give the title compound (123 mg, 90%) as a pink solid. $^1$H NMR (DMSO-d$_6$): δ 9.37 (s, 1H), 8.24 (s, 1H), 7.46-7.31 (m, 7H), 6.99-6.92 (m, 3H), 6.48 (dd, 1H, J=12.5, 2.7 Hz), 6.39 (dd, 1H, J=8.6, 2.7 Hz), 5.97 (s, 1H), 5.39 (br s, 2H), 5.08 (s, 2H); MS(ESI$^+$) m/z 403.09 (M+H)$^+$.

C) N$^1$-(4-(6-(4-(Benzyloxy)phenylamino)pyrimidin-4-yloxy)-3-fluorophenyl)-N$^3$-(4-fluorophenyl)malonamide The title compound was prepared from a mixture 6-(4-amino-2-fluorophenoxy)-N-(4-(benzyloxy)phenyl)pyrimidin-4-amine (45 mg, 0.11 mmol), 3-(4-fluorophenylamino)-3-oxopropanoic acid (Compound B of Example 1, 24 mg, 0.12 mmol), TBTU (48 mg, 0.15 mmol), DIPEA (0.26 mL, 0.15 mmol), and DMF (1 mL) using a similar procedure described for the preparation of Compound C of Example 1. The crude product was triturated with isopropyl ether to give the title compound (56 mg, 88%) as a pink solid. $^1$H NMR (DMSO-d$_6$) δ 10.47 (s, 1H), 10.27 (s, 1H), 9.45 (s, 1H), 8.25 (s, 1H), 7.77 (dd, 1H, J=12.7, 2.0 Hz), 7.65-7.62 (m, 2H), 7.46 (d, 4H, J=7.3 Hz), 7.40 (dd, 2H, J=7.6, 7.3 Hz), 7.37-7.29 (m, 3H), 7.17 (dd, 2H, J=9.0, 8.3 Hz), 7.00 (d, 2H, J=9.0 Hz) 6.09 (s, 1H), 5.09 (s, 2H) 3.49 (s, 2H); MS(ESI$^+$) m/z 582.3 (M+H)$^+$.

Example 30

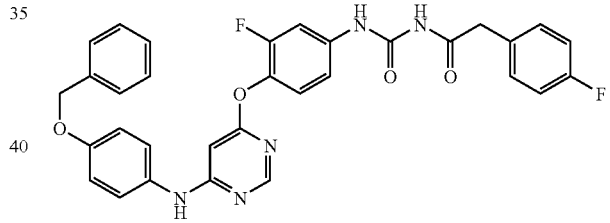

1-(4-(6-(4-(Benzyloxy)phenylamino)pyrimidin-4-yloxy)-3-fluorophenyl)-3-(2-(4-fluorophenyl)acetyl)urea The title compound was prepared from 6-(4-amino-2-fluorophenoxy)-N-(4-(benzyloxy)phenyl)pyrimidin-4-amine (Compound B of Example 29, 45 mg, 0.11 mmol) and a solution of 2-(4-fluorophenyl)acetyl isocyanate in toluene (Compound D of Example 11, 0.13 mmol) in THF using a similar procedure described for the preparation of Compound E of Example 11. The crude product was triturated with isopropyl ether to give the title compound (58 mg, 90%) as a pink solid. $^1$H NMR (DMSO-d$_6$) δ 11.02 (s, 1H), 10.54 (s, 1H), 9.46 (s, 1H), 8.24 (s, 1H), 7.70 (dd, 1H, J=12.7, 2.4 Hz), 7.46-7.26 (m, 9H), 7.18 (dd, 2H, J=9.6, 8.3 Hz), 7.00 (d, 2H, J=9.6 Hz), 6.11 (s, 1H), 5.09 (s, 2H), 3.75 (s, 2H); MS(ESI$^+$) m/z 582.3 (M+H)$^+$.

Example 31

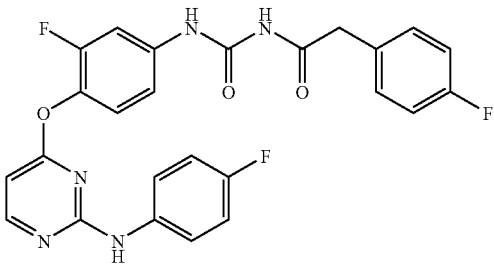

1-(3-Fluoro-4-(2-(4-fluorophenylamino)pyrimidin-4-yloxy)phenyl)-3-(2-(4-fluorophenyl)acetyl)urea

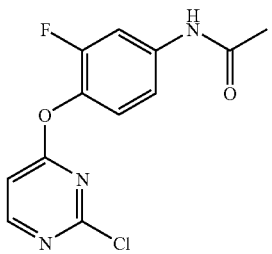

A) N-(4-(2-Chloropyrimidin-4-yloxy)-3-fluorophenyl)acetamide

A mixture of 2,4-dichloropyrimidine (Aldrich, 1.5 g, 10.0 mmol), N-(3-fluoro-4-hydroxyphenyl)acetamide (0.85 g, 5.0 mmol), $K_2CO_3$ (0.76 g, 5.5 mmol), and $CH_3CN$ (100 mL) was heated at reflux for 2 h. The mixture was concentrated and the residue partitioned between EtOAc and saturated $NaHCO_3$ solution. The EtOAc phase was washed with sat $NaHCO_3$ solution, brine, dried ($MgSO_4$) and concentrated in vacuo. The crude product was purified by flash chromatography using a gradient form 30% EtOAc in hexanes to 100% EtOAc to give the title compound (1.1 g, 78%) as a white solid. $^1$H NMR (DMSO-$d_6$) δ 10.22 (s, 1H), 8.63 (d, 1H, J=5.6 Hz), 7.74 (dd, 1H, J=12.6, 2.4 Hz), 7.34-7.26 (m, 3H), 2.01 (s, 3H).

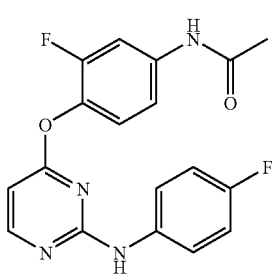

B) N-(3-Fluoro-4-(2-(4-fluorophenylamino)pyrimidin-4-yloxy)phenyl)acetamide

A mixture of N-(4-(2-chloropyrimidin-4-yloxy)-3-fluorophenyl)acetamide (100 mg, 0.36 mmol), 4-fluoroaniline (Aldrich, 40 mg, 0.36 mmol), and 1,4-dioxane (3 mL) was heated at reflux for 2 h. The mixture was concentrated in vacuo and the residue triturated with ether to give a gray solid. The product was dissolved in MeOH, treated with silica gel (150 mg) and the mixture concentrated to dryness. The compound was concentrated down on silica gel and applied to a silica gel column and eluted first with EtOAc then with 100:1 MeOH/$NH_4OH$ in $CH_2Cl_2$ to give the title compound (40 mg, 31%) as a white solid. $^1$H NMR (DMSO-$d_6$) δ 10.19 (s, 1H), 9.61 (s, 1H), 8.33 (d, 1H, J=5.6 Hz), 7.71 (d, 1H, J=12.7 Hz), 7.40 (s, 2H), 7.30-7.26 (m, 2H), 6.86 (dd, 2H, J=8.3, 8.3 Hz), 6.50 (d, 1H, J=5.4 Hz), 2.05 (s, 3H); MS(ESI$^+$) m/z 357.13 (M+H)$^+$.

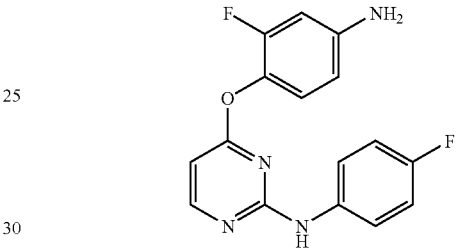

C) 4-(4-Amino-2-fluorophenoxy)-N-(4-fluorophenyl)pyrimidin-2-amine

A mixture of N-(3-fluoro-4-(2-(4-fluorophenylamino)pyrimidin-4-yloxy)phenyl)acetamide (32 mg, 0.09 mmol), 6 M HCl (0.2 mL) and MeOH (2 mL) was heated at reflux for 2 h. The mixture was cooled, diluted with EtOAc (20 mL), washed with saturated $NaHCO_3$ solution and brine, dried ($MgSO_4$), and concentrated in vacuo. Flash chromatography on $SiO_2$ using 30-40% EtOAc in hexanes containing 1% $Et_3N$ gave the title compound (15 mg, 46%) as a white solid. $^1$H NMR (DMSO-$d_6$) δ 9.55 (s, 1H), 8.25 (d, 1H, J=5.5 Hz), 7.43 (br s, 2H), 6.92-6.85 (m, 3H), 6.45 (dd, 1H, J=13.5, 2.1 Hz), 6.38-6.35 (m, 2H), 5.35 (br s, 2H). MS(ESI$^+$) m/z 315.17 (M+H)$^+$.

D) 1-(3-Fluoro-4-(2-(4-fluorophenylamino)pyrimidin-4-yloxy)phenyl)-3-(2-(4-fluorophenyl)acetyl)urea A solution of 4-(4-amino-2-fluorophenoxy)-N-(4-fluorophenyl)pyrimidin-2-amine (10 mg, 0.032 mmol) in THF (1 mL) was cooled in an ice bath and treated with a solution of 2-(4-fluorophenyl)acetyl isocyanate in toluene (Compound D of Example of 11, 228 μL, 0.064 mmol) and stirred at RT for 2 h. The reaction mixture was concentrated in vacuo and the residue triturated with isopropyl ether to give the title compound (15 mg, 93%) as a white solid. $^1$H NMR (DMSO-$d_6$) δ 11.06 (s, 1H), 10.56 (s, 1H), 9.68 (s, 1H), 8.39 (d, 1H, J=5.7 Hz), 7.76 (dd, 1H, J=13.5, 2.1 Hz), 7.43 (br s, 2H), 7.46-7.35 (m, 6H), 7.18 (dd, 2H, J=8.8, 8.8 Hz), 6.57 (d, 1H, J=5.4 Hz), 3.76 (s, 2H); MS(ESI$^+$) m/z 492.0 (M+H)$^+$.

Example 32

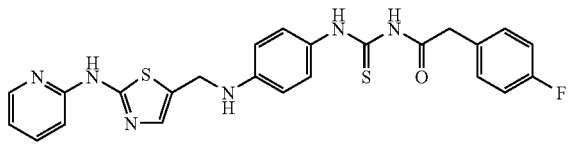

1-(2-(4-Fluorophenyl)acetyl)-3-(4-((2-(pyridin-2-ylamino)thiazol-5-yl)methylamino)phenyl)thiourea

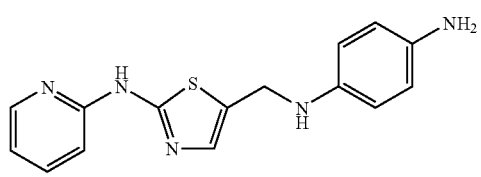

A) N$^1$-((2-(Pyridin-2-ylamino)thiazol-5-yl)methyl)benzene-1,4-diamine

A solution of 2-(pyridine-2-ylamino)-thiazole-5-carbaldehyde (0.10 g, 0.49 mmol, WO2004/001059), benzene-1,4-diamine (0.105 g, 0.97 mmol) and triethylsilane (0.19 mL, 1.2 mmol) in CH$_2$Cl$_2$-TFA (3:1, 4 mL) was stirred at ambient temperature for 4 h. The reaction mixture was concentrated in vacuo and the residue partitioned between CH$_2$Cl$_2$ and saturated aqueous NaHCO$_3$ solution. The organic phase was washed with saturated aqueous NaHCO$_3$ solution, brine, dried (MgSO$_4$) and concentrated in vacuo. The crude product which contained the title compound along with the starting aldehyde and benzene-1,4-diamine was carried on directly into the next step.

B) 1-(2-(4-Fluorophenyl)acetyl)-3-(4-((2-(pyridin-2-ylamino)thiazol-5-yl)methylamino)phenyl)thiourea 4-Fluorophenylacetyl chloride (7.4 µL, 0.053 mmol) was added to a suspension of NaSCN (4.5 mg, 0.055 mmol) in EtOAc (0.5 mL) and the resulting mixture was stirred at RT for 30 min. This mixture was then added to a solution of the above mixture obtained in A (14.5 mg) in CH$_2$Cl$_2$ (0.5 ml) and the resulting mixture was stirred at ambient temperature for 2 h. The reaction mixture was concentrated in vacuo and the residue was purified by flash chromatography on SiO$_2$ using a 2-5% MeOH—CHCl$_3$ gradient elution to give the title compound (2 mg) as an orange film. MS(ESI$^+$) m/z 493.2 (M+H)$^+$.

Example 33

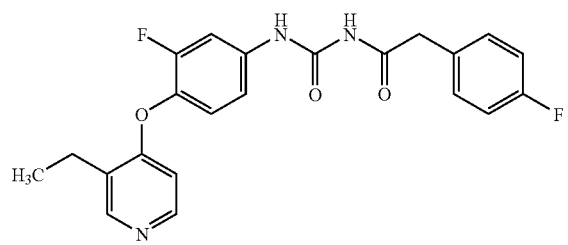

1-(4-(3-Ethylpyridin-4-yloxy)-3-fluorophenyl)-3-(2-(4-fluorophenyl)acetyl)urea, hydrochloride salt

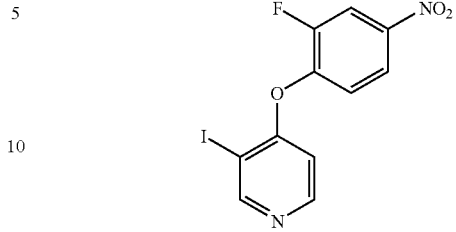

A) 4-(2-Fluoro-4-nitrophenoxy)-3-iodopyridine

A mixture of 4-chloro-3-iodopyridine (1.50 g, 6.30 mmol, prepared according to Tabanella, S. et al. *Org. Biomol. Chem.* 2003, 1, 4254-4261.), 2-fluoro-nitrophenol (Lancaster, 2.0 g, 12.7 mmol), DIPEA (5 mL), and NMP (10 mL) was heated at 150° C. After 12 h, more 2-fluoro-nitrophenol (0.50 g, 3.18 mmol) was added to the reaction mixture and heating was continued for 4 h. Most of the volatile components were removed under vacuum at 75° C., the residue treated with saturated aq. NaHCO$_3$ solution (150 mL) and extracted with EtOAc (2×100 mL). The combined extracts were washed with brine, dried (MgSO$_4$) and concentrated in vacuo to give the crude product. Purification by flash chromatography on silica gel, using 0-100% CH$_2$Cl$_2$/hexanes then 2% MeOH/CH$_2$Cl$_2$ gave the title compound (1.0 g, 43%) as a yellow solid. $^1$H NMR (DMSO-d$_6$) δ 8.96 (s, 1H), 8.47 (d, 2H, J=5.5 Hz), 8.44 (dd, 1H, J=2.7, 9.2 Hz), 7.49 (dd, 1H, J=8.8, 8.2 Hz), 7.07 (d, 1H, J=5.5 Hz); MS(ESI$^+$): m/z 361.05 (M+H)$^+$.

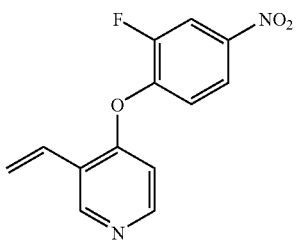

B) 4-(2-Fluoro-4-nitrophenoxy)-3-vinylpyridine

A solution of 4-(2-fluoro-4-nitrophenoxy)-3-iodopyridine (200 mg, 0.56 mmol), tributylvinyltin (212 mg, 0.67 mmol) in DMF (1 mL) was treated with CsF (169 mg, 1.12 mmol) followed by (Ph$_3$P)$_4$Pd (36 mg, 0.031 mmol) and CuI (10 mg, 0.056 mmol) and the mixture was heated at 45° C. for 1 h. The mixture was cooled, diluted with CH$_2$Cl$_2$ (15 mL) and H$_2$O (10 µL), shaken vigorously and then filtered through Celite®. The filter cake was washed with 1:1 CH$_2$Cl$_2$/EtOAc and the washings were combined with the filtrate. The solution was washed with brine, dried (MgSO$_4$) and concentrated in vacuo to give a brown oil. The crude product was purified by flash chromatography on SiO$_2$ using 0-2% MeOH/CH$_2$Cl$_2$ to give a semi-pure product. The product was treated with 2 M HCl/Et$_2$O (10 mL) and the precipitated hydrochloride derivative collected by filtration and washed with Et$_2$O and EtOAc to a yellow solid (145 mg, 87%). $^1$H NMR (DMSO-d$_6$) δ 9.11 (s, 1H), 8.64 (s, 1H), 8.51-8.48 (m, 1H), 8.24 (d, 1H, J=7.7 Hz), 7.83-7.79 (m, 1H), 7.28 (d, 1H, J=6.0 Hz), 7.02-6.95 (m, 1H), 6.24 (d, 1H, J=17.6 Hz), 5.68 (d, 1H, 11.5 Hz); MS(ESI$^+$): m/z 261.18 (M+H)$^+$.

The above hydrochloride salt was converted to the freebase as follows: The pyridine hydrochloride (230 mg) was stirred with NaHCO$_3$ (25 mL) and EtOAc (20 mL) until homogeneous and the EtOAc phase separated, washed with brine, dried (MgSO$_4$) and concentrated. The title compound (190 mg) was obtained as a yellow oil.

1-(4-(2-Amino-3-ethylpyridin-4-yloxy)-3-fluorophenyl)-3-(2-(4-fluorophenyl)acetyl)urea, trifluoroacetic acid salt

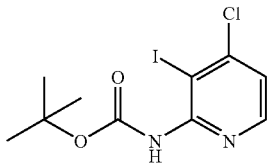

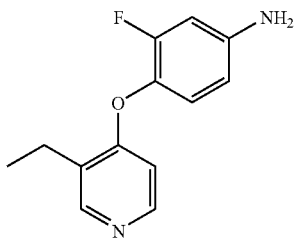

A) (4-Chloro-3-iodopyridin-2-yl)-carbamic acid tert-butyl ester

C) 4-(3-Ethylpyridin-4-yloxy)-3-fluorobenzenamine

A solution of 4-(2-fluoro-4-nitrophenoxy)-3-vinylpyridine (80 mg, 0.30 mmol) in 1:1 EtOAc/MeOH (2 mL) was hydrogenated over 10% palladium-carbon (30 mg) for 1 h using H$_2$ from a latex balloon. Pt$_2$O (10 mg) was added to the mixture and the reaction continued for 1 h. The mixture was filtered through Celite® and concentrated in vacuo to give the title compound (50 mg, 63%) as a yellow oil. $^1$H NMR (DMSO-d$_6$) δ 8.33 (s, 1H), 8.22 (d, 1H, J=5.6 Hz), 6.96 (dd, 1H, J=8.7, 9.1 Hz), 6.50 (dd, 1H, J=2.0, 13.7 Hz), 6.56 (d, 1H, J=5.6 Hz), 6.41 (dd, 1H, J=2.5, 6.1 Hz), 2.69 (q, 2H, J=7.6 Hz), 1.21 (t, 31H, J=7.6 Hz).

D) 1-(4-(3-Ethylpyridin-4-yloxy)-3-fluorophenyl)-3-(2-(4-fluorophenyl)acetyl)urea, hydrochloride salt A solution of 4-(3-ethylpyridin-4-yloxy)-3-fluorobenzenamine (23 mg, 0.10 mmol) in CH$_2$Cl$_2$ (1 mL) was treated with a solution of 0.3 M solution of 2-(4-fluorophenyl)acetyl isocyanate in toluene (Compound D of Example 11, 0.33 mL, 0.11 mmol) and the mixture was stirred at room temperature for 2.5 h. The mixture was concentrated under vacuum and the residue triturated with 1:1 isopropyl ether/EtOAc to give a yellow solid. The product was treated with absolute MeOH (1 mL) and 2 M HCl/Et$_2$O (1 mL), stirred at room temperature for 5 min and concentrated under vacuum to give the title compound (15 mg, 36%) as a pale yellow solid. $^1$H NMR (DMSO-d$_6$) δ 11.04 (s, 1H), 10.57 (s, 1H), 8.41 (s, 1H), 8.26 (d, 1H, J=5.6 Hz), 7.76 (dd, 1H, J=2.0, 12.7 Hz), 7.40-7.28 (m, 4H), 7.19-7.14 (m, 3H), 6.54 (d, 1H, J=5.6 Hz), 3.73 (s, 2H), 2.72 (q, 2H, J=7.6 Hz), 1.23 (t, 3H, J=7.6 Hz); MS(ESI$^+$): m/z 412.20 (M+H)$^+$.

Example 34

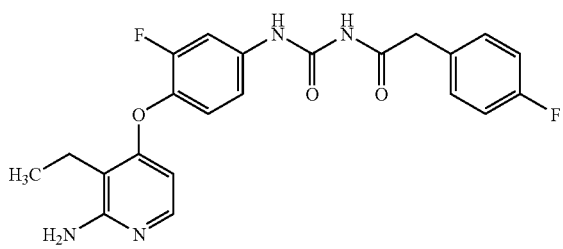

A solution of (4-chloro-pyridin-2-yl)-carbamic acid tert-butyl ester (CB Research and Development Inc., 5.0 g, 22.0 mmol), TMEDA (8 mL) in anhydrous THF (100 mL) was placed under a nitrogen atmosphere and cooled to −70° C. and treated dropwise with 2.5 M n-BuLi in hexanes (22.0 mL, 54.8 mmol) over a period of 30 min. The mixture was stirred at −70° C. for 1 h then treated dropwise with a solution of I$_2$ (14 g, 110 mmol) in anhydrous THF (16 mL) at −70° C. After the addition was complete, the reaction was stirred at −70° C. for 30 min then allowed to warm to room temperature. The mixture was treated with a solution of sodium hydrogensulfite (16 g) in H$_2$O (100 mL) and stirred for 30 min then extracted with EtOAc. The extract was washed with brine, dried (MgSO$_4$) and concentrated in vacuo. The product was purified by flash chromatography on SiO$_2$ eluting with 0-5% MeOH/CH$_2$Cl$_2$ to give the title compound (5.8 g, 78%) as white solid. $^1$H NMR (DMSO-d$_6$) δ 9.46 (s, 1H), 8.29 (d, 1H, J=5.6 Hz), 7.46 (d, 1H, J=5.0 Hz), 1.44 (s, 9H); MS(ESI$^-$): m/z 352.99 (M−H)$^-$.

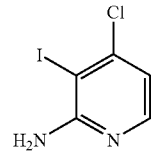

B) 4-Chloro-3-iodopyridin-2-amine

A suspension of (4-chloro-3-iodo-pyridin-2-yl)-carbamic acid tert-butyl ester (5.6 g, 15.8 mmol) in 48% hydrobromic acid was heated at 100° C. for 10 min to give a clear solution. The mixture was cooled, treated with crushed ice and made basic with 6 M NaOH. The precipitated product was collected by vacuum filtration, washed with H$_2$O and sucked partially on the funnel to give a white solid. The product was dissolved in THF and the solution dried over MgSO$_4$ and concentrated in vacuo to give the title compound (3.7 g, 93%) as a white solid. $^1$H NMR (DMSO-d$_6$) δ 7.84 (d, 1H, J=5.1 Hz), 6.73 (d, 1H, J=5.6 Hz), 6.51 (br s, 2H); MS(ESI$^+$): m/z 254.97 (M+H)$^+$.

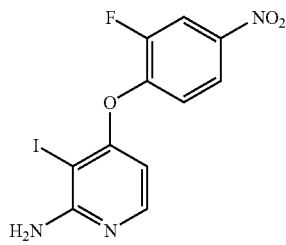

C) 4-(2-Fluoro-4-nitrophenoxy)-3-iodopyridin-2-amine

A mixture of 4-chloro-3-iodopyridin-2-amine (3.6 g, 14.2 mmol) and 2-fluoro-4-nitrophenol (Lancaster, 4.5 g, 28.4 mmol), DIPEA (3.6 mL, 20.7 mmol) and NMP (8 mL) was placed in a glass pressure vessel and heated rapidly to 170° C. and the heating continued for 18 h. The volatile components were distilled off under reduced pressure and the viscous residue poured into ice-water (150 mL). The mixture was sonicated for 15 min in order to break up the gummy solid and the pH of the mixture was adjusted to 7.5 with saturated aq. NaHCO$_3$ solution. The solid was collected by vacuum filtration, washed with H$_2$O, sucked partially dry on the funnel. The partially dried solid was suspended in toluene (150 mL) and the mixture concentrated in vacuo and the process repeated 3 times to give a brown solid. The product was dissolved in MeOH (150 mL), treated with 4 M HCl/1,4-dioxane (8 mL) and stirred at room temperature for 5 min and then the mixture was concentrated in vacuo. The hydrochloride thus obtained was washed and triturated with EtOAc and partitioned between EtOAc and saturated aq. NaHCO$_3$ solution. The EtOAc phase was separated washed with brine, and then dried (MgSO$_4$). The EtOAc solution was treated with activated charcoal, stirred at room temperature for 10 min and the charcoal filtered off. The solution was concentrate in vacuo to give the title compound (3.9 g, 74%) as a yellow solid. $^1$H NMR (DMSO-d$_6$) δ 8.39 (dd, 1H, J=2.5, 10.7 Hz), 8.12 (dd, 1H, J=1.5, 9.2 Hz), 7.86 (d, 1H, J=5.6 Hz), 7.32 (dd, 1H, J=8.6, 8.6 Hz), 6.40 (br s, 2H), 6.18 (d, 1H, J=5.6 Hz).

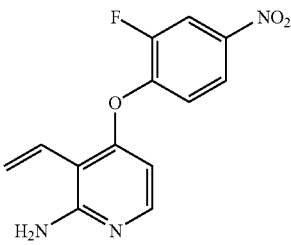

D) 4-(2-Fluoro-4-nitrophenoxy)-3-vinylpyridin-2-amine

The title compound was prepared from 4-(2-fluoro-4-nitrophenoxy)-3-iodopyridin-2-amine and tributylvinyltin via a Stille coupling reaction in the same manner as described in Step B of Example 33. $^1$H NMR (DMSO-d$_6$) δ 8.35 (dd, 1H, J=10.7, 3.1 Hz), 8.09 (d, 1H, J=9.2 Hz), 7.85 (d, 1H, J=5.6 Hz), 7.31-7.15 (m, 1H), 6.54 (dd, 1H, J=17.8, 11.7 Hz), 6.24 (br s, 2H), 6.20 (d, 1H, J=5.6 Hz), 5.71 (d, 1H, J=17.8 Hz), 5.46 (d, 1H, J=11.7 Hz); MS(ESI$^+$): m/z 276.17 (M+H)$^+$.

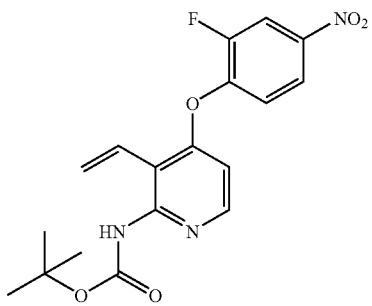

E) tert-Butyl 4-(2-fluoro-4-nitrophenoxy)-3-vinylpyridin-2-ylcarbamate

A solution of 4-(2-fluoro-4-nitrophenoxy)-3-vinylpyridin-2-amine (60 mg, 0.22 mmol) in 1,4-dioxane (0.5 mL) and tert-butyl alcohol (1.5 mL) was treated with Boc$_2$O (140 mg, 0.64 mmol) and heated at 65° C. for 5 h. The mixture was cooled, partitioned between EtOAc and saturated aq. NaHCO$_3$ solution. The EtOAc phase was separated, washed with brine, dried (MgSO$_4$) and concentrated in vacuo. The crude product was purified by flash chromatography on SiO$_2$ to give the title compound (50 mg, 60%) as a yellow solid. $^1$H NMR (DMSO-d$_6$) δ 9.37 (s, 1H), 8.41 (dd, 1H, J=10.7, 2.5 Hz), 8.22 (d, 1H, J=5.6 Hz), 8.15 (d, 1H, J=8.6 Hz), 7.42 (t, 1H, J=8.6 Hz), 6.86 (d, 1H, J=5.6 Hz), 6.58 (dd, 1H, J=17.8, 11.7 Hz), 5.82 (d, 1H, J=16.3 Hz), 5.52 (d, 1H, J=11.7 Hz), 1.42 (s, 9H); MS(ESI$^+$): m/z 376.18 (M+H)$^+$.

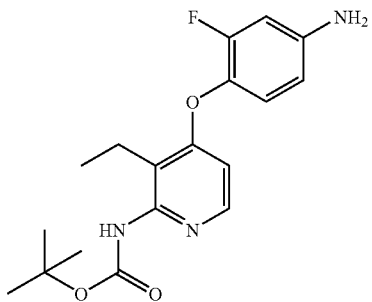

F) tert-Butyl 4-(4-amino-2-fluorophenoxy)-3-ethylpyridin-2-ylcarbamate

A solution of tert-butyl 4-(2-fluoro-4-nitrophenoxy)-3-vinylpyridin-2-ylcarbamate (48 mg, 0.13 mmol) was hydrogenated over 10% palladium-carbon (10 mg) and Pt$_2$O (5 mg) for 1.5 h using H$_2$ from a rubber balloon. The mixture was filtered through Celite® and the filtrate concentrated in vacuo to give the title compound (40 mg, 89%) as a pale yellow solid. $^1$H NMR (DMSO-d$_6$) δ 9.04 (s, 1H), 8.03 (d, 1H, J=5.6 Hz), 6.95 (dd, 1H, J=8.6, 8.6 Hz), 6.50 (dd, 1H, J=2.5, 13.2 Hz), 6.41 (dd, 1H, J=2.5, 9.4 Hz), 6.36 (d, 1H, J=5.6 Hz), 5.44 (s, 2H), 2.67-2.62 (m, 2H), 1.43 (s, 9H), 1.11 (t, 3H, J=7.1 Hz); MS(ESI$^+$): m/z 348.22 (M+H)$^+$.

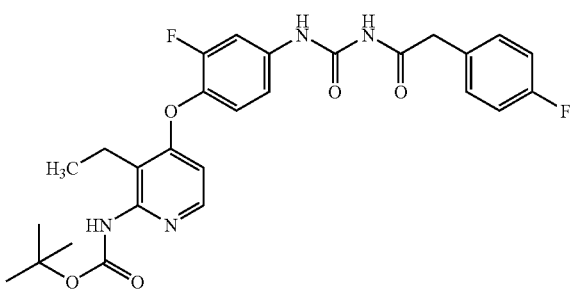

G) tert-Butyl 3-ethyl-4-(2-fluoro-4-(3-(2-(4-fluorophenyl)acetyl)ureido)phenoxy)pyridin-2-ylcarbamate The title compound was prepared from tert-butyl 4-(4-amino-2-fluorophenoxy)-3-ethylpyridin-2-ylcarbamate (20 mg, 0.058 mmol) and 0.3 M solution of 2-(4-fluorophenyl)acetyl isocyanate in toluene (232 μL, 0.070 mmol) in THF in the same manner as Step D of Example 33. MS(ESI+): m/z 527.31 (M+H)+.

H) 1-(4-(2-Amino-3-ethylpyridin-4-yloxy)-3-fluorophenyl)-3-(2-(4-fluorophenyl)acetyl)urea, trifluoroacetic acid salt A solution of tert-butyl 3-ethyl-4-(2-fluoro-4-(3-(2-(4-fluorophenyl)acetyl)ureido)phenoxy)pyridin-2-ylcarbamate (16 mg, 0.03 mmol) was dissolved in anhydrous THF (0.5 mL) and treated with 4 M HCl/1,4-dioxane (1.5 mL) and stirred at room temperature for 3 h. The mixture was concentrated in vacuo and the product purified by preparative HPLC method A to give the title compound (5 mg, 36%) as a white solid. $^1$H NMR (DMSO-d$_6$) δ 11.06 (s, 1H), 10.6 (s, 1H), 7.80-7.79 (m, 4H), 7.43-7.33 (m, 4H), 7.16 (dd, 2H, J=8.9, 8.9 Hz), 6.19 (d, 1H, J=7.1 Hz), 3.73 (s, 2H), 2.71-2.66 (m, 2H), 1.10 (t, 3H, J=7.1 Hz); MS(ESI+): m/z 427.18 (M+H)+.

Example 35

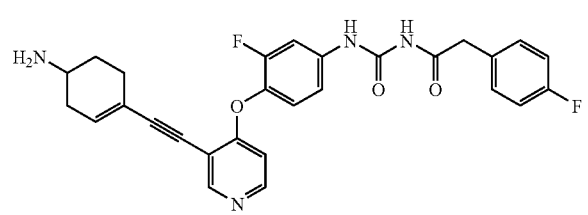

1-(4-(3-(2-(4-Aminocyclohex-1-enyl)ethynyl)pyridin-4-yloxy)-3-fluorophenyl)-3-(2-(4-fluorophenyl)acetyl)urea

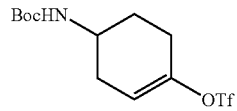

A) 4-(tert-Butoxycarbonyl)cyclohex-1-enyl trifluoromethanesulfonate

A solution of N-Boc-4-aminocyclohexanone (Astatech Inc., 213 mg, 1.0 mmol) in THF (7 mL) was cooled to –70° C. and treated with a solution 0.5 M KHMDS in toluene (2.4 ml, 1.2 mmol). The mixture was stirred at –70° C. for 20 min, treated dropwise with a solution of phenyltrifluoromethanesulfonimide (392 mg, 1.1 mmol) in THF (4 mL) and stirred at –70° C. for 25 min. The mixture was quenched with saturated aq. NH$_4$Cl solution, diluted with EtOAc, washed with 10% Na$_2$CO$_3$ and brine, dried (MgSO$_4$) and concentrated in vacuo. The crude product was purified by flash chromatography on SiO$_2$ eluting with 10-25% EtOAc/hexanes to give the title compound (180 mg, 52%) as a white solid. $^1$H NMR (DMSO-d$_6$) δ 5.68 (s, 1H), 4.50 (s, 1H), 3.82 (s, 1H), 2.68-2.25 (m, 3H), 2.22-1.89 (m, 2H), 1.87-1.63 (m, 1H), 1.43 (s, 9H).

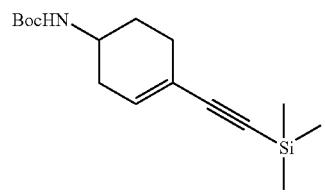

B) tert-Butyl 4-(2-(trimethylsilyl)ethynyl)cyclohex-3-enylcarbamate

A mixture of 4-(tert-butoxycarbonyl)cyclohex-1-enyl trifluoromethanesulfonate (170 mg, 0.49 mmol), trimethylsilylacetylene (138 μL, 0.98 mmol), Et$_3$N (0.68 mL) and THF (8 mL) in a reaction flask was purged with argon and treated in turn with CuI (14 mg, 0.072 mmol) and (Ph$_3$P)$_4$Pd (27 mg, 0.024 mmol). The reaction mixture was stirred at room temperature for 25 min, and then diluted with EtOAc (50 mL), washed with saturated aq. NaHCO$_3$ solution and brine, dried (MgSO$_4$) and concentrated in vacuo. The crude product was purified by flash chromatography on SiO$_2$ eluting with 0-25% EtOAc/hexanes to give the title compound (116 mg, 81%) as a yellow solid. $^1$H NMR (DMSO-d$_6$) δ 6.06 (s, 1H), 4.50 (s, 1H), 3.76 (s, 1H), 2.46 (d, 1H, J=18.8 Hz), 2.36-2.14 (m, 2H), 2.00-1.78 (m, 2H), 1.66-1.50 (m, 1H), 1.43 (s, 9H), 0.27-0.05 (m, 9H).

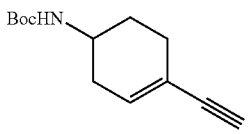

C) tert-Butyl 4-ethynylcyclohex-3-enylcarbamate

A solution of tert-butyl 4-(2-(trimethylsilyl)ethynyl)cyclohex-3-enylcarbamate (112 mg, 0.38 mmol) in THF was cooled to −15° C., treated with 1.0 M tetrabutylammonium fluoride in THF (Aldrich, 440 μL, 0.44 mmol) and the mixture stirred at −15° C. for 40 min. The mixture was treated with 5% $Na_2CO_3$ (25 mL) and extracted with ether. The ether extract was washed with 5% $Na_2CO_3$ and brine, dried ($MgSO_4$) and concentrated in vacuo to give the title compound (83 mg, 99%) as a brown oil. $^1$H NMR (DMSO-$d_6$) δ 6.09 (s, 1H), 4.51 (s, 1H), 3.77 (s, 1H), 2.82 (s, 1H), 2.47 (d, 1H, J=18.3 Hz), 2.35-2.16 (m, 2H), 2.04-1.79 (m, 2H), 1.72-1.51 (m, 1H), 1.43 (s, 9H).

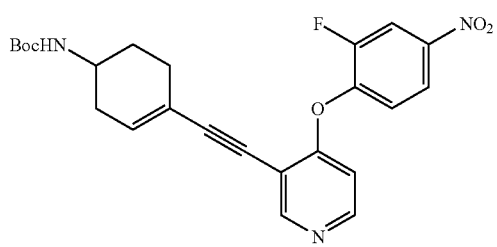

D) tert-Butyl 4-(2-(4-(2-fluoro-4-nitrophenoxy)pyridin-3-yl)ethynyl)cyclohex-3-enylcarbamate A solution of 4-(2-fluoro-4-nitrophenoxy)-3-iodopyridine (Compound A of Example 33, 130 mg, 0.36 mmol) and N-Boc-4-ethynylcyclohex-3-enamine (80 mg, 0.36 mmol) in anhydrous THF (2 mL) was treated with $Et_3N$ (2 mL) and the degassed by vacuum/argon purge. The solution was treated with tetrakistriphenylphosphine palladium (20 mg, 0.0018 mmol) and CuI (10 mg, 0.054 mmol) and then heated at reflux for 2 h. The mixture was cooled and partitioned between saturated aq. $NaHCO_3$ solution and EtOAc. The EtOAc phase was separated, washed with brine, dried ($MgSO_4$) and concentrated in vacuo. The crude product was purified by flash chromatography on silica gel eluting with 0-40% EtOAc/hexanes to give the title compound (124 mg, 76%) as a yellow solid. $^1$H NMR (DMSO-$d_6$) δ 8.68 (s, 1H), 8.51 (d, 1H, J=5.6 Hz), 8.43 (dd, 1H, J=2.5, 10.7 Hz), 8.15 (d, 1H, J=9.2 Hz), 7.49 (dd, 1H, J=8.6, 8.6 Hz), 7.14 (d, 1H, J=5.6 Hz), 6.85 (d, 1H, J=7.1 Hz), 6.04-6.00 (m, 1H), 3.48-3.35 (m, 1H), 2.36-2.25 (m, 1H), 2.17-2.04 (m, 2H), 2.03-1.89 (m, 1H), 1.78-1.69 (m, 1H), 1.46-1.35 (m, 1H), 1.36 (s, 9H); MS(ESI$^+$): m/z 454.27 (M+H)$^+$.

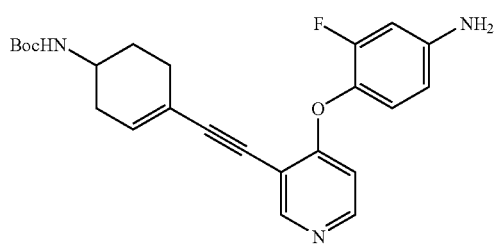

E) tert-Butyl 4-(2-(4-(4-amino-2-fluorophenoxy)pyridin-3-yl)ethynyl)cyclohex-3-enylcarbamate A mixture of tert-butyl 4-(2-(4-(2-fluoro-4-nitrophenoxy)pyridin-3-yl)ethynyl)cyclohex-3-enylcarbamate (110 mg, 0.24 mmol), iron powder, ~325 mesh (150 mg, 2.7 mmol), $NH_4Cl$ (280 mg, 5.3 mmol), DMF (1 mL), $H_2O$ (1 mL) and EtOH (1 mL) was heated at 100° C. for 30 minutes. The mixture was filtered through a pad of Celite® using DMF to wash the filter cake and the filtrate made basic to pH 8 with saturated aq. $NaHCO_3$ solution. The mixture was extracted twice with EtOAc and dried ($MgSO_4$) and concentrated in vacuo to give the title compound (105 mg) which was used without any further purification. MS(ESI$^+$): m/z 424.27 (M+H)$^+$.

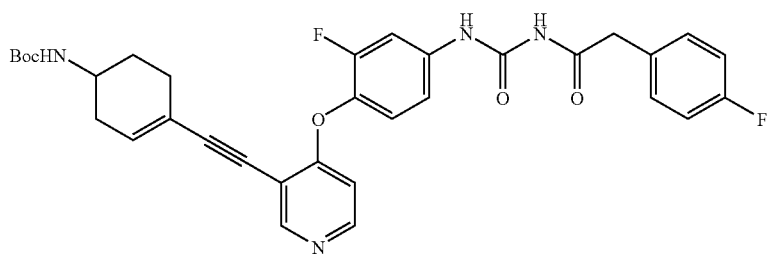

F) tert-Butyl 4-(2-(4-(2-fluoro-4-(3-(2-(4-fluorophenyl)acetyl)ureido)phenoxy)pyridin-3-yl)ethynyl)cyclohex-3-enylcarbamate A solution of tert-butyl 4-(2-(4-(4-amino-2-fluorophenoxy)pyridin-3-yl)ethynyl)cyclohex-3-enylcarbamate (50 mg, 0.12 mmol) in dry $CH_2Cl_2$ (2 mL) was treated with a 0.3 M solution of 2-(4-fluorophenyl)acetyl isocyanate in toluene (Compound D of Example 11, 0.8 mL, 0.24 mmol) and the mixture stirred at rt for 1 h. The solvents were evaporated under vacuum and the residue purified by flash chromatography on silica gel eluting with 10-60% EtOAc/hexanes to give the title compound (50 mg, 69%) as a white solid. $^1$H NMR (DMSO-d$_6$) δ 11.03 (s, 1H), 10.57 (s, 1H), 8.57 (s, 1H), 8.36 (d, 1H, J=5.7 Hz), 7.78 (dd, 1H, J=1.8, 13.1 Hz), 7.41-7.29 (m, 3H), 7.16 (dd, 3H, J=8.6, 8.6 Hz), 6.85 (d, 1H, J=8.3 Hz), 6.70 (d, 1H, J=5.7 Hz), 6.13-6.08 (m, 1H), 3.73 (s, 2H), 3.51-3.41 (m, 1H), 2.38-2.27 (m, 1H), 2.27-2.20 (m, 2H), 1.82-1.72 (m, 1H), 1.54-1.28 (m, 2H), 1.37 (s, 9H); ESI MS: m/z 603.24 (M+H)$^+$.

G) 1-(4-(3-(2-(4-Aminocyclohex-1-enyl)ethynyl)pyridin-4-yloxy)-3-fluorophenyl)-3-(2-(4-fluorophenyl)acetyl)urea, dihydrochloride salt A solution of tert-butyl 4-(2-(4-(2-fluoro-4-(3-(2-(4-fluorophenyl)acetyl)ureido)phenoxy)pyridin-3-yl)ethynyl)cyclohex-3-enylcarbamate (40 mg, 0.066 mol) in anhydrous 1,4-dioxane (2 mL) was cooled to −10° C. and treated with 4 M HCl/1,4-dioxane (4 mL). The mixture was stirred at −5° C. for 2.5 h then at rt for 1 h. The mixture was concentrated under vacuum without any heating to give the title compound (32 mg, 84%) as a yellow solid. $^1$H NMR (DMSO-d$_6$) δ 11.05 (s, 1H), 10.61 (s, 1H), 8.69 (s, 1H), 8.44 (d, 1H, J=6.1 Hz), 8.06 (d, 1H, J=2.0 Hz), 7.80 (dd, 1H, J=12.7, 2.0 Hz), 7.46-7.38 (m, 1H), 7.35 (dd, 1H, J=8.6, 5.6 Hz), 7.19-7.13 (m, 1H), 6.82 (d, 1H, J=5.6 Hz), 6.17 (s, 1H), 3.74 (s, 2H), 3.73-3.62 (m, 2H), 3.62-3.54 (m, 1H), 3.34-3.22 (m, 1H), 2.31 (s, 1H), 1.99-1.96 (m, 1H), 1.71-1.66 (m, 1H); MS(ESI$^+$): m/z 503.12 (M+H)$^+$.

Example 36

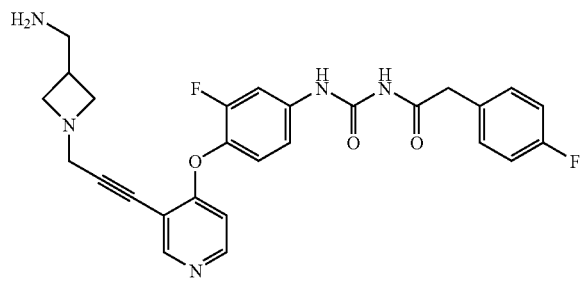

1-(4-(3-(3-(3-(Aminomethyl)azetidin-1-yl)prop-1-ynyl)pyridin-4-yloxy)-3-fluorophenyl)-3-(2-(4-fluorophenyl)acetyl)urea, trihydrochloride salt

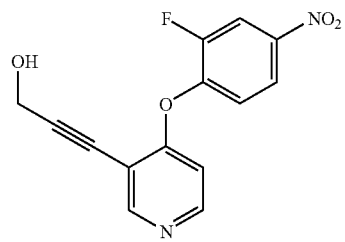

A) 3-(4-(2-Fluoro-4-nitrophenoxy)pyridin-3-yl)prop-2-yn-1-ol

A solution of 4-(2-fluoro-4-nitrophenoxy)-3-iodopyridine (Compound A of Example 33, 300 mg, 0.83 mmol), propargylalcohol (Aldrich, 145 μL, 2.50 mmol), Et$_3$N (2 mL) and anhydrous THF (2 mL) was degassed by vacuum/argon purge and treated with Pd(Ph$_3$P)$_4$ (31 mg, 0.027 mmol) and CuI (10 mg, 0.054 mmol). The mixture was heated at reflux under argon atmosphere for 10 min, cooled to rt and diluted with EtOAc (25 mL) and H$_2$O (20 mL). The EtOAc phase was washed with water and brine, dried (MgSO$_4$) and concentrated in vacuo. The crude residue was purified by flash chromatography on silica gel using 0-3% MeOH/CH$_2$Cl$_2$ to give the desired product (185 mg, 77%) as a pale yellow solid. $^1$H NMR (DMSO-d$_6$) δ 8.69 (s, 1H), 8.49 (d, 1H, J=5.6 Hz), 8.43 (dd, 1H, J=10.7, 2.5 Hz), 8.17 (d, 1H, J=9.2 Hz), 7.57 (t, 1H, J=8.6 Hz), 7.04 (d, 1H, J=5.6 Hz), 5.40 (t, 1H, J=6.1), 4.28 (d, 2H, J=6.1 Hz); MS(ESI$^+$): m/z 289.13 (M+H)$^+$.

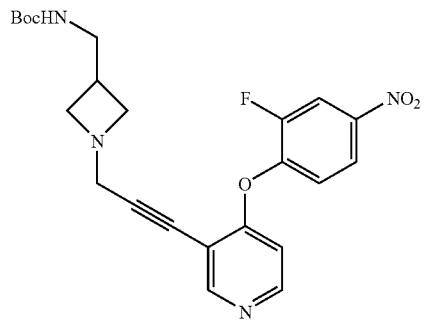

B) tert-Butyl(1-(3-(4-(2-fluoro-4-nitrophenoxy)pyridin-3-yl)prop-2-ynyl)azetidin-3-yl)methylcarbamate A solution of 3-(4-(2-fluoro-4-nitrophenoxy)pyridin-3-yl)prop-2-yn-1-ol (43 mg, 0.15 mmol) and DIPEA (45 μL, 0.26 mmol) in anhydrous THF (1.5 mL) was cooled to 0° C. and treated with methanesulfonyl chloride (15 mg, 0.11 mmol) in portions. After stirring at 0° C. for 1 h, the mixture was concentrated under reduced pressure. The residue was treated with DMF (1.0 mL), DIPEA (45 μL, 0.26 mmol) and azetidin-3-ylmethyl-carbamic acid tert-butyl ester (Beta Pharma Inc., 145 mg, 0.78 mmol) and stirred at rt for 2 h. The reaction mixture was partitioned between EtOAc and saturated aq. NaHCO$_3$ solution and the EtOAc phase separated, washed with brine dried (MgSO$_4$) and concentrated in vacuo. The residue was purified by flash chromatography on SiO$_2$ eluting with 1-5% MeOH/CH$_2$Cl$_2$ to afford the title compound (33 mg, 48%) as a colorless oil. $^1$H NMR (DMSO-d$_6$) δ 8.74 (s, 1H), 8.51 (d, 1H, J=5.6 Hz), 8.41 (dd, 1H, J=10.7, 2.5 Hz), 8.15 (d, 1H, J=9.2 Hz), 7.53 (t, 1H, J=8.6 Hz), 7.09 (d, 1H, J=6.1 Hz), 6.86 (t, 1H, J=5.6 Hz), 3.39 (s, 2H), 3.24-3.14 (m, 2H), 3.07-2.98 (m, 2H), 2.94-2.87 (m, 2H), 2.37-2.26 (m, 1H), 1.33 (s, 9H); MS(ESI$^+$): m/z 401.20 (100), [(M-C$_4$H$_9$)]+; m/z 457.20 (25), (M+H)$^+$.

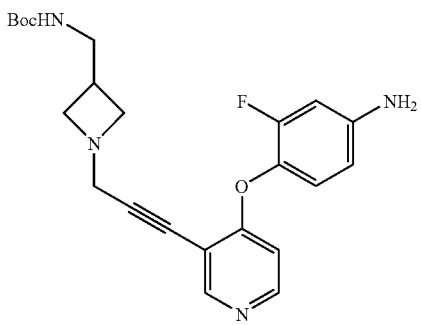

C) tert-Butyl(1-(3-(4-(4-amino-2-fluorophenoxy) pyridin-3-yl)prop-2-ynyl)azetidin-3-yl)methylcarbamate The title compound was prepared by the reduction of tert-butyl(1-(3-(4-(2-fluoro-4-nitrophenoxy)pyridin-3-yl)prop-2-ynyl)azetidin-3-yl)methylcarbamate (30 mg, 0.66 mmol) in the same manner as in Step E of Example 35 using Fe powder (50 g, 0.091 mmol) and NH$_4$Cl (96 mg, 1.82 mmol). The product was used in subsequent reactions without any purification. MS(ESI$^+$): m/z 371.24 (100), [(M-C$_4$H$_9$)]+; m/z 427.27 (25), (M+H)$^+$.

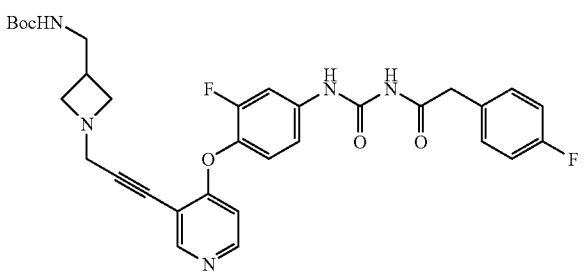

D) tert-Butyl(1-(3-(4-(2-fluoro-4-(3-(2-(4-fluorophenyl)acetyl)ureido)phenoxy)pyridin-3-yl)prop-2-ynyl) azetidin-3-yl)methylcarbamate The title compound was prepared from tert-butyl(1-(3-(4-(4-amino-2-fluorophenoxy)pyridin-3-yl)prop-2-ynyl)azetidin-3-yl)methylcarbamate (25 mg, 0.059 mmol) and a 0.3 M solution of 2-(4-fluorophenyl)acetyl isocyanate in toluene (Compound D of Example 11, 0.37 mL, 0.11 mmol) in the same manner as Step D of Example 33 to give the title compound as a white solid (20 mg, 57%). $^1$H NMR (DMSO-d$_6$) δ 11.04 (s, 1H), 10.58 (s, 1H), 8.63 (s, 1H), 8.37 (d, 1H, J=5.5 Hz), 7.78 (d, 1H, J=12.6 Hz), 7.40-7.33 (m, 4H), 7.16 (dd, 2H, J=8.8, 8.9 Hz), 6.89-6.87 (m, 1H), 6.68 (d, 1H, J=5.5 Hz), 3.73 (s, 2H), 3.45 (s, 2H), 3.26-3.24 (m, 2H), 3.07-3.04 (m, 2H), 2.98-2.96 (m, 2H), 2.38-2.35 (m, 2H), 1.32 (s, 9H); MS(ESI$^+$): m/z 606.26 (M+H)$^+$.

E) 1-(4-(3-(3-(3-(Aminomethyl)azetidin-1-yl)prop-1-ynyl)pyridin-4-yloxy)-3-fluorophenyl)-3-(2-(4-fluorophenyl)acetyl)urea, trihydrochloride salt tert-Butyl(1-(3-(4-(2-fluoro-4-(3-(2-(4-fluorophenyl) acetyl)ureido)phenoxy)pyridin-3-yl)prop-2-ynyl)azetidin-3-yl)methylcarbamate (20 mg, 0.033 mmol) was dissolved in CH$_2$Cl$_2$ (2 mL) and treated with TFA (0.5 mL) and the mixture stirred at room temperature for 1.5 h. The mixture was concentrated in vacuo and purified by preparative HPLC (Column A) to give the TFA salt. The TFA salt was dissolved in absolute MeOH and treated with 1.0 M HCl/ether stirred for 5 min and concentrated in vacuo to give the title compound (9 mg, 45%) as a white solid. $^1$H NMR (DMSO-d$_6$) δ 11.07 (s, 1H), 10.06 (s, 1H), 8.96 (m, 1H), 8.61-8.52 (m, 1H), 8.36-8.25 (s, 2H), 7.82 (d, 1H, J=12.2 Hz), 7.45-7.42 (m, 2H), 7.37-7.33 (m, 2H), 7.18-7.14 (m, 2H), 6.92 (d, 1H, J=6.1 Hz), 4.48 (s, 2H), 4.27-3.98 (m, 2H), 3.76 (s, 2H), 3.30-3.20 (m, 1H), 3.16-3.00 (m, 2H); MS(ESI$^+$): m/z 506.18 (M+H)$^+$.

Examples 37-40 were prepared in a similar manner to that which is described in Example 36.

Example 37

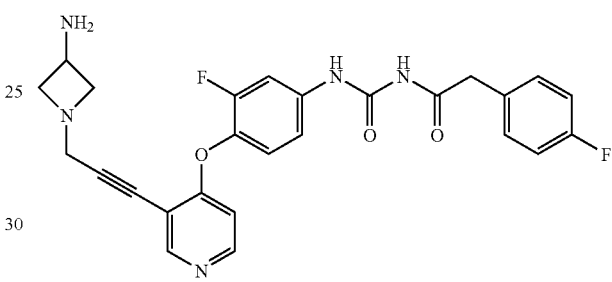

1-(4-(3-(3-(3-Aminoazetidin-1-yl)prop-1-ynyl)pyridin-4-yloxy)-3-fluorophenyl)-3-(2-(4-fluorophenyl) acetyl)urea, trihydrochloride salt MS(ESI$^+$): m/z 492.17 (M+H)$^+$ Example 38

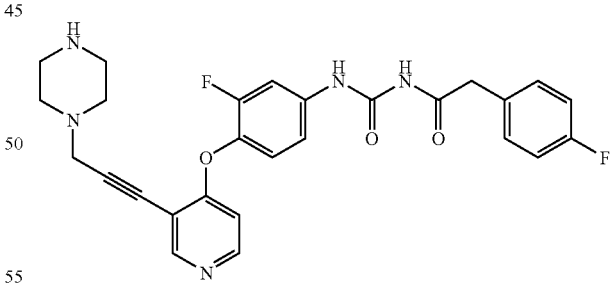

1-(3-Fluoro-4-(3-(3-(piperazin-1-yl)prop-1-ynyl) pyridin-4-yloxy)phenyl)-3-(2-(4-fluorophenyl) acetyl)urea, trihydrochloride salt $^1$H NMR (DMSO-d$_6$) δ 11.07 (s, 1H), 10.63 (s, 1H), 9.44 (s, 1H), 8.91 (s, 1H), 8.50 (d, 1H, J=6.2 Hz), 7.84-7.78 (m, 1H), 7.45-7.39 (m, 2H), 7.38-7.32 (m, 2H), 7.16 (t, 2H, J=8.8 Hz), 6.85 (d, 1H, J=6.2 Hz), 4.26 (s, 2H), 3.75 (s, 2H), 3.34 (br s, 4H), 2.49 (br s, 4H); MS(ESI$^+$): m/z 506.23 (M+H)$^+$.

Example 39

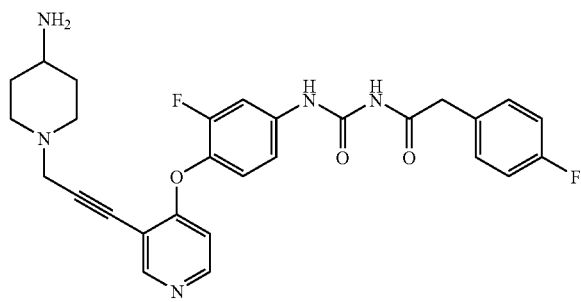

1-(4-(3-(3-(4-Aminopiperidin-1-yl)prop-1-ynyl)pyridin-4-yloxy)-3-fluorophenyl)-3-(2-(4-fluorophenyl)acetyl)urea, trihydrochloride salt ¹H NMR (DMSO-d₆) δ 11.07 (s, 1H), 10.62 (s, 1H), 8.81 (s, 1H), 8.48 (d, 1H, J=6.1 Hz), 8.31 (s, 2H), 7.80 (dd, 1H, J=2.2, 12.7 Hz), 7.44-7.33 (m, 4H), 7.19-7.13 (m, 2H), 6.78 (d, 1H, J=5.7 Hz), 4.40 (s, 2H), 3.74 (s, 2H), 3.64-3.60 (m, 2H), 3.34-3.22 (m, 1H), 3.19-3.13 (m, 2H), 2.16-2.13 (m, 2H), 1.99-1.88 (m, 2H); MS(ESI⁺): m/z 506.23 (M+H)⁺.

Example 40

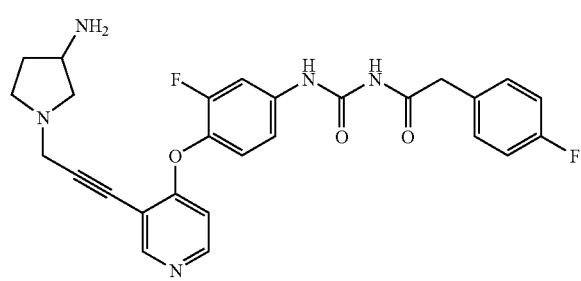

(±)-1-(4-(3-(3-(3-Aminopyrrolidin-1-yl)prop-1-ynyl)pyridin-4-yloxy)-3-fluorophenyl)-3-(2-(4-fluorophenyl)acetyl)urea, trihydrochloride salt ¹H NMR (DMSO-d₆) δ 11.08 (s, 1H), 10.65 (s, 1H), 8.96 (s, 1H), 8.54 (d, 1H, J=6.1 Hz), 7.83 (d, 1H, J=12.7 Hz), 7.43 (s, 2H), 7.37-7.33 (m, 2H), 7.16-7.14 (m, 2H), 6.90 (d, 1H, J=5.6 Hz), 4.62 (s, 2H), 4.06-3.87 (m, 1H), 3.75 (s, 2H), 3.70-3.55 (m, 3H), 3.49-3.44 (m, 2H), 2.25-2.08 (m, 1H); MS(ESI⁺): m/z 506.22 (M+H)⁺.

Example 41

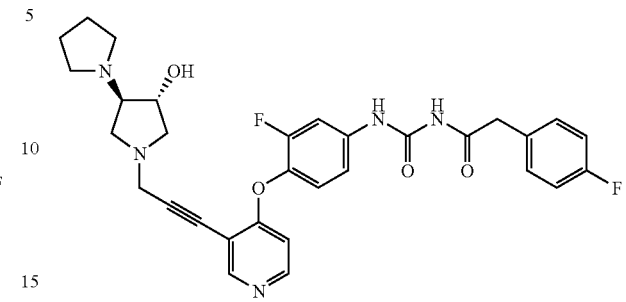

1-(3-Fluoro-4-(3-(3-((3R,4R)-3-hydroxy-4-(pyrrolidin-1-yl)pyrrolidin-1-yl)prop-1-ynyl)pyridin-4-yloxy)phenyl)-3-(2-(4-fluorophenyl)acetyl)urea, trihydrochloride salt

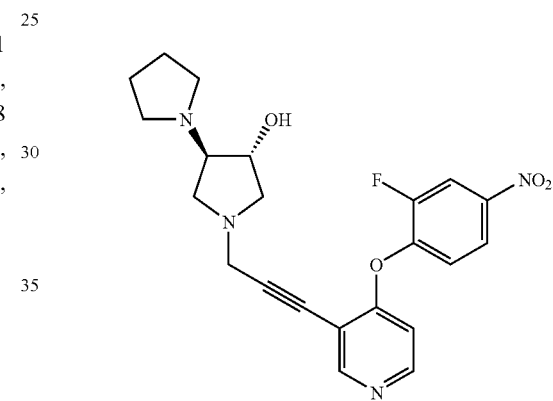

A) (3R,4R)-1-(3-(4-(2-Fluoro-4-nitrophenoxy)pyridin-3-yl)prop-2-ynyl)-4-(pyrrolidin-1-yl)pyrrolidin-3-ol A solution of 3-(4-(2-fluoro-4-nitrophenoxy)pyridin-3-yl)prop-2-yn-1-ol (Compound A of Example 36, 43 mg, 0.15 mmol) and DIPEA (45 μL, 0.26 mmol) in anhydrous THF (1.5 mL) was cooled to 0° C. and treated with methanesulfonyl chloride (15 mg, 0.11 mmol) in portions. After stirring at 0° C. for 1 h, the mixture was concentrated under reduced pressure. The residue was treated with DMF (1.0 mL), DIPEA (45 μL, 0.26 mmol) and (3R,4R)-4-(pyrrolidin-1-yl)pyrrolidin-3-ol (Lexicon Pharmaceutical Corp., 94 mg, 0.6 mmol) and stirred at rt for 2 h. The reaction mixture was partitioned between EtOAc and saturated aq. NaHCO₃ solution and the EtOAc phase separated, washed with brine, dried (MgSO₄) and concentrated in vacuo. The crude product was purified by flash chromatography on SiO₂ eluting with 0-1.5% MeOH/CH₂Cl₂ to give the title compound (38 mg, 59%) as a brown oil. ¹H NMR (DMSO-d₆) δ 8.72 (s, 1H), 8.54 (d, 1H, J=5.6 Hz), 8.40 (dd, 1H, J=10.7, 2.5 Hz), 8.14 (d, 1H, J=9.2 Hz), 7.43 (t, 1H, J=8.6 Hz), 7.15 (d, 1H, J=5.6 Hz), 4.99-4.81 (m, 1H), 4.11-4.10 (m, 0.5H), 3.92-3.84 (m, 1H), 3.54 (s, 2H), 3.59-3.50 (m, 0.5H), 3.16-3.15 (m, 1H), 2.79-2.75 (m, 1H), 2.60-2.32 (m, 4H), 1.70-1.59 (m, 4H); MS(ESI+): m/z 427.24 (M+H)+.

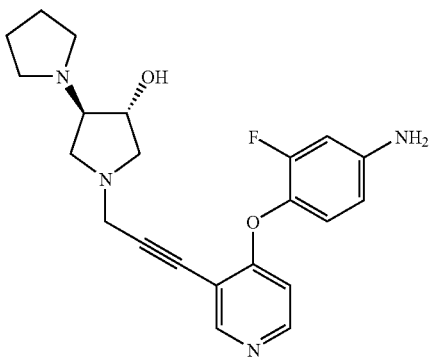

B) (3R,4R)-1-(3-(4-(4-Amino-2-fluorophenoxy)pyridin-3-yl)prop-2-ynyl)-4-(pyrrolidin-1-yl)pyrrolidin-3-ol A mixture of (3R,4R)-1-(3-(4-(2-fluoro-4-nitrophenoxy)pyridin-3-yl)prop-2-ynyl)-4-(pyrrolidin-1-yl)pyrrolidin-3-ol (35 mg, 0.082 mmol), DMF (1 mL), EtOH (1 mL) and H₂O (1 mL) was treated with Fe powder (67 mg, 1.2 mmol, 2.4 mmol) and heated at 100° C. for 45 min. The mixture was filtered through Celite®, made basic with NaHCO₃ and concentrate in vacuo. The residue was partitioned between EtOAc and saturated aq. NaHCO₃ solution. The EtOAc phase was dried (MgSO₄) and concentrated in vacuo to give the crude aniline (16 mg, 50%) which was used directly in the next step without further purification. MS(ESI+): m/z 397.28 (M+H)+.

C) 1-(3-Fluoro-4-(3-(3-((3R,4R)-3-hydroxy-4-(pyrrolidin-1-yl)pyrrolidin-1-yl)prop-1-ynyl)pyridin-4-yloxy)phenyl)-3-(2-(4-fluorophenyl)acetyl)urea, trihydrochloride salt The title compound was prepared from (3R,4R)-1-(3-(4-(4-amino-2-fluorophenoxy)pyridin-3-yl)prop-2-ynyl)-4-(pyrrolidin-1-yl)pyrrolidin-3-ol (16 mg, 0.04 mmol) and a 0.3 M solution of 2-(4-fluorophenyl)acetyl isocyanate in toluene (Compound D of Example 11, 0.13 mL, 0.04 mmol) in a manner similar to that of Step D of Example 33. The product was purified by preparative HPLC (Column A) and converted to the hydrochloride salt in the same manner as in Step E of Example 36 to give the title compound (9 mg, 33%) as a white solid. ¹H NMR (DMSO-d₆) δ 11.06 (s, 1H), 10.62 (s, 1H), 8.86 (s, 1H), 8.45 (d, 1H, J=6.1 Hz), 7.81 (d, 1H, J=12.2 Hz), 7.45-7.40 (m, 4H), 7.33-7.28 (m, 4H), 7.16 (dd, 2H, J=9.2, 8.6 Hz), 6.80 (d, 1H, J=6.1 Hz), 4.64 (s, 1H), 4.34 (s, 2H), 3.84-3.70 (m, 4H), 2.70-3.55 (m, 2H), 3.55-2.98 (m, 3H), 2.08-1.92 (m, 2H), 1.92-1.75 (m, 2H); MS(ESI+): m/z 576.25 (M+H)+.

Example 42

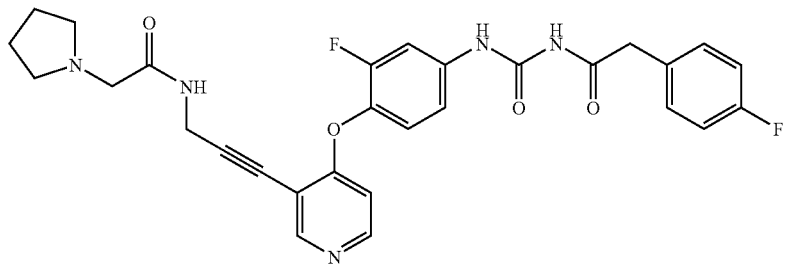

1-(3-Fluoro-4-(3-(3-(2-(pyrrolidin-1-yl)acetamido)prop-1-ynyl)pyridin-4-yloxy)phenyl)-3-(2-(4-fluorophenyl)acetyl)urea, dihydrochloride salt

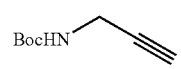

A) N-Boc-propargylamine

Di-tert-butyl-dicarbonate (21.8 mg, 100.0 mmol) was dissolved in THF (25 mL) and the solution cooled to 0° C. and treated dropwise with a solution of propargylamine (Aldrich, 5.0 g, 90.0 mmol) keeping the temperature below 15° C. The mixture was stirred at rt for 1.5 h then concentrated under vacuum. The residue was dissolved in hexanes and filtered through a column of silica gel using 0-100% CH₂Cl₂/hexanes to elute the product. The eluent containing the product was concentrated in vacuo to give a colorless oil which was dissolved in hexanes (150 mL) and cooled to 0° C. to give white crystals. The crystals were collected by filtration and dried under vacuum to give the title compound (10.5 g, 75%). ¹H NMR (CDCl₃) δ 4.75 (s, 1H), 3.95 (s, 2H), 2.25-2.24 (m, 1H), 1.48 (s, 9H).

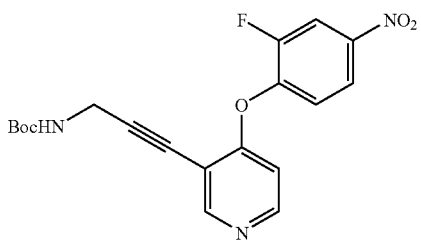

B) tert-Butyl 3-(4-(2-fluoro-4-nitrophenoxy)pyridin-3-yl)prop-2-ynylcarbamate

The title compound was prepared from N-Boc-propargylamine (98 mg, 0.63 mmol) and 4-(2-fluoro-4-nitrophenoxy)-3-iodopyridine (Compound A of Example 33, 150 mg, 0.42 mmol) via a Sonagashira cross coupling reaction using Pd(Ph$_3$P)$_4$ (9 mg, 0.008 mmol) and CuI (1.5 mg, 0.008 mmol) in 1:1 Et$_3$N/THF (3 mL) according to Step C of Example 35. The title compound (124 mg, 76%) was obtained as a red oil. $^1$H NMR (DMSO-d$_6$) δ 8.66 (s, 1H), 8.50 (d, 1H, J=5.6 Hz), 8.40 (dd, 1H, J=2.5, 10.7 Hz), 8.15 (d, 1H, J=9.2 Hz), 7.52 (dd, 1H, J=8.1, 8.6 Hz), 7.33-7.30 (m, 1H), 7.07 (d, 1H, J=5.6 Hz), 3.95 (d, 2H, J=5.6 Hz), 1.35 (s, 9H); MS(ESI$^+$): m/z 388.21 (M+H)$^+$.

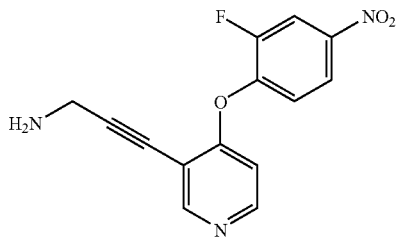

C) 3-(4-(2-Fluoro-4-nitrophenoxy)pyridin-3-yl)prop-2-yn-1-amine

A solution of tert-butyl 3-(4-(2-fluoro-4-nitrophenoxy)pyridin-3-yl)prop-2-ynylcarbamate (300 mg, 0.78 mmol) in CH$_2$Cl$_2$ (10 mL) was treated with TFA (2 mL) and stirred at rt for 45 min. The mixture was concentrated under vacuum and the residue was partitioned between EtOAc and saturated aq. NaHCO$_3$ solution. The EtOAc phase was separated and washed with brine, dried (MgSO$_4$) and concentrated in vacuo to give the title compound (180 mg, 80%) as a red oil. $^1$H NMR (DMSO-d$_6$) 68.65 (s, 1H), 8.47 (d, 1H, J=5.6 Hz), 8.43 (dd, 1H, J=10.7, 2.5 Hz), 8.17 (d, 1H, J=8.6 Hz), 7.54 (t, 1H, J=8.6 Hz), 7.04 (d, 1H, J=5.6 Hz), 3.49 (s, 2H); MS(ESI$^+$): m/z 288.17 (M+H)$^+$.

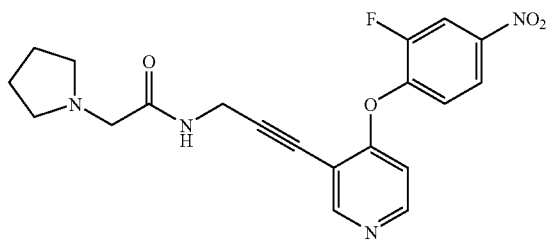

D) N-(3-(4-(2-Fluoro-4-nitrophenoxy)pyridin-3-yl)prop-2-ynyl)-2-(pyrrolidin-1-yl)acetamide A solution of 3-(4-(2-fluoro-4-nitrophenoxy)pyridin-3-yl)prop-2-yn-1-amine (80 mg, 0.26 mmol) in anhydrous CH$_2$Cl$_2$ (2.5 mL) was cooled to 0° C. and treated with chloroacetyl chloride (40 mg, 0.37 mmol) the mixture was stirred at rt for 1 h. The mixture was concentrated under vacuum to removed the solvent and excess reagent and the residue redissolved in CH$_3$CN (1.5 mL), treated with pyrrolidone (55 mg, 0.78 mmol) and stirred at rt for 4 h. The mixture was partitioned between EtOAc and saturated aq. NaHCO$_3$ solution and the organic phase separated, washed with brine, dried (MgSO$_4$) and concentrated to give crude product. The residue was purified by flash chromatography on silica gel eluting with 0-10% MeOH/CH$_2$Cl$_2$ to afford the title compound (40 mg, 39%) as a brown oil. $^1$H NMR (DMSO-d$_6$) δ 8.66 (s, 1H), 8.50 (d, 1H, J=6.1 Hz), 8.41 (dd, 1H, J=2.8, 10.4 Hz), 8.18-8.15 (m, 2H), 7.51 (dd, 1H, J=8.3, 8.8 Hz), 7.06 (d, 1H, J=5.5 Hz) 4.10 (d, 2H, J=5.5 Hz), 3.01 (s, 2H), 2.47-2.43 (m, 4H), 1.67-1.63 (m, 4H); MS(ESI$^+$): m/z 399.27 (M+H)$^+$.

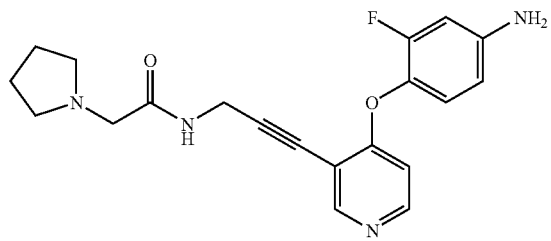

E) N-(3-(4-(4-Amino-2-fluorophenoxy)pyridin-3-yl)prop-2-ynyl)-2-(pyrrolidin-1-yl)acetamide The title compound was prepared by the reduction of N-(3-(4-(2-fluoro-4-nitrophenoxy)pyridin-3-yl)prop-2-ynyl)-2-(pyrrolidin-1-yl)acetamide (35 mg, 0.088 mmol) in the manner similar to that of Step E of Example 35 using Fe powder (67 mg, 1.21 mmol) and NH$_4$Cl (128 mg, 2.42 mmol). The product was used in subsequent reactions without any purification. Yellow oil (30 mg, 93%). MS(ESI$^+$): m/z 319.24 (M+H)$^+$.

F) 1-(3-Fluoro-4-(3-(3-(2-(pyrrolidin-1-yl)acetamido)prop-1-ynyl)pyridin-4-yloxy)phenyl)-3-(2-(4-fluorophenyl)acetyl)urea, dihydrochloride salt The title compound was prepared from N-(3-(4-(4-amino-2-fluorophenoxy)pyridin-3-yl)prop-2-ynyl)-2-(pyrrolidin-1-yl)acetamide (32 mg, 0.088 mmol) and 0.3 M solution of 2-(4-fluorophenyl)acetyl isocyanate in toluene (Compound D of Example 11, 0.40 ml, 0.12 mmol) using THF (0.5 ml) in a manner similar to that of Step D of Example 33. The product was purified by preparative HPLC (Column B). The fraction containing the product was treated with excess 1 M hydrochloric acid, concentrated in vacuo and lyophilized to give the title compound (30 mg, 63%) as a pale yellow solid. $^1$H NMR (DMSO-d$_6$) δ 11.07 (s, 1H), 10.62 (s, 1H), 10.09 (s, 1H), 9.17-9.14 (m, 1H), 8.65 (s, 1H), 8.43 (d, 1H, J=5.6 Hz), 7.81 (dd, 1H, J=2.5, 12.7 Hz), 7.44-7.33 (m, 4H), 7.19-7.12 (m, 2H), 4.31 (d, 2H, J=5.6 Hz), 4.05 (d, 2H, J=5.6 Hz), 3.74 (s, 2H), 3.56-3.51 (m, 2H), 3.05-2.99 (m, 2H), 1.96-1.90 (m, 2H), 1.88-1.79 (m, 2H); MS(ESI$^+$): m/z 548.26 (M+H)$^+$.

Example 43

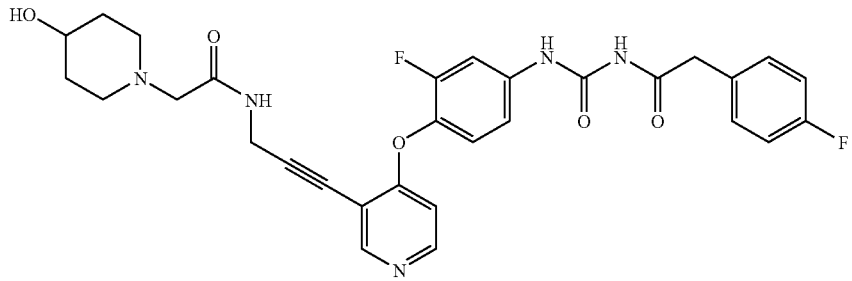

1-(3-Fluoro-4-(3-(3-(2-(4-hydroxypiperidin-1-yl)acetamido)prop-1-ynyl)pyridin-4-yloxy)phenyl)-3-(2-(4-fluorophenyl)acetyl)urea, dihydrochloride salt

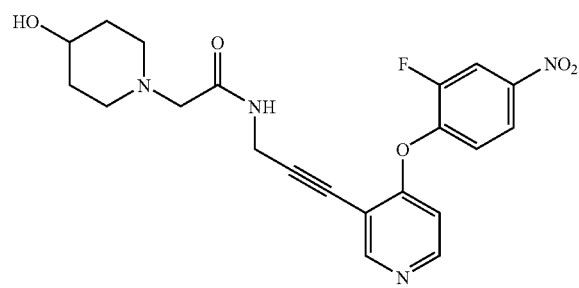

A) N-(3-(4-(2-Fluoro-4-nitrophenoxy)pyridin-3-yl)prop-2-ynyl)-2-(4-hydroxypiperidin-1-yl)acetamide The title compound was prepared from 3-(4-(2-fluoro-4-nitrophenoxy)pyridin-3-yl)prop-2-yn-1-amine (Compound A of Example 36, 80 mg, 0.26 mmol), 4-hydroxypiperidine (79 mmol, 0.78 mmol) and chloroacetyl chloride (40 mg, 0.36 mmol) in the same manner as for Step D of Example 42. The residue was purified by flash chromatography on silica gel eluting with 1-3% MeOH/CH$_2$Cl$_2$ to give a white foam (40 mg, 36%). $^1$H NMR (DMSO-d$_6$) δ 8.65 (s, 1H), 8.49 (d, 1H, J=5.5 Hz), 8.41 (dd, 1H, J=10.4, 2.7 Hz), 8.18-8.12 (m, 2H), 7.55-7.50 (m, 1H), 7.05 (d, 1H, J=6.0 Hz), 4.54 (d, 1H, J=3.8 Hz), 4.11 (d, 2H, J=6.0 Hz), 3.43-3.36 (m, 1H), 2.86 (s, 2H), 2.64-2.58 (m, 2H), 2.12-2.05 (m, 2H), 1.67-1.61 (m, 2H), 1.44-1.36 (m, 2H); MS(ESI$^+$): m/z 429.18 (M+H)$^+$.

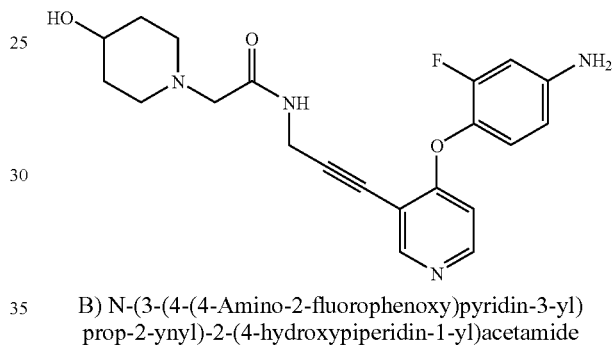

B) N-(3-(4-(4-Amino-2-fluorophenoxy)pyridin-3-yl)prop-2-ynyl)-2-(4-hydroxypiperidin-1-yl)acetamide The title compound was prepared by the reduction N-(3-(4-(2-fluoro-4-nitrophenoxy)pyridin-3-yl)prop-2-ynyl)-2-(4-hydroxypiperidin-1-yl)acetamide (33 mg, 0.077 mmol) in a manner similar to that of Step E of Example 35 using Fe (powder, 67 mg, 1.21 mmol), NH$_4$Cl (128 mg, 2.42 mmol). The product (30 mg, 100%) was obtained as a yellow oil which was used directly in the subsequent step. MS(ESI$^+$): m/z 399.27 (M+H)$^+$.

C) 1-(3-Fluoro-4-(3-(3-(2-(4-hydroxypiperidin-1-yl)acetamido)prop-1-ynyl)pyridin-4-yloxy)phenyl)-3-(2-(4-fluorophenyl)acetyl)urea, dihydrochloride salt The title compound was prepared from N-(3-(4-(4-amino-2-fluorophenoxy)pyridin-3-yl)prop-2-ynyl)-2-(4-hydroxypiperidin-1-yl)acetamide (25 mg, 0.063 mmol) and 0.3 M solution of 2-(4-fluorophenyl)acetyl isocyanate in toluene (Compound D of Example 11, 0.40 mL, 0.12 mmol) using THF (0.5 ml) in a manner similar to that of Step D of Example 33. The product was purified by preparative HPLC (Column B). The fraction containing the product was treated with excess 1 N hydrochloric acid, concentrated and lyophilized to give the title compound (10 mg, 30%) as a pale yellow solid. $^1$H NMR (DMSO-d$_6$) δ 11.08 (s, 1H), 10.64 (s, 1H), 9.83-9.72 (m, 1H), 9.25-9.20 (m, 1H), 8.66 (s, 1H), 8.45 (d, 1H, J=6.1 Hz), 7.83 (dd, 1H, J=2.0, 13.2 Hz), 7.46-7.35 (m, 3H), 7.21-7.11 (m, 2H), 6.77 (d, 1H, J=6.1 Hz), 4.33-4.31 (m, 2H), 3.99-3.94 (m, 2H), 3.92-3.89 (m, 1H), 3.76 (s, 2H), 3.46-3.40 (m, 2H), 3.29-3.21 (m, 2H), 3.10-3.00 (m, 1H), 1.98-1.87 (m, 2H), 1.72-1.62 (m, 2H); MS(ESI$^+$): m/z 528.25 (M+H)$^+$.

Example 44

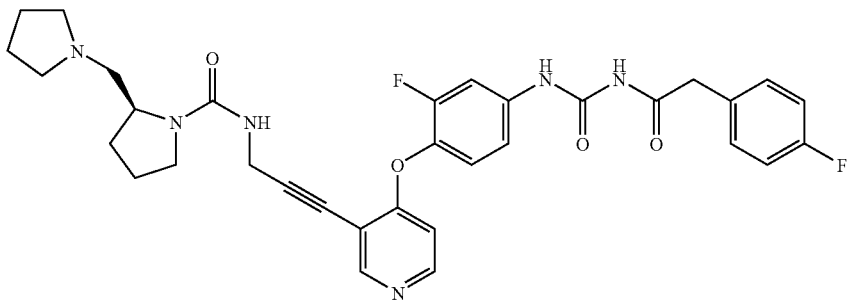

(S)-1-(3-Fluoro-4-(3-(3-(2-(pyrrolidin-1-ylmethyl)
pyrrolidine-1-carboxamido)prop-1-ynyl)pyridin-4-
yloxy)phenyl)-3-(2-(4-fluorophenyl)acetyl)urea,
dihydrochloride salt

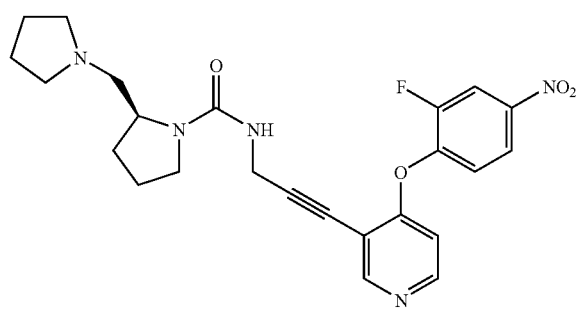

A) (S)-N-(3-(4-(2-Fluoro-4-nitrophenoxy)pyridin-3-
yl)prop-2-ynyl)-2-(pyrrolidin-1-ylmethyl)pyrroli-
dine-1-carboxamide 3-(4-(2-Fluoro-4-nitrophenoxy)pyridin-3-yl)prop-2-yn-1-amine (Compound A of Example 36, 55 mg, 0.19 mmol) was dissolved in $CH_2Cl_2$ (5 mL), treated with 4-nitrophenyl chloroformate (0.38 mg, 0.19 mmol) and pyridine (15 μL, 0.19 mmol). The reaction mixture was stirred at rt. After 1 h, the mixture was treated with $Et_3N$ (30 mL, 0.20 mmol) and (S)-(+)-1-(2-pyrrolidinylmethyl)pyrrolidone (Aldrich, 32 mg, 0.21 mmol) and stirred at rt for 15 h. The mixture was then diluted with $CH_2Cl_2$ (50 mL), washed with 1 M NaOH and brine, dried ($MgSO_4$) and concentrated in vacuo to give the crude product. The residue was purified by flash chromatography on silica gel eluting with 0-10% MeOH/$CH_2Cl_2$ to give the title compound (53 mg, 60%) as a yellow oil. $^1H$ NMR (DMSO-$d_6$) δ 8.65 (s, 1H), 8.49 (d, 1H, J=6.1 Hz), 8.41 (dd, 1H, J=2.8 Hz, 10.5 Hz), 8.16 (d, 1H, J=7.7 Hz), 7.52 (dd, 1H, J=8.3, 8.8 Hz), 7.05 (d, 1H, J=6.1 Hz), 4.11-4.06 (m, 2H), 3.99-3.95 (m, 2H), 3.76 (s, 2H), 3.16-3.11 (m, 2H), 2.57-2.48 (m, 2H), 2.43-2.41 (m, 2H), 3.36-2.34 (m, 2H), 1.90-1.86 (m, 2H), 1.76-1.62 (m, 3H); MS(ESI$^+$): m/z 468.27 (M+H)$^+$.

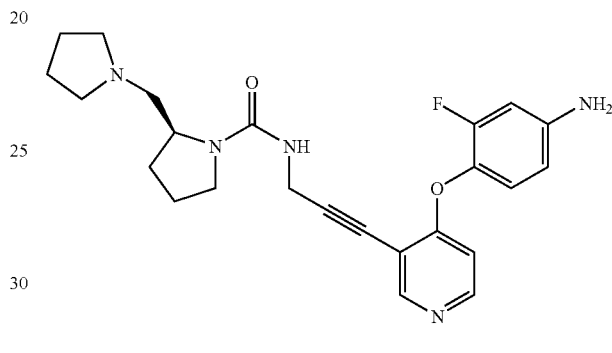

B) (S)-N-(3-(4-(4-Amino-2-fluorophenoxy)pyridin-
3-yl)prop-2-ynyl)-2-(pyrrolidin-1-ylmethyl)pyrroli-
dine-1-carboxamide The title compound was prepared by the reduction of (S)-N-(3-(4-(2-fluoro-4-nitrophenoxy)pyridin-3-yl)prop-2-ynyl)-2-(pyrrolidin-1-ylmethyl)pyrrolidine-1-carboxamide (50 mg, 0.11 mmol) in a manner similar to that of Step E of Example 35 using Fe (powder, 67 mg, 1.21 mmol), $NH_4Cl$ (128 mg, 2.42 mmol). The product (36 mg, 75%) was obtained as a yellow oil which was used directly in the subsequent step. MS(ESI$^+$): m/z 438.30 (M+H)$^+$.

C) (S)-1-(3-Fluoro-4-(3-(3-(2-(pyrrolidin-1-ylm-
ethyl)pyrrolidine-1-carboxamido)prop-1-ynyl)pyri-
din-4-yloxy)phenyl)-3-(2-(4-fluorophenyl)acetyl)
urea, dihydrochloride salt The title compound was prepared from (S)-N-(3-(4-(4-amino-2-fluorophenoxy)pyridin-3-yl)prop-2-ynyl)-2-(pyrrolidin-1-ylmethyl)pyrrolidine-1-carboxamide (36 mg, 0.057 mmol) and 0.3 M solution of 2-(4-fluorophenyl)acetyl isocyanate in toluene (Compound D of Example 11, 0.37 mL, 0.11 mmol) in the same manner as in Step D of Example 33. The product was purified by preparative HPLC (Column B) and converted to its hydrochloride according to Step C of Example 43 to give the title compound (10 mg, 25%) as an amber colored oil. $^1H$ NMR (DMSO-$d_6$) δ 11.06 (s, 1H), 10.60 (s, 1H), 9.56 (s, 1H), 8.58 (s, 1H), 8.38 (d, 1H, J=5.6 Hz), 7.80 (dd, 1H, J=2.6, 12.7 Hz), 7.42 (dm, 1H, J=10.6 Hz), 7.38-7.31 (m, 2H), 7.30-7.25 (m, 1H), 7.20-7.10 (m, 2H), 6.69 (d, 1H, J=6.1 Hz), 4.26-4.12 (m, 2H), 3.79-3.69 (m, 3H), 3.56 (s, 2H), 3.31-3.18 (m, 2H), 3.17-2.93 (m, 2H), 2.14-2.02 (m, 4H), 2.03-1.76 (m, 5H), 1.71-1.61 (m, 1H); MS(ESI⁺): m/z 617.20 (M+H)⁺.

Example 45

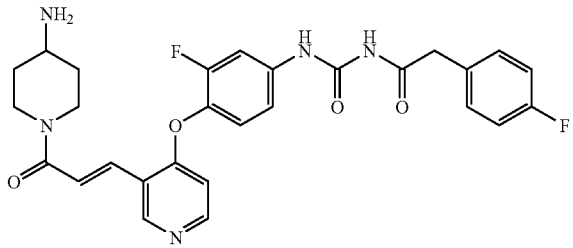

(E)-1-(4-(3-(3-(4-Aminopiperidin-1-yl)-3-oxoprop-1-enyl)pyridin-4-yloxy)-3-fluorophenyl)-3-(2-(4-fluorophenyl)acetyl)urea, ditrifluoroacetic acid salt

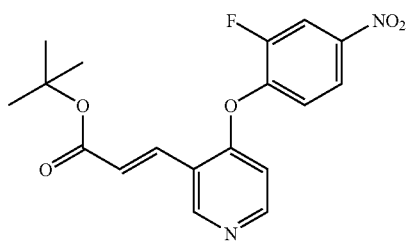

A) (E)-tert-Butyl 3-(4-(2-fluoro-4-nitrophenoxy) pyridin-3-yl)acrylate

A mixture of 4-(2-fluoro-4-nitrophenoxy)-3-iodopyridine (Compound A of Example 33, 150 mg, 0.42 mmol), tert-butylacrylate (Aldrich, 107 mg, 0.84 mmol), tri-n-butylamine (0.21 mL, 0.92 mmol) and DMF (2 mL) was degassed by vacuum/argon purge and then treated with Pd(OAc)₂ (17 mg, 0.078 mmol). The mixture was heated at 100-130° C. for under argon for 45 min, then the mixture was cooled to rt, partitioned between EtOAc and saturated aq. NaHCO₃ solution. The phases were separated and the EtOAc extracts were washed with saturated aq. NaHCO₃ solution and brine, dried (MgSO₄) and concentrated in vacuo. The crude product was purified by flash chromatography on SiO₂ eluting with 0-20% EtOAc/CH₂Cl₂ to give the title compound (118 mg, 78%) as a pale yellow oil which solidified at room temperature. ¹H NMR (DMSO-d₆) δ 9.02 (s, 1H), 8.49 (d, 1H, J=5.5 Hz), 8.46 (dd, 1H, J=2.5, 11.7 Hz), 8.21 (dm, 1H, J=9.2 Hz), 7.74 (d, 1H, J=16.3 Hz), 7.65 (dd, 1H, J=8.1, 8.6 Hz), 6.95 (d, 1H, J=6.1 Hz), 6.77 (d, 1H, J=16.3 Hz), 1.47 (s, 9H); MS(ESI⁺): m/z 361.15 (M+H)⁺.

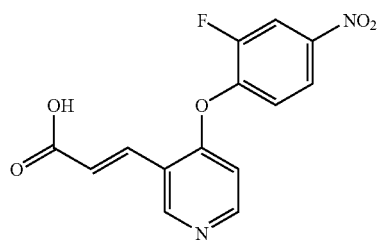

B) (E)-3-(4-(2-Fluoro-4-nitrophenoxy)pyridin-3-yl) acrylic acid (E)-tert-Butyl 3-(4-(2-fluoro-4-nitrophenoxy)pyridin-3-yl)acrylate (115 mg, 0.32 mmol) was treated with 1:1 TFA/CH₂Cl₂ (6 mL) and stirred at room temperature for 1.5 h. The mixture was concentrated under vacuum and the residue treated with MeOH (5 mL) and 2 M HCl/Et₂O (15 mL) and concentrated under vacuum. A second treatment with MeOH (5 mL) and 2 M HCl/Et₂O (15 mL) and reconcentration gave the title compound (120 mg). ¹H NMR (DMSO-d₆) δ 9.17 (s, 1H), 8.62 (d, 1H, J=6.6 Hz), 8.50 (dd, 1H, J=2.6, 10.1 Hz), 8.25 (d, 1H, J=9.1 Hz), 7.78 (d, 1H, J=16.3 Hz), 7.74 (dd, 1H, J=8.1, 8.6 Hz), 7.17 (d, 1H, J=6.1 Hz), 6.87 (d, 1H, J=16.3 Hz); MS(ESI⁺): m/z 305.11 (M+H)⁺.

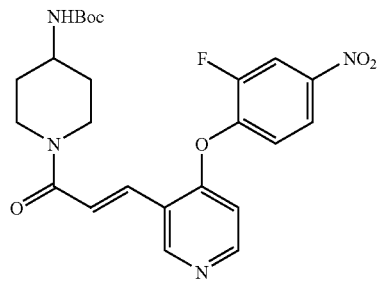

C) (E)-tert-Butyl 1-(3-(4-(2-fluoro-4-nitrophenoxy) pyridin-3-yl)acryloyl)piperidin-4-ylcarbamate A solution of (E)-3-(4-(2-fluoro-4-nitrophenoxy)pyridin-3-yl)acrylic acid (143 mg, 0.42 mmol), 4-N-Boc-aminopiperidine (Aldrich, 84 mg, 0.42 mmol) in DMF (1.5 mL) was treated with DIPEA (160 μL, 0.92 mmol), and TBTU (160 mg, 0.50 mmol) and the mixture stirred at rt for 2 h. The mixture was diluted with EtOAc, washed with saturated aq. NaHCO₃ solution and brine, dried (MgSO₄) and concentrated in vacuo. The crude product was purified by flash chromatography on silica gel eluting first with 30-100% EtOAc/hexanes then 5% MeOH/CH₂Cl₂ to give the title compound (110 mg, 54%) as a light brown solid. ¹H NMR (DMSO-d₆) δ 9.15 (s, 1H), 8.48 (d, 1H, J=5.6 Hz), 8.44 (dd, 1H, J=2.5, 10.5 Hz), 8.18 (d, 1H, J=9.2 Hz), 7.69 (d, 1H, J=15.3 Hz), 7.58 (dd, 1H, J=8.6, 8.6 Hz), 7.50 (d, 1H, J=15.7 Hz), 6.97 (d, 1H, J=5.6

Hz), 6.89 (d, 1H, J=7.6 Hz), 4.31-4.16 (m, 2H), 3.55-3.46 (m, 1H), 3.20-3.14 (m, 1H), 2.83-2.81 (m, 1H), 1.82-1.71 (m, 2H), 1.34-1.18 (m, 2H), 1.37 (s, 9H); MS(ESI$^+$): m/z 431.04 (100) [(M-C$_4$H$_9$)$^+$H]$^+$; m/z 487.10 (90) (M+H)$^+$.

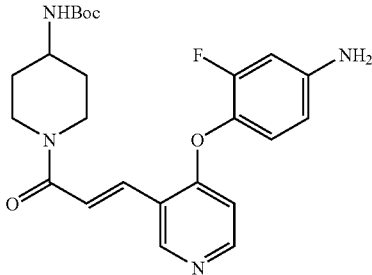

D) (E)-tert-Butyl 1-(3-(4-(4-amino-2-fluorophenoxy)pyridin-3-yl)acryloyl)piperidin-4-ylcarbamate The title compound was prepared by the reduction of (E)-tert-butyl 1-(3-(4-(2-fluoro-4-nitrophenoxy)pyridin-3-yl)acryloyl)piperidin-4-ylcarbamate (100 mg, 0.21 mmol) in a manner similar to that of Step E of Example 35 using Fe powder (55 mg, 2.7 mmol), NH$_4$Cl (280 mg, 5.3 mmol). The product (90 mg, 95%) was obtained as a light brown solid which was used directly in the subsequent step. MS(ESI$^+$): m/z 457.18 (M+H)$^+$.

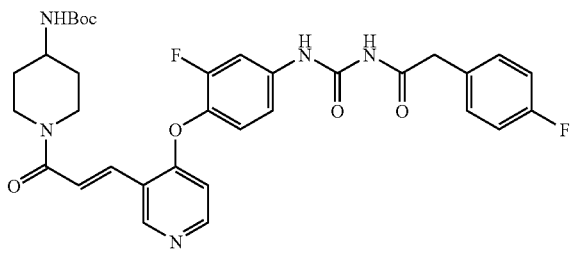

E) (E)-tert-Butyl 1-(3-(4-(2-fluoro-4-(3-(2-(4-fluorophenyl)acetyl)ureido)phenoxy)pyridin-3-yl)acryloyl)piperidin-4-ylcarbamate The title compound was prepared from (E)-tert-butyl 1-(3-(4-(4-amino-2-fluorophenoxy)pyridin-3-yl)acryloyl)piperidin-4-ylcarbamate (42 mg, 0.092 mmol) and 0.3 M solution of 2-(4-fluorophenyl)acetyl isocyanate in toluene (Compound D of Example 11, 0.50 mL, 0.15 mmol) in a manner similar to that of Step D of Example 33. The crude product was adsorbed onto silica gel and purified by flash chromatography eluting with 0-5% MeOH/EtOAc to give the product (20 mg, 33%) as a white solid. $^1$H NMR (DMSO-d$_6$) δ 11.05 (s, 1H), 10.59 (s, 1H), 9.03 (s, 1H), 8.37 (d, 1H, J=5.6 Hz), 7.82-7.74 (m, 2H), 7.47 (d, 1H, J=15.8 Hz), 7.42-7.33 (m, 4H), 7.20-7.13 (m, 2H), 6.89 (d, 1H, J=8.1 Hz), 6.63 (d, 1H, J=5.6 Hz), 4.31 (d, 1H, J=13.7 Hz), 4.19 (d, 1H, J=12.7 Hz), 3.74 (s, 2H), 3.56-3.47 (m, 1H), 3.22-3.13 (m, 1H), 2.84-2.76 (m, 1H), 1.76 (s, 2H), 1.37 (s, 9H), 1.32-1.20 (m, 2H); MS(ESI$^+$): m/z 636.23 (M+H)$^+$.

F) (E)-1-(4-(3-(3-(4-Aminopiperidin-1-yl)-3-oxoprop-1-enyl)pyridin-4-yloxy)-3-fluorophenyl)-3-(2-(4-fluorophenyl)acetyl)urea, ditrifluoroacetic acid salt (E)-tert-Butyl 1-(3-(4-(2-fluoro-4-(3-(2-(4-fluorophenyl)acetyl)ureido)phenoxy)pyridin-3-yl)acryloyl)piperidin-4-ylcarbamate (15 mg, 0.024 mmol) was dissolved in anhydrous MeOH (0.5 mL), treated with 4 M HCl/1,4-dioxane (1.5 mL) and stirred at rt for 1 h. The mixture was concentrated under vacuum to give the crude product which was purified by preparative HPLC (Column A). The fraction containing the product was treated with excess 1 M hydrochloric acid, concentrated and lyophilized to give the title compound (8 mg, 44%) as a pale yellow solid. $^1$H NMR (DMSO-d$_6$) δ 11.07 (s, 1H), 10.61 (s, 1H), 9.10 (s, 1H), 8.44 (s, 1H), 7.91 (m, 3H), 7.86-7.69 (m, 2H), 7.55-7.28 (m, 5H), 7.23-7.08 (m, 2H), 6.80-6.72 (m, 1H), 5.61-5.33 (m, 1H), 4.45-4.20 (m, 2H), 3.74 (s, 2H), 3.39-3.07 (m, 2H), 2.82-2.68 (m, 1H), 1.91-1.51 (m, 2H), 1.50-1.15 (m, 1H); MS(ESI$^+$): m/z 536.16 (M+H)$^+$.

Example 46

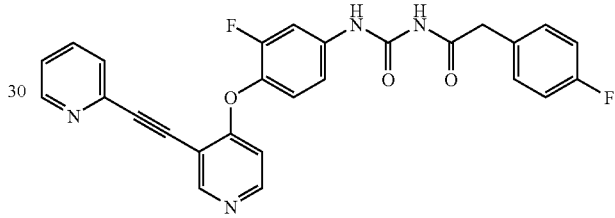

1-(3-Fluoro-4-(3-(2-(pyridin-2-yl)ethynyl)pyridin-4-yloxy)phenyl)-3-(2-(4-fluorophenyl)acetyl)urea, dihydrochloride salt

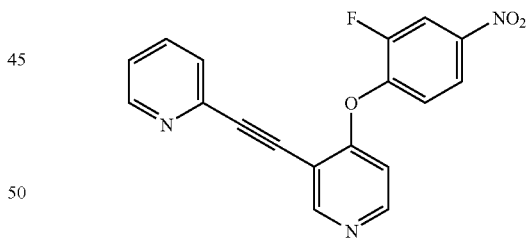

A) 2-(2-(4-(2-Fluoro-4-nitrophenoxy)pyridin-3-yl)ethynyl)pyridine

A mixture of 4-(2-fluoro-4-nitrophenoxy)-3-iodopyridine (Compound A of Example 33, 50 mg, 0.14 mmol) and 2-ethynylpyridine (Aldrich, 57 mg, 0.54 mmol), THF (1 mL) and Et$_3$N (1 mL) was degassed by vacuum/argon purge and treated in turn with CuI (3 mg, 0.016 mmol) and (Ph$_3$P)$_4$Pd (10 mg, 0.009 mmol). The mixture was heated at 60° C. 45 minutes, cooled, partitioned between EtOAc and saturated sodium bicarbonate and the EtOAc phase dried (MgSO$_4$) and concentrated in vacuo to give the crude product. Purification of the residue by flash column chromatography on SiO$_2$ eluting with 0-1.5% MeOH/CH$_2$Cl$_2$ gave the title compound (42 mg, 89%) as a brown solid. $^1$H NMR (DMSO-d$_6$) δ 8.91 (s, 1H), 8.60 (d, 1H, J=4.5 Hz), 8.45 (dd, 1H, J=2.6, 10.7 Hz), 8.19 (d, 1H, J=9.1 Hz), 7.86-7.83 (m, 1H), 7.66 (dd, 1H, J=8.7, 8.7 Hz), 7.57 (d, 1H, J=7.6 Hz), 7.45-7.42 (m, 2H), 7.14 (d, 1H, J=4.5 Hz); MS(ESI$^+$): m/z 336.20 (M+H)$^+$.

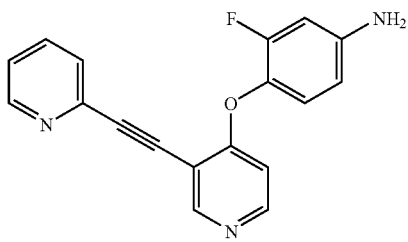

B) 3-Fluoro-4-(3-(2-(pyridin-2-yl)ethynyl)pyridin-4-yloxy)benzenamine

The title compound was prepared from 2-(2-(4-(2-fluoro-4-nitrophenoxy)pyridin-3-yl)ethynyl)pyridine (30 mg, 0.090 mmol) in a manner similar to that of Step E of Example 35 to give the title compound (20 mg) as a brown solid. MS(ESI$^+$): m/z 306.20 (M+H)$^+$.

C) 1-(3-Fluoro-4-(3-(2-(pyridin-2-yl)ethynyl)pyridin-4-yloxy)phenyl)-3-(2-(4-fluorophenyl)acetyl) urea, dihydrochloride salt The title compound was prepared from 3-fluoro-4-(3-(2-(pyridin-2-yl)ethynyl)pyridin-4-yloxy)benzenamine (19 mg, 0.062 mmol) and 0.3 M solution of 2-(4-fluorophenyl)acetyl isocyanate in toluene (Compound D of Example 11, 0.50 mL, 0.15 mmol) in a manner similar to that of Step D of Example 33. Purification of the reaction mixture by flash chromatography on SiO$_2$ eluting with 0-100% EtOAc/CH$_2$Cl$_2$ gave a white solid which was converted to the hydrochloride in a manner similar to Step D of Example 33 to give the title compound (19 mg, 60%) as a white solid. $^1$H NMR (DMSO-d$_6$) δ 11.07 (s, 1H), 10.61 (s, 1H), 8.79 (s, 1H), 8.63 (d, 1H, J=5.6 Hz), 8.47 (d, 1H, J=5.6 Hz), 7.89-7.86 (m, 1H), 7.83 (dd, 1H, J=1.5, 12.7 Hz), 7.67 (d, 1H, J=7.6 Hz), 7.47-7.43 (m, 2H), 7.39-7.35 (m, 1H), 7.30-7.27 (m, 1H), 7.20-7.16 (m, 2H), 7.14-7.10 (m, 1H), 6.77 (d, 1H, J=5.6 Hz), 3.75 (s, 2H); MS(ESI$^+$): m/z 485.17 (M+H)$^+$.

Example 47

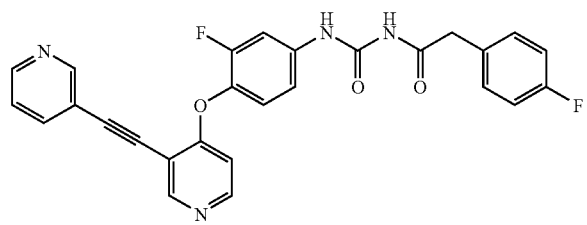

1-(3-Fluoro-4-(3-(2-(pyridin-3-yl)ethynyl)pyridin-4-yloxy)phenyl)-3-(2-(4-fluorophenyl)acetyl)urea, dihydrochloride salt

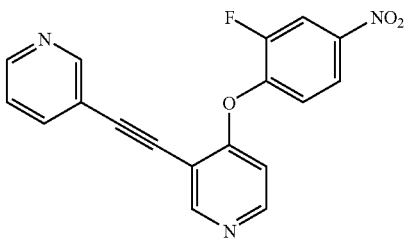

A) 3-(2-(4-(2-Fluoro-4-nitrophenoxy)pyridin-3-yl) ethynyl)pyridine

A mixture of 4-(2-fluoro-4-nitrophenoxy)-3-iodopyridine (Compound A of Example 33, 50 mg, 0.14 mmol) and 3-ethynylpyridine (57 mg, 0.54 mmol), THF (1 mL) and Et$_3$N (1 mL) was degassed by vacuum/argon purge and treated in turn with CuI (3 mg, 0.016 mmol), and (Ph$_3$P)$_4$Pd (10 mg, 0.009 mmol). The mixture was heated at 60° C. 45 minutes, cooled, partitioned between EtOAc and saturated sodium bicarbonate and the EtOAc phase dried (MgSO$_4$) and concentrated in vacuo. Purification of the residue by flash chromatography on SiO$_2$ eluting with 0-1.5% MeOH/CH$_2$Cl$_2$ gave the title compound (33 mg, 77%) as a brown solid. $^1$H NMR (DMSO-d$_6$) δ 8.86 (s, 1H), 8.65 (s, 1H), 8.61-8.57 (m, 2H), 8.45 (dd, 1H, J=2.6, 10.7 Hz), 8.18 (d, 1H, J=9.2 Hz), 7.90 (d, 1H, J=9.2 Hz), 7.62 (dd, 1H, J=8.7, 8.7 Hz), 7.46 (dd, 1H, J=4.6, 8.1 Hz), 7.17 (d, 1H, J=5.6 Hz); MS(ESI$^+$): m/z 336.19 (M+H)$^+$.

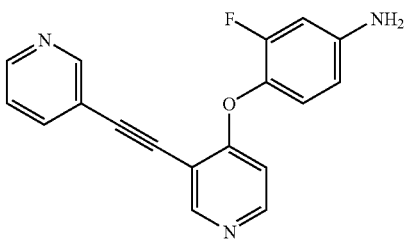

B) 3-Fluoro-4-(3-(2-(pyridin-3-yl)ethynyl)pyridin-4-yloxy)benzenamine

The title compound was prepared from 3-(2-(4-(2-fluoro-4-nitrophenoxy)pyridin-3-yl)ethynyl)pyridine (30 mg, 0.090 mmol) in a manner similar to Step E of Example 35 to give the title compound as a brown solid (25 mg, 93%). MS(ESI$^+$): m/z 306.20 (M+H)$^+$.

C) 1-(3-Fluoro-4-(3-(2-(pyridin-3-yl)ethynyl)pyridin-4-yloxy)phenyl)-3-(2-(4-fluorophenyl)acetyl) urea, dihydrochloride salt The title compound was prepared from 3-fluoro-4-(3-(2-(pyridin-3-yl)ethynyl)pyridin-4-yloxy)benzenamine (22 mg, 0.072 mmol) and 0.3 M solution of 2-(4-fluorophenyl)acetyl isocyanate in toluene (Compound D of Example 11, 0.50 mL, 0.15 mmol) in a manner similar to that of Step D of Example 33.

Purification of the reaction mixture by flash column chromatography on SiO$_2$ eluting with 0-100% EtOAc/CH$_2$Cl$_2$ gave a white solid which was converted to the hydrochloride in a manner similar to Step D of Example 33 to give the title compound (15 mg, 38%) as a white solid. $^1$H NMR (DMSO-d$_6$) δ 11.04 (s, 1H), 10.59 (s, 1H), 8.76 (s, 1H), 8.74 (d, 1H, J=1.1 Hz), 8.60 (dd, 1H, J=5.6, 1.1 Hz), 8.45 (d, 1H, J=6.1 Hz), 7.98 (d, 1H, J=7.7 Hz), 7.80 (d, 1H, J=12.1 Hz), 7.47-7.45 (m, 1H), 7.41 (s, 2H), 7.36-7.34 (m, 2H), 7.16 (dd, 2H, J=8.8, 8.9 Hz), 6.78 (d, 1H, J=5.5 Hz), 3.74 (s, 2H); MS(ESI$^+$): 485.13 m/z.

Example 48

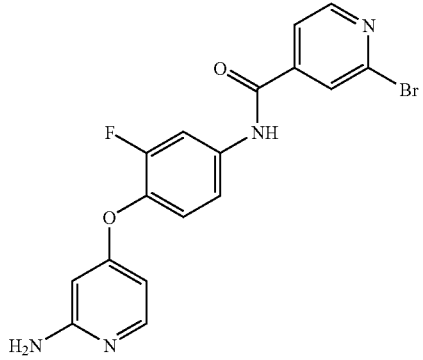

N-(4-(2-Aminopyridin-4-yloxy)-3-fluorophenyl)-2-bromoisonicotinamide, trifluoroacetic acid salt

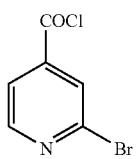

A) 2-Bromo-isonicotinicacyl chloride

A solution of 2-bromo-isonicotinic acid (Lancaster, 70 mg, 0.34 mmol) in thionyl chloride (1.2 mL) was heated at reflux temperature for 1.5 h. The mixture was concentrated and the crude product of 2-bromoisonicotinoyl chloride was used directly in the next step without further purification.

B) N-(4-(2-Aminopyridin-4-yloxy)-3-fluorophenyl)-2-bromoisonicotinamide

To the above residue was added a solution of 4-(4-amino-2-fluorophenoxy)pyridine-2-amine (Compound B of Example 24, 70 mg, 0.32 mmol) in CH$_2$Cl$_2$ (3 mL) at rt, and the reaction was stirred for 1 h. The reaction mixture was concentrated and the residue was purified by preparative HPLC to obtain the title compound (75 mg, 45%) as a yellow solid (TFA salt). $^1$H NMR (DMSO-d$_6$) δ 11.03 (s, 1H), 8.62 (d, 1H, J=5.0 Hz), 8.17 (s, 1H), 7.89-8.04 (m, 4H), 7.71 (d, 1H, J=8.8 Hz), 7.51 (t, 1H, J=9.3 Hz), 6.72 (dd, 1H, J=7.1, 2.2 Hz), 6.18 (d, 1H, J=2.2 Hz); MS(ESI$^+$) m/z 403, 405 (M+H)$^+$.

Example 49

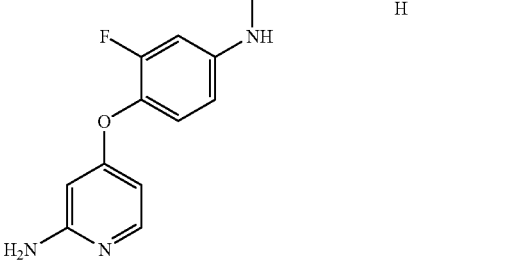

N-(4-(2-Aminopyridin-4-yloxy)-3-fluorophenyl)-2-(4-fluorophenylamino) isonicotinamide, bis-trifluoroacetic acid salt

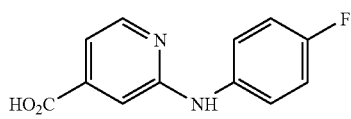

A) 2-(4-Fluorophenylamino)isonicotinic acid

To a mixture of 2-fluoro-isonicotinic acid (Aldrich, 423 mg, 3.0 mmol) and 4-fluoroaniline (555 mg, 5.0 mmol) in DMF (18 mL) at rt was added NaH (500 mg of 60% in oil), and the mixture was heated at 85° C. for 75 min. Acetic acid (0.7 mL) was added to the reaction mixture and it was concentrated in vacuo. To the residue were added EtOAc (100 mL) and water (20 mL), stirred for 20 min and the solid was filtered, washed with EtOAc and dried to obtain the desired product (600 mg, 50%) as a tan solid. $^1$H NMR (DMSO-d$_6$) δ 8.98 (s, 1H), 8.43 (s, 1H), 8.04 (d, 1H, J=4.9 Hz), 7.69 (dd, 2H, J=8.8, 4.9 Hz), 7.24 (s, 1H), 7.05 (dd, 2H, J=8.2, 6.0 Hz); MS(ESI$^+$) m/z 233.3 (M+H)$^+$.

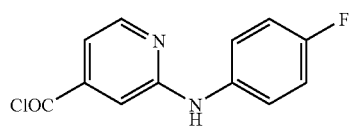

B) 2-(4-Fluorophenylamino)isonicotinicacyl chloride

A mixture of 2-(4-fluorophenylamino)isonicotinic acid (464 mg, 2.0 mmol) and thionyl chloride (10 mL) was heated at reflux temperature for 2 h. The reaction was concentrated in vacuo, and the crude product was used directly in the next step.

C) N-(4-(2-Aminopyridin-4-yloxy)-3-fluorophenyl)-2-(4-fluorophenylamino)isonicotinamide A solution of 4-(4-amino-2-fluorophenoxy)pyridine-2-amine (Compound B of Example 24, 450 mg, 2.1 mmol) in 1,2-dichloroethane (10 mL) was added slowly to a solution of acylchloride obtained above in 1,2-dichloroethane (10 mL) at ice bath temperature with stirring. The reaction mixture was allowed to stand at rt overnight. To the reaction mixture were added EtOAc (150 mL) and saturated aq. NaHCO$_3$ solution (50 mL). The EtOAc layer was separated, dried over MgSO$_4$ and concentrated in vacuo. The residue was purified by preparative HPLC to obtain the title compound (69 mg, 6.3%) as a yellow solid (bis-TFA salt). $^1$H NMR (DMSO-d$_6$) δ 10.90 (s, 1H), 9.32 (s, 1H), 8.27 (d, 1H, J=5.5 Hz), 7.92-7.07 (m, 11H), 6.68 (dd, 1H, J=7.1, 2.2 Hz), 6.10 (d, 1H, J=2.2 Hz); MS(ESI$^+$) m/z 217.9 (M+H)$^+$.

Example 50

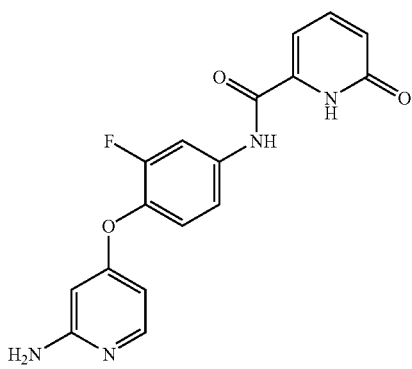

N-(4-(2-Aminopyridin-4-yloxy)-3-fluorophenyl)-6-oxo-1,6-dihydropyridine-2-carboxamide, trifluoroacetic acid salt To a solution of 6-hydroxypicolinic acid (Aldrich, 28 mg, 0.20 mmol) and HOBt (28 mg, 0.21 mmol) in DMF (2 mL) at rt was added EDCI.HCl (50 mg, 0.26 mmol) followed by 4-(4-amino-2-fluorophenoxy)pyridine-2-amine (Compound B of Example 24, 42 mg, 0.19 mmol), and the reaction mixture was stirred overnight at rt. Purification of the reaction mixture by preparative HPLC afforded the desired product (24 mg, 25%) as a light brown solid (TFA salt). $^1$H NMR (CD$_3$OD) δ 8.03 (dd, 1H, J=12.6, 2.2 Hz), 7.79-7.36 (m, 5H), 6.85 (d, 1H, J=8.8 Hz), 6.67 (dd, 1H, J=7.2, 4.4 Hz), 6.22 (d, 1H, J=2.2 Hz); MS(ESI$^+$) m/z 341.3 (M+H)$^+$.

Example 51

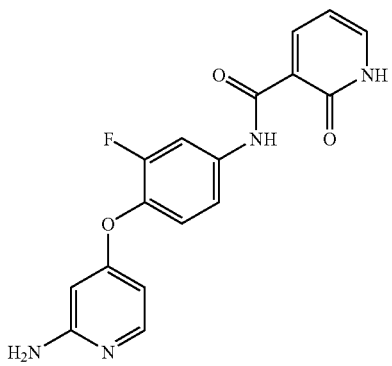

N-(4-(2-aminopyridin-4-yloxy)-3-fluorophenyl)-2-oxo-1,2-dihydropyridine-3-carboxamide, trifluoroacetic acid salt To a solution of 2-hydroxynicotinic acid (Aldrich, 42 mg, 0.30 mmol) and HOBt (18 mg) in DMF (2 mL) at rt was added EDCI.HCl (80 mg, 0.42 mmol) followed by 4-(4-amino-2-fluorophenoxy)pyridine-2-amine (Compound B of Example 24, 65 mg, 0.30 mmol), and the reaction mixture was stirred for 20 h at rt. Purification of the reaction mixture by preparative HPLC afforded the desired product (70 mg, 49%) as a beige-colored solid (TFA salt). $^1$H NMR (CD$_3$OD) δ 8.59 (dd, 1H, J=7.1, 2.2 Hz), 8.03 (dd, 1H, J=12.6, 2.2 Hz), 7.83 (d, 1H, J=7.7 Hz), 7.75 (dd, 1H, J=6.6, 2.2 Hz), 7.44 (d, 1H, J=8.8 Hz), 7.32 (t, 1H, J=8.8 Hz), 6.67 (m, 2H), 6.21 (d, 1H, J=2.2 Hz); MS(ESI$^+$) m/z 341.2 (M+H)$^+$.

Example 52

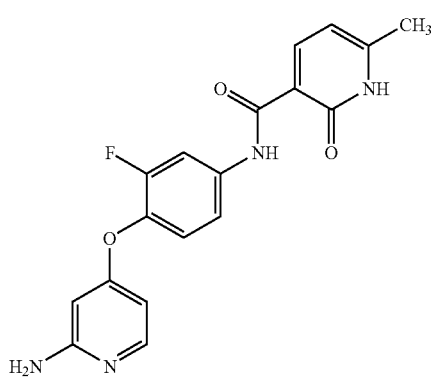

N-(4-(2-Aminopyridin-4-yloxy)-3-fluorophenyl)-6-methyl-2-oxo-1,2-dihydropyridine-3-carboxamide, trifluroacetic acid salt To a solution of 2-hydroxy-6-methylnicotinic acid (Lancaster, 72 mg, 0.47 mmol) and HOBt (50 mg) in DMF (5 mL) at rt was added EDCI.HCl (130 mg, 0.68 mmol) followed by 4-(4-amino-2-fluorophenoxy)pyridine-2-amine (Compound B of Example 24, 110 mg, 0.50 mmol), and the reaction mixture was stirred at rt over 72 h. Purification of the reaction mixture by preparative HPLC afforded the desired product (125 mg, 55%) as a beige-colored solid (TFA salt). $^1$H NMR (CD$_3$OD) δ 8.46 (d, 1H, J=7.9 Hz), 8.03 (dd, 1H, J=12.7, 2.8 Hz), 7.83 (d, 1H, J=7.1 Hz), 7.44 (dd, 1H, J=8.8, 2.2 Hz), 7.33 (t, 1H, J=8.8 Hz), 6.67 (dd, 1H, J=7.7, 2.7 Hz), 6.45 (d, 1H, J=7.7 Hz), 6.21 (d, 1H, J=2.8 Hz), 2.40 (s, 3H); MS(ESI$^+$) m/z 355.2 (M+H)$^+$.

Example 53

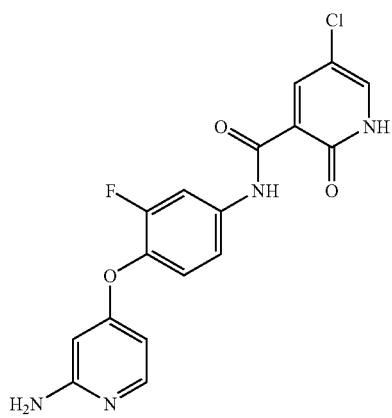

N-(4-(2-Aminopyridin-4-yloxy)-3-fluorophenyl)-5-chloro-2-oxo-1,2-dihydropyridine-3-carboxamide, trifluoroacetic acid salt To a solution of 2-hydroxy-5-chloronicotinic acid (Avocado, 87 mg, 0.50 mmol) and HOBt (40 mg) in DMF (4 mL) at rt was added EDCI.HCl (130 mg, 0.68 mmol) followed by 4-(4-amino-2-fluorophenoxy)pyridine-2-amine (Compound B of Example 24, 110 mg, 0.50 mmol), and the reaction mixture was stirred for 72 h. Purification of the reaction mixture by preparative HPLC afforded the desired product (115 mg, 45%) as a beige-colored solid (TFA salt). $^1$H NMR (CD$_3$OD) δ 8.50 (d, 1H, J=3.3 Hz), 8.03 (dd, 1H, J=12.6, 2.1 Hz), 7.84 (m, 2H), 7.46 (d, 1H, J=8.8 Hz), 7.34 (t, 1H, J=8.8 Hz), 6.67 (dd, 1H, J=7.2, 2.2 Hz), 6.21 (d, 1H, J=2.2 Hz); MS(ESI$^+$) m/z 375.1, 377.1 (M+H)$^+$.

Example 54

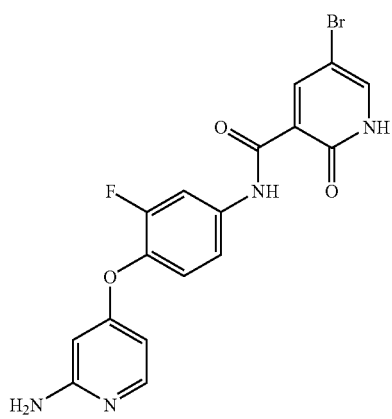

N-(4-(2-Aminopyridin-4-yloxy)-3-fluorophenyl)-5-bromo-2-oxo-1,2-dihydropyridine-3-carboxamide, trifluoroacetic acid salt To a solution of 2-hydroxy-5-bromo-nicotinic acid (147 mg, 0.67 mmol, Syn. Comm., 1989, 19, 553-559) and HOBt (30 mg) in DMF (4 mL) at rt was added EDCI.HCl (160 mg, 0.83 mmol) followed by 4-(4-amino-2-fluorophenoxy)pyridine-2-amine (Compound B of Example 24, 147 mg, 0.67 mmol), and the reaction mixture was stirred at rt overnight. Purification of the reaction mixture by preparative HPLC afforded the title compound (120 mg, 33%) as a beige-colored solid (TFA salt). $^1$H NMR (DMSO-d$_6$) δ 13.22 (s, 1H), 12.23 (s, 1H), 8.40 (d, 1H, J=2.8 Hz), 8.14 (d, 1H, J=2.8 Hz), 8.12-7.46 (m, 5H), 6.68 (dd, 1H, J=7.2, 2.2 Hz), 6.14 (d, 1H, J=2.2 Hz); MS(ESI$^+$) m/z 419/421 (M+H)$^+$.

Example 55

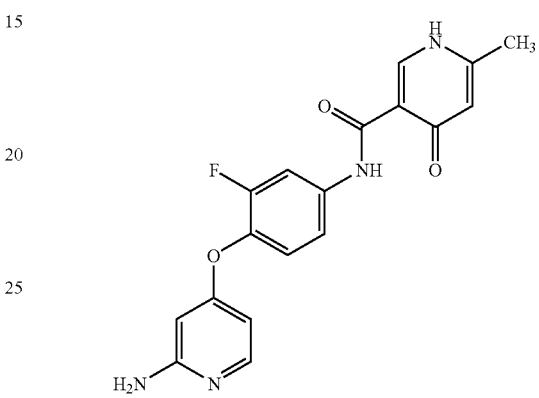

N-(4-(2-Aminopyridin-4-yloxy)-3-fluorophenyl)-6-methyl-4-oxo-1,4-dihydropyridine-3-carboxamide, trifluoroacetic acid salt To a solution of 4-hydroxy-6-methyl-nicotinic acid (Wako, 77 mg, 0.50 mmol) and HOBt (50 mg) in DMF (5 mL) at rt was added EDCI.HCl (130 mg, 0.68 mmol) followed by 4-(4-amino-2-fluorophenoxy)pyridine-2-amine (Compound B of Example 24, 110 mg, 0.50 mmol), and the reaction mixture was stirred at rt overnight, and then heated at 75° C. for 1.5 h. After cooling the reaction mixture to rt purification by preparative HPLC afforded the title compound (70 mg, 29%) as a white solid (TFA salt). $^1$H NMR (DMSO-d$_6$) δ 13.22 (br s, 1H), 12.53 (s, 1H), 8.47 (d, 1H, J=5.5 Hz), 8.04 (d, 1H, J=2.2 Hz), 7.95 (d, 1H, J=8.2 Hz), 7.82 (s, 2H), 7.46-7.42 (m, 2H), 6.70 (dd, 1H, J=7.7, 2.7 Hz), 6.39 (s, 1H), 6.14 (d, 1H, J=2.2 Hz); MS(ESI+) m/z 355.3 (M+H)$^+$.

Example 56

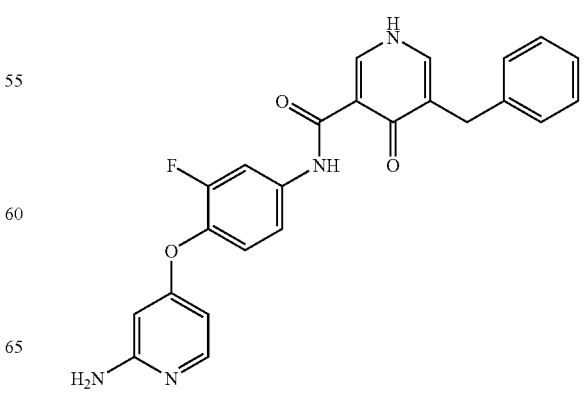

N-(4-(2-Aminopyridin-4-yloxy)-3-fluorophenyl)-5-benzyl-4-oxo-1,4-dihydropyridine-3-carboxamide, trifluoroacetic acid salt

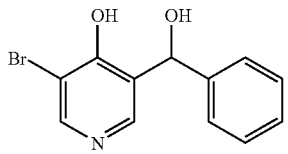

A) 3-Bromo-5-(hydroxy(phenyl)methyl)pyridin-4-ol

To a heterogeneous mixture of 3,5-dibromo-4-hydroxypyridine (2.53 g, 10 mmol, prepared following the procedure in *Synthesis,* 2001, 14, 2175-2179) in anhydrous THF (20 mL) at −78° C. under Ar-atm was added phenylmagnesium bromide solution (11 mL of 1 M solution in THF, 11 mmol). After stirring for 15 min. was added n-BuLi solution (5.5 mL of 2 M solution in cyclohexane), and the reaction mixture was stirred for 15 min at −78° C. under Ar-atm. To this mixture benzaldehyde (2.15 mL) was added and the reaction mixture was stirred for 2 h −78° C. under Ar-atm. The reaction mixture was quenched by adding HOAc (3 mL) and TFA (3 mL), concentrated in vacuo and the residue was purified by flash column chromatography on silica gel eluting with hexane/EtOAc/MeOH//750:250:50 followed by hexane/EtOAc/MeOH/Et$_3$N//460:460:50:10 to afford the desired product (2.85 g, 91%) as a white solid. $^1$H NMR (CD$_3$OD) δ 8.13 (s, 1H), 8.04 (s, 1H), 7.41-7.20 (m, 5H), 5.94 (s, 1H); MS(ESI$^+$) m/z 280, 282 (M+H)$^+$.

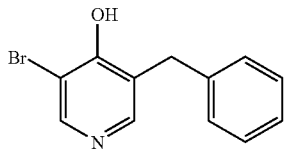

B) 3-Benzyl-5-bromopyridin-4-ol

A mixture of 3-bromo-5-(hydroxy(phenyl)methyl)pyridin-4-ol (2.55 g, 91 mmol), TFA (16 mL) and Et$_3$SiH in CH$_2$Cl$_2$ (30 mL) was stirred at rt for 10 h. The reaction mixture was concentrated in vacuo and the residue was purified by flash column chromatography on silica gel eluting with hexane/EtOAc/MeOH//600:300:50 followed by hexane/EtOAc/MeOH 11400:400:50:10 to afford an impure product which was triturated with a small amount of MeOH and Et$_2$O to obtain the desired product (255 mg, 10%) as a white solid. $^1$H NMR (DMSO-d$_6$) δ 11.75 (br s, 1H), 8.13 (s, 1H), 7.54 (s, 1H), 7.26-7.14 (m, 5H), 2.49 (s, 2H).

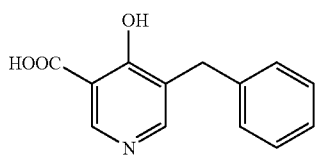

C) 5-Benzyl-4-hydroxynicotinic acid

To a solution of 3-benzyl-5-bromopyridin-4-ol (220 mg, 0.83 mmol) in anhydrous THF (8 mL) at −78° C. under Ar-atm was added MeLi solution (0.61 mL of 1.5 M solution in THF, 0.92 mmol). After stirring for 5 min. n-BuLi solution (0.5 mL of 2 M solution in cyclohexane, 1.0 mmol) was added and the mixture was stirred for 15 min at −78° C. under Ar-atm. Carbon dioxide was bubbled through the reaction mixture for 20 min at −78° C. The reaction mixture was then quenched by adding HOAc (2 mL), concentrated in vacuo and the residue was purified by by preparative HPLC to afford the desired product (100 mg, 35%) as a white solid (TFA salt). $^1$H NMR (DMF-d$_7$) δ 12.99 (br s, 1H), 8.69 (s, 1H), 8.28 (s, 1H), 7.35-7.19 (m, 5H), 3.90 (s, 2H); MS(ESI$^+$) m/z 230.1 (M+H)$^+$.

D) N-(4-(2-Aminopyridin-4-yloxy)-3-fluorophenyl)-5-benzyl-4-oxo-1,4-dihydropyridine-3-carboxamide, trifluoroacetic acid salt To a solution of 4-hydroxy-5-benzylnicotinic acid (35 mg, 0.15 mmol) and HOBt (30 mg) in DMF (2.5 mL) at rt was added EDCI.HCl (80 mg, 0.42 mmol) followed by 4-(4-amino-2-fluorophenoxy)pyridine-2-amine (Compound B of Example 24, 35 mg, 0.16 mmol), and the reaction mixture was stirred for 40 h at rt. Purification of the reaction mixture by preparative HPLC afforded the desired product (35 mg, 43%) as a white TFA solid salt. $^1$H NMR (DMSO-d$_6$) δ 13.25 (br s, 1H), 12.44 (s, 1H), 8.59 (d, 1H, J=4.9 Hz), 8.08 (dd, 1H, J=13.2, 2.2 Hz), 7.97 (d, 1H, J=7.1 Hz), 7.81 (d, 1H, J=9.4 Hz), 7.52-7.19 (m, 7H), 6.72 (dd, 1H, J=7.2, 2.2 Hz), 6.15 (d, 1H, J=2.5 Hz), 3.81 (s, 2H), 3.51 (br s, 2H); MS(ESI$^+$) m/z 431.2 (M+H)$^+$.

Example 57

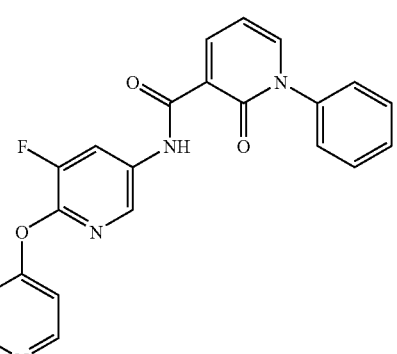

121

N-(4-(2-Aminopyridin-4-yloxy)-3-fluorophenyl)-2-oxo-1-phenyl-1,2-dihydropyridine-3-carboxamide, trifluoroacetic acid salt

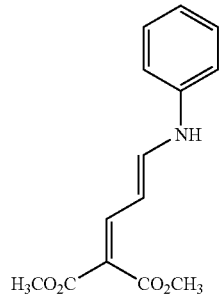

A) (E)-Dimethyl 2-(3-(phenylamino)allylidene)malonate

To a solution of 2-(3-methoxyallylidene)malonic acid dimethyl ester (Acros Organics, 200 mg, 1.0 mmol) in THF (2 mL) at rt was added aniline (300 mg, 3.2 mmol) and the reaction mixture was heated at 60° C. for 8.5 h. Purification of the reaction mixture by preparative HPLC provided the desired product (150 mg, 57%) as a yellow solid. $^1$H NMR (DMSO-$d_6$) δ 10.16 (d, 1H, J=12.7 Hz), 8.06 (t, 1H, J=12.7 Hz), 7.74 (d, 1H, J=12.7 Hz), 7.30 (t, 2H, J=8.7 Hz), 7.16 (d, 2H, J=7.7 Hz), 6.98 (t, 1H, J=7.7 Hz), 6.35 (t, 1H, J=12.1 Hz), 3.69 (s, 3H), 3.65 (s, 3H).

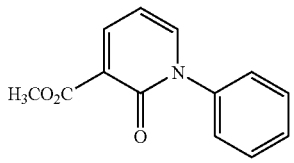

B) Methyl 2-oxo-1-phenyl-1,2-dihydropyridine-3-carboxylate

To a solution of the aniline adduct obtained above (130 mg, 0.50 mmol) in methanol (8 mL) at rt was added NaH (50 mg of the 60% NaH in oil, 1.2 mmol) and the mixture was stirred at rt for 3 h. Acetic acid (0.3 mL) was added to the mixture, concentrated to a volume of ~4 mL, and purification of the reaction mixture by preparative HPLC provided the desired product (105 mg, 92%) as a yellow solid. $^1$H NMR (CD$_3$OD) δ 8.30 (dd, 1H, J=7.2, 2.2 Hz), 7.87 (dd, 1H, J=6.6, 1.7 Hz), 7.57-7.38 (m, 5H), 6.53 (t, 1H, J=7.0 Hz), 3.84 (s, 3H); MS(ESI$^+$) m/z 230.3 (M+H)$^+$.

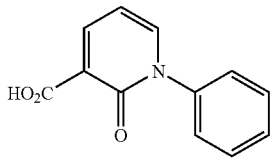

122

C) 2-Oxo-1-phenyl-1,2-dihydropyridine-3-carboxylic acid

A mixture of methyl 2-oxo-1-phenyl-1,2-dihydropyridine-3-carboxylate (70 mg, 0.31 mmol) and LiOH (40 mg) in methanol (6 mL) and water (1 mL) was stirred at rt overnight. To the reaction mixture were added EtOAc (50 mL) and 1 N aq HCl (15 mL). The EtOAc layer was separated, dried over MgSO$_4$, and concentrated in vacuo to afford the product (55 mg, 83%) as a light yellow solid. $^1$H NMR (DMF-$d_7$) δ 11.77 (br s, 1H), 8.57 (dd, 1H, J=7.4, 2.0 Hz), 8.26 (dd, 1H, J=6.6, 1.6 Hz), 7.64-7.55 (m, 5H), 6.88 (t, 1H, J=7.0 Hz); MS(ESI$^+$) m/z 216.2 (M+H)$^+$.

D) N-(4-(2-Aminopyridin-4-yloxy)-3-fluorophenyl)-2-oxo-1-phenyl-1,2-dihydropyridine-3-carboxamide To a solution of 2-oxo-1-phenyl-1,2-dihydropyridine-3-carboxylic acid (36 mg, 0.17 mmol) and HOBt (18 mg) in DMF (3 mL) at rt was added EDCI.HCl (45 mg, 0.23 mmol) followed by 4-(4-amino-2-fluorophenoxy)pyridine-2-amine (Compound B of Example 24, 36 mg, 0.17 mmol), and the reaction mixture was stirred at rt overnight. Purification of the reaction mixture by preparative HPLC afforded the title compound (32 mg, 36%) as a beige colored solid (TFA salt). $^1$H NMR (DMSO-$d_6$) δ 13.35 (br s, 1H), 12.11 (s, 1H), 8.52 (dd, 1H, J=7.3, 2.1 Hz), 8.08 (dd, 1H, J=6.6, 2.1 Hz), 8.03 (d, 1H, J=2.3 Hz), 7.89 (d, 1H, J=7.2 Hz), 7.81 (s, 1H), 7.54-7.36 (m, 6H), 6.69-6.63 (m, 2H), 6.08 (d, 1H, J=2.4 Hz), 3.55 (br s, 1H); MS(ESI$^+$) m/z 417.2 (M+H)$^+$.

Example 58

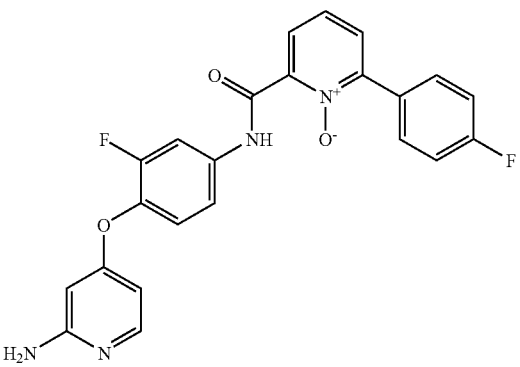

N-(4-(2-Aminopyridin-4-yloxy)-3-fluorophenyl)-6-(4-fluorophenyl)pyridyl-N-oxide-amide, trifluoroacetic acid salt

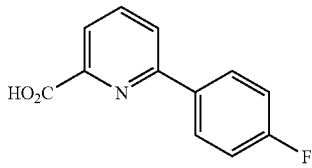

A) 6-(4-Fluorophenyl)picolinic acid

A solution of 2-bromo-picolinic acid (Aldrich, 2.02 g, 10 mmol) in DME containing 4 mL of 10% aq $Na_2CO_3$ was purged with Ar gas. To this mixture was added $Pd(PPh_3)_4$ followed by 2-(4-fluorophenyl)-5,5-dimethyl-1,3,2-dioxaborinane (Aldrich, 2.40 g, 11.5 mmol) and EtOH (20 mL), and the mixture was purged with Ar gas. The reaction mixture was heated at 100° C. for 2.5 h in a sealed tube. Additional 2-bromo-picolinic acid (900 mg) and $Pd(PPh_3)_4$ was added, and after purging with Ar gas it was heated at 100° C. for 4.5 h. Trifluoroacetic acid (20 mL) was added to the reaction and the mixture was concentrated in vacuo. MeOH (150 mL) was added to the residue and the insoluble material was filtered, and the filtrate solution was concentrated in vacuo. Purification of the resulting residue by flash column chromatography on silica gel eluting with EtOAc/MeOH//900:100 followed by EtOAc/MeOH/HOAc//700:1500:50 provided the desired product (1.0 g, 40% based on borinane starting material) as a white solid. $^1H$ NMR ($CD_3OD$) δ 8.01 (d, 1H, J=7.7 Hz), 7.94-7.87 (m, 3H), 7.73 (d, 1H, J=7.7 Hz), 7.13 (t, 2H, J=8.8 Hz); MS($ESI^+$) m/z 234 (M+H)$^+$.

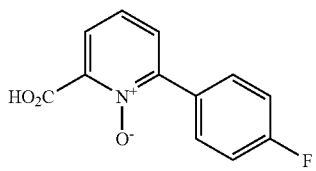

B) 6-(4-Fluorophenyl)picolinic acid-N-oxide

A mixture of picolinic acid derivative (1.0 g, 4.6 mmol), $Na_2HPO_4$ (1.2 g) and m-CPBA (1.1 g, ~70% from Aldrich) in $CH_2ClCH_2Cl$ (30 mL) was stirred at rt for 2 h. Additional $Na_2HPO_4$ (0.8 g) and m-CPBA (1.0 g) was added to the reaction mixture and it was stirred for 3 h at rt. Another $Na_2HPO_4$ (0.5 g) and m-CPBA (0.5 g) was added to the reaction mixture and it was stirred at rt overnight. $CHCl_3$ (160 mL) and 2 N aq. HCl solution (50 mL) were added to the reation mixture and the organic layer was separated, dried over $MgSO_4$ and concentrated in vacuo. The residue was purified by flash column chromatography on silica gel eluting with EtOAc/MeOH/HOAc//700:240:60 to obtain the desired product which was contaminated with m-CPBA. This impure material was purified by preparative HPLC to obtain the desired product (175 mg, 16%) as a white solid. $^1H$ NMR (DMF-$d_7$) 8.45 (dd, 1H, J=8.3, 2.2 Hz), 8.15 (d, 1H, J=2.2 Hz), 8.13-8.00 (m, 4H), 7.45 (t, 2H, J=8.7 Hz).

C) N-(4-(2-Aminopyridin-4-yloxy)-3-fluorophenyl)-6-(4-fluorophenyl)pyridyl-N-oxide-amide, trifluoroaacetic acid salt To a solution of 6-(4-fluorophenyl)picolinic acid-N-oxide (23 mg, 0.1 mmol) and HOBt (10 mg) in DMF (2 mL) at rt was added EDCI.HCl (30 mg, 0.16 mmol) followed by 4-(4-amino-2-fluorophenoxy)pyridine-2-amine (Compound B of Example 24, 22 mg, 0.1 mmol), and the reaction mixture was stirred at rt overnight. Purification of the reaction mixture by preparative HPLC afforded the title compound (25 mg, 46%) as a white solid (TFA salt). $^1H$ NMR (DMF-$d_7$) δ 14.00 (s, 1H), 8.43 (dd, 1H, J=8.0, 2.2 Hz), 8.15 (d, 1H, J=12.8, 2.4 Hz), 8.08 (d, 1H, J=7.1 Hz), 7.99-7.37 (m, 9H), 6.72 (dd, 1H, J=7.0, 2.4 Hz), 6.32 (d, 1H, J=2.3 Hz), 3.7 (br s, 2H); MS($ESI^+$) m/z 417.2 (M+H)$^+$.

Example 59

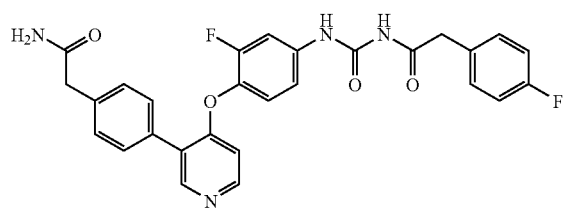

1-(4-(3-(4-(2-Amino-2-oxoethyl)phenyl)pyridin-4-yloxy)-3-fluorophenyl)-3-(2-(4-fluorophenyl)acetyl)urea, hydrochloride salt

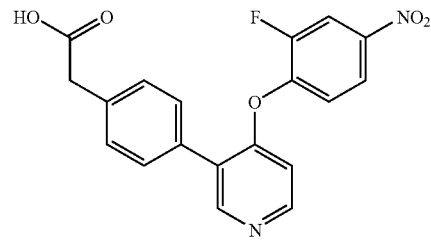

A) 2-(4-(4-(2-Fluoro-4-nitrophenoxy)pyridin-3-yl)phenyl)acetic acid

A 25 mL round bottom flask was charged with 4-(2-fluoro-4-nitrophenoxy)-3-iodopyridine (Compound A of Example 33, 120 mg, 0.33 mmol), 2-(4-(4,4,5,5-tetramethyl-1,3,2-dioxaborolan-2-yl)phenyl)acetic acid (Frontier Scientific, 131 mg, 0.50 mmol), tetrakis(triphenylphosphine)palladium(0) (Strem Chemicals, 38 mg, 0.033 mmol), and sodium carbonate (245 mg, 2.3 mmol). The flask was flushed with nitrogen and then charged with dioxane and water (1 mL each). After stirring at 80° C. for 10 h, the mixture was cooled to room temperature and then concentrated in vacuo. The crude product was purified by flash column chromatography on silica gel (30% MeOH/EtOAc) to give the title compound (120 mg, 99%) as a white solid. $^1H$ NMR ($CD_3OD$) δ 8.61 (s, 1H), 8.48 (d, 1H, J=5.6 Hz), 8.22 (dd, 1H, J=10.4, 2.8 Hz), 8.14-8.11 (m, 1H), 7.54 (d, 2H, J=8.1 Hz), 7.41 (d, 2H, J=8.0 Hz), 7.40 (m, 1H), 7.05 (d, 1H, J=5.7 Hz), 3.56 (s, 2H); MS($ESI^+$) m/z 369.16 (M+H)$^+$.

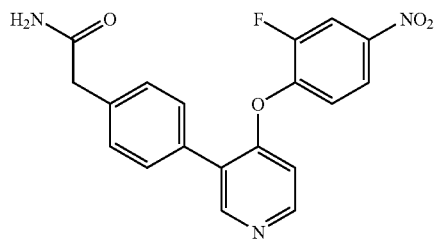

B) 2-(4-(4-(2-Fluoro-4-nitrophenoxy)pyridin-3-yl)phenyl)acetamide

A 25 mL round bottom flask was charged with 2-(4-(4-(2-fluoro-4-nitrophenoxy)pyridin-3-yl)phenyl)acetic acid (50 mg, 0.136 mmol), HOBT (46 mg, 0.34 mmol), and EDCI (65 mg, 0.34 mmol). The flask was flushed with nitrogen and then DMF was added (1 mL). After stirring at rt for 1 h, the solution was cooled to 0° C. and then charged with ammonium hydroxide (0.5 mL). The reaction was stirred at 0° C. for 1 h and was then diluted with brine (5 mL) and extracted with ethyl acetate (3×5 mL). The combined organic extracts were dried over anhydrous $Na_2SO_4$ and concentrated in vacuo. The crude product was purified by flash column chromatography on silica gel (20% MeOH/EtOAc) to give the title compound (33 mg, 66%) as a colorless oil. $^1$H NMR ($CD_3OD$) δ 8.49 (s, 1H), 8.38 (d, 1H, J=5.6 Hz), 8.10 (dd, 1H, J=10.4, 2.4 Hz), 7.99 (m, 1H), 7.45 (d, 2H, J=8.2 Hz), 7.30 (d, 2H, J=8.2 Hz), 7.28 (m, 1H), 6.93 (d, 1H, J=5.6 Hz), 3.44 (s, 2H); MS(ESI$^+$) m/z 368.18 (M+H)$^+$.

C) 1-(4-(3-(4-(2-Amino-2-oxoethyl)phenyl)pyridin-4-yloxy)-3-fluorophenyl)-3-(2-(4-fluorophenyl)acetyl)urea A solution of 2-(4-(4-(2-flouro-4-nitrophenoxy)pyridin-3-yl)phenyl)acetamide (33 mg, 0.09 mmol) in THF (0.8 mL) and methanol (1.2 mL) was treated with Zn dust (59 mg, 0.9 mmol) followed by ammonium chloride (48 mg, 0.9 mmol). The mixture was stirred at rt for 4 h and was then filtered through a thin pad of Celite® with methanol. The filtrate was concentrated and the residue partitioned between EtOAc and saturated aqueous sodium bicarbonate solution. The EtOAc phase was dried over anhydrous $Na_2SO_4$ and concentrated in vacuo to give the crude product (25 mg, 82%) as a yellow oil which was sufficiently pure to use in the next step without further purification. $^1$H NMR ($CD_3OD$) δ 8.33 (s, 1H), 8.19 (d, 1H, J=5.6 Hz), 7.49 (d, 2H, J=8.1 Hz), 7.32 (d, 2H, J=8.2 Hz), 6.82 (t, 1H, J=8.8 Hz), 6.61 (d, 1H, J=5.6 Hz), 6.44 (qd, 1H, J=12.8, 2.8 Hz), 3.48 (s, 2H); MS(ESI$^+$)m/z 338.25 (M+H)$^+$.

The above amine was dissolved in THF (1 mL) and then charged with 2-(4-fluorophenyl)acetyl isocyanate (Compound D of Example 11, 250 uL, 0.074 mmol, 0.3 M in toluene). After stirring at rt for 1 h, the reaction was purified directly by flash chromatography on silica gel (10% MeOH/EtOAc) to give the title compound as a white solid. The solid was dissolved in dioxane (2 mL) and cooled to 0° C. Anhydrous HCl (2 mL, 1 N in ether) was added. After stirring at 0° C. for 5 min, the solution was concentrated in vacuo. The resulting HCl salt was lyophilized from acetonitrile/water to give the title compound (23 mg, 57%) as a white solid. $^1$H NMR (DMSO-$d_6$) δ 11.02 (s, 1H), 10.59 (s, 1H), 8.83 (s, 1H), 8.58 (d, 1H, J=6.4 Hz), 7.79 (dd, 1H, J=12.8, 2.4 Hz), 7.60 (d, 2H, J=8.4 Hz), 7.46-7.34 (m, 4H), 7.31-7.28 (m, 2H), 7.11 (t, 2H, J=8.7 Hz), 6.88 (d, 1H, J=5.6 Hz), 3.70 (s, 2H), 3.40 (s, 2H); MS(ESI$^+$) m/z 517.19 (M+H)$^+$.

Example 60

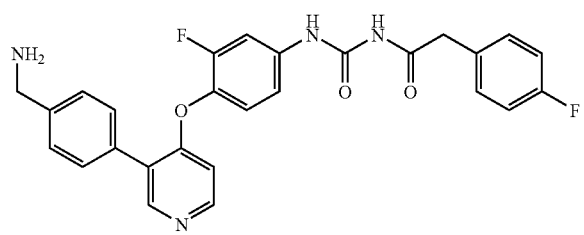

1-(4-(3-(4-(Aminomethyl)phenyl)pyridin-4-yloxy)-3-fluoro phenyl)-3-(2-(4-fluorophenyl)acetyl)urea, trifluoroacetic acid salt

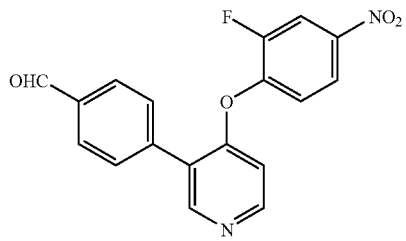

A) 4-(4-(2-Fluoro4-nitrophenoxy)pyridin-3-yl)benzaldehyde

Prepared in a similar manner as Step A of Example 59 to give the title compound (86%) as a colorless oil. $^1$H NMR ($CD_3OD$) δ 9.92 (s, 1H), 8.56 (s, 1H), 8.41 (d, 1H, J=6 Hz), 8.12 (dd, 1H, J=10.3, 2.6 Hz), 8.05-8.01 (m, 1H), 7.90 (d, 2H, J=8.3 Hz), 7.73 (d, 2H, J=8.2 Hz), 7.35 (t, 1H, J=8.4 Hz), 6.95 (d, 1H, J=6 Hz); MS(ESI$^+$) m/z 339.19 (M+H)$^+$.

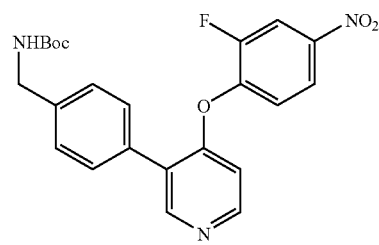

B) tert-Butyl 4-(4-(2-fluoro-4-nitrophenoxy)pyridin-3-yl)benzylcarbamate

To 4-(4-(2-fluoro-4-nitrophenoxy)pyridin-3-yl)benzaldehyde (81 mg, 0.24 mmol) in methanol (2 mL) was added ammonium acetate (185 mg, 2.4 mmol) followed by sodium cyanoborohydride (16 mg, 0.24 mmol). The reaction was stirred at rt for 4 h and was then concentrated in vacuo. The residue was dissolved in water (5 mL) and extracted with EtOAc (2×5 mL). The combined organic extracts were washed with saturated aqueous sodium bicarbonate solution, dried over anhydrous $Na_2SO_4$, and concentrated in vacuo. The crude product was dissolved in dichloromethane (2 mL) and then triethylamine (50 uL, 0.36 mmol), DMAP (spatula tip), and di-tert-butyl dicarbonate (Aldrich, 57 mg, 0.26 mmol) were added sequentially. The reaction was stirred at rt for 2 h and was then purified directly by flash column chromatography on silica gel (EtOAc) to give the title compound (13 mg, 12%) as a colorless oil. $^1$H NMR ($CD_3OD$) δ 8.50 (s, 1H), 8.37 (d, 1H, J=5.6 Hz), 8.09 (dd, 1H, J=6.1, 2.6 Hz), 8.01-7.99 (m, 1H), 7.45 (d, 2H, J=8 Hz), 7.26 (d, 2H, J=8.2 Hz), 7.25 (m, 1H), 6.95 (d, 1H, J=5.6 Hz), 4.16 (s, 2H), 1.35 (s, 9H); MS(ESI$^+$) m/z 440.19 (M+H)$^+$.

C) 1-(4-(3-(4-(Aminomethyl)phenyl)pyridin-4-yloxy)-3-fluorophenyl)-3-(2-(4-fluorophenyl)acetyl) urea Prepared in a similar manner as Step C of Example 59. After acylurea formation, 4 N HCl in dioxane (5 mL) was added. After stirring at rt for 5 min, the reaction was concentrated in vacuo. The residue was suspended in EtOAc, washed with saturated aqueous sodium bicarbonate solution, dried over anhydrous Na$_2$SO$_4$, and concentrated in vacuo. The crude material was purified by prep HPLC. The appropriate fractions were concentrated in vacuo to remove methanol. Toluene was added and then concentrated (2×5 mL). The resulting solid was lyophilized from acetonitrile/water to give the TFA salt of the title compound (6 mg, 25%) as a white solid. $^1$H NMR (DMSO-d$_6$) δ 11.00 (s, 1H), 10.53 (s, 1H), 8.55 (s, 1H), 8.40 (d, 1H, J=4 Hz), 7.73 (dd, 1H, J=12, 4 Hz), 7.67 (d, 2H, J=8 Hz), 7.51 (d, 2H, J=8 Hz), 7.34-7.27 (m, 4H), 7.13-7.09 (m, 2H), 6.73 (d, 1H, J=4 Hz), 4.03 (s, 2H), 3.68 (s, 2H); MS(ESI$^+$) m/z 489.18 (M+H)$^+$.

Example 61

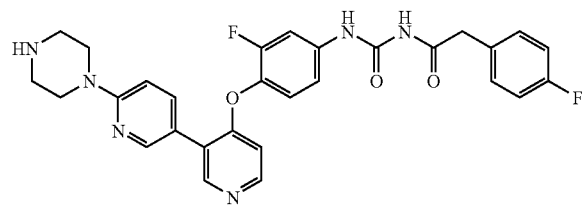

1-(3-Fluoro-4-(3-(6-(piperazin-1-yl)pyridin-3-yl) pyridin-4-yloxy)phenyl)-3-(2-(4-fluorophenyl) acetyl)urea, hydrochloride salt

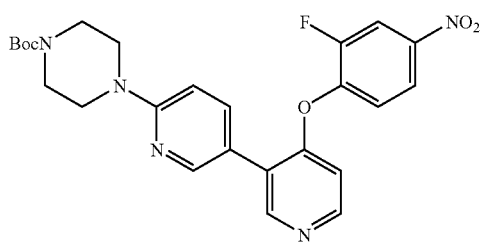

A) tert-Butyl 4-(5-(4-(2-fluoro-4-nitrophenoxy)pyridin-3-yl)pyridin-2-yl)piperazine-1-carboxylate Prepared in a similar manner as Step A of Example 59 to give the title compound (87%) as a colorless oil. $^1$H NMR (CD$_3$OD) δ 8.62 (s, 1H), 8.46 (d, 1H, J=6 Hz), 8.36 (d, 1H, J=2.4 Hz), 8.24 (dd, 1H, J=10.4, 2.8 Hz), 8.15-8.11 (m, 1H), 7.84 (dd, 1H, J=8.8, 2.4 Hz), 7.41 (t, 1H, J=8.4 Hz), 7.04 (d, 1H, J=5.6 Hz), 6.92 (d, 1H, J=8.8 Hz), 3.61-3.59 (m, 4H), 3.56-3.54 (m, 4H), 1.50 (s, 9H); MS(ESI$^+$) m/z 496.23 (M+H)$^+$.

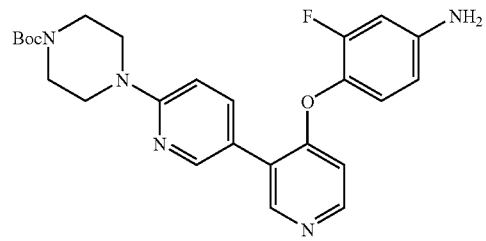

B) tert-Butyl 4-(5-(4-(4-amino-2-fluorophenoxy) pyridin-3-yl)pyridin-2-yl)piperazine-1-carboxylate Prepared in a similar manner as Step C of Example 59 to give the title compound (96%) as a colorless oil. $^1$H NMR (CD$_3$OD) δ 8.34 (s, 1H), 8.29 (d, 1H, J=2 Hz), 8.18 (d, 1H, J=6 Hz), 7.78 (dd, 1H, J=9.2, 2.8 Hz), 6.87-6.83 (m, 2H), 6.61 (d, 1H, J=5.6 Hz), 6.48 (dd, 1H, J=12.8, 2.8 Hz), 6.44-6.41 (m, 1H), 3.50-3.46 (m, 8H), 1.38 (s, 9H); MS(ESI$^+$) m/z 466.25 (M+H)$^+$.

C) 1-(3-Fluoro-4-(3-(6-(piperazin-1-yl)pyridin-3-yl) pyridin-4-yloxy)phenyl)-3-(2-(4-fluorophenyl) acetyl)urea Prepared in a similar manner as Step C of Example 59 to give the title compound (28%) as the HCl salt. $^1$H NMR (DMSO-d$_6$) δ 11.33 (s, 1H), 10.76 (s, 1H), 9.09 (s, 1H), 8.74 (d, 1H, J=6.8 Hz), 8.57 (d, 1H, J=2.4 Hz), 8.16 (dd, 1H, J=8.8, 2 Hz), 7.91 (dd, 1H, J=12.8, 2 Hz), 7.61 (t, 1H, J=8.8 Hz), 7.55-7.50 (m, 1H), 7.42-7.38 (m, 2H), 7.28 (d, 1H, J=6.5 Hz), 7.27-7.18 (m, 3H), 3.98 (m, 4H), 3.82 (s, 2H), 3.23 (m, 4H); MS(ESI$^+$) m/z 545.19 (M+H)$^+$.

Example 62

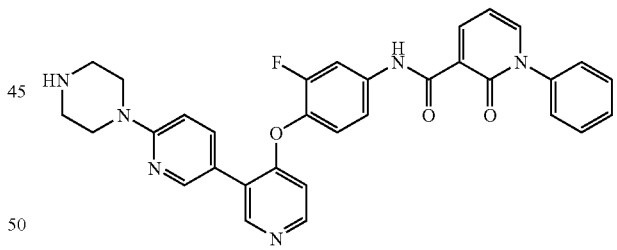

N-(3-Fluoro-4-(3-(6-(piperazin-1-yl)pyridin-3-yl) pyridin-4-yloxy)phenyl)-2-oxo-1-phenyl-1,2-dihydropyridine-3-carboxamide, hydrochloride salt To tert-butyl 4-(5-(4-(4-amino-2-fluorophenoxy)pyridin-3-yl)pyridin-2-yl)piperazine-1-carboxylate (Compound B of Example 61, 32 mg, 0.069 mmol) in THF/DMF (1 mL each) was added 2-oxo-1-phenyl-1,2-dihydropyridine-3-carboxylic acid (Compound C of Example 57, 15 mg, 0.069 mmol), DIPEA (60 uL, 0.35 mmol), then TBTU (Fluka, 33 mg, 0.10 mmol). After stirring at rt for 18 h, the reaction was diluted with EtOAc (5 mL), washed with 10% aqueous lithium chloride solution (2×5 mL) followed by saturated sodium bicarbonate solution (1×5 mL), dried over anhydrous Na$_2$SO$_4$, and concentrated in vacuo. The residue was suspended in ether, cooled to 0° C., and treated with 4 N HCl in dioxane (5 mL). The solution was allowed to warm to rt and then stirred at rt for 2 h. The solution was concentrated in vacuo and the resulting crude product was purified by prep HPLC. The appropriate fractions were concentrated to remove methanol and then made basic with saturated aqueous sodium bicarbonate solution. The aqueous solution was extracted with EtOAc (2×10 mL) and the pooled organic extracts were dried over anhydrous Na$_2$SO$_4$ and then concentrated in vacuo. The residue was dissolved in THF (2 mL), cooled to 0° C., and treated with 1N HCl in ether (0.5 mL). After stirring at 0° C. for 5 min, the mixture was concentrated. The resulting white solid was lyophilized from acetonitrile/water to give the HCl salt of the title compound (26 mg, 56%) as a pale yellow solid. $^1$H NMR (DMSO-d$_6$) δ 12.16 (s, 1H), 8.92 (s, 1H), 8.59 (d, 1H, J=6.4 Hz), 8.53 (dd, 1H, J=7.2, 2 Hz), 8.47 (d, 1H, J=2.4 Hz), 8.10 (dd, 1H, J=6.4, 2 Hz), 8.04 (d, 1H, J=12 Hz), 7.99 (dd, 1H, J=8.8, 2.4 Hz), 7.54-7.46 (m, 7H), 7.20 (d, 1H, J=6.4 Hz), 7.97 (d, 1H, J=9.2 Hz), 6.68 (t, 1H, J=6.8 Hz), 3.82-3.80 (m, 4H), 3.12 (m, 4H); MS(ESI$^+$) m/z 545.19 (M+H)$^+$.

Example 63

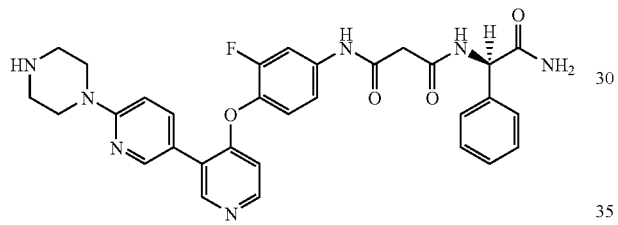

N$^1$-((R)-2-Amino-2-oxo-1-phenylethyl)-N$^3$-(3-fluoro-4-(3-(6-(piperazin-1-yl)pyridin-3-yl)pyridin-4-yloxy)phenyl)malonamide, hydrochloride salt To tert-butyl 4-(5-(4-(4-amino-2-fluorophenoxy)pyridin-3-yl)pyridin-2-yl)piperazine-1-carboxylate (Compound B of Example 61, 32 mg, 0.069 mmol) in THF (1 mL) was added DIPEA (60 uL, 0.35 mmol) then ethyl 3-chloro-3-oxopropanoate (Aldrich, 10 uL, 0.076 mmol). After stirring at rt for 2 h, the reaction was diluted with EtOAc (5 mL), washed with saturated aqueous sodium bicarbonate solution (1×5 mL), dried over anhydrous Na$_2$SO$_4$, and concentrated in vacuo. The resulting yellow oil (65 mg) was dissolved in THF (2 mL) and then charged with 1 N aqueous sodium hydroxide solution (2 mL). The solution was stirred at rt for 6 h. The solution was concentrated to remove THF and then acidified to pH 4-5 with 1 N aqueous HCl solution. The solid was collected by vacuum filtration and washed with water to give the corresponding acid as a white solid (30 mg, 78% 2 steps). MS(ESI$^+$) m/z 552.21 (M+H)$^+$.

The above acid was coupled with D(–)-phenylglycinamide (Bachem) using TBTU as described above to give the HCl salt of the title compound (32%) as a white solid. $^1$H NMR (DMSO-d$_6$) δ 10.64 (s, 1H), 8.89 (s, 1H), 8.74 (d, 1H, J=8 Hz), 8.56 (d, 1H, J=5.6 Hz), 8.46 (d, 1H, J=2.4 Hz), 7.96 (d, 1H, J=8.8 Hz), 7.84 (d, 1H, J=12 Hz), 7.74 (s, 1H), 7.46-7.37 (m, 4H), 7.31-7.22 (m, 5H), 7.06 (d, 1H, J=9.2 Hz), 5.34 (d, 1H, J=8 Hz), 3.81-3.78 (m, 4H), 3.40 (s, 2H), 3.12 (m, 4H); MS(ESI$^+$) m/z 584.25 (M+H)$^+$.

Example 64

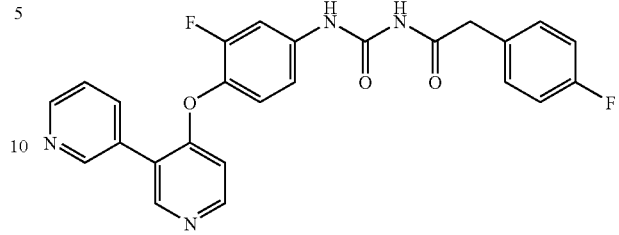

1-(3-Fluoro-4-(3-(pyridin-3-yl)pyridin-4-yloxy)phenyl)-3-(2-(4-fluorophenyl)acetyl)urea, hydrochloride salt

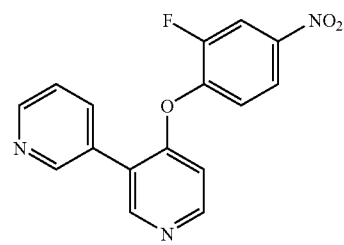

A) 3-(4-(2-Fluoro-4-nitrophenoxy)pyridin-3-yl)pyridine

Prepared in a similar manner as Step A of Example 59 give the title compound as a colorless oil. $^1$H NMR (CD$_3$OD) δ 8.83 (d, 1H, J=1.6 Hz), 8.69 (s, 1H), 8.61 (d, 1H, J=5 Hz), 8.56 (d, 1H, J=5.8 Hz), 8.27 (dd, 1H, J=10.4, 2.8 Hz), 8.20-814 (m, 2H), 7.72-7.55 (m, 1H), 7.53 (t, 1H, J=8.6 Hz), 7.08 (d, 1H, J=6 Hz); MS(ESI$^+$) m/z 312.15 (M+H)$^+$.

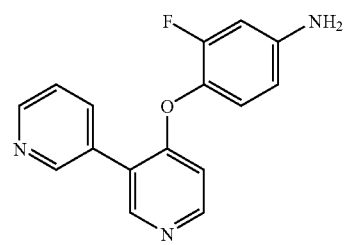

B) 3-Fluoro-4-(3-(pyridin-3-yl)pyridin-4-yloxy)benzenamine

Prepared in a similar manner as Step C of Example 59 give the title compound as a colorless oil. MS(ESI$^+$) m/z 282.12 (M+H)$^+$.

C) 1-(3-Fluoro-4-(3-(pyridin-3-yl)pyridin-4-yloxy) phenyl)-3-(2-(4-fluorophenyl)acetyl)urea Prepared in a similar manner as Step C of Example 59 give to give the HCl salt of the title compound (47% combined yield for Steps B and C) as a yellow solid. ¹H NMR (DMSO-d₆) δ 11.14 (s, 1H), 10.73 (s, 1H), 9.16 (d, 1H, J=1.6 Hz), 9.08 (s, 1H), 8.90 (dd, 1H, J=5.2, 1.2 Hz), 8.78 (d, 1H, J=6.4 Hz), 8.56 (d, 1H, J=8 Hz), 7.95-7.90 (m, 2H), 7.60 (t, 1H, J=8.8 Hz), 7.55-7.52 (m, 1H), 7.44-7.41 (m, 2H), 7.26-7.21 (m, 3H), 3.82 (s, 2H); MS(ESI⁺) m/z 461.16 (M+H)⁺.

Example 65

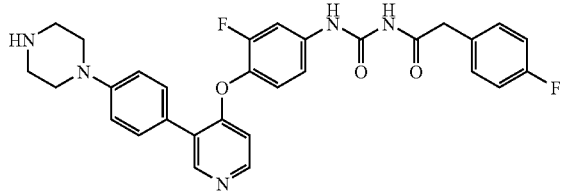

1-(3-Fluoro-4-(3-(4-(piperazin-1-yl)phenyl)pyridin-4-yloxy)phenyl)-3-(2-(4-fluorophenyl)acetyl)urea, trihydrochloride salt

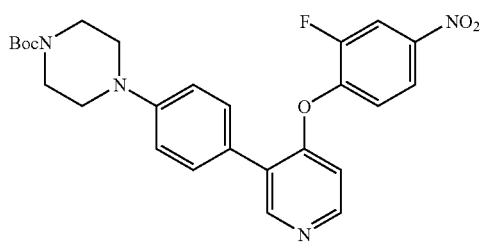

A) tert-Butyl 4-(4-(4-(2-fluoro-4-nitrophenoxy)pyridin-3-yl)phenyl)piperazine-1-carboxylate Prepared in a similar manner as Step A of Example 59 give the title compound as a colorless oil. ¹H NMR (CD₃OD) δ 8.48 (s, 1H), 8.32 (d, 1H, J=5.6 Hz), 8.08 (dd, 1H, J=12, 4 Hz), 7.97 (d, 1H, J=8 Hz), 7.38 (d, 2H, J=8.8 Hz), 7.21-7.18 (m, 1H), 6.95-6.92 (m, 3H), 3.46 (m, 4H), 3.09-3.06 (m, 4H), 1.10 (s, 9H); MS(ESI⁺) m/z 495.23 (M+H)⁺.

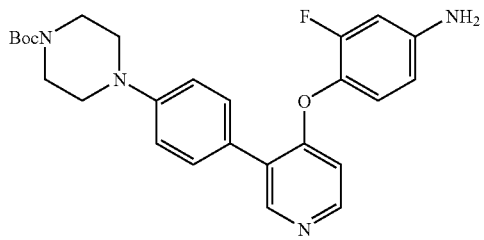

B) tert-Butyl 4-(4-(4-(4-amino-2-fluorophenoxy)pyridin-3-yl)phenyl)piperazine-1-carboxylate Prepared in a similar manner as Step C of Example 59 to give the title compound (94% combined yield for Steps A and B) as a colorless oil. ¹H NMR (CD₃OD) δ 8.30 (s, 1H), 8.14 (d, 1H, J=5.6 Hz), 7.45 (d, 2H, J=8.8 Hz), 6.98 (d, 2H, J=8.8 Hz), 6.83 (t, 1H, J=8.8 Hz), 6.58 (d, 1H, J=5.6 Hz), 6.48 (dd, 1H, J=12.8, 2.4 Hz), 6.43-6.41 (m, 1H), 3.49 (m, 4H), 3.11-3.09 (m, 4H), 1.16 (s, 9H); MS(ESI⁺) m/z 465.24 (M+H)⁺.

C) 1-(3-Fluoro-4-(3-(4-(piperazin-1-yl)phenyl)pyridin-4-yloxy)phenyl)-3-(2-(4-fluorophenyl)acetyl)urea Prepared in a similar manner as Step C of Example 59 to give the HCl salt of the title compound (37%) as a pale yellow solid. ¹H NMR (DMSO-d₆) δ 11.01 (s, 1H), 10.60 (s, 1H), 8.77 (s, 1H), 8.51 (d, 1H, J=6.4 Hz), 7.78 (d, 1H, J=12 Hz), 7.59 (d, 2H, J=8.4 Hz), 7.44-7.40 (m, 2H), 7.31-7.28 (m, 2H), 7.13-7.08 (m, 4H), 7.03 (d, 1H, J=6.4 Hz), 3.70 (s, 2H), 3.42 (m, 4H), 3.15 (m, 4H); MS(ESI⁺) m/z 544.26 (M+H)⁺.

Example 66

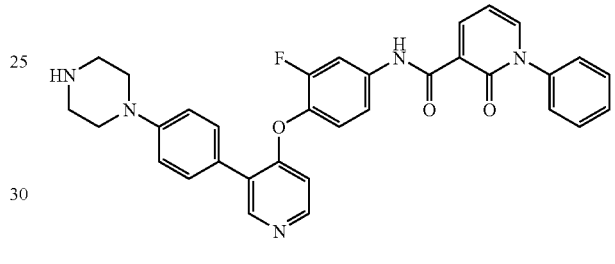

N-(3-Fluoro-4-(3-(4-(piperazin-1-yl)phenyl)pyridin-4-yloxy)phenyl)-2-oxo-1-phenyl-1,2-dihydropyridine-3-carboxamide, trihydrochloride salt Prepared in a manner similar to that of Example 62 to give the HCl salt of the title compound (43%) as a pale yellow solid. ¹H NMR (DMSO-d₆) δ 12.15 (s, 1H), 8.83 (s, 1H), 8.56-8.52 (m, 2H), 8.10 (dd, 1H, J=6.8, 2.4 Hz), 8.04 (dd, 1H, J=11.6, 2 Hz), 7.61 (d, 2H, J=8.8 Hz), 7.55-7.45 (m, 7H), 7.15 (d, 1H, J=6.8 Hz), 7.09 (d, 2H, J=8.8 Hz), 6.61 (t, 1H, J=6.8 Hz), 3.44 (m, 4H), 3.15 (m, 4H); MS(ESI⁺) m/z 562.36 (M+H)⁺.

Example 67

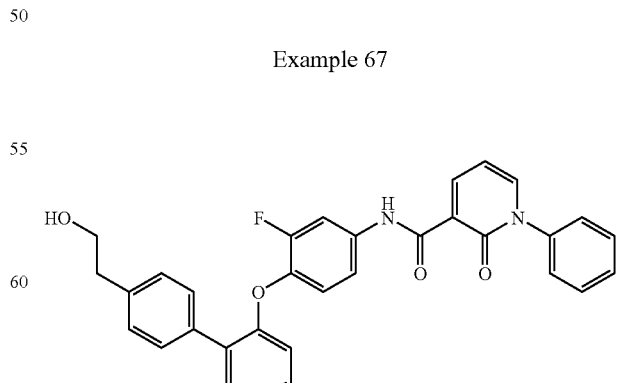

133

N-(3-Fluoro-4-(3-(4-(2-hydroxyethyl)phenyl)pyridin-4-yloxy)phenyl)-2-oxo-1-phenyl-1,2-dihydropyridine-3-carboxamide

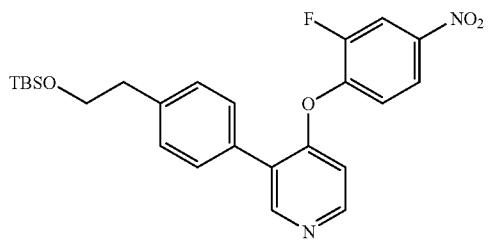

A) 3-(4-(2-(tert-Butyldimethylsilyloxy)ethyl)phenyl)-4-(2-fluoro-4-nitrophenoxy)pyridine Prepared in a similar manner as Step A of Example 59 to give the title compound (77%) as a colorless oil. $^1$H NMR (CD$_3$OD) δ 8.67 (s, 1H), 8.56 (d, 1H, J=8 Hz), 8.27 (dd, 1H, J=12, 4 Hz), 8.16 (d, 1H, J=8 Hz), 7.58 (d, 2H, J=8 Hz), 7.39 (d, 2H, J=8 Hz), 7.36 (m, 1H), 7.15 (d, 1H, J=4 Hz), 3.91 (t, 2H, J=8 Hz), 2.90 (t, 2H, J=8 Hz), 0.90 (s, 9H), 0.00 (s, 6H); MS(ESI$^+$) m/z 469.25 (M+H)$^+$.

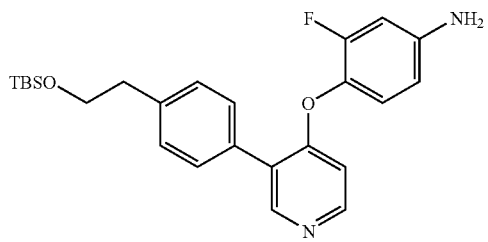

B) 3-(4-(2-(tert-Butyldimethylsilyloxy)ethyl)phenyl)-4-(2-fluoro-4-nitrophenoxy)pyridine Prepared in a similar manner as Step C of Example 59 to give the title compound (76%) as a pale yellow oil. $^1$H NMR (CD$_3$OD) δ 8.44 (s, 1H), 8.32 (d, 1H, J=4 Hz), 7.57 (d, 2H, J=8 Hz), 7.36 (d, 2H, J=8.4 Hz), 6.95 (t, 1H, J=8 Hz), 6.75 (d, 1H, J=4 Hz), 6.61 (d, 1H, J=8 Hz), 6.55 (d, 1H, J=4 Hz), 3.90 (t, 2H, J=6.8 Hz), 2.89 (t, 2H, J=6.4 Hz), 0.87 (s, 9H), 0.00 (s, 6H); MS(ESI$^+$) m/z 439.26 (M+H)$^+$.

C) N-(3-Fluoro-4-(3-(4-(2-hydroxyethyl)phenyl)pyridin-4-yloxy)phenyl)-2-oxo-1-phenyl-1,2-dihydropyridine-3-carboxamide Prepared in a similar manner as Step C of Example 62. After amide formation, the resulting yellow oil was dissolved in THF (2 mL) and then treated with TBAF (Aldrich, 180 uL, 1 M in THF) at rt for 1 h. The reaction was diluted with EtOAc (10 mL), washed successively with water and brine (5 mL each), dried over anhydrous Na$_2$SO$_4$, and concentrated in vacuo. The crude product was purified by flash chromatography on silica gel (10% methanol/EtOAc) to give the title compound (72%) as a pale yellow solid. $^1$H NMR (CD$_3$OD) δ 8.59 (dd, 1H, J=7.6, 2.0 Hz), 8.41 (s, 1H), 8.26 (d, 1H, J=5.6 Hz), 7.91-7.85 (m, 2H), 7.55-7.46 (m, 5H), 7.41 (d, 2H, J=6.7 Hz), 7.29 (d, 2H, J=8.1 Hz), 7.26 (m, 1H), 7.13 (t, 1H, J=8.7 Hz), 6.69 (d, 1H, J=6 Hz), 6.64 (t, 1H, J=7.2 Hz), 3.73 (t, 2H, J=7.2 Hz), 2.82 (t, 2H, J=6.8 Hz); MS(ESI$^+$) m/z 522.27 (M+H)$^+$.

Example 68

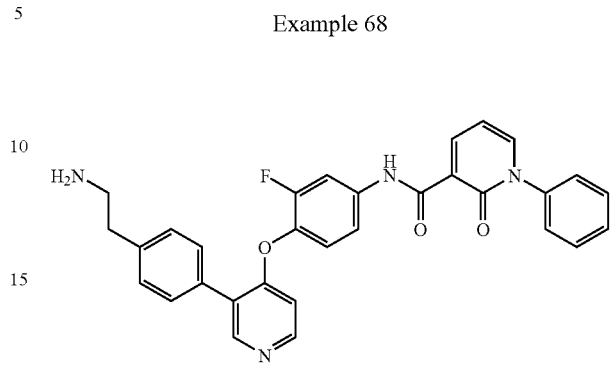

N-(4-(3-(4-(2-Aminoethyl)phenyl)pyridin-4-yloxy)-3-fluorophenyl)-2-oxo-1-phenyl-1,2-dihydropyridine-3-carboxamide, dihydrochloride salt To N-(3-fluoro-4-(3-(4-(2-hydroxyethyl)phenyl)pyridin-4-yloxy)phenyl)-2-oxo-1-phenyl-1,2-dihydropyridine-3-carboxamide (Compound C of Example 67, 40 mg, 0.077 mmol) in THF (1 mL) was added DIPEA (27 uL, 0.154 mmol) followed by methanesulfonyl chloride (Aldrich, 7 uL, 0.092 mmol). After stirring at rt for 30 min, the reaction was concentrated in vacuo. The residue was dissolved in 3 mL of ethanol and transferred to a pressure tube. Ammonium hydroxide (7 mL) was added and the tube was sealed and heated at 50° C. for 8 h. After cooling to rt, the reaction was diluted with EtOAc (10 mL), washed with water (2×10 mL) then brine (1×10 mL), dried over anhydrous Na$_2$SO$_4$, and concentrated in vacuo. The crude product was purified by prep HPLC. The appropriate fractions were concentrated to remove methanol and basified with saturated sodium bicarbonate solution. The aqueous layer was extracted with EtOAc (2×20 mL) and the pooled organic extracts were washed with brine (1×10 mL), dried over anhydrous Na$_2$SO$_4$, and concentrated. The residue was dissolved in dioxane (2 mL) and charged with 1N HCl in ether (1 mL). The solution was concentrated and the resulting solid was lyophilized from acetonitrile/water to give the HCl salt of the title compound (24 mg, 53%) as a white solid. $^1$H NMR (DMSO-d$_6$) δ 12.13 (s, 1H), 8.74 (s, 1H), 8.55-8.51 (m, 2H), 8.09 (dd, 1H, J=6.4, 2 Hz), 8.03 (m, 1H), 7.64 (d, 2H, J=6 Hz), 7.63 (m, 1H), 7.54-7.41 (m, 6H), 7.38 (d, 2H, J=8.4 Hz), 7.04 (d, 1H, J=6 Hz), 6.68 (t, 1H, J=6.8 Hz), 3.02 (m, 2H), 2.89 (m, 2H); MS(ESI$^+$) m/z 521.27 (M+H)$^+$.

Example 69

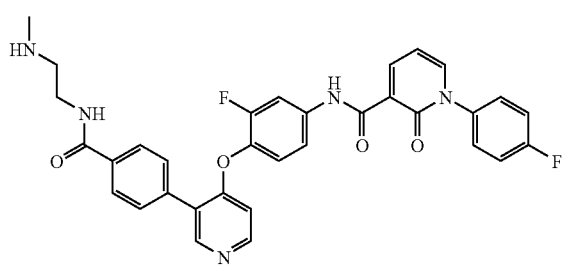

N-(4-(3-(4-((2-(Methylamino)ethyl)carbamoyl)phenyl)pyridin-4-yloxy)-3-fluorophenyl)-1-(4-fluorophenyl)-2-oxo-1,2-dihydropyridine-3-carboxamide, dihydrochloride salt

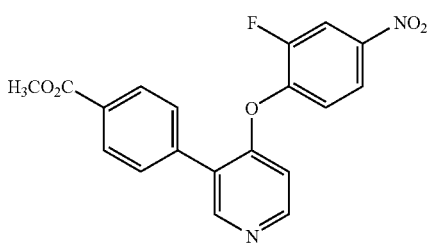

A) Methyl 4-(4-(2-fluoro-4-nitrophenoxy)pyridin-3-yl)benzoate

Prepared in a similar manner as Step A of Example 59 to give the title compound (77%) as a colorless oil. $^1$H NMR (CD$_3$OD) δ 8.66 (s, 1H), 8.52 (d, 1H, J=6 Hz), 8.22 (dd, 1H, J=10.4, 2.8 Hz), 8.16-8.13 (m, 1H), 8.10 (d, 2H, J=8.4 Hz), 7.97 (d, 2H, J=8 Hz), 7.44 (t, 1H, J=8.5 Hz), 7.06 (d, 1H, J=6 Hz), 3.93 (s, 3H); MS(ESI$^+$) m/z 369.22 (M+H)$^+$.

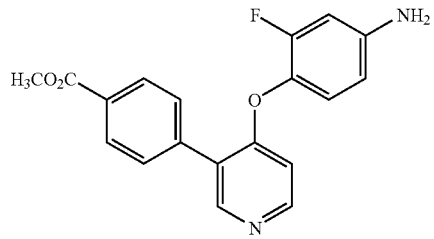

B) Methyl 4-(4-(4-amino-2-fluorophenoxy)pyridin-3-yl)benzoate

Prepared in a similar manner as Step C of Example 59 to give the title compound (99%) as a yellow oil. $^1$H NMR (CD$_3$OD) δ 8.38 (s, 1H), 8.24 (d, 1H, J=6 Hz), 8.01 (d, 2H, J=8.4 Hz), 7.66 (d, 2H, J=8.4 Hz), 6.85 (t, 1H, J=9.2 Hz), 6.65 (d, 1H, J=6 Hz), 6.48 (dd, 1H, J=12.8, 2.4 Hz), 6.43 (d, 1H, J=2.8 Hz), 3.82 (s, 3H); MS(ESI$^+$) m/z 339.28 (M+H)$^+$.

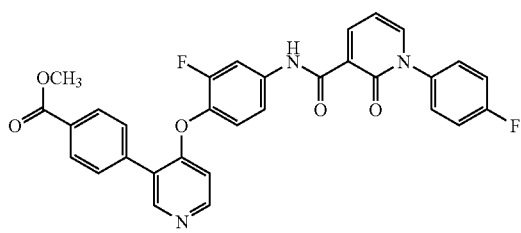

C) Methyl 4-(4-(2-fluoro-4-(1-(4-fluorophenyl)-2-oxo-1,2-dihydropyridine-3-carboxamido)phenoxy)pyridin-3-yl)benzoate Prepared in a similar manner as Step C of Example 62 to give the title compound (81%) as a yellow oil. $^1$H NMR (CD$_3$OD) δ 8.66 (dd, 1H, J=7.2, 2 Hz), 8.56 (s, 1H), 8.40 (d, 1H, J=6 Hz), 8.13 (d, 2H, J=8.4 Hz), 7.97-7.95 (m, 2H), 7.78 (d, 2H, J=8.4 Hz), 7.55-7.52 (m, 2H), 7.38-7.31 (m, 3H), 7.26 (t, 1H, J=7.2 Hz), 6.82 (d, 1H, J=5.6 Hz), 6.72 (t, 1H, J=6.7 Hz), 3.94 (s, 3H); MS(ESI$^+$) m/z 554.21 (M+H)$^+$.

D) N-(4-(3-(4-((2-(Methylamino)ethyl)carbamoyl) phenyl)pyridin-4-yloxy)-3-fluorophenyl)-1-(4-fluorophenyl)-2-oxo-1,2-dihydropyridine-3-carboxamide To the above ester (159 mg, 0.29 mmol) in THF (5 mL) was added 1 N aqueous NaOH (5 mL). After stirring at rt for 20 h, the reaction was concentrated to remove THF. The aqueous solution was acidified to pH 4 with 1 N aqueous HCl. The acid was collected by filtration and washed with water to give the desired product (144 mg, 92%) as a tan solid. MS(ESI$^+$) m/z 540.21 (M+H)$^+$.

The amide was prepared as described above using TBTU to give the HCl salt of the title compound (62%) as a white solid. $^1$H NMR (DMSO-d$_6$) δ 12.21 (s, 1H), 8.93-8.90 (m, 2H), 8.68-8.64 (m, 2H), 8.21 (dd, 1H, J=6.4, 2 Hz), 8.16 (m, 1H), 8.11 (d, 2H, J=8 Hz), 7.90 (d, 2H, J=8.4 Hz), 7.69-7.65 (m, 2H), 7.60-7.47 (m, 4H), 7.16 (d, 1H, J=5.6 Hz), 6.80 (t, 1H, J=7 Hz), 3.64 (t, 2H, J=5.2 Hz), 3.17 (t, 2H, J=5.2 Hz), 2.65 (s, 3H); MS(ESI$^+$) m/z 596.37 (M+H)$^+$.

Example 70

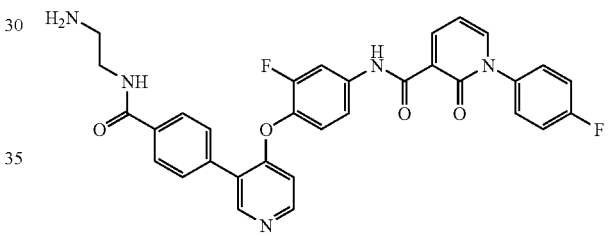

N-(4-(3-(4-((2-Aminoethyl)carbamoyl)phenyl)pyridin-4-yloxy)-3-fluorophenyl)-1-(4-fluorophenyl)-2-oxo-1,2-dihydropyridine-3-carboxamide, dihydrochloride salt Prepared in a similar manner as Example 69 to give the HCl salt of the title compound as an off-white solid. $^1$H NMR (DMSO-d$_6$) δ 12.17 (s, 1H), 8.87-8.85 (m, 2H), 8.64 (d, 1H, J=6.4 Hz), 8.59 (dd, 1H, J=7.6, 2.4 Hz), 8.16 (dd, 1H, J=6.8, 2.4 Hz), 8.10 (m, 1H), 8.06 (d, 2H, J=8.4 Hz), 8.00 (br s, 2H), 7.85 (d, 2H, J=8.4 Hz), 7.64-7.60 (m, 2H), 7.55-7.42 (m, 4H), 7.13 (d, 1H, J=6 Hz), 6.75 (t, 1H, J=7.2 Hz), 3.56-3.53 (m, 2H), 3.04-2.99 (m, 2H); MS(ESI$^+$) m/z 582.32 (M+H)$^+$.

Example 71

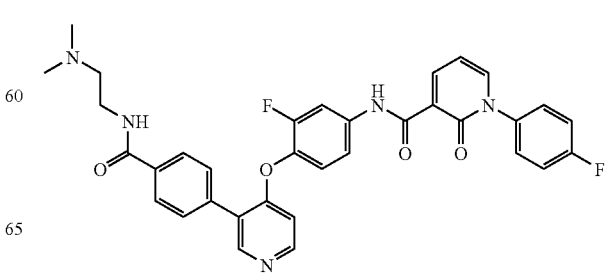

N-(4-(3-(4-((2-(Dimethylamino)ethyl)carbamoyl)
phenyl)pyridin-4-yloxy)-3-fluorophenyl)-1-(4-fluo-
rophenyl)-2-oxo-1,2-dihydropyridine-3-carboxam-
ide, dihydrochloride salt Prepared in a similar manner as Example 69 to give the HCl salt of the title compound (56%) as an off-white solid. ¹H NMR (DMSO-d₆) δ 12.08 (s, 1H), 8.87 (br s, 1H), 8.75 (s, 1H), 8.54-8.51 (m, 2H), 8.08 (dd, 1H, J=6.8, 2.4 Hz), 8.02 (m, 1H), 7.99 (d, 2H, J=8.4 Hz), 7.77 (d, 2H, J=8.4 Hz), 7.56-7.53 (m, 2H), 7.47-7.34 (m, 4H), 6.99 (d, 1H, J=5.6 Hz), 6.67 (t, 1H, J=6.8 Hz), 3.61-3.57 (m, 2H), 3.23-3.21 (m, 2H), 2.77 (s, 3H), 2.76 (s, 3H); MS(ESI⁺) m/z 610.30 (M+H)⁺.

Example 72

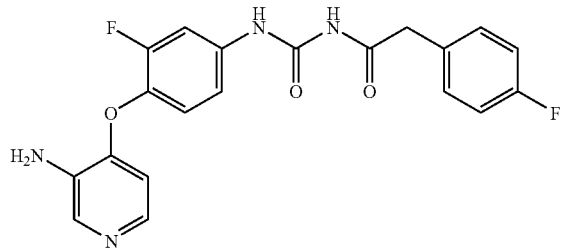

1-(4-(3-Aminopyridin-4-yloxy)-3-fluorophenyl)-3-
(2-(4-fluorophenyl)acetyl)urea

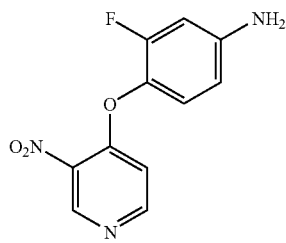

A) 3-Fluoro-4-(3-nitropyridin-4-yloxy)benzenamine

To 4-amino-2-fluorophenol (see Step A of Example 19, 127 mg, 1.0 mmol) in DMF (5 mL) at rt under nitrogen was added sodium hydride (80 mg, 2 mmol, 60%). After stirring at rt for 10 min, 4-chloro-3-nitropyridine hydrochloride (Lancaster, 195 mg, 1.0 mmol) was added. The mixture was stirred at rt for 1 h and was then diluted with EtOAc (50 mL) and washed with water, 10% aqueous lithium chloride solution, and then brine (1×30 mL each). The organic layer was dried over anhydrous Na₂SO₄ and concentrated in vacuo. The crude product was purified by flash column chromatography on silica gel eluting with EtOAc to give the title compound (150 mg, 60%) as a yellow-orange solid. ¹H NMR (DMSO-d₆) δ 9.13 (s, 1H), 8.63 (d, 1H, J=6 Hz), 7.09 (t, 1H, J=9.2 Hz), 6.92 (d, 1H, J=6 Hz), 6.55 (dd, 1H, J=13.2, 2.4 Hz), 6.45 (dd, 1H, J=9.2, 2.4 Hz), 5.61 (s, 2H); MS(ESI⁺) m/z 250.18 (M+H)⁺.

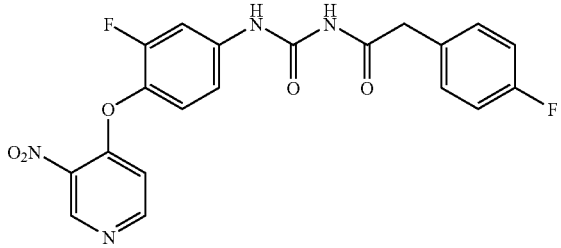

B) 1-(3-Fluoro-4-(3-nitropyridin-4-yloxy)phenyl)-3-
(2-(4-fluorophenyl)acetyl)urea A solution of 3-fluoro-4-(3-nitropyridin-4-yloxy)benzenamine (158 mg, 0.63 mmol) in THF (3 mL) was treated with a solution of solution of 2-(4-fluorophenyl)acetyl isocyanate in toluene (Compound D of Example 11, 1.3 mmol) and stirred at room temperature for 2 h then at 50° C. for 5 min. The mixture was concentrated and the residue treated with DMF (15 mL) and SiO₂ (150 mg) and the mixture concentrated to dryness under vacuum and applied to a SiO₂ column. The column was eluted with 20-60% EtOAc/hexanes to give the product, which was further purified by trituration with isopropyl ether to give a pale yellow solid (120 mg, 25%). ¹H NMR (DMSO-d₆) δ 11.07 (s, 1H), 10.63 (s, 1H), 9.19 (s, 1H), 8.67 (d, 1H, J=5.6 Hz), 7.85 (d, 1H, J=11.7 Hz), 7.46-7.45 (m, 2H), 7.39-7.35 (m, 2H), 7.18 (dd, 2H, J=8.6, 8.6 Hz), 7.01 (d, 1H, J=6.1 Hz), 3.76 (s, 2H).

C) 1-(4-(3-Aminopyridin-4-yloxy)-3-fluorophenyl)-
3-(2-(4-fluorophenyl)acetyl)urea A suspension of 1-(3-fluoro-4-(3-nitropyridin-4-yloxy) phenyl)-3-(2-(4-fluorophenyl)acetyl)urea (125 mg, 0.29 mmol) in 3:1 MeOH/THF (20 mL) was hydrogenated over Pt₂O (50 mg) using H₂ from a latex balloon for 6 h. The catalyst was filtered off with the aid of Celite® and the filtrate concentrated to give the title compound (85 mg, 74%) as a white solid. ¹H NMR (DMSO-d₆) δ 11.03 (s, 1H), 10.55 (s, 1H), 8.03 (s, 1H), 7.75 (dd, 1H, J=2.5, 13.2 Hz), 7.65 (d, 1H, J=5.1 Hz), 7.38-7.35 (m, 3H), 7.23-7.16 (m, 3H), 6.42 (d, 1H, J=5.1 Hz), 5.26 (s, 2H), 3.75 (s, 2H); MS(ESI⁺): m/z 399.35 (M+H)⁺.

Example 73

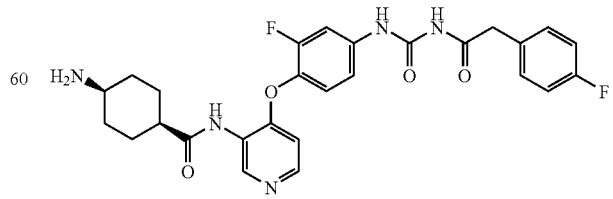

1-(4-(3-((1S,4S)-4-Aminocyclohexanecarboxamido)
pyridin-4-yloxy)-3-fluorophenyl)-3-(2-(4-fluorophe-
nyl)acetyl)urea, trifluoroacetic acid salt

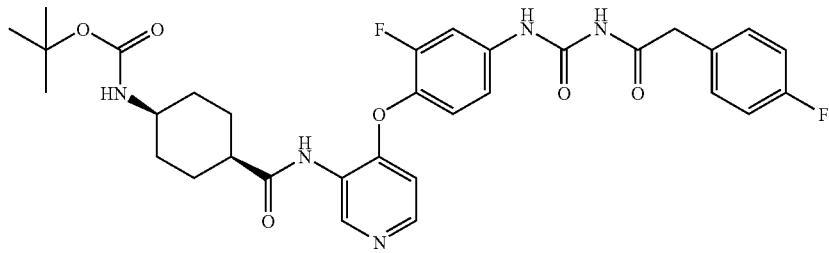

A) tert-Butyl(1S,4S)-4-((4-(2-fluoro-4-(3-(2-(4-fluo-
rophenyl)acetyl)ureido)phenoxy)pyridin-3-yl)car-
bamoyl)cyclohexylcarbamate A solution of N-Boc-cis-1,4-diaminocyclohexane carboxylic acid (Chem-Imprex International, 24 mg, 0.10 mmol) in THF (1 mL) was cooled to 0° C., and treated with Et$_3$N and then isobutylchloroformate. After 5 min, the mixture was treated with a solution of 1-(4-(3-aminopyridin-4-yloxy)-3-fluorophenyl)-3-(2-(4-fluorophenyl)acetyl)urea (Compound C of Example 72, 27 mg, 0.068 mmol) in THF (0.5 mL) and the stirring continued at 0° C. for 10 min and then at room temperature for 2 h. The mixture was partitioned between EtOAc and saturated aq. NaHCO$_3$ solution and the EtOAc phase separated, dried (MgSO$_4$) and concentrated in vacuo to give the crude product. Purification of the residue by flash column chromatography on SiO$_2$ eluting with 50-100% EtOAc/hexanes gave the title compound (13 mg, 21%) as a white solid. MS(ESI$^+$): m/z 624.25 (M+H)$^+$.

B) 1-(4-(3-((1S,4S)-4-Aminocyclohexanecarboxa-
mido)pyridin-4-yloxy)-3-fluorophenyl)-3-(2-(4-fluo-
rophenyl)acetyl)urea, trifluoroacetic acid salt A solution of tert-butyl(1S,4S)-4-((4-(2-fluoro-4-(3-(2-(4-fluorophenyl)acetyl)ureido)phenoxy)pyridin-3-yl)carbamoyl)cyclohexylcarbamate (10 mg, 0.016 mmol) in anhydrous MeOH (0.5 mL) was cooled to 0° C. and treated with 4 M HCl/1,4-dioxane (2 mL). The mixture was stirred at 0° C. for 1.5 h and then at room temperature for 20 min and finally concentrated in vacuo to give the crude product. Purification of the residue by preparative HPLC (Column A) gave the title compound (4 mg, 33%) as a yellow solid. $^1$H NMR (DMSO-d$_6$) δ 11.07 (s, 1H), 10.64 (s, 1H), 9.28 (s, 1H), 8.40-8.37 (m, 1H), 7.94 (s, 1H), 7.83 (dd, 1H, J=2.1, 12.7 Hz), 7.47-7.33 (m, 5H), 7.19-7.14 (m, 3H), 7.07-7.02 (m, 1H), 3.75 (s, 2H), 3.25-3.15 (m, 1H), 2.85-2.76 (m, 1H), 1.97-1.84 (m, 2H), 1.85-1.61 (m, 5H); MS(ESI$^+$): m/z 524.26 (M+H)$^+$.

Example 74

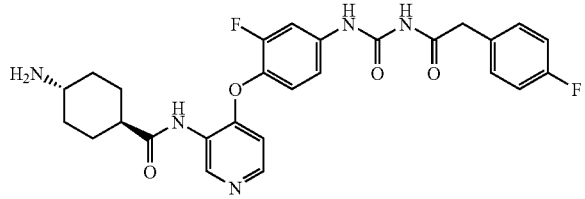

1-(4-(3-((1R,4R)-4-Aminocyclohexanecarboxamido)
pyridin-4-yloxy)-3-fluorophenyl)-3-(2-(4-fluorophe-
nyl)acetyl)urea, bis-trifluoroacetic acid salt

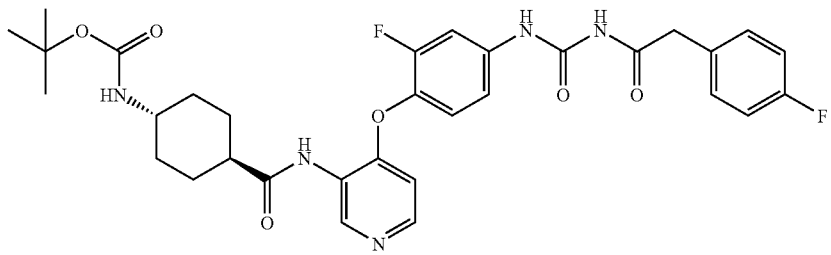

A) tert-Butyl(1R,4R)-4-((4-(2-fluoro-4-(3-(2-(4-fluorophenyl)acetyl)ureido)phenoxy)pyridin-3-yl)carbamoyl)cyclohexylcarbamate The title compound was prepared from 1-(4-(3-aminopyridin-4-yloxy)-3-fluorophenyl)-3-(2-(4-fluorophenyl)acetyl)urea (Compound C of Example 72, 57 mg, 0.14 mmol) and N-Boc-trans-4-aminocyclohexane-1-carboxylic acid (Anaspec Inc., 51 mg, 0.21 mmol) in a similar manner as described for Step A of Example 73 to give the title compound (32 mg, 66%) as white solid. MS(ESI⁺): m/z 624.41 (M+H)⁺.

B) 1-(4-(3-((1R,4R)-4-Aminocyclohexanecarboxamido)pyridin-4-yloxy)-3-fluorophenyl)-3-(2-(4-fluorophenyl)acetyl)urea, bis-trifluoroacetic acid salt The title compound was prepared from tert-butyl(1S,4S)-4-((4-(2-fluoro-4-(3-(2-(4-fluorophenyl)acetyl)ureido)phenoxy)pyridin-3-yl)carbamoyl)cyclohexylcarbamate (25 mg) in a similar manner as described for Example 73. Purification of the reaction mixture by preparative HPLC (Column A) gave the title compound (7 mg, 23%) as a white solid. ¹H NMR (DMSO-d₆) δ 11.06 (s, 1H), 10.61 (s, 1H), 9.94 (s, 1H), 9.19 (s, 1H), 8.28 (d, 1H, J=5.6 Hz), 7.82 (dd, 1H, J=2.0, 13.2 Hz), 7.79-7.76 (m, 3H), 7.43 (dd, 1H, J=2.0, 8.6 Hz), 7.38-7.33 (m, 2H), 7.17 (dd, 2H, J=9.2, 6.6 Hz), 6.86 (d, 1H, J=5.6 Hz), 3.74 (s, 2H), 3.08-2.95 (m, 1H), 2.67-2.43 (m, 1H), 2.01-1.88 (m, 4H), 1.53-1.43 (m, 2H), 1.37-1.27 (m, 2H); MS(ESI⁺): m/z 524.35 (M+H)⁺.

Example 75

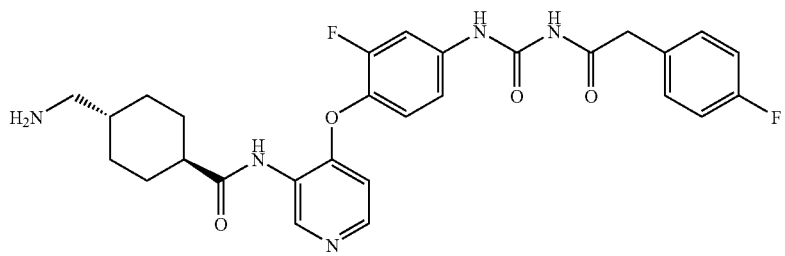

1-(4-(3-((1R,4R)-4-(Aminomethyl)cyclohexanecarboxamido)pyridin-4-yloxy)-3-fluorophenyl)-3-(2-(4-fluorophenyl)acetyl)urea

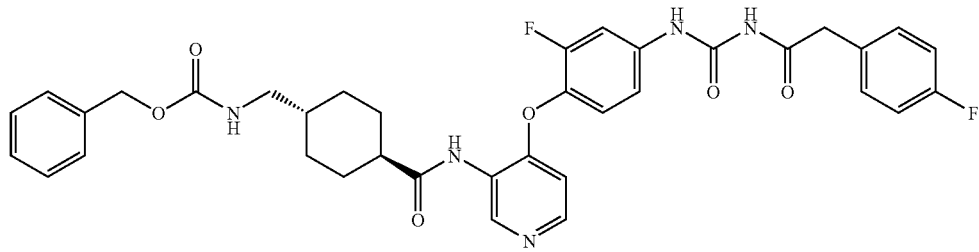

A) Benzyl((1R,4R)-4-((4-(2-fluoro-4-(3-(2-(4-fluorophenyl)acetyl)ureido) phenoxy)pyridin-3-yl) carbamoyl)cyclohexyl)methylcarbamate The title compound was prepared from 1-(4-(3-aminopyridin-4-yloxy)-3-fluorophenyl)-3-(2-(4-fluorophenyl)acetyl)urea (Compound C of Example 72, 50 mg, 0.13 mmol) and trans-4-((benzyloxycarbonyl)methyl)cyclohexanecarboxylic acid (40 mg, 0.14 mmol, prepared according to the synthetic route described in Schaus, J. M. et al. *J. Med. Chem.* 1998, 41, 1943-1955) according to Step A of Example 73 to give the title compound (30 mg, 34%) as white solid. MS(ESI+): m/z 672.34 (M+H)+.

B) 1-(4-(3-((1R,4R)-4-(Aminomethyl)cyclohexanecarboxamido)pyridin-4-yloxy)-3-fluorophenyl)-3-(2-(4-fluorophenyl)acetyl)urea A solution of benzyl((1R,4R)-4-((4-(2-fluoro-4-(3-(2-(4-fluorophenyl) acetyl)ureido)phenoxy)pyridin-3-yl)carbamoyl)cyclohexyl)methylcarbamate (25 mg 0.037 mmol) in MeOH (1.5 mL) was hydrogenated over 10% palladium-carbon (15 mg) for 4 h using H₂ form a rubber balloon. The catalyst was filtered off and the filtrate concentrated in vacuo to give the title compound (18 mg, 90%) as a yellow solid. ¹H NMR (DMSO-d₆) δ 10.62 (s, 1H), 9.64 (s, 1H), 9.01 (s, 1H), 8.17 (d, 1H, J=5.6 Hz), 7.79 (dd, 1H, J=2.5, 12.7 Hz), 7.42-7.35 (m, 4H), 7.30 (dd, 1H, J=8.6, 9.2 Hz), 7.18 (m, 2H), 6.66 (d, 1H, J=5.6 Hz), 3.75 (s, 2H), 2.39 (d, 2H, J=6.6 Hz), 1.87-1.81 (m, 4H), 1.46-1.35 (m, 1H), 1.33-1.10 (m, 1H), 0.95-0.77 (m, 4H); MS(ESI+): m/z 538.28 (M+H)+.

Example 76

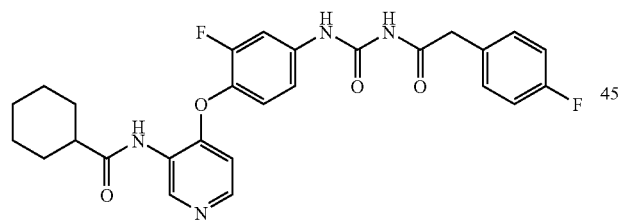

1-(4-(3-(Cyclohexanecarboxamido)pyridin-4-yloxy)-3-fluorophenyl)-3-(2-(4-fluorophenyl)acetyl)urea A solution of 1-(4-(3-aminopyridin-4-yloxy)-3-fluorophenyl)-3-(2-(4-fluorophenyl)acetyl)urea (Compound C of Example 72, 25 mg, 0.062 mmol) in CH₂Cl₂ (2 mL) was treated with Et₃N (10 μL, 0.074 mmol) and cyclohexanecarbonyl chloride (Aldrich, 11 mg, 0.074 mmol) and stirred at rt for 2 h. An additional portion of cyclohexanecarbonyl chloride (11 mg, 0.074 mmol) was added to the mixture and the reaction continued for 18 h. The mixture was diluted with CH₂Cl₂, washed with saturated aq. NaHCO₃ solution, dried (MgSO₄) and concentrated in vacuo. The residue was purified by flash column chromatography on SiO₂ eluting with 50-100% EtOAc/hexanes to give the title compound (19 mg, 61%) as a white solid. ¹H NMR (DMSO-d₆) δ 11.03 (s, 1H), 10.57 (m, 1H), 9.60 (m, 1H), 8.99 (s, 1H), 8.15 (d, 1H, J=5.6 Hz), 7.76 (dd, 1H, J=2.0, 13.2 Hz), 7.39-7.33 (m, 3H), 7.28 (dd, 1H, J=8.6, 9.2 Hz), 7.18-7.14 (m, 2H), 6.65 (d, 1H, J=5.1 Hz), 3.73 (s, 2H), 1.81-1.71 (m, 5H), 1.64-1.61 (m, 1H), 1.43-1.34 (m, 2H), 1.29-1.14 (m, 3H); MS(ESI+): m/z 509.27 (M+H)+.

Example 77

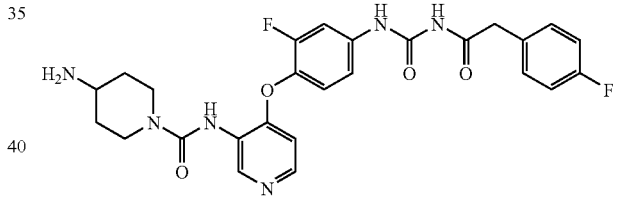

1-(4-(3-(4-Aminopiperidine-1-carboxamido)pyridin-4-yloxy)-3-fluorophenyl)-3-(2-(4-fluorophenyl)acetyl)urea, bis-trifluoroacetic acid salt

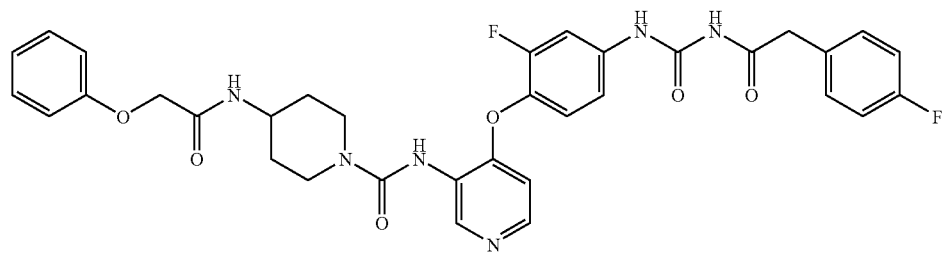

A) 1-(3-Fluoro-4-(3-(4-(2-phenoxyacetamido)piperidine-1-carboxamido)pyridin-4-yloxy)phenyl)-3-(2-(4-fluorophenyl)acetyl)urea A solution of triphosgene (50 mg, 0.17 mmol), in CH$_2$Cl$_2$ (0.4 mL) was cooled to −10° C. and treated with a solution of 1-(4-(3-aminopyridin-4-yloxy)-3-fluorophenyl)-3-(2-(4-fluorophenyl)acetyl)urea (Compound C of Example 72, 67 mg, 0.17 mmol) and DIPEA (65 μL, 0.37 mmol) in CH$_2$Cl$_2$ (0.4 mL). The mixture was stirred at −10° C. for 10 min and then treated with a solution of 4-((carbobenzyloxy)amido)piperidine (40 mg, 0.17 mmol, prepared using the procedure describe in Schaus, J. M. et al. *J. Med. Chem.* 1998, 41, 1943-1955) and DIPEA (65 μl, 0.37 mmol) in CH$_2$Cl$_2$ (0.4 mL). After stirring for 2 minutes, the mixture was warmed to room temperature then heated to 40° C. for 10 min. The mixture was diluted with EtOAc, washed with saturated aq. NaHCO$_3$ and brine, dried (MgSO$_4$) and concentrated in vacuo. The product was purified by flash column chromatography on SiO$_2$ eluting with 0-5% MeOH/CH$_2$Cl$_2$ to give the title compound (50 mg, 45%) as yellow solid. MS(ESI$^+$) m/z 659.29 (M+H)$^+$.

B) 1-(4-(3-(4-Aminopiperidine-1-carboxamido)pyridin-4-yloxy)-3-fluorophenyl)-3-(2-(4-fluorophenyl)acetyl)urea, bis-trifluoroacetic acid salt A solution of 1-(3-fluoro-4-(3-(4-(2-phenoxyacetamido)piperidine-1-carboxamido)pyridin-4-yloxy)phenyl)-3-(2-(4-fluorophenyl)acetyl)urea (45 mg, 0.068 mmol) in absolute MeOH (2.5 mL) was hydrogenated over 10% palladium-carbon (15 mg) using H$_2$ from a rubber balloon for 2.5 h. The catalyst was filtered and the filtrate concentrated in vacuo and the residue was purified by preparative HPLC (Column A) to afford the title compound. $^1$H NMR (DMSO-d$_6$) δ 10.57 (s, 1H), 8.55 (s, 1H), 8.27 (m, 1H), 8.14 (d, 1H, J=5.6 Hz), 7.75 (dd, 1H, J=2.0, 12.7 Hz), 7.37-7.33 (m, 3H), 7.23-7.14 (m, 3H), 6.65 (d, 1H, J=5.1 Hz), 4.05-3.98 (m, 2H), 3.73 (s, 2H), 3.05-2.91 (m, 1H), 2.88-2.83 (m, 2H), 1.83-1.74 (m, 2H), 1.34-1.20 (m, 2H); MS(ESI$^+$) m/z 525.35 (M+H)$^+$.

Example 78

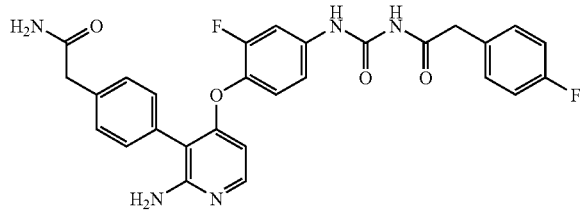

1-(4-(2-Amino-3-(4-(2-amino-2-oxoethyl)phenyl)pyridin-4-yloxy)-3-fluorophenyl)-3-(2-(4-fluorophenyl)acetyl)urea, trifluoroacetic acid salt

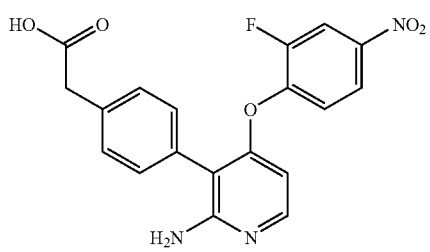

A) 2-(4-(2-Amino-4-(2-fluoro-4-nitrophenoxy)pyridin-3-yl)phenyl)acetic acid

A mixture of 4-(2-fluoro-4-nitrophenoxy)-3-iodopyridin-2-amine (Compound C of Example 34, 88 mg, 0.23 mmol), 4-(dihydroxyborane)phenylacetic acid pinacol ester (Frontier Scientific Inc., 92 mg, 0.35 mmol), Na$_2$CO$_3$ (170 mg, 1.61 mmol), 1,4-dioxane (2 mL) and H$_2$O (2 mL) was degassed by vacuum/argon purge and treated with tetrakis(triphenylphosphine)palladium (27 mg, 0.023 mmol). After heating at 100° C. for 3 h, the pH of the mixture was adjusted to pH 6 using 1 N hydrochloric acid. The mixture was concentrated in vacuo and the residue partitioned between EtOAc and pH 7 phosphate buffer. The aqueous phase was extracted with EtOAc and the combined extracts were dried (MgSO$_4$) and concentrated in vacuo to give the crude product. The product was triturated with 2:1 EtOAc/MeOH to give the desired product (70 mg, 80%) as an orange-brown solid. $^1$H NMR (DMSO-d$_6$) δ 12.34 (s, 1H), 8.23 (dd, 1H, J=3.1, 10.5 Hz), 8.05 (d, 1H, J=10.2 Hz), 7.94 (d, 1H, J=6.1 Hz), 7.32-7.25 (m, 5H), 6.26 (d, 1H, J=6.1 Hz), 5.62 (s, 2H), 3.57 (s, 2H); MS(ESI$^+$): m/z 384.16 (M+H)$^+$.

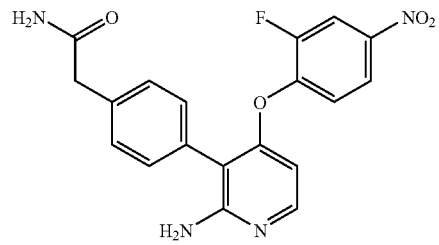

B) 2-(4-(2-Amino-4-(2-fluoro-4-nitrophenoxy)pyridin-3-yl)phenyl)acetamide

A solution of 2-(4-(2-amino-4-(2-fluoro-4-nitrophenoxy)pyridin-3-yl)phenyl)acetic acid (65 mg, 0.17 mmol) in anhydrous DMF (1.2 mL) was treated with PyBOP (125 mg, 0.24 mmol) and HOBt (32 mg, 0.24 mmol) followed by DIPEA (60 μL, 0.35 mmol) and NH$_4$Cl (19 mg, 0.35 mmol). After stirring at room temperature for 20 min, the mixture was concentrated under vacuum and the residue partitioned between EtOAc and saturated aq. NaHCO$_3$ solution. The EtOAc phase was washed with brine, dried (MgSO$_4$) and concentrated in vacuo. The product was purified by flash column chromatography on SiO$_2$ eluting with 0-8% MeOH/CH$_2$Cl$_2$ to give the title compound (40 mg, 62%) as an amber colored oil. $^1$H NMR (DMSO-d$_6$) δ 8.23 (dd, 1H, J=10.7, 2.5 Hz), 8.05 (d, 1H, J=9.2 Hz), 7.93 (d, 1H, J=6.1 Hz), 7.42-7.32 (m, 2H), 7.33-7.25 (m, 4H), 6.92 (s, 1H), 6.25 (d, 1H, J=5.6 Hz), 5.64 (s, 2H), 3.36 (s, 2H); MS(ESI$^+$): m/z 383.17 (M+H)$^+$.

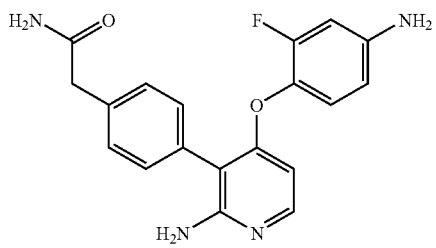

C) 2-(4-(2-Amino-4-(4-amino-2-fluorophenoxy) pyridin-3-yl)phenyl)acetamide

A mixture of 2-(4-(2-amino-4-(2-fluoro-4-nitrophenoxy) pyridin-3-yl)phenyl)acetamide (32 mg, 0.086 mmol), DMF (1 mL), EtOH (1 mL) and H$_2$O (1 mL) was treated with Fe powder (67 mg, 1.2 mmol), and NH$_4$Cl (128 mg, 2.4 mmol) and the mixture heated at 100° C. for 20 min. The mixture was filtered through Celite®, the pH of the filtrate adjusted to pH 7 using phosphate buffer and then the mixture was extracted with EtOAc. The organic extract was dried (MgSO$_4$) and concentrated to give the desired product (20 mg, 67%) as a yellow-brown solid. MS(ESI$^+$): m/z 353.32 (M+H)$^+$.

D) 1-(4-(2-Amino-3-(4-(2-amino-2-oxoethyl)phenyl) pyridin-4-yloxy)-3-fluorophenyl)-3-(2-(4-fluorophenyl)acetyl)urea trifluoroacetic acid salt The title compound was prepared form 2-(4-(2-amino-4-(4-amino-2-fluorophenoxy)pyridin-3-yl)phenyl)acetamide (19 mg, 0.054 mmol) and 0.3 M solution of 2-(4-fluorophenyl)acetyl isocyanate in toluene (Compound D of Example 11, 0.27 mL, 0.081 mmol) in a similar manner as that described for Step D of Example 33. Purification of the reaction mixture by preparative HPLC (Column A) gave the title compound (9 mg, 26%) as a white solid. $^1$H NMR (DMSO-d$_6$): δ 11.03 (s, 1H), 10.57 (s, 1H), 7.93 (d, 1H, J=7.1 Hz), 7.76 (dd, 1H, J=2.0, 13.2 Hz), 7.44-7.42 (m, 3H), 7.37-7.29 (m, 6H), 7.16 (dd, 2H, J=8.6, 8.8 Hz), 6.94 (s, 1H), 6.31 (d, 1H, J=7.1 Hz), 3.72 (s, 2H), 3.43 (s, 2H); MS(ESI$^+$): m/z 532.24 (M+H)$^+$.

Example 79

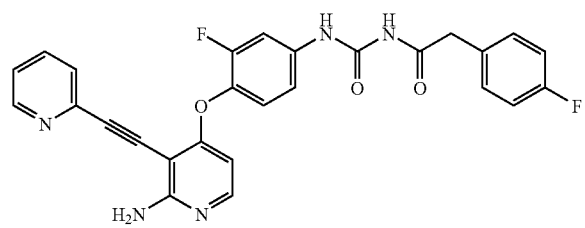

1-(4-(2-Amino-3-(2-(pyridin-2-yl)ethynyl)pyridin-4-yloxy)-3-fluorophenyl)-3-(2-(4-fluorophenyl)acetyl) urea, dihydrochloride salt

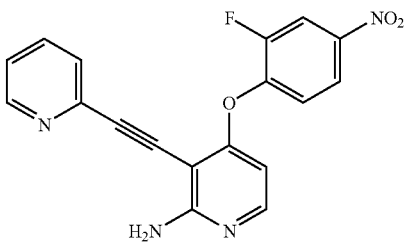

A) 4-(2-Fluoro-4-nitrophenoxy)-3-(2-(pyridin-2-yl) ethynyl)pyridin-2-amine

A mixture of 4-(2-fluoro-4-nitrophenoxy)-3-iodopyridin-2-amine (Compound C of Example 34, 100 mg, 0.27 mmol) and 2-ethynylpyridine (Aldrich, 57 mg, 0.54 mmol), THF (2 mL) and Et$_3$N (2 mL) was degassed by vacuum/argon purge and treated in turn with CuI (6 mg, 0.032 mmol) and (Ph$_3$P)$_4$Pd (20 mg, 0.017 mmol). The mixture was heated at 60° C. for 45 minutes, cooled, partitioned between EtOAc and saturated aq. sodium bicarbonate solution. The organic phase was dried (MgSO$_4$) and concentrated in vacuo to give the crude product. Purification of the residue by flash column chromatography on SiO$_2$ eluting with 0-1.5% MeOH/CH$_2$Cl$_2$ gave the title compound (55 mg, 58%) as a brown solid. $^1$H NMR (DMSO-d$_6$) δ 8.53 (d, 1H, J=5.1 Hz), 8.39 (dd, 1H, J=2.5, 10.7 Hz), 8.15 (dm, 1H, J=8.1 Hz), 7.97 (d, 1H, J=5.6 Hz), 7.81 (d, 1H, J=8.1 Hz), 7.71 (d, 1H, J=7.6 Hz), 7.52 (dd, 1H, J=8.6, 8.6 Hz), 7.38-7.34 (m, 1H), 6.71 (s, 2H), 6.21 (d, 1H, J=5.6 Hz); MS(ESI$^+$): m/z 351.25 (M+H)$^+$.

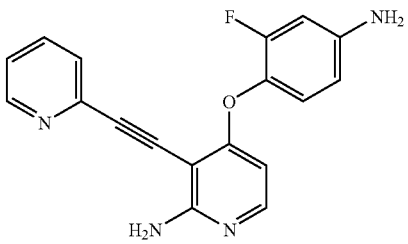

B) 4-(4-Amino-2-fluorophenoxy)-3-(2-(pyridin-2-yl) ethynyl)pyridin-2-amine

A mixture of 4-(2-fluoro-4-nitrophenoxy)-3-(2-(pyridin-2-yl)ethynyl)pyridin-2-amine (35 mg, 0.1 mmol), THF (1.5 mL) and MeOH (1.5 ml) was treated with zinc dust (65 mg, 1.0 mmol) and NH$_4$Cl (53 mg, 1.0 mmol) and heated at 60° C. for 45 min. The reaction mixture was cooled, filtered and concentrated under vacuum. The residue was partitioned between EtOAc and saturated aq. NaHCO$_3$ solution. The organic phase was separated, washed with brine, dried (MgSO$_4$) and concentrated to give the title compound (25 mg, 78%) as a brown solid. MS(ESI$^+$): m/z 321.2 (M+H)$^+$.

C) 1-(4-(2-Amino-3-(2-(pyridin-2-yl)ethynyl)pyridin-4-yloxy)-3-fluorophenyl)-3-(2-(4-fluorophenyl)acetyl)urea, dihydrochloride salt A solution of 4-(4-amino-2-fluorophenoxy)-3-(2-(pyridin-2-yl)ethynyl)pyridin-2-amine (25 mg, 0.078 mmol) in THF (2 mL) was cooled to 0° C. and treated with 0.3 M solution of 2-(4-fluorophenyl)acetyl isocyanate in toluene (Compound D of Example 11, 0.26 mL, 0.078 mmol). After 1 h, the mixture was warmed to room temperature and stirred for 15 min. The mixture was concentrated under vacuum and the residue purified by preparative HPLC (Column A) to give the title compound as a TFA salt. The TFA salt was dissolved in anhydrous MeOH and treated with 1 M HCl/Et$_2$O at 0° C. and stirred for 5 min. The mixture was then concentrated in vacuo to give the title compound (18 mg, 41%) as a brown solid. $^1$H NMR (DMSO-d$_6$) δ 11.06 (s, 1H), 10.63 (s, 1H), 8.62 (d, 1H, J=4.5 Hz), 8.22 (s, 2H), 7.99 (d, 1H, J=7.1 Hz), 7.94-7.81 (m, 3H), 7.48-7.44 (m, 3H), 7.37-7.33 (m, 2H), 7.16 (dd, 2H, J=6.2, 9.2 Hz), 6.30 (d, 1H, J=7.1 Hz), 3.74 (s, 2H); MS(ESI$^+$): m/z 500.21 (M+H)$^+$.

Example 80

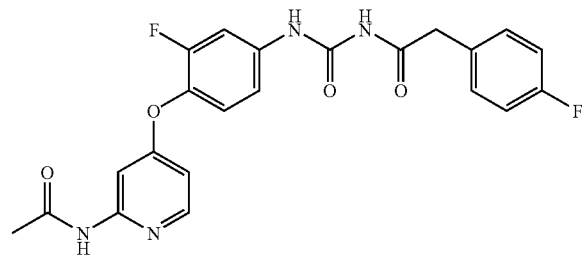

1-(4-(2-Acetamidopyridin-4-yloxy)-3-fluorophenyl)-3-(2-(4-fluorophenyl)acetyl)urea, hydrochloride salt

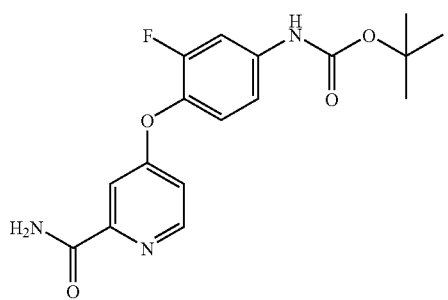

A) tert-Butyl 4-(2-carbamoylpyridin-4-yloxy)-3-fluorophenylcarbamate

A mixture of 4-(4-amino-2-fluorophenoxy)picolinamide (Compound B' of Example 24, 190 mg, 0.76 mmol), tert-butyl alcohol (2 mL), 1,4-dioxane (1 mL), DMF (1 mL) and Boc$_2$O (167 mg, 0.76 mmol) was heated at 65° C. for 16 h. Additional portions of Boc$_2$O (85 mg and 60 mg) were added after 16 h and 32 h, respectively and the mixture heated for a total of 40 h. The mixture was concentrated under vacuum and the residue partitioned between EtOAc and saturated aq. NaHCO$_3$ solution. The EtOAc phase was dried (MgSO$_4$) and concentrated in vacuo to give the crude product. Purification of the residue by flash column chromatography on SiO$_2$ eluting with 30-60% EtOAc/hexanes gave the title compound (180 mg, 68%) as a brown solid. $^1$H NMR (DMSO-d$_6$) δ 9.74 (s, 1H), 8.52 (d, 1H, J=5.6 Hz), 8.13 (s, 1H), 7.72 (s, 1H), 7.62 (d, 1H, J=13.7 Hz), 7.35-7.31 (m, 3H), 7.18 (dd, 1H, J=5.6, 2.5 Hz), 1.39 (s, 9H); MS(ESI$^+$): m/z 348.22 (M+H)$^+$.

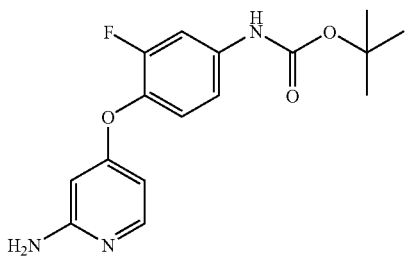

B) tert-Butyl 4-(2-aminopyridin-4-yloxy)-3-fluorophenylcarbamate

A solution of KOH (280 mg, 5.0 mmol) in H$_2$O (2 mL) was cooled to 0-5° C. and treated dropwise with bromine (162 mg, 1.0 mmol) and the mixture stirred for 5 min. tert-Butyl 4-(2-carbamoylpyridin-4-yloxy)-3-fluorophenylcarbamate (347 mg, 1.0 mmol) was added to the mixture in one portion as a solid and then 1,4-dioxane (3 mL) was added to dissolve the solids. The reaction mixture was stirred at room temperature for 30 min then at 55° C. for 45 min. The mixture was then cooled to room temperature, treated with HOAc (0.5 mL) and stirred until the foaming subsided. The mixture was reheated to 55° C. for 20 min, cooled to room temperature, treated with KOH (350 mg) and extracted with CH$_2$Cl$_2$. The organic extract was dried (MgSO$_4$) and concentrated under vacuum. The residue was purified by flash column chromatography on SiO$_2$ eluting with 30-70% EtOAc/hexanes to give the title compound (265 mg, 83%). $^1$H NMR (DMSO-d$_6$) δ 9.67 (s, 1H), 7.77 (d, 1H, J=6.1 Hz), 7.56 (d, 1H, J=11.7 Hz), 7.26-7.18 (m, 2H), 6.12 (dd, 1H, J=2.0, 6.1 Hz), 5.93 (s, 2H), 5.74 (d, 1H, J=2.5 Hz), 1.47 (s, 9H); MS(ESI$^+$): m/z 320.23 (M+H)$^+$.

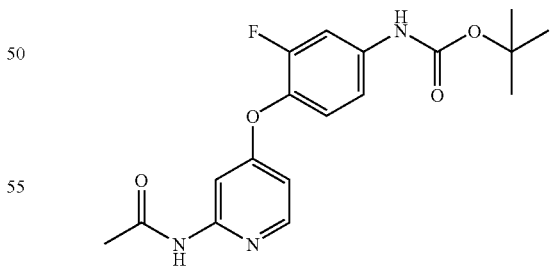

C) tert-Butyl 4-(2-acetamidopyridin-4-yloxy)-3-fluorophenylcarbamate

A tert-butyl 4-(2-aminopyridin-4-yloxy)-3-fluorophenylcarbamate (150 mg, 0.47 mmol) in anhydrous pyridine (0.5 mL) was cooled to 10° C. and treated with acetyl chloride (33 µL, 0.47 nmol) and the mixture stirred for 45 min. An additional portion of acetyl chloride (16 μL, 0.24 mmol) was added to the reaction and stirring continued for 25 min. The mixture was diluted with EtOAc (20 mL), washed with brine, dried (MgSO₄) and concentrated under vacuum to give the title compound (115 mg, 68%). $^1$H NMR (DMSO-$d_6$) δ 10.55 (s, 1H), 9.71 (s, 1H), 8.16 (d, 1H, J=5.5 Hz), 7.63-7.55 (m, 2H), 7.29-7.23 (m, 2H), 6.68-6.63 (m, 1H), 2.02 (s, 3H), 1.48 (s, 9H); MS(ESI⁺): m/z 362.22 (M+H)⁺.

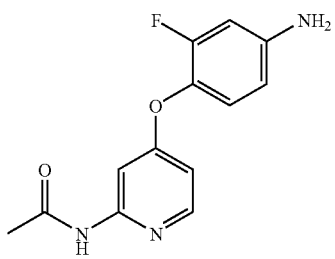

D) N-(4-(4-Amino-2-fluorophenoxy)pyridin-2-yl) acetamide

A solution of tert-butyl 4-(2-acetamidopyridin-4-yloxy)-3-fluorophenylcarbamate (110 mg, 0.30 mmol) in 4 M HCl/1,4-dioxane (1.5 mL) was stirred at 0° C. for 20 min then at room temperature for 25 min. The mixture was diluted with EtOAc (25 mL) and saturated aq. NaHCO₃ solution (20 mL), and stirred vigorously for 5 min. The EtOAc phase was washed with brine, dried (MgSO₄) and concentrated in vacuo to give the title compound (69 mg, 87%) as a yellow solid. $^1$H NMR (DMSO-$d_6$) δ 10.49 (s, 1H), 8.13 (d, 1H, J=5.6 Hz), 7.60 (m, 1H), 6.95 (dd, 1H, J=8.6, 9.2 Hz), 6.60 (dd, 1H, J=2.5, 5.6 Hz), 6.48 (dd, 1H, J=2.5, 13.2 Hz), 6.40 (dd, 1H, J=2.0, 8.6 Hz), 5.44 (s, 2H), 2.02 (s, 3H).

E) 1-(4-(2-Acetamidopyridin-4-yloxy)-3-fluorophenyl)-3-(2-(4-fluorophenyl)acetyl)urea, hydrochloride salt A solution of N-(4-(4-amino-2-fluorophenoxy)pyridin-2-yl)acetamide (20 mg, 0.077 mmol) in THF (1 mL) was treated with 0.3 M solution of 2-(4-fluorophenyl)acetyl isocyanate in toluene (Compound D of Example 11, 0.26 mL, 0.77 mmol) and the mixture was stirred at room temperature for 1 h. The mixture was concentrated under vacuum and the residue purified by preparative HPLC (Column A) to give the title compound as a TFA salt. The TFA salt was dissolved in anhydrous MeOH and treated with 1 M HCl/Et₂O at 0° C. and stirred for 5 min. The mixture was then concentrated in vacuo to give the title compound (12 mg, 33%) as a white solid. $^1$H NMR (DMSO-$d_6$): δ 11.04 (s, 1H), 10.65 (s, 1H), 10.58 (s, 1H), 8.18 (d, 1H, J=6.1 Hz), 7.77 (dd, 1H, J=2.0, 12.7 Hz), 7.56 (m, 1H), 7.40-7.30 (m, 5H), 7.18-7.14 (m, 2H), 6.71 (dd, 1H, J=2.5, 6.1 Hz), 3.74 (s, 2H), 2.03 (s, 3H); MS(ESI⁺): m/z 441.18 (M+H)⁺.

Example 81

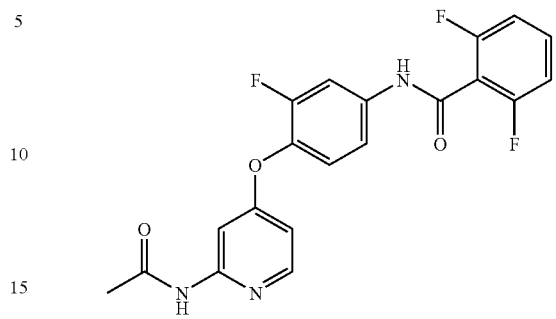

N-(4-(2-Acetamidopyridin-4-yloxy)-3-fluorophenyl)-2,6-difluorobenzamide, hydrochloride salt A solution of N-(4-(4-amino-2-fluorophenoxy)pyridin-2-yl)acetamide (Compound B' of Example 24, 15 mg, 0.057 mmol) in THF (0.5 mL) was treated with DIPEA (15 μL, 0.086 mmol) and 2-6-diflurobenzoyl chloride (10 mg, 0.057 mmol) and the mixture stirred at room temperature for 1.5 h. The mixture was concentrated under vacuum and the residue purified by preparative HPLC (Column A) to give the title compound as a TFA salt. The TFA salt was dissolved in anhydrous MeOH and treated with 1 M HCl/Et₂O at 0° C. and stirred for 5 min. The mixture was then concentrated in vacuo to give the title compound (15 mg, 60%) as a off-white solid. $^1$H NMR (DMSO-$d_6$) δ 11.17 (s, 1H), 10.79 (s, 1H), 8.21 (d, 1H, J=6.1 Hz), 7.89 (dd, 1H, J=2.0, 12.7 Hz), 7.66-7.59 (m, 1H), 7.53-7.50 (m, 2H), 7.42 (dd, 1H, J=8.6, 9.2 Hz), 7.28 (dd, 2H, J=8.1, 8.1 Hz), 6.80 (dd, 1H, J=2.0, 6.1 Hz), 2.06 (s, 3H); MS(ESI⁺): m/z 402.13 (M+H)⁺.

Example 82

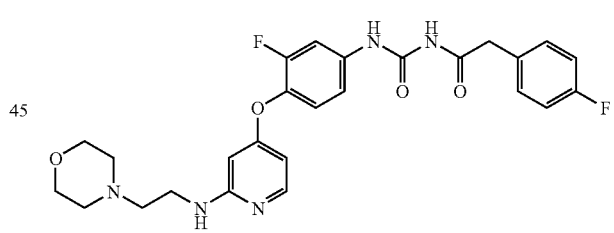

1-(3-Fluoro-4-(2-(2-morpholinoethylamino)pyridin-4-yloxy)phenyl)-3-(2-(4-fluorophenyl)acetyl)urea, dihydrochloride salt

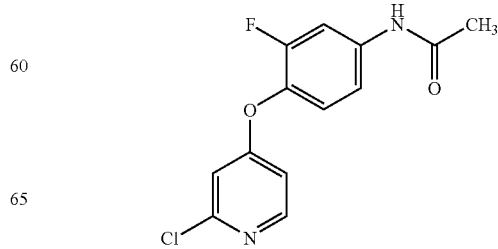

A) N-(4-(2-Chloropyridin-4-yloxy)-3-fluorophenyl)acetamide

A mixture of N-(3-fluoro-4-hydroxyphenyl)acetamide (Compound A of Example 13, 1.33 g, 7.87 mmol), 2-chloro-4-nitropyridine (Aldrich, 1.24 g, 7.87 mmol), $K_2CO_3$ (1.6 g, 11.8 mmol), and DMF (25 mL) was heated at 100° C. for 9 h. The mixture was concentrated in vacuo and the residue was partitioned between EtOAc and saturated aq. $NaHCO_3$ solution. The EtOAc phase was washed with brine, dried ($MgSO_4$), and concentrated in vacuo. The residue was purified by flash column chromatography on $SiO_2$ eluting with 30-80% EtOAc in hexanes to give the title compound (1.6 g, 73%) as a pale yellow solid. $^1H$ NMR (DMSO-$d_6$) δ 10.25 (s, 1H), 8.35 (d, 1H, J=7 Hz), 7.80 (d, 1H, J=14 Hz), 7.50 (d, 1H, J=3 Hz), 7.33 (m, 2H), 7.02 (m, 1H), 2.06 (s, 3H); MS(ESI$^+$): m/z 281.16 (M+H)$^+$.

and absolute EtOH was heated at reflux 16 h. The reaction mixture was concentrated in vacuo, and the residue was treated with $H_2O$ (3 mL) and applied to a 10 g Varian C-18 cartridge. The cartridge was eluted first with $H_2O$ then with 30% MeOH in $H_2O$. The eluent which contained the desired product was pooled, concentrated to 5 mL volume, and extracted 3 times with EtOAc. The combined extracts were washed with brine, dried ($MgSO_4$) and concentrated in vacuo to give the title compound (100 mg, 40%). $^1H$ NMR (DMSO-$d_6$) δ 10.22 (s, 1H), 7.84 (d, 1H, J=6 Hz), 7.77 (dd, 1H, J=2, 12 Hz), 7.31 (dd, 1H, J=2, 9 Hz), 7.24 (dd, 1H, J=9, 9 Hz), 6.41 (m, 1H), 6.13 (dd, 1H, J=2, 6 Hz), 5.81 (d, 1H, J=2.5 Hz), 3.56-3.48 (m, 2H), 3.31-3.19 (m, 4H), 2.38 (t, 2H, J=7 Hz), 2.40-2.28 (m, 4H), 2.06 (s, 3H); MS(ESI$^+$): m/z 405.22 (M+H)$^+$.

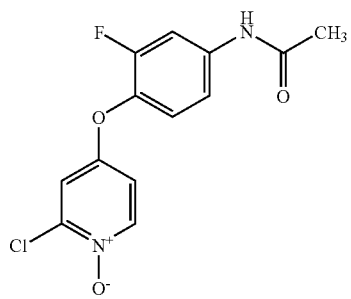

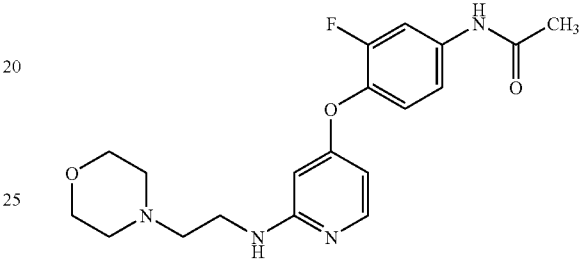

D) N-(3-Fluoro-4-(2-(2-morpholinoethylamino)pyridin-4-yloxy)phenyl)acetamide, trifluoroacetic acid salt A mixture of N-(3-fluoro-4-(2-(2-morpholinoethylamino)pyridin-4-yloxy-1-oxide)phenyl)acetamide (100 mg, 0.26 mmol), and triphenylphosphine polymer supported (1.4-2.0 mmol/g) on polystyrene (500 mg) and DMF (2 mL) was stirred at 135° C. for 15 h. The mixture was filtered to remove the resin and the resin washed with DMF and EtOAc. The filtrate and washings were combined and concentrated. The crude product was purified by preparative HPLC (Column A) to give the title compound (45 mg, 24%) as a white solid. $^1H$ NMR (DMSO-$d_6$) δ 10.33 (s, 1H), 8.02 (d, 1H, J=7 Hz) 7.84 (dd, 1H, J=2, 13 Hz), 7.39-7.31 (m, 2H), 6.52 (s, 1H), 6.10 (s, 1H), 3.83 (s, 4H), 3.60-3.48 (m, 2H), 3.32-3.18 (m, 6H), 2.08 (s, 3H); MS(ESI$^+$): m/z 375.12 (M+H)$^+$.

B) N-(4-(2-Chloropyridin-4-yloxy-1-oxide)-3-fluorophenyl)acetamide

A mixture of N-(4-(2-chloropyridin-4-yloxy)-3-fluorophenyl)acetamide (0.98 g, 3.5 mmol), >90%, m-chloroperoxybenzoic acid (1.3 g, 7.6 mmol), and $CHCl_3$ (50 mL) was stirred at rt for 60 h. The mixture was concentrated in vacuo and the residue triturated with $Et_2O$ (2×100 mL) to give the title compound (0.89 g, 86%) as a pale yellow solid. $^1H$ NMR (DMSO-$d_6$) δ 10.25 (s, 1H), 8.35 (d, 1H, J=7.3 Hz), 7.80 (d, 1H, J=13 Hz), 7.33-7.32 (m, 3H), 7.02 (dd, 1H, J=3.5, 7.5 Hz), 2.06 (s, 3H); MS(ESI$^-$): m/z 295.04 (M+H)$^+$.

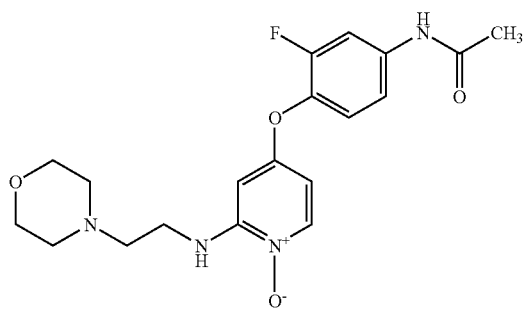

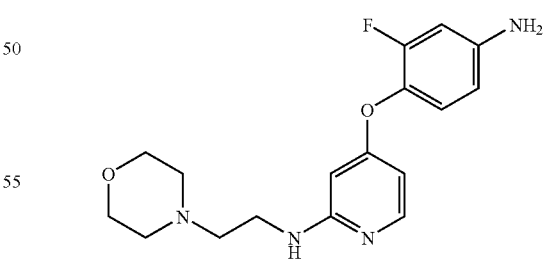

E) 4-(4-Amino-2-fluorophenoxy)-N-(2-morpholinoethyl)pyridin-2-amine, hydrochloride salt

C) N-(3-Fluoro-4-(2-(2-morpholinoethylamino)pyridin-4-yloxy-1-oxide)phenyl)acetamide A mixture of N-(4-(2-chloropyridin-4-yloxy-1-oxide)-3-fluorophenyl)acetamide hydrochloride (205 mg, 0.62 mmol), 4-(2-aminoethyl)morpholine (Aldrich, 169 mg, 1.30 mmol), A mixture of N-(3-fluoro-4-(2-(2-morpholinoethylamino)pyridin-4-yloxy)phenyl)acetamide trifluoroacetate (40 mg), MeOH (1 mL), and 6 M HCl (0.2 mL) was heated at reflux for 3 h. The mixture was concentrated on a rotary evaporator and the residue was lyophilized to give the title compound (30 mg) as a white solid. $^1$H NMR (DMSO-$d_6$) δ 11.12 (s, 1H), 8.85 (s, 1H), 7.95 (d, 1H, J=7 Hz), 7.08 (dd, 1H, J=9, 9 Hz), 6.65-6.63 (m, 2H), 6.54 (d, 1H, J=8 Hz), 6.31 (s, 1H), 3.90-3.75 (m 6H), 3.37-3.21 (m, 6H); MS(ESI$^-$): m/z 373.14 (M+H)$^+$.

F) 1-(3-Fluoro-4-(2-(2-morpholinoethylamino)pyridin-4-yloxy)phenyl)-3-(2-(4-fluorophenyl)acetyl) urea, dihydrochloride salt A solution of 4-(4-amino-2-fluorophenoxy)-N-(2-morpholinoethyl)pyridin-2-amine hydrochloride (15 mg, 0.045 mmol) in MeOH (5 mL) was treated with Et$_3$N (2 mL) and the mixture stirred at room temperature for 5 min. The mixture was concentrated in vacuo to remove the MeOH, the residue suspended in THF (1 mL) and treated with a solution of 0.3 M solution of 2-(4-fluorophenyl)acetyl isocyanate in toluene (Compound D of Example 11, 180 mL, 0.054 mmol). After stirring, the mixture was concentrated in vacuo and the residue partitioned between EtOAc and saturated NaHCO$_3$. The EtOAc phase was separated, washed with brine, dried (MgSO$_4$) and concentrated. The mixture was concentrated under vacuum and the residue purified by preparative HPLC (Column A) to give the title compound as a TFA salt. The TFA salt was dissolved in anhydrous MeOH and treated with 1 N HCl/Et$_2$O at 0° C. and stirred for 5 min. The mixture was then concentrated in vacuo to give the title compound (10 mg, 43%) as a white solid. $^1$H NMR (DMSO-$d_6$) δ 11.05 (s, 1H), 10.61 (s, 1H), 7.98 (d, 1H, J=7.1 Hz), 7.86-7.73 (m, 1H), 7.48-7.38 (m, 1H), 7.37-7.30 (m, 3H), 7.24-7.04 (m, 2H), 6.60 (s, 1H), 6.26 (s, 1H), 3.98-3.60 (m, 8H), 3.74 (s, 2H), 3.39-3.19 (m, 4H); MS(ESI$^+$): m/z 512.2 (M+H)$^+$.

Examples 83-85 were prepared in a similar manner as described for Example 82.

Example 83

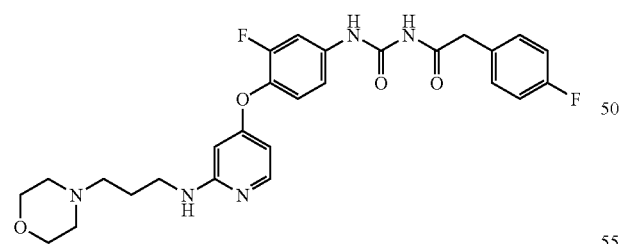

1-(3-Fluoro-4-(2-(3-morpholinopropylamino)pyridin-4-yloxy)phenyl)-3-(2-(4-fluorophenyl)acetyl) urea, hydrochloride salt $^1$H NMR (DMSO-$d_6$) δ 11.06 (s, 1H), 10.62 (s, 1H), 7.93 (d, 1H, J=7.1 Hz), 7.83 (d, 1H, J=12.7 Hz), 7.45-7.33 (m, 4H), 7.16 (dd, 2H, J=8.6, 9.2 Hz), 6.64 (s, 1H), 6.23 (s, 1H), 3.95-3.76 (m, 4H), 3.74 (s, 2H), 3.70-3.48 (m, 4H), 3.48-3.35 (m, 2H), 3.20-3.-04 (m, 2H), 2.02-1.93 (m, 2H).

Example 84

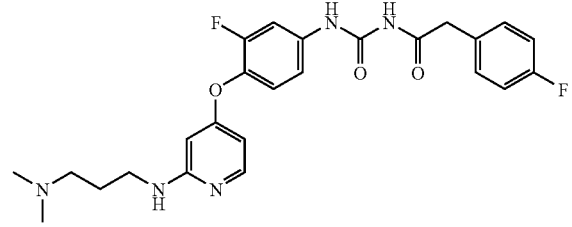

1-(4-(2-(3-(Dimethylamino)propylamino)pyridin-4-yloxy)-3-fluorophenyl)-3-(2-(4-fluorophenyl)acetyl) urea, hydrochloride salt $^1$H NMR (DMSO-$d_6$) δ 11.06 (s, 1H), 10.62 (s, 1H), 10.37 (s, 1H), 7.93 (d, 1H, J=7.1 Hz), 7.82 (dd, 1H, J=2.0, 12.7 Hz), 7.45 (dd, 1H, J=2.6, 8.6 Hz), 7.40 (d, 1H, J=8.6 Hz), 7.37-7.33 (m, 2H), 7.16 (dd, 2H, J=8.7, 9.1 Hz), 6.65 (s, 1H), 6.24 (s, 1H), 3.75 (s, 2H), 3.45-3.36 (m, 2H), 3.13-3.03 (m, 2H), 2.73 (s, 3H), 2.72 (s, 3H), 1.94-1.90 (m, 2H).

Example 85

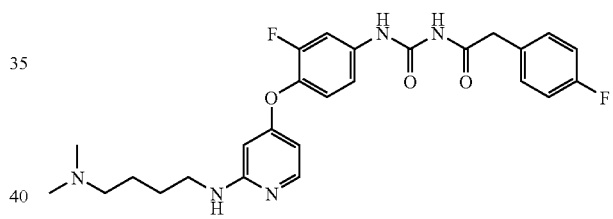

1-(4-(2-(4-(Dimethylamino)butylamino)pyridin-4-yloxy)-3-fluorophenyl)-3-(2-(4-fluorophenyl)acetyl) urea, hydrochloride salt MS(ESI$^+$): m/z 498.2 (M+H)$^+$.

Example 86

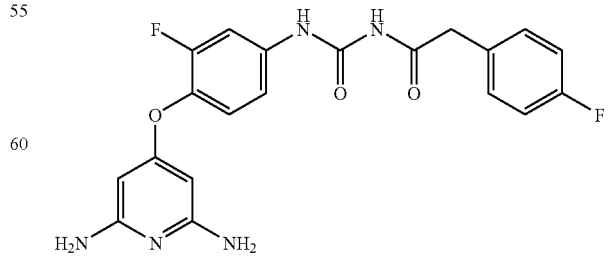

1-(4-(2,6-Diaminopyridin-4-yloxy)-3-fluorophenyl)-
3-(2-(4-fluorophenyl)acetyl)urea, hydrochloride salt

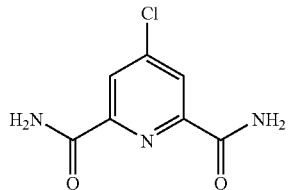

A) 4-Chloropyridine-2,6-dicarboxamide

A mixture of chelidamic acid (3.19 g, 17.0 mmol), PCl$_5$ (2.1 g) and CCl$_4$ (30 mL) was refluxed for 6 h and then cooled to 65° C. and treated with MeOH (5 mL) under gentle reflux. The mixture was refluxed for 5 h and then concentrated in vacuo. The residue was treated with ice-water (50 mL) and the precipitated solid was collected by filtration and sucked dry on the funnel to give white needles of 2,6-biscarbomethoxy-4-chloropyridine (2.4 g). The product was treated with ~7 M NH$_3$/MeOH and stirred at room temperature for 1 h. The mixture was filtered to collect the title compound as a white solid (1.8 g, 53%). $^1$H NMR (DMSO-d$_6$) δ 8.91 (s, 2H), 8.15 (s, 2H), 7.87 (s, 2H).

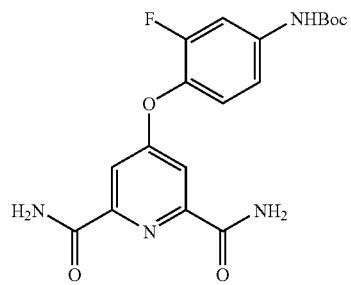

B) tert-Butyl 4-(2,6-dicarbamoylpyridin-4-yloxy)-3-fluorophenylcarbamate

A solution of N-Boc-4-amino-2-fluorophenol (228 mg, 1.0 mmol) in DMF (2 mL) was treated with t-BuOK (124 mg, 1.1 mmol) and the mixture stirred at room temperature for 2 h. The mixture was treated with 4-chloropyridine-2,6-dicarboxamide (200 mg, 1.0 mmol) and K$_2$CO$_3$ (35 mg, 0.5 mmol) and heated at 80° C. for 1.5 h. The mixture was concentrated in vacuo, treated with EtOAc (10 mL) and H$_2$O (10 mL) and filtered to remove the insoluble material. The EtOAc phase was washed with brine, dried (MgSO$_4$) and concentrated in vacuo. Purification of the residue by flash column chromatography on SiO$_2$ eluting with 30-100% EtOAc/hexanes gave the title compound (170 mg, 44%) as a white solid containing 10% of the starting chloropyridine. $^1$H NMR (DMSO-d$_6$) δ 9.77 (s, 1H), 8.86 (s, 2H), 7.87 (s, 1H), 7.63 (d, 1H, J=12.1 Hz), 7.55 (s, 2H), 7.38-7.31 (m, 2H), 1.48 (s, 9H).

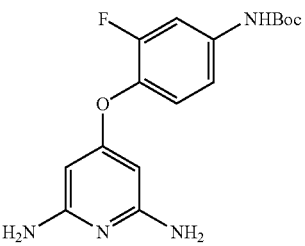

C) tert-Butyl 4-(2,6-diaminopyridin-4-yloxy)-3-fluorophenylcarbamate

The title compound was prepared from tert-butyl 4-(2,6-dicarbamoylpyridin-4-yloxy)-3-fluorophenylcarbamate (110 mg, 0.28 mmol) using a similar procedure as described for Step B of Example 80. Flash chromatography on SiO$_2$ eluting with 0-2% MeOH/EtOAc gave the title compound (60 mg, 63%) as a white solid. $^1$H NMR (DMSO-d$_6$) δ 9.60 (s, 1H), 7.50 (dd, 1H, J=1.8, 13.6 Hz), 7.21 (dd, 1H, J=2.2, 8.7 Hz), 7.13 (dd, 1H, J=8.7, 9.2 Hz), 5.40 (s, 4H), 5.13 (s, 2H), 1.47 (s, 9H); MS(ESI$^+$): m/z 335.23 (M+H)$^+$.

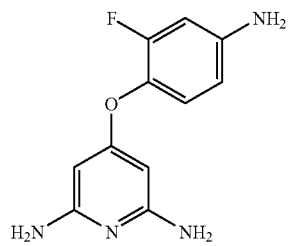

D) 4-(4-Amino-2-fluorophenoxy)pyridine-2,6-diamine

The title compound was prepared form tert-butyl 4-(2,6-diaminopyridin-4-yloxy)-3-fluorophenylcarbamate (30 mg, 0.089 mmol) in a manner similar to that is described in Step D of Example 80 to give a clear oil (20 mg, 100%). MS(ESI$^+$): m/z 235.22 (M+H)$^+$.

E) 1-(4-(2,6-Diaminopyridin-4-yloxy)-3-fluorophenyl)-3-(2-(4-fluorophenyl)acetyl)urea, hydrochloride salt The title compound was prepared from 4-(4-amino-2-fluorophenoxy)pyridine-2,6-diamine (19 mg, 0.081 mmol) and a solution of 2-(4-fluorophenyl)acetyl isocyanate in toluene (0.3 M, Compound D of Example 11, 0.27 mL, 0.081 mmol) in a similar manner as Step D of Example 33. The reaction mixture was purified by preparative HPLC (Column A) to give the title compound as a TFA salt. The TFA salt was dissolved in anhydrous MeOH and treated with 1 M HCl/Et$_2$O at 0° C. and stirred for 5 min. The mixture was then concentrated in vacuo to give the title compound (8 mg, 24%) as a pale yellow solid. $^1$H NMR (DMSO-d$_6$) δ 11.01 (s, 1H), 10.51 (s, 1H), 7.68 (dd, 1H, J=2.6, 12.7 Hz), 7.36-7.30 (m, 3H), 7.22-7.14 (m, 3H), 5.52 (s, 4H), 5.15 (s, 2H), 3.73 (s, 2H); MS(ESI+): m/z 414.09 (M+H)+. Example 87

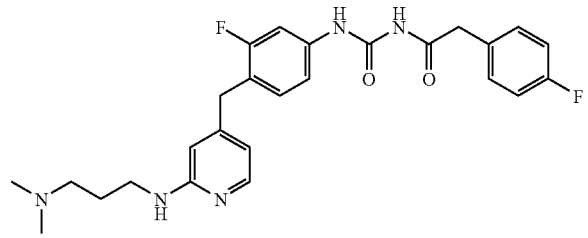

1-(4-((2-(3-(Dimethylamino)propylamino)pyridin-4-yl)methyl)-3-fluorophenyl)-3-(2-(4-fluorophenyl)acetyl)urea, dihydrochloride salt

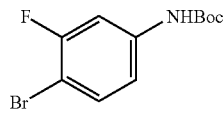

A) tert-Butyl 4-bromo-3-fluorophenylcarbamate

To a solution of 4-bromo-3-fluorobenzenamine (Lancaster, 7.05 g, 37.1 mmol) in anhydrous tetrahydrofuran (40 mL) at room temperature was added (Boc)₂O (8.10 g, 37.1 mmol) and triethylamine (5.17 mL, 37.1 mmol). The reaction mixture was heated at reflux overnight. After cooling down, the reaction mixture was concentrated under reduced pressure. The residue was purified by flash column chromatography on SiO₂ eluting with 20% dichloromethane in hexane, then 20% ethyl acetate in hexane to give tert-butyl 4-bromo-3-fluorophenylcarbamate (5.30 g, 49% yield). MS(ESI+): m/z 290.2 (M+H)+.

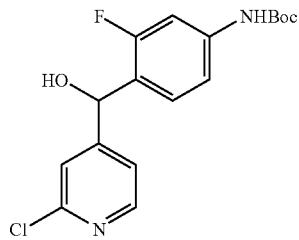

B) tert-Butyl 4-((2-chloropyridin-4-yl)(hydroxy)methyl)-3-fluorophenylcarbamate

To a solution of tert-butyl 4-bromo-3-fluorophenylcarbamate (2.60 g, 9.0 mmol) in anhydrous THF (30 mL) at −78° C. was added MeMgBr (3.0 M in Et₂O, 3.1 mL, 9.3 mmol) via syringe. The solution was stirred for 10 min at that temperature, and then warmed to 0° C. for 0.5 h. After the solution was cooled back to −78° C., a solution of t-BuLi (1.7 M in hexane, 10.6 mL, 18.1 mmol) was added over 4 min. The resulting solution was allowed to stir for 5 min before a solution of 2-chloroisonicotinaldehyde (1.41 g, 10 mmol) (for preparation, see Frey, L. F. et al. *Tetrahedron Lett.* 2001, 42, 6815) in anhydrous THF (25 mL) was added in 3 min. The reaction mixture was stirred at −78° C. for 20 min and 2.0 mL of MeOH was added. The solution was then concentrated under reduced pressure and the residue was dissolved in 200 mL of EtOAc. It was subsequently washed with H₂O (2×50 mL), brine (2×50 mL) and dried over MgSO₄. After filtration and concentration, the residue was purified by flash chromatography on SiO₂ eluting with 0%-50% EtOAc in hexane to give tert-butyl 4-((2-chloropyridin-4-yl)(hydroxy)methyl)-3-fluorophenylcarbamate (1.30 g, 41% yield). MS(ESI+): m/z 353.28/355.24 (M+H)+.

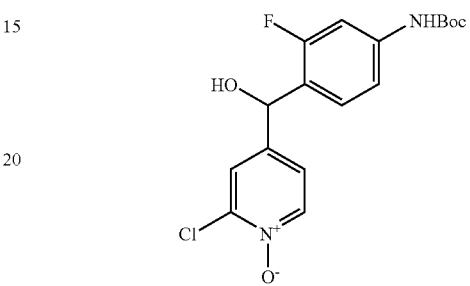

C) tert-Butyl 4-((2-chloropyridin-N-oxide-4-yl)(hydroxy)methyl)-3-fluorophenylcarbamate To a solution of tert-butyl 4-((2-chloropyridin-4-yl)(hydroxy)methyl)-3-fluorophenylcarbamate (1.20 g, 3.40 mmol) in a mixture of dichloromethane (100 mL) and ethyl acetate (10 mL) was added m-CPBA (70%, 2.34 g, 9.48 mmol). The reaction mixture was stirred at room temperature for 2 h, and then heated at reflux for 5 h. The solvent was removed under reduced pressure and the residue was purified by flash chromatography on SiO₂ eluting with 50% EtOAc in hexane, 100% EtOAc and then 10% MeOH in EtOAc, to give tert-butyl 4-((2-chloropyridin-N-oxide-4-yl)(hydroxy)methyl)-3-fluorophenylcarbamate (840 mg, 67% yield). MS(ESI+): m/z 369.13/371.13 (M+H)+.

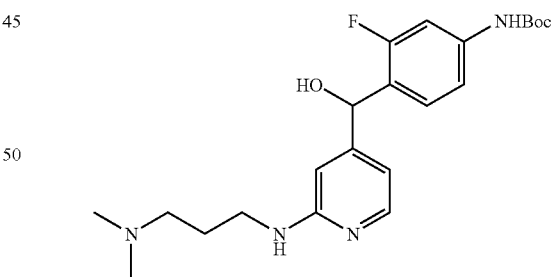

D) tert-Butyl 4-((2-(3-(dimethylamino)propylamino)pyridine-4-yl)(hydroxy)methyl)-3-fluorophenylcarbamate To a solution of tert-butyl 4-((2-chloropyridin-N-oxide-4-yl)(hydroxy)methyl)-3-fluorophenylcarbamate (80 mg, 0.22 mmol) in EtOH (2.0 mL) was added N¹,N¹-dimethylpropane-1,3-diamine (225 mg, 2.2 mmol). The reaction mixture was heated at 80° C. for 12 h and the solvent was removed to provide crude tert-butyl 4-((2-(3-(dimethylamino)propylamino)pyridine-N-oxide-4-yl)(hydroxy)methyl)-3-fluorophenylcarbamate, which was directly used in the next step. MS(ESI+): m/z 435.37 (M+H)+.

To a solution of tert-butyl 4-((2-(3-(dimethylamino)propylamino)pyridine-N-oxide-4-yl)(hydroxy)methyl)-3-fluorophenylcarbamate (~0.22 mmol) in MeOH (2.0 mL) was added zinc (114 mg, 1.75 mmol) and NH$_4$CO$_2$H (139 mg, 2.20 mmol). The suspension was refluxed overnight. More zinc (114 mg) and NH$_4$CO$_2$H (139 mg) were added and the suspension was refluxed for 2 h. After cooling down, the solution was filtered and the filtrate was concentrated under reduced pressure. The residue was then purified by flash chromatography on SiO$_2$ eluting with 10-30% MeOH in DCM to give tert-butyl 4-((2-(3-(dimethylamino)propylamino)pyridine-4-yl)(hydroxy)methyl)-3-fluorophenylcarbamate (80 mg, 87% yield). MS(ESI+): m/z 419.34 (M+H)+.

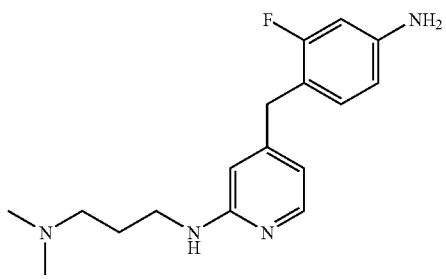

E) 4-(4-Amino-2-fluorobenzyl)-N-(3-(dimethylamino)propyl)pyridin-2-amine

To a solution of tert-butyl 4-((2-(3-(dimethylamino)propylamino)pyridine-4-yl)(hydroxy)methyl)-3-fluorophenylcarbamate (80 mg, 0.19 mmol) in MeOH (5.0 mL) was added 2 mL of conc. HCl and palladium on charcoal (10%, 200 mg). The suspension was heated at 75° C. under H$_2$ atmosphere for 24 h. The mixture was cooled down, filtered and concentrated in vacuo. The residue was dissolved in 1 mL of conc. NH$_4$OH and it was extracted with DCM (5×5 mL). The combined organic layer was dried over Na$_2$SO$_4$. After filtration, it was concentrated in vacuo to give 4-(4-amino-2-fluorobenzyl)-N-(3-(dimethylamino)propyl)pyridin-2-amine (31 mg, 40% yield). MS(ESI+): m/z 303.31 (M+H)+.

F) 1-(4-((2-(3-(Dimethylamino)propylamino)pyridin-4-yl)methyl)-3-fluorophenyl)-3-(2-(4-fluorophenyl)acetyl)urea, dihydrochloride salt To a solution of 4-(4-amino-2-fluorobenzyl)-N-(3-(dimethylamino)propyl)pyridin-2-amine (30 mg, 0.1 mmol) in DCM (2 mL) was added a solution of 2-(4-fluorophenyl)acetyl isocyanate (Compound D of Example 11, 0.347 M in toluene, 0.25 mL). The mixture was stirred at room temperature for 0.5 h before it was quenched with MeOH. The solution was concentrated in vacuo and the residue was purified by prep. HPLC. The desired fractions were collected and concentrated in vacuo. The residue was dissolved in MeOH and polymer bound diethylene triamine (50 mg) was added to remove trifluoroacetic acid. After filtration and concentration, the residue was converted to a hydrochloride salt by the addition of 1 N HCl (0.5 mL) and lyophilized to give 1-(4-((2-(3-(dimethylamino)propylamino)pyridin-4-yl)methyl)-3-fluorophenyl)-3-(2-(4-fluorophenyl)acetyl)urea hydrochloride (8.0 mg, 14% yield). MS(ESI+): m/z 482.24 (M+H)+.

Example 88

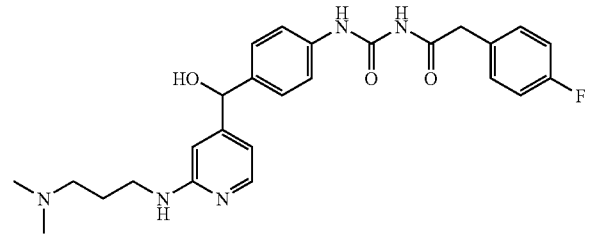

1-(4-((2-(3-(Dimethylamino)propylamino)pyridin-4-yl)(hydroxy)methyl)phenyl)-3-(2-(4-fluorophenyl)acetyl)urea

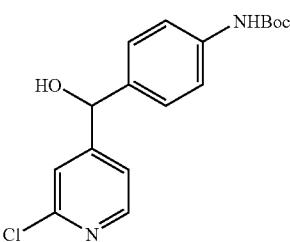

A) tert-Butyl 4-((2-chloropyridin-4-yl)(hydroxy)methyl)phenylcarbamate

Prepared in a manner similar to that which is described in Step B of Example 87. 2-Chloroisonicotinaldehyde (141 mg, 1.0 mmol) was converted to tert-butyl 4-((2-chloropyridin-4-yl)(hydroxy)methyl)phenylcarbamate (190 mg, 57% yield). MS(ESI+): m/z 335.27/337.27 (M+H)+.

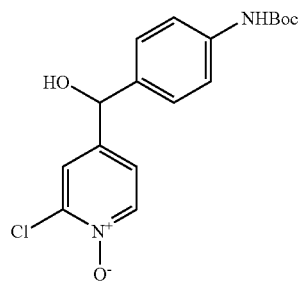

B) tert-Butyl 4-((2-chloropyridin-N-oxide-4-yl)(hydroxy)methyl) phenylcarbamate

Prepared in a manner similar to that which is described in Step C of Example 87. tert-Butyl 4-((2-chloropyridin-4-yl)(hydroxy)methyl)phenylcarbamate (78 mg, 0.23 mmol) was converted to tert-butyl 4-((2-chloropyridin-N-oxide-4-yl)(hydroxy)methyl)phenylcarbamate (36 mg, 44% yield). MS(ESI+): m/z 351.28/353.27 (M+H)+.

163 / 164

Example 89

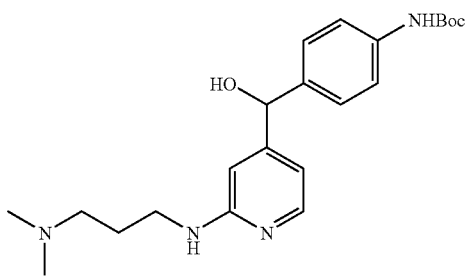

C) tert-Butyl 4-((2-(3-(dimethylamino)propylamino)pyridin-4-yl)(hydroxy)methyl)phenylcarbamate Prepared in a manner similar to that which is described in Step D of Example 87. tert-Butyl 4-((2-chloropyridin-N-oxide-4-yl)(hydroxy)methyl) phenylcarbamate (36 mg, 0.1 mmol) was converted to tert-butyl 4-((2-(3-(dimethylamino)propylamino)pyridin-4-yl)(hydroxy)methyl)phenylcarbamate (16 mg, 40% yield). MS(ESI+): m/z 401.38 (M+H)+.

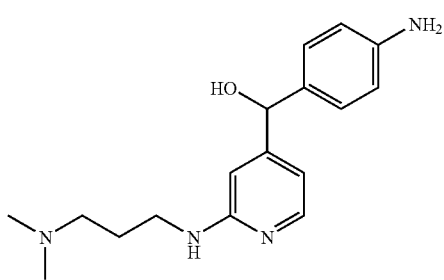

D) (4-Aminophenyl)(2-(3-(dimethylamino)propylamino)pyridin-4-yl)methanol

To a solution of tert-butyl 4-((2-(3-(dimethylamino)propylamino)pyridin-4-yl)(hydroxy)methyl)phenylcarbamate (16 mg, 0.04 mmol) in 1 mL of DCM were added Et₃SiH (0.1 mL)/TFA in DCM (10%, 0.2 mL). The mixture was stirred for 1 hr and no reaction was detected by LC-MS. Another 0.1 mL of Et₃SiH and 0.8 mL of TFA in DCM (10%) were added and the mixture was stirred for 2 h. The solvent was removed and was purified by solid extraction (Waters Oasis®MCX extraction cartridge) to give (4-aminophenyl)(2-(3-(dimethylamino)propylamino)pyridin-4-yl)methanol (6.0 mg, 50% yield). MS(ESI+): m/z 301.40 (M+H)+.

E) 1-(4-((2-(3-(Dimethylamino)propylamino)pyridin-4-yl)(hydroxy)methyl)phenyl)-3-(2-(4-fluorophenyl)acetyl)urea Prepared in a manner similar to that which is described in Step F of Example 87. 4-Aminophenyl-(2-(3-(dimethylamino)propylamino)pyridin-4-yl)methanol (6.0 mg, 0.02 mmol) was converted to 1-(4-((2-(3-(dimethylamino)propylamino)pyridin-4-yl)(hydroxy)methyl)phenyl)-3-(2-(4-fluorophenyl)acetyl)urea, bis-trifluoroacetic acid (6.1 mg, 43% yield). ¹H NMR (CD₃OD) δ 7.82 (d, 1H, J=6.4 Hz), 7.50 (m, 2H), 7.36 (m, 4H), 7.07 (m, 3H), 6.75 (m, 1H), 5.68 (s, 1H), 3.71 (s, 2H), 3.21-3.49 (m, 4H), 2.90 (s, 6H), 2.08 (m, 2H); MS(ESI+): m/z 480.31 (M+H)+.

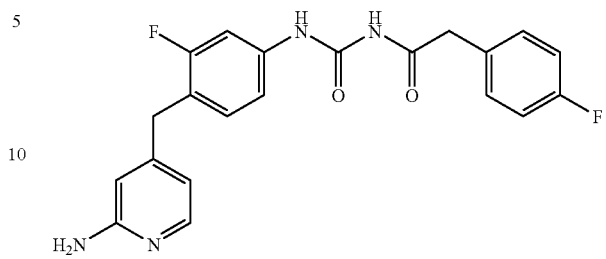

1-(4-((2-Aminopyridin-4-yl)methyl)-3-fluorophenyl)-3-(2-(4-fluorophenyl)acetyl)urea, trifluoroacetic acid salt

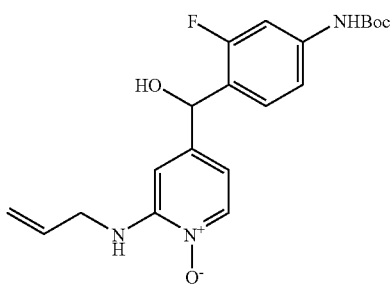

A) tert-Butyl 4-((2-(allylamino)pyridin-N-oxide-4-yl)(hydroxy)methyl)-3-fluorophenylcarbamate To a solution of tert-butyl 4-((2-chloropyridin-N-oxide-4-yl)(hydroxy)methyl)-3-fluorophenylcarbamate (Step C of Example 87, 500 mg, 1.36 mmol) in EtOH (14 mL) was added allylamine (1.0 mL, 13.6 mmol). The mixture was heated at 80° C. overnight. After cooling down, the solvent was removed and the residue was purified by flash chromatography on SiO₂ eluting with 0%-15% MeOH in DCM to give tert-butyl 4-((2-(allylamino)pyridin-N-oxide-4-yl)(hydroxy)methyl)-3-fluorophenylcarbamate (440 mg, 83% yield). MS(ESI+): m/z 390.19 (M+H)+.

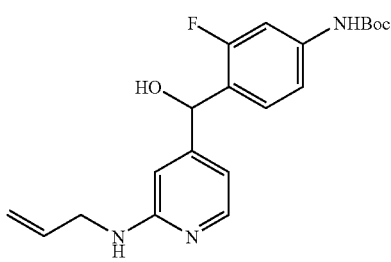

B) tert-Butyl 4-((2-(allylamino)pyridin-4-yl)(hydroxy)methyl)-3-fluorophenylcarbamate Prepared in a manner similar to that which is described in Step D of Example 87. tert-Butyl 4-((2-(allylamino)pyridin- N-oxide-4-yl)(hydroxy)methyl)-3-fluorophenylcarbamate (440 mg, 1.13 mmol) was converted to tert-butyl 4-((2-(allylamino)pyridin-4-yl)(hydroxy)methyl)-3-fluorophenylcarbamate (400 mg, 95% yield). MS(ESI+): m/z 374.33 (M+H)+.

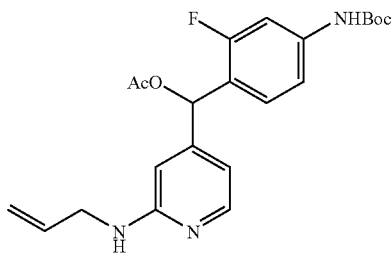

C) (2-(Allylamino)pyridin-4-yl)(4-(tert-butoxycarbonyl)-2-fluorophenyl)methyl acetate To a solution of tert-butyl 4-((2-(allylamino)pyridin-4-yl)(hydroxy)methyl)-3-fluorophenylcarbamate (400 mg, 1.1 mmol) in THF (10 mL) were added diisopropylethylamine (DIEA) (0.2 mL, 1.1 mmol), 4-dimethylaminopyridine (DMAP) (360 mg, 3.0 mmol) and Ac$_2$O (0.29 μL, 3.0 mmol). The mixture was stirred overnight and then heated at reflux for 1 h. After cooling down, the solvent was removed under reduced pressure and the residue was purified by flash chromatography on SiO$_2$ eluting with 0%-100% EtOAc in hexane to give (2-(allylamino)pyridin-4-yl)(4-(tert-butoxycarbonyl)-2-fluorophenyl)methyl acetate (390 mg, 85% yield). MS(ESI+): m/z 416.33 (M+H)+.

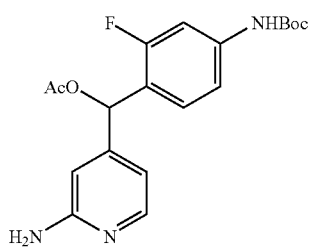

D) (2-Aminopyridin-4-yl)(4-(tert-butoxycarbonyl)-2-fluorophenyl)methyl acetate

A solution of (2-(allylamino)pyridin-4-yl)(4-(tert-butoxycarbonyl)-2-fluorophenyl)methyl acetate (380 mg, 0.91 mmol) in a mixture of EtOH/H$_2$O (10:1, 40 mL) was degassed via bubbling N$_2$ into the solution for 1 h. To the mixture was added Rh(PPh$_3$)$_3$Cl (80 mg, 0.09 mmol). The solution was refluxed to remove the solvent and the residue was purified by flash chromatography on SiO$_2$, followed by preparitve HPLC purification, to give (2-aminopyridin-4-yl)(4-(tert-butoxycarbonyl)-2-fluorophenyl)methyl acetate, trifluoroacetic acid salt (185 mg, 42% yield). MS(ESI+): m/z 376.26 (M+H)+.

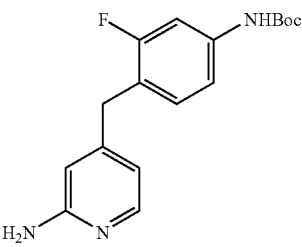

E) tert-Butyl 4-((2-aminopyridin-4-yl)methyl)-3-fluorophenylcarbamate

To a solution of (2-aminopyridin-4-yl)(4-(tert-butoxycarbonyl)-2-fluorophenyl)methyl acetate as a TFA salt (180 mg, 0.37 mmol) in MeOH (10 mL) was added 10% Pd/C (90 mg). The suspension was stirred under H$_2$ atmosphere for 1 h. The catalyst was removed and the filtrate was concentrated in vacuo. The residue was then purified by flash chromatography on SiO$_2$ eluting with 3% MeOH in DCM, to give tert-butyl 4-((2-aminopyridin-4-yl)methyl)-3-fluorophenylcarbamate as a TFA salt (73 mg, 46% yield). MS(ESI+): m/z 318.24 (M+H)+.

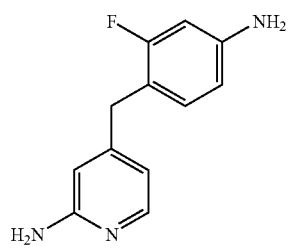

F) 4-(4-Amino-2-fluorobenzyl)pyridin-2-amine

To a solution of tert-butyl 4-((2-aminopyridin-4-yl)methyl)-3-fluorophenylcarbamate as a TFA salt (73 mg, 0.17 mmol) in DCM (4.0 mL) was added TFA (1.0 mL). The solution was stirred at room temperature for 2 h and the solvent was removed in vacuo to give 4-(4-amino-2-fluorobenzyl)pyridin-2-amine, bis-trifluoroacetic acid (70 mg, 93% yield). MS(ESI+): m/z 218.12 (M+H)+.

G) 1-(4-((2-Aminopyridin-4-yl)methyl)-3-fluorophenyl)-3-(2-(4-fluorophenyl)acetyl)urea, trifluoroacetic acid salt Prepared in a manner similar to that which is described in Step F of Example 87. 4-(4-Amino-2-fluorobenzyl)pyridin-2-amine as 2 TFA salt (19 mg, 0.042 mmol) was converted to 1-(4-((2-aminopyridin-4-yl)methyl)-3-fluorophenyl)-3-(2-(4-fluorophenyl)acetyl)urea, trifluoroacetic acid salt (19 mg, 88% yield). $^1$H NMR (DMSO-d$_6$) δ 10.94 (s, 1H), 10.47 (s, 1H), 7.76 (m, 3H), 7.50 (d, 1H, J=11.5 Hz), 7.10-7.26 (m, 4H), 7.10 (m, 2H), 6.65 (d, 1H, J=6.5 Hz), 6.55 (s, 1H), 3.89 (s, 2H), 3.65 (s, 2H); MS(ESI+): m/z 397.26 (M+H)+.

Example 90

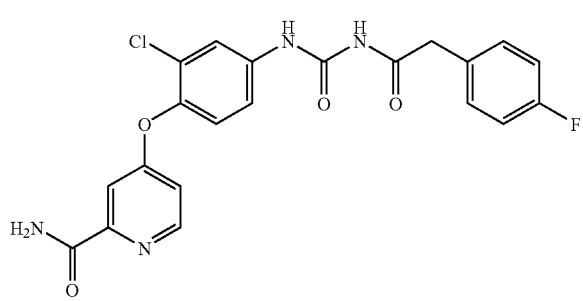

1-(4-(2-Carbamoylpyridin-4-yloxy)-3-chlorophenyl)-3-(2-(4-fluorophenyl)acetyl)urea

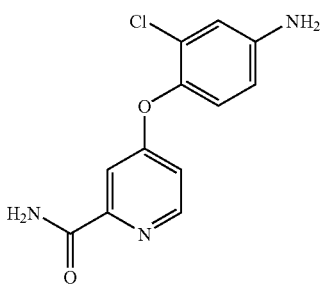

A) 4-(4-Amino-2-chlorophenoxy)picolinamide

To a solution of 4-amino-2-chlorophenol (Aldrich, 430 mg, 3.0 mmol) in DMF (2.0 mL) at room temperature was added KOt-Bu (352 mg, 3.2 mmol). The mixture was allowed to stir at room temperature for 1 h. To the solution were then added 4-chloropicolinamide (468 mg, 3.0 mmol) and K$_2$CO$_3$ (221 mg, 1.6 mmol). The resulting suspension was heated at 90° C. overnight. After cooling down, the suspension was diluted with 100 mL of EtOAc and 50 mL of H$_2$O. The organic layer was separated and washed with brine (2×25 mL) and dried over MgSO$_4$. After filtration and concentration, the solid was triturated with 50 mL of DCM. The solid was then collected and washed with DCM (2×20 mL), EtOAc (5.6 mL) and dried to give 4-(4-amino-2-chlorophenoxy)picolinamide (320 mg, 40% yield). MS(ESI$^+$): m/z 264.12/266.07 (M+H)$^+$.

B) 1-(4-(2-Carbamoylpyridin-4-yloxy)-3-chlorophenyl)-3-(2-(4-fluorophenyl)acetyl)urea Prepared in a manner similar to that which is described in Step F of Example 87. 4-(4-Amino-2-chlorophenoxy)picolinamide (79 mg, 0.30 mmol) in DMF (1.0 mL) was converted to 1-(4-(2-carbamoylpyridin-4-yloxy)-3-chlorophenyl)-3-(2-(4-fluorophenyl)acetyl)urea (65 mg, 49% yield). $^1$H NMR (DMSO-d$_6$) δ 11.05 (s, 1H), 10.58 (s, 1H), 8.52 (d, 1H, J=4.5 Hz), 8.15 (s, 1H), 7.98 (s, 1H), 7.70 (s, 1H), 7.55 (m, 1H), 7.39 (m, 3H), 7.27 (m, 1H), 7.16 (m, 3H), 3.73 (s, 2H); MS(ESI$^+$): m/z 443.17 (M+H)$^+$.

Example 91

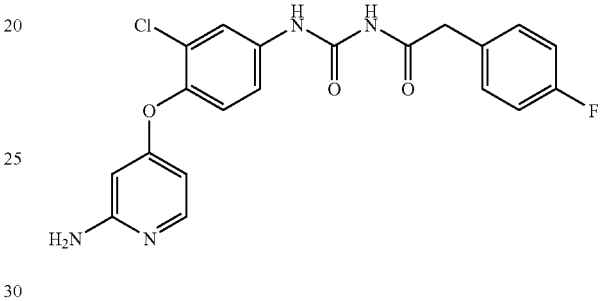

1-(4-(2-Aminopyridin-4-yloxy)-3-chlorophenyl)-3-(2-(4-fluorophenyl)acetyl)urea, hydrochloride salt To a solution of 1-(4-(2-carbamoylpyridin-4-yloxy)-3-chlorophenyl)-3-(2-(4-fluorophenyl)acetyl)urea (Example 90, 27 mg, 0.06 mmol) in DMF (1.0 mL) were added H$_2$O (2.2 mg, 0.12 mmol), pyridine (0.04 mL) and bis(trifluoroacetoxy)iodobenzene (Aldrich, 39 mg, 0.09 mmol) at room temperature. The solution was allowed to stir overnight and then it was purified on prep HPLC to give the desired product, which was further converted to 1-(4-(2-aminopyridin-4-yloxy)-3-chlorophenyl)-3-(2-(4-fluorophenyl)acetyl)urea hydrochloride (19 mg, 70% yield) by the addition of 1N HCl solution (0.5 mL). $^1$H NMR (DMSO-d$_6$) δ 13.50 (s, 1H), 11.02 (s, 1H), 10.57 (s, 1H), 7.80-7.95 (m, 4H), 7.55 (m, 1H), 7.37 (m, 1H), 7.30 (m, 2H), 7.11 (m, 2H), 6.60 (m, 1H), 6.00 (s, 1H), 3.70 (s, 2H); MS(ESI$^+$): m/z 415.16 (M+H)$^+$.

Example 92

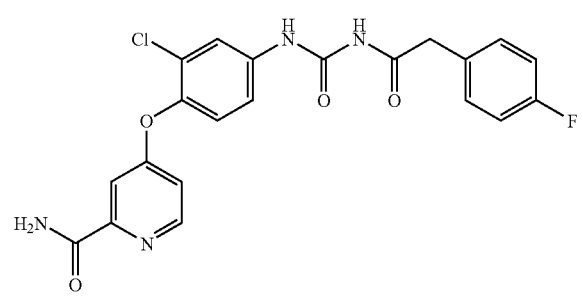

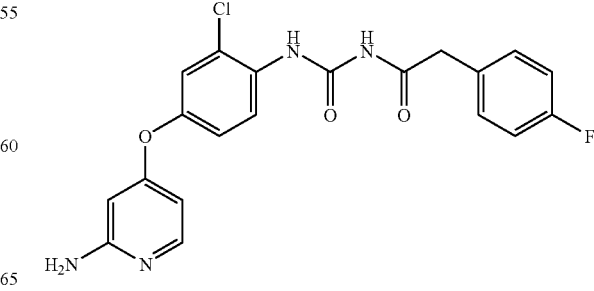

1-(4-(2-Aminopyridin-4-yloxy)-2-chlorophenyl)-3-(2-(4-fluorophenyl)acetyl)urea

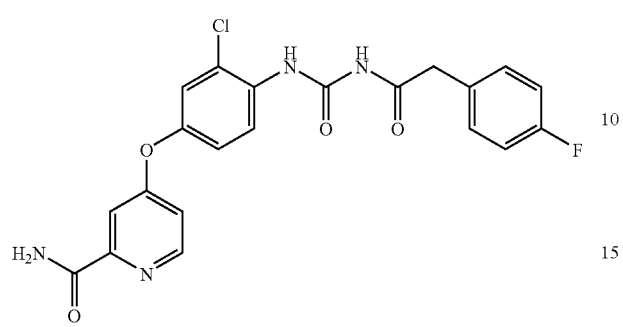

A) 1-(4-(2-Carbamoylpyridin-4-yloxy)-2-chlorophenyl)-3-(2-(4-fluorophenyl)acetyl)urea Prepared in a manner similar to that which is described in Step A of Example 90. 4-(4-Amino-3-chlorophenoxy)picolinamide (39 mg, 0.19 mmol) in DMF (1.0 mL) was converted to 1-(4-(2-carbamoylpyridin-4-yloxy)-2-chlorophenyl)-3-(2-(4-fluorophenyl)acetyl)urea (18 mg, 41% yield) after prep HPLC purification. MS(ESI$^+$): m/z 443.13/445.14 (M+H)$^+$.

B) 1-(4-(2-Aminopyridin-4-yloxy)-2-chlorophenyl)-3-(2-(4-fluorophenyl)acetyl)urea Prepared in a manner similar to that which is described for Example 91. 1-(4-(2-Carbamoylpyridin-4-yloxy)-2-chlorophenyl)-3-(2-(4-fluorophenyl)acetyl)urea (18 mg, 0.04 mmol) in DMF (1.0 mL) was converted to 1-(4-(2-aminopyridin-4-yloxy)-2-chlorophenyl)-3-(2-(4-fluorophenyl)acetyl)urea (10 mg, 55% yield). $^1$H NMR (DMSO-d$_6$) δ 13.47 (s, 1H), 11.26 (s, 1H), 11.08 (s, 1H), 8.37 (d, 1H, J=8.5 Hz), 7.95 (d, 1H, J=7.5 Hz), 7.88 (s, 2H), 7.62 (s, 1H), 7.35 (m, 3H), 7.17 (m, 2H), 6.64 (d, 1H, J=7.5 Hz), 6.13 (s, 1H), 3.76 (s, 2H); MS(ESI$^+$): m/z 415.18/417.17 (M+H)$^+$.

Example 93

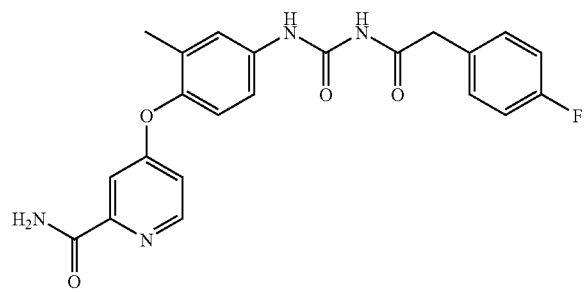

1-(4-(2-Carbamoylpyridin-4-yloxy)-3-methylphenyl)-3-(2-(4-fluorophenyl)acetyl)urea

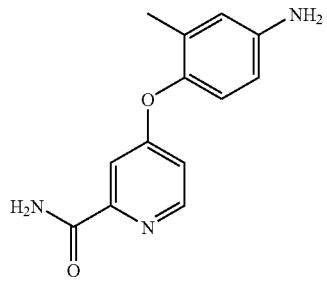

A) 4-(4-Amino-2-methylphenoxy)picolinamide

Prepared in a manner similar to that which is described in Step A of Example 90. 4-Amino-2-methylphenol (246 mg, 2.0 mmol) was converted to 4-(4-amino-2-methylphenoxy)picolinamide (230 mg, 47% yield). MS(ESI$^+$): m/z 244.15 (M+H)$^+$.

B) 1-(4-(2-Carbamoylpyridin-4-yloxy)-3-methylphenyl)-3-(2-(4-fluorophenyl)acetyl)urea Prepared in a manner similar to that which is described in Step F of Example 87. 4-(4-Amino-2-methylphenoxy)picolinamide (48 mg, 0.2 mmol) in DMF (1.0 mL) was converted to 1-(4-(2-carbamoylpyridin-4-yloxy)-3-methylphenyl)-3-(2-(4-fluorophenyl)acetyl)urea (35 mg, 41% yield. $^1$H NMR (DMSO-d$_6$) δ 10.92 (s, 1H), 10.44 (s, 1H), 8.44 (d, 1H, J=5.5 Hz), 8.06 (s, 1H), 7.63 (s, 1H), 7.50 (s, 1H), 7.42 (m, 1H), 7.31 (m, 2H), 7.24 (d, 1H, J=2.0 Hz), 7.06-7.12 (m, 4H), 3.69 (s, 2H), 2.02 (s, 3H); –. MS(ESI$^+$): m/z 423.17 (M+H)$^+$.

Example 94

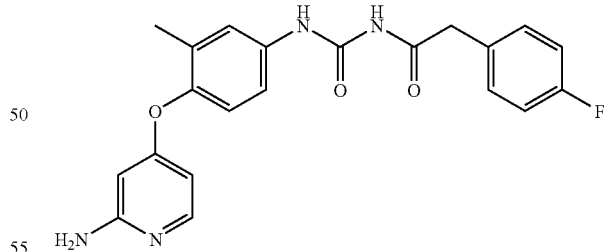

1-(4-(2-Aminopyridin-4-yloxy)-3-methylphenyl)-3-(2-(4-fluorophenyl)acetyl)urea, hydrochloride salt Prepared in a manner similar to that which is described in Step A of Example 91. 1-(4-(2-Carbamoylpyridin-4-yloxy)-3-methylphenyl)-3-(2-(4-fluorophenyl)acetyl)urea (27 mg, 0.06 mmol) in DMF (1.0 mL) was converted to 1-(4-(2-aminopyridin-4-yloxy)-3-methylphenyl)-3-(2-(4-fluorophenyl)acetyl)urea, hydrochloride salt (24 mg, 88% yield) after HPLC purification. $^1$H NMR (DMSO-$d_6$) δ 13.18 (s, 1H), 10.93 (s, 1H), 10.45 (s, 1H), 7.88 (d, 1H, J=7.0 Hz), 7.73 (s, 2H), 7.50 (m, 2H), 7.29 (m, 2H), 7.10 (m, 3H), 6.56 (d, 1H, J=7.0 Hz), 5.91 (d, 1H, J=2.5 Hz), 3.68 (s, 2H), 2.02 (s, 3H); MS(ESI$^+$): m/z 395.20 (M+H)$^+$.

Example 95

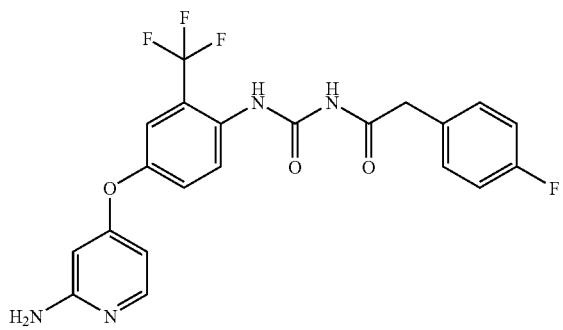

1-(4-(2-Aminopyridin-4-yloxy)-2-(trifluoromethyl)phenyl)-3-(2-(4-fluorophenyl)acetyl)urea, hydrochloride salt

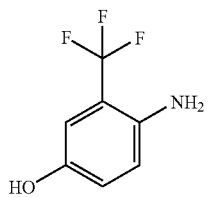

A) 4-Amino-3-(trifluoromethyl)phenol

A solution of 4-nitro-3-(trifluoromethyl)phenol (Aldrich, 414 mg, 2.0 mmol) in 10 mL of MeOH was added 10% Pd/C (100 mg). The suspension was stirred under H$_2$ atmosphere for 12 h and it was then filtered and concentrated in vacuo to give 4-amino-3-(trifluoromethyl)phenol (350 mg, 95% yield), which was sufficiently pure to use in the next step. MS(ESI$^+$): m/z 178.02 (M+H)$^+$.

B) 4-(4-Amino-3-(trifluoromethyl)phenoxy)picolinamide

Prepared in a manner similar to that which is described in Step A of Example 90. 4-Amino-3-(trifluoromethyl)phenol (177 mg, 1.0 mmol) in DMF (2.0 mL) was converted to 4-(4-amino-3-(trifluoromethyl)phenoxy)picolinamide (180 mg, 61% yield). MS(ESI$^+$): m/z 298.20 (M+H)$^+$.

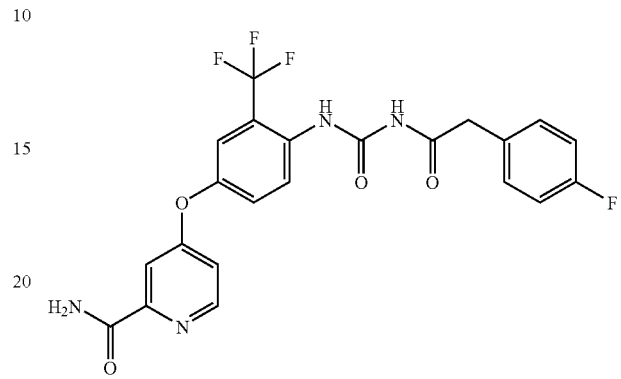

C) 1-(4-(2-Carbamoylpyridin-4-yloxy)-2-(trifluoromethyl)phenyl)-3-(2-(4-fluorophenyl)acetyl)urea Prepared in a manner similar to that which is described in Step F of Example 87. 4-(4-Amino-3-(trifluoromethyl)phenoxy)picolinamide (30 mg, 0.1 mmol) in DMF (1.0 mL) was converted to 1-(4-(2-carbamoylpyridin-4-yloxy)-2(trifluoromethyl)phenyl)-3-(2-(4-fluorophenyl)acetyl)urea (30 mg, 63% yield). MS(ESI$^+$): m/z 477.12 (M+H)$^+$.

D) 1-(4-(2-Aminopyridin-4-yloxy)-2-(trifluoromethyl)phenyl)-3-(2-(4-fluorophenyl)acetyl)urea Prepared in a manner similar to that which is described in Step A of Example 91. 1-(4-(2-Carbamoylpyridin-4-yloxy)-2-(trifluoromethyl)phenyl)-3-(2-(4 fluorophenyl)acetyl)urea (26 mg, 0.055 mmol) in DMF (1.0 mL) was converted to 1-(4-(2-aminopyridin-4-yloxy)-2-(trifluoromethyl)phenyl)-3-(2-(4-fluorophenyl)acetyl)urea hydrochloride (15 mg, 56% yield) after prep. HPLC purification. $^1$H NMR (DMSO-$d_6$) δ 13.40 (s, 1H), 11.28 (s, 1H), 10.95 (s, 1H), 8.25 (d, 1H, J=8.5 Hz), 7.97 (d, 1H, J=7.0 Hz), 7.88 (s, 2H), 7.72 (d, 1H, J=2.5 Hz), 7.65 (m, 1H), 7.35 (m, 2H), 7.19 (m, 2H), 6.66 (d, 1H, J=2.5 Hz), 3.75 (s, 2H); MS(ESI$^+$): m/z 449.14 (M+H)$^+$.

Example 96

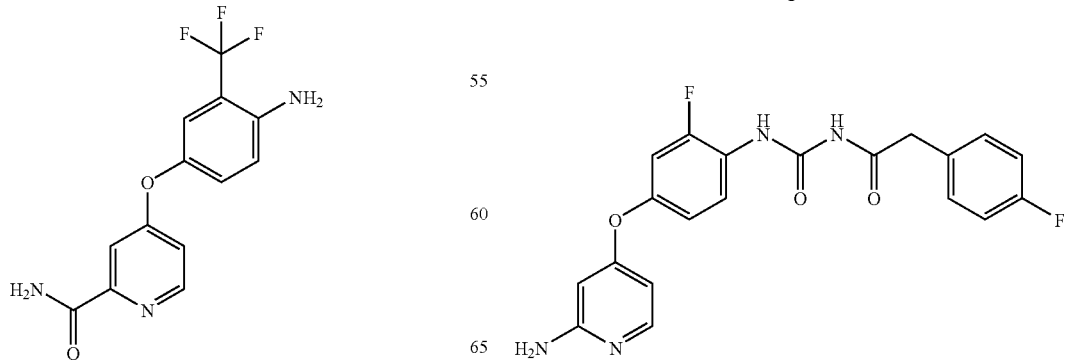

1-(4-(2-Aminopyridin-4-yloxy)-2-fluorophenyl)-3-(2-(4-fluorophenyl)acetyl)urea, trifluoroacetic acid salt

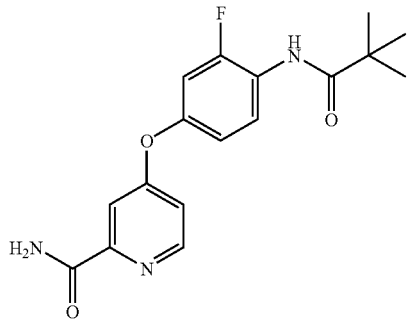

A) 4-(3-Fluoro-4-pivalamidophenoxy)picolinamide

To a solution of 4-amino-3-fluorophenol (Oakwood Products Inc., 252 mg, 2.0 mmol) in NMP (4.0 mL) were added 4-chloropicolinamide (312 mg, 2.0 mmol) and DIEA (0.3 mL). The solution was heated at 250° C. in a microwave oven. After cooling down, the solution was diluted with $H_2O$ and the solution was extracted with EtOAc (3×40 mL). The combined organic layers were washed with brine, dried over $MgSO_4$. After filtration and concentration, the residue was purified by flash chromatography on $SiO_2$ eluting with 0-30% MeOH in DCM to give a fraction containing 4-(4-amino-3-fluorophenoxy)picolinamide (50% pure, HPLC-UV detection). MS(ESI$^+$): m/z 248.12 (M+H)$^+$.

To a solution of 4-(4-amino-3-fluorophenoxy)picolinamide, obtained from previous step in THF (3.0 mL) and DCM (10.0 mL) were added 1 N NaOH (5.0 mL) and trimethylacetyl chloride (0.25 mL, 2 mmol) at room temperature. The solution was stirred for 2 h and was then extracted with EtOAc. The organic layer was washed with brine and dried over $MgSO_4$. After filtration and concentration, the residue was purified by flash chromatography on $SiO_2$ eluting with 0%-100% EtOAc in hexane to give 4-(3-fluoro-4-pivalamidophenoxy)picolinamide (110 mg, 17% yield for two steps). MS(ESI$^+$): m/z 332.18 (M+H)$^+$.

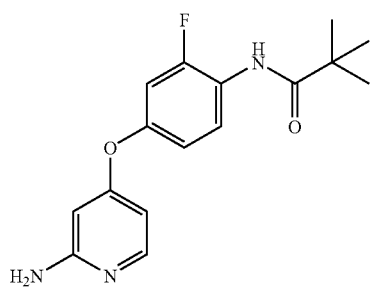

B) N-(4-(2-Aminopyridin-4-yloxy)-2-fluorophenyl)pivalamide

Prepared in a manner similar to that which is described in Step A of Example 91. 4-(3-Fluoro-4-pivalamidophenoxy)picolinamide (110 mg, 0.33 mmol) in acetonitrile (4 mL) was converted to N-(4-(2-aminopyridin-4-yloxy)-2-fluorophenyl)pivalamide (70 mg, 70% yield). MS(ESI$^+$): m/z 304.21 (M+H)$^+$.

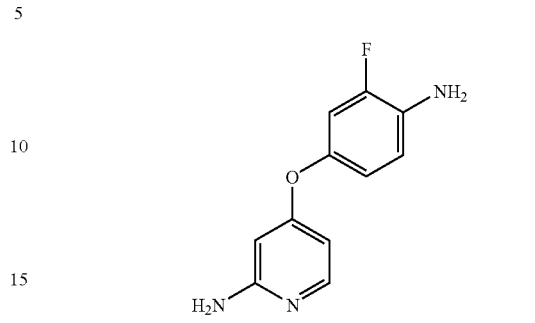

C) 4-(4-Amino-3-fluorophenoxy)pyridin-2-amine

A solution of N-(4-(2-aminopyridin-4-yloxy)-2-fluorophenyl)pivalamide (70 mg, 0.23 mmol) in 3 mL of MeOH was added 2 mL of 6 N HCl. The mixture was then heated at reflux for 48 h. After cooling down, the solvent was removed under reduced pressure and the residue was purified by solid extraction (Waters Oasis®MCX extraction cartridge) to give 4-(4-amino-3-fluorophenoxy)pyridin-2-amine (27 mg, 54% yield). MS(ESI$^+$): m/z 220.21 (M+H)$^+$.

D) 1-(4-(2-Aminopyridin-4-yloxy)-2-fluorophenyl)-3-(2-(4-fluorophenyl)acetyl)urea, trifluoroacetic acid salt Prepared in a manner similar to that which is described in Step F of Example 87. 4-(4-Amino-3-fluorophenoxy)pyridin-2-amine (28 mg, 0.095 mmol) in THF (2.0 mL) was converted to 1-(4-(2-aminopyridin-4-yloxy)-2-fluorophenyl)-3-(2-(4-fluorophenyl)acetyl)urea trifluoroacetic acid (23 mg, 47% yield) after prep. HPLC purification. $^1$H NMR (DMSO-$d_6$) δ 11.20 (s, 1H), 10.77 (s, 1H), 8.23 (m, 1H), 7.94 (d, 1H, J=6.5 Hz), 7.70 (s, 2H), 7.45 (m, 1H), 7.35 (m, 2H), 7.16 (m, 3H), 6.64 (d, 1H, J=2.5 Hz), 6.11 (s, 1H), 3.75 (s, 2H); MS(ESI$^+$): m/z 399.12 (M+H)$^+$.

Example 97

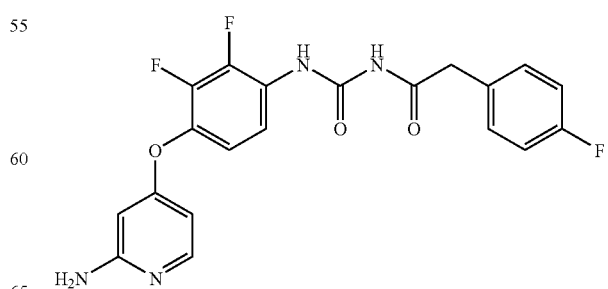

1-(4-(2-Aminopyridin-4-yloxy)-2,3-difluorophenyl)-3-(2-(4-fluorophenyl)acetyl)urea, trifluoroacetic acid salt

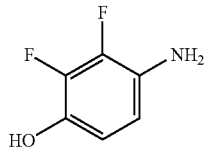

A) 4-Amino-2,3-difluorophenol

To a solution of 1,2,3-trifluoro-4-nitrobenzene (Aldrich, 15.0 g, 84.7 mmol) in DMF (25.0 mL) were added $K_2CO_3$ (17.6 g, 127.8 mmol) and benzylalcohol (8.8 mL, 85.0 mmol). The suspension was stirred overnight. To the reaction mixture was then added $H_2O$ (100 mL) and the solution was kept at 4° C. overnight. The precipitate was then collected and washed with $H_2O$ to give a mixture of two isomers (22.4 g) [1-(benzyloxy)-2,3-difluoro-4-nitrobenzene and 2-(benzyloxy)-3,4-difluoro-1-nitrobenzene in a ratio of 1:1].

To a solution of [1-(benzyloxy)-2,3-difluoro-4-nitrobenzene and 2-(benzyloxy)-3,4-difluoro-1-nitrobenzene] (22.4 g, 84.5 mmol) in EtOAc (20.0 mL) and MeOH (100.0 mL) was added 10% Pd/C (1.0 g). The suspension was stirred under $H_2$ atmosphere for 12 h. The suspension was then filtered and concentrated in vacuo to give a mixture of two isomers (12.6 g) [4-amino-2,3-difluorophenol and 6-amino-2,3-difluorophenol in a ratio of 1:1]. MS(ESI$^+$): m/z 146.00 (M+H)$^+$.

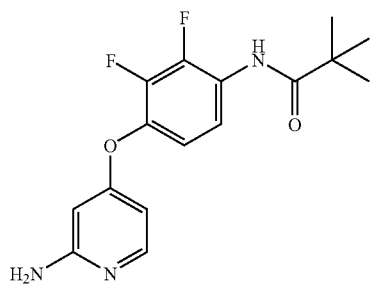

B) N-(4-(2-Aminopyridin-4-yloxy)-2,3-difluorophenyl)pivalamide

Prepared in a manner similar to that which is described in Step A of Example 90. A mixture of 4-amino-2,3-difluorophenol and 6-amino-2,3-difluorophenol (580 mg, 4.0 mmol) in DMF (3.0 mL) was converted to a mixture of 4-(4-amino-2,3-difluorophenoxy)picolinamide and 4-(6-amino-2,3-difluorophenoxy)picolinamide (300 mg). MS(ESI$^+$): m/z 266.13 (M+H)$^+$.

Prepared in a manner similar to that which is described in Step A of Example 96. A mixture of 4-(4-amino-2,3-difluorophenoxy)picolinamide and 4-(6-amino-2,3-difluorophenoxy)picolinamide (300 mg, 1.13 mmol) was converted to a mixture of 4-(2,3-difluoro-4-pivalamidophenoxy)picolinamide and 4-(2,3-difluoro-6-pivalamidophenoxy)picolinamide (406 mg). MS(ESI$^+$): m/z 350.20 (M+H)$^+$.

Prepared in a manner similar to that which is described in Step A of Example 91. A mixture of 4-(2,3-difluoro-4-pivalamidophenoxy)picolinamide and 4-(2,3-difluoro-6-pivalamidophenoxy)picolinamide (400 mg) was reacted with bis(trifluoroacetoxy)iodobenzene to give N-(4-(2-aminopyridin-4-yloxy)-2,3-difluorophenyl)pivalamide, trifluoroacetic acid salt (120 mg, 24% yield) after prep. HPLC purification. MS(ESI$^+$): m/z 322.23 (M+H)$^+$.

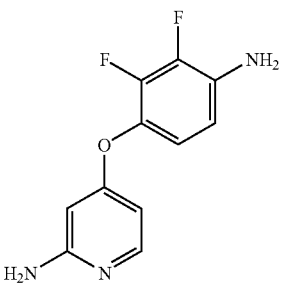

C) 4-(4-Amino-2,3-difluorophenoxy)pyridin-2-amine

Prepared in a manner similar to that which is described in Step C of Example 96. N-(4-(2-Aminopyridin-4-yloxy)-2,3-difluorophenyl)pivalamide, trifluoroacetic acid salt (120 mg, 0.27 mmol) was converted to 4-(4-amino-2,3-difluorophenoxy)pyridin-2-amine (52 mg, 81% yield). MS(ESI$^+$): m/z 238.11 (M+H)$^+$.

D) 1-(4-(2-Aminopyridin-4-yloxy)-2,3-difluorophenyl)-3-(2-(4-fluorophenyl)acetyl)urea, trifluoroacetic acid salt Prepared in a manner similar to that which is described in Step F of Example 87. 4-(4-Amino-2,3-difluorophenoxy)pyridin-2-amine (24 mg, 0.10 mmol) in THF (3.0 mL) was converted to 1-(4-(2-aminopyridin-4-yloxy)-2,3-difluorophenyl)-3-(2-(4-fluorophenyl)acetyl)urea, trifluoroacetic acid (21 mg, 40% yield). $^1$H NMR (DMSO-d$_6$) δ 11.27 (s, 1H), 10.84 (s, 1H), 8.02 (m, 1H), 7.96 (d, 1H, J=8.5 Hz), 7.73 (s, 2H), 7.34 (m, 3H), 7.17 (m, 2H), 6.70 (m, 1H), 6.20 (d, 1H, J=2.0 Hz), 3.75 (s, 2H); MS(ESI$^+$): m/z 417.10 (M+H)$^+$.

Example 98

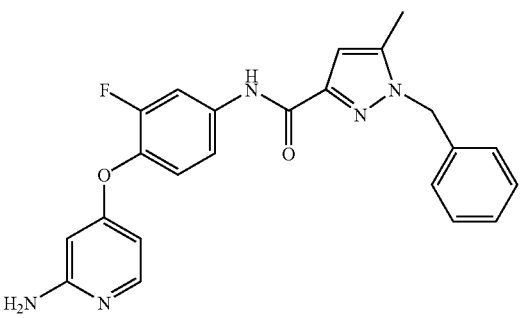

N-(4-(2-Aminopyridin-4-yloxy)-3-fluorophenyl)-1-benzyl-5-methyl-1H-pyrazole-3-carboxamide, hydrochloride salt

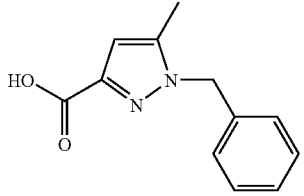

A) 1-Benzyl-5-methyl-1H-pyrazole-3-carboxylic acid

To a solution of 1-benzylhydrazine dihydrochloride (Aldrich, 0.98 g, 5.0 mmol) in EtOH (30 mL) were added DIEA (2.0 mL) and ethyl 2,4-dioxopentanoate (0.70 mL, 5.0 mmol). The mixture was stirred at room temperature for 12 h and was concentrated in vacuo. The residue was dissolved in 1 N NaOH (10 mL). The solution was heated at 60° C. for 1 h. After cooling down, the solution was extracted with DCM (3×50 mL). The aqueous layer was neutralized to pH 2.0 and then was extracted with EtOAc. The organic layer was washed with brine and dried over MgSO$_4$. It was filtered and concentrated to give 1-benzyl-5-methyl-1H-pyrazole-3-carboxylic acid (1.0 g, 92% yield). MS(ESI$^+$): m/z 217.12 (M+H)$^+$.

B) N-(4-(2-Aminopyridin-4-yloxy)-3-fluorophenyl)-1-benzyl-5-methyl-1H-pyrazole-3-carboxamide, hydrochloride salt 4-(4-Amino-2-fluorophenoxy)pyridin-2-amine (Compound B of Example 24, 25 mg, 0.11 mmol) was coupled with 1-benzyl-5-methyl-1H-pyrazole-3carboxylic acid (25 mg, 0.11 mmol) in a manner similar to that which is described in Step C of Example 1 to give N-(4-(2-aminopyridin-4-yloxy)-3-fluorophenyl)-1-benzyl-5-methyl-1H-pyrazole-3-carboxamide hydrochloride (10 mg, 20% yield) after prep HPLC purification. $^1$H NMR (DMSO-d$_6$) δ 10.64 (s, 1H), 7.8-7.98 (m, 3H), 7.00-7.65 (m, 9H), 6.71 (m, 1H), 6.15 (s, 1H), 5.65 (s, 2H), 2.24 (s, 3H); MS(ESI$^+$): m/z 418.21 (M+H)$^+$.

Example 99

2-(4-Fluorobenzylsulfinyl)-N-(4-(2-aminopyridin-4-yloxy)-3-fluorophenyl)acetamide, hydrochloride salt

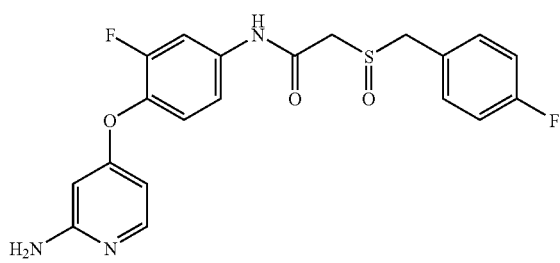

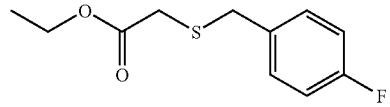

A) Ethyl 2-(4-fluorobenzylthio)acetate

To a solution of ethyl 2-mercaptoacetate (Aldrich, 1.0 mL, 9.1 mmol) in acetonitrile (10.0 mL) were added K$_2$CO$_3$ (2.76 g, 20.0 mmol) and 1-(bromomethyl)-4-fluorobenzene (2.27 g, 12.0 mmol). The mixture was stirred at room temperature for 12 h. After filtration and concentration, the residue was purified by flash column chromatography on SiO$_2$ to give ethyl 2-(4-fluorobenzylthio)acetate (1.89 g, 91% yield). MS(ESI$^+$): m/z 251.08 (M+H)$^+$.

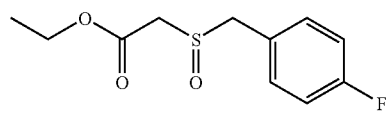

B) Ethyl 2-(4-fluorobenzylsulfinyl)acetate

To a solution of ethyl 2-(4-fluorobenzylthio)acetate (1.89 g, 8.29 mmol) in DCM (20.0 mL) at −40° C. was added a solution of m-CPBA (77%, 1.86 g, 8.29 mmol) in DCM (20.0 mL) dropwise. The solution was stirred from −40° C. to room temperature overnight. The solution was then quenched with polymer bound diethylene triamine. After filtration and concentration, the residue was purified by flash chromatography on SiO$_2$ to give ethyl 2-(4-fluorobenzylsulfinyl)acetate (2.0 g, 98% yield). MS(ESI+): m/z 267.09 (M+H)$^+$.

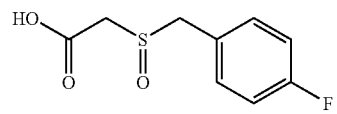

C) 2-(4-Fluorobenzylsulfinyl)acetic acid

To a solution of ethyl 2-(4-fluorobenzylsulfinyl)acetate (1.60 g, 6.55 mmol) in THF (10.0 mL) and MeOH (20.0 mL) was added 1 N NaOH (20.0 mmol). The mixture was stirred at room temperature for 2 h. After removal of organic solvent under reduced pressure, the remaining aqueous solution was neutralized with 1 N HCl (25.0 mL). It was extracted with EtOAc (3×100 mL) and the combined organic layer was dried over MgSO$_4$. The solution was then filtered and concentrated in vacuo to give 2-(4-fluorobenzylsulfinyl)acetic acid (1.25 g, 88% yield). MS(ESI$^+$): m/z 217.05 (M+H)$^+$.

D) 2-(4-Fluorobenzylsulfinyl)-N-(4-(2-aminopyridin-4-yloxy)-3-fluorophenyl)acetamide, hydrochloride salt 4-(4-Amino-2-fluorophenoxy)pyridin-2-amine dihydrochloride (Compound B of Example 24, 29 mg, 0.10 mmol) was coupled with 2-(4-fluorobenzylsulfinyl)acetic acid (22 mg, 0.1 mmol) in a manner similar to that which is described in Step C of Example 1 to give 2-(4-fluorobenzylsulfinyl)-N-(4-(2-aminopyridin-4-yloxy)-3-fluorophenyl)acetamide, hydrochloride salt (17 mg, 37% yield). $^1$H NMR (DMSO-$d_6$) δ 10.94 (s, 1H), 7.97 (d, 1H, J=7.5 Hz), 7.85 (m, 3H), 7.39-7.45 (m, 4H), 7.23 (t, 2H, J=7.5 Hz), 6.70 (m, 1H), 6.13 (d, 1H, J=2.5 Hz), 4.32 (d, 1H, J=11.0 Hz), 4.11 (d, 1H, J=11.0 Hz), 3.98 (d, 1H, J=13.0 Hz), 3.65 (d, 1H, J=13.0 Hz); MS(ESI$^+$): m/z 418.26 (M+H)$^+$.

Example 100

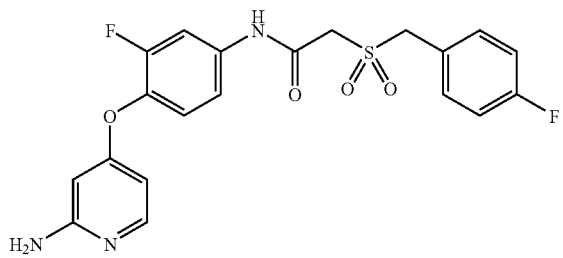

2-(4-Fluorobenzylsulfonyl)-N-(4-(2-aminopyridin-4-yloxy)-3-fluorophenyl)acetamide, hydrochloride salt

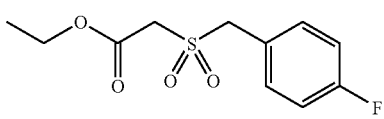

A) Ethyl 2-(4-fluorobenzylsulfonyl)acetate

To a solution of ethyl 2-(4-fluorobenzylsulfinyl)acetate (370 mg, 1.52 mmol) in DCM (5.0 mL) was added m-CPBA (77%, 450 mg, 2.0 mmol). The mixture was stirred at room temperature for 2 h and was then quenched with polymer bound diethylene triamine (1.5 g). The reaction mixture was filtered and concentrated in vacuo to give ethyl 2-(4-fluorobenzylsulfonyl)acetate (360 mg, 91% yield). MS(ESI$^+$): m/z 283.10 (M+H)$^+$.

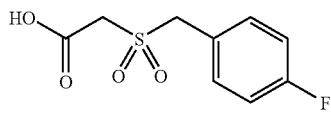

B) 2-(4-Fluorobenzylsulfonyl)acetic acid

Prepared in a manner similar to that which is described in Step C of Example 99. Ethyl 2-(4-fluorobenzylsulfonyl)acetate (340 mg, 1.31 mmol) was converted to 2-(4-fluorobenzylsulfonyl)acetic acid (270 mg, 81% yield). MS(ESI$^+$): m/z 255.05 (M+H)$^+$.

C) 2-(4-Fluorobenzylsulfonyl)-N-(4-(2-aminopyridin-4-yloxy)-3-fluorophenyl)acetamide, hydrochloride salt 4-(4-Amino-2-fluorophenoxy)pyridin-2-amine dihydrochloride (50 mg, 0.17 mmol) was coupled with 2-(4-fluorobenzylsulfonyl)acetic acid (33 mg, 0.14 mmol) in a manner similar to that which is described in Step C of Example 1 to give 2-(4-fluorobenzylsulfonyl)-N-(4-(2-aminopyridin-4-yloxy)-3-fluorophenyl)acetamide, hydrochloride salt (30 mg, 45% yield). $^1$H NMR (DMSO-$d_6$) δ 13.40 (s, 1H), 11.15 (s, 1H), 7.97 (d, 1H, J=7.0 Hz), 7.80-7.90 (m, 3H), 7.47 (m, 4H), 7.26 (t, 2H, J=8.5 Hz), 6.72 (d, 1H, J=7.0 Hz), 6.14 (d, 1H, J=2.0 Hz), 4.69 (s, 2H), 4.27 (s, 2H); MS(ESI$^+$): m/z 434.15 (M+H)$^+$.

Example 101

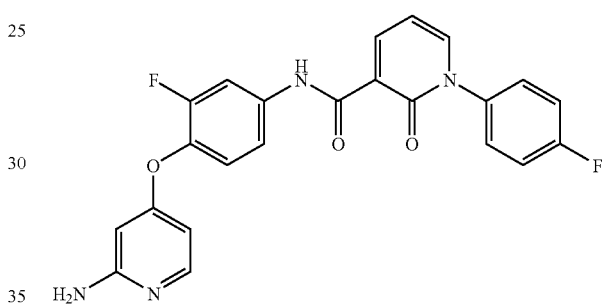

N-(4-(2-Aminopyridin-4-yloxy)-3-fluorophenyl)-1-(4-fluorophenyl)-2-oxo-1,2-dihydropyridine-3-carboxamide, hydrochloride salt

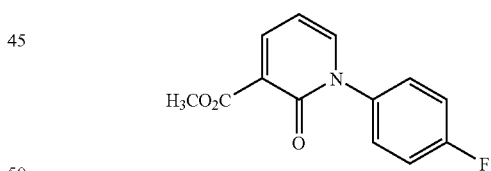

A) Methyl 1-(4-fluorophenyl)-2-oxo-1,2-dihydropyridine-3-carboxylate

To a solution of methyl 2-oxo-2H-pyran-3-carboxylate (Aldrich, 2.31 g, 15 mmol) in THF (40 mL) and DMF (10 mL) at rt was added 4-fluoroaniline (1.67 g, 15 mmol), and the reaction mixture was stirred for 2.5 h. Solid precipitation was observed. To the 4-fluoroaniline adduct intermediate formed via Michael addition obtained in situ was added EDCI.HCl (3.85 g, 20 mmol) and DMAP (120 mg) at rt. The reaction mixture was stirred at rt overnight. To the reaction mixture were added 1N aq HCl (50 mL) and EtOAc (150 mL), the EtOAc layer was separated, and the aqueous layer was washed with EtOAc (150 mL), the combined EtOAc layer was dried over MgSO$_4$ and concentrated in vacuo to obtain a semi-solid material (~4.4 g). To this crude product were added ether (100 mL) and methanol (15 mL), stirred, and the solid was filtered to obtain the undesired solid product (870 mg). The filtrate solution was concentrated to obtain a semi-solid crude desired product (2.95 g, crude 80%) which was pure enough to use in the next step without further purification. $^1$H NMR (DMSO-d$_6$) δ 8.23 (dd, 1H, J=7.2, 2.2 Hz), 7.57 (dd, 1H, J=6.6, 1.7 Hz), 7.32-7.34 (m, 2H), 7.17 (t, 2H, J=8.8 Hz), 6.32 (t, 1H, J=7.1 Hz), 3.89 (s, 3H); MS(ESI$^+$) m/z 248.2 (M+H)$^+$.

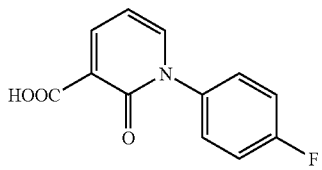

B) 1-(4-Fluorophenyl)-2-oxo-1,2-dihydropyridine-3-carboxylic acid

A mixture of methyl 1-(4-fluorophenyl)-2-oxo-1,2-dihydropyridine-3-carboxylate (crude 2.45 g, 12 mmol) and 6 N aq NaOH (2.5 mL) in methanol (60 mL) was stirred at rt for 4 h. To the reaction mixture was added conc HCl (1 mL) slowly with stirring at rt, and the precipitated solid was filtered, washed with a small amount water and dried to obtain the desired acid product (2.1 g) as a yellow solid. The filtrate solution was concentrated in vacuo. The residue was mixed with water (50 mL) and washed with EtOAc (2×130 mL). The EtOAc layers were dried over MgSO$_4$ and concentrated in vacuo. The residue was triturated with a small amount of ether to obtain the 2$^{nd}$ crop of product (195 mg, total 2.30 g, 82%). $^1$H NMR (DMSO-d$_6$) δ 8.47 (dd, 1H, J=7.2, 2.2 Hz), 8.19 (dd, 1H, J=6.6, 1.7 Hz), 7.62-7.60 (m, 2H), 7.42 (t, 2H, J=8.8 Hz), 6.78 (t, 1H, J=7.1 Hz); MS(ESI$^+$) m/z 234.2 (M+H)$^+$.

C) N-(4-(2-Aminopyridin-4-yloxy)-3-fluorophenyl)-1-(4-fluorophenyl)-2-oxo-1,2-dihydropyridine-3-carboxamide, hydrochloride salt 4-(4-Amino-2-fluorophenoxy)pyridin-2-amine (Compound B of Example 24, 58 mg, 0.20 mmol) was coupled with 1-(4-fluorophenyl)-2-oxo-1,2-dihydropyridine-3-carboxylic acid (47 mg, 0.20 mmol) in a manner similar to that which is described in Step C of Example 1 to give N-(4-(2-aminopyridin-4-yloxy)-3-fluorophenyl)-1-(4-fluorophenyl)-2-oxo-1,2-dihydropyridine-3-carboxamide, hydrochloride salt (22 mg, 23% yield). $^1$H NMR (DMSO-d$_6$) δ 13.40 (s, 1H), 12.13 (s, 1H), 8.58 (d, 1H, J=5.0 Hz), 8.13 (d, 1H, J=5.0 Hz), 8.07 (d, 1H, J=10.0 Hz), 7.98 (d, 1H, J=7.5 Hz), 7.89 (s, 2H), 7.40-7.60 (m, 6H), 6.72 (m, 2H), 6.17 (d, 1H, J=2.5 Hz); MS(ESI$^+$) m/z 435.18 (M+H)$^+$.

Example 102

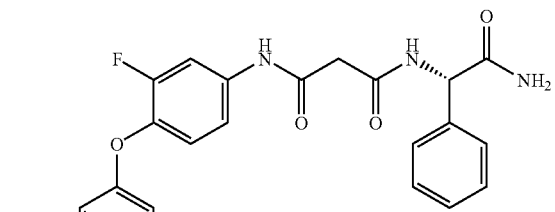

(S)—N$^1$-(2-Amino-2-oxo-1-phenylethyl)-N$^3$-(4-(2-aminopyridin-4-yloxy)-3-fluorophenyl)malonamide, hydrochloride salt

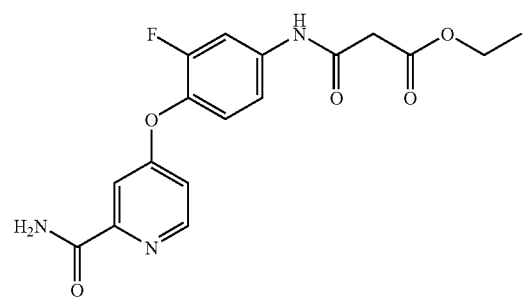

A) Ethyl 3-(4-(2-carbamoylpyridin-4-yloxy)-3-fluorophenylamino)-3-oxopropanoate To a solution of 4-(4-amino-2-fluorophenoxy)picolinamide (Compound B' of Example 24, 1.0 g, 4.0 mmol) in DMF (10.0 mL) were added DIEA (2.0 mL) and ethyl 3-chloro-3-oxopropanoate (Aldrich, 0.75 mL, 6.0 mmol). The mixture was stirred at room temperature for 12 h and more ethyl 3-chloro-3-oxopropanoate (0.20 mL, 1.6 mmol) was added. The mixture was stirred for 2 h and was then diluted with EtOAc (200 mL). It was washed with H$_2$O and brine and then dried over MgSO$_4$. After filtration and concentration, the residue was triturated with DCM and filtered to give ethyl 3-(4-(2-carbamoylpyridin-4-yloxy)-3-fluorophenylamino)-3-oxopropanoate (900 mg, 62% yield). MS(ESI$^+$) m/z 362.28 (M+H)$^+$.

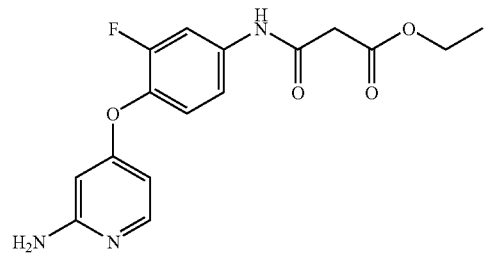

B) Ethyl 3-(4-(2-aminopyridin-4-yloxy)-3-fluorophenylamino)-3-oxopropanoate

Prepared in a manner similar to that which is described in Step A of Example 91. Ethyl 3-(4-(2-carbamoylpyridin-4-yloxy)-3-fluorophenylamino)-3-oxopropanoate (900 mg, 2.5 mmol) in DMF (10.0 mL) was converted to ethyl 3-(4-(2-aminopyridin-4-yloxy)-3-fluorophenylamino)-3-oxopropanoate (710 mg, 86% yield). MS(ESI$^+$) m/z 334.26 (M+H)$^+$.

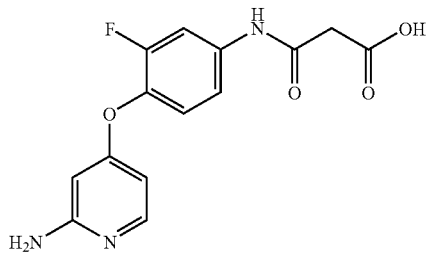

C) 3-(4-(2-Aminopyridin-4-yloxy)-3-fluorophenylamino)-3-oxopropanoic acid

Prepared in a manner similar to that which is described in Step C of Example 99. Ethyl 3-(4-(2-aminopyridin-4-yloxy)-3-fluorophenylamino)-3-oxopropanoate (700 mg, 2.10 mmol) was converted to 3-(4-(2-aminopyridin-4-yloxy)-3-fluorophenylamino)-3-oxopropanoic acid (630 mg, 98% yield). MS(ESI$^+$) m/z 306.20 (M+H)$^+$.

D) (S)—N$^1$-(2-Amino-2-oxo-1-phenylethyl)-N$^3$-(4-(2-aminopyridin-4-yloxy)-3-fluorophenyl)malonamide, hydrochloride salt 3-(4-(2-Aminopyridin-4-yloxy)-3-fluorophenylamino)-3-oxopropanoic acid (30 mg, 0.10 mmol) was coupled with (S)-2-amino-2-phenylacetamide hydrochloride (Acros, 28 mg, 0.15 mmol) in a manner similar to that which is described in Step C of Example 1 to give (S)-N-(2-amino-2-oxo-1-phenylethyl)-N$^3$(4-(2-aminopyridin-4-yloxy)-3-fluorophenyl)malonamide, hydrochloride salt (25 mg, 53% yield). $^1$H NMR (DMSO-d$_6$) δ 10.68 (s, 1H), 8.80 (d, 1H, J=8.0 Hz), 7.96 (d, 1H, J=7.5 Hz), 7.77-7.90 (m, 4H), 7.20-7.45 (m, 8H), 6.70 (m, 1H), 6.12 (s, 1H), 5.39 (d, 1H, J=7.5 Hz), 3.48 (d, 1H, J=15.0 Hz), 3.41 (d, 1H, J=15.0 Hz); MS(ESI$^+$) m/z 438.26 (M+H)$^+$.

Example 103

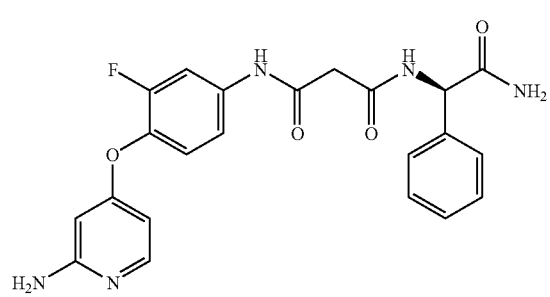

(R)-N$^1$-(2-Amino-2-oxo-1-phenylethyl)-N$^3$-(4-(2-aminopyridin-4-yloxy)-3-fluorophenyl)malonamide, hydrochloride salt 3-(4-(2-Aminopyridin-4-yloxy)-3-fluorophenylamino)-3-oxopropanoic acid (Compound C of Example 102, 30 mg, 0.10 mmol) was coupled with (R)-2-amino-2-phenylacetamide hydrochloride (Bachem, 28 mg, 0.15 mmol) in a manner similar to that which is described in Step C of Example 1 to give (R)-N$^1$-(2-amino-2-oxo-1-phenylethyl)-N$^3$-(4-(2-aminopyridin-4-yloxy)-3-fluorophenyl)malonamide, hydrochloride salt (14 mg, 30% yield). $^1$H NMR (DMSO-d$_6$) δ 10.65 (s, 1H), 8.76 (d, 1H, J=8.0 Hz), 7.92 (d, 1H, J=7.0 Hz), 7.75-7.88 (m, 4H), 7.20-7.43 (m, 8H), 6.66 (m, 1H), 6.09 (s, 1H), 5.35 (d, 1H, J=8.0 Hz), 3.45 (d, 1H, J=15.0 Hz), 3.37 (d, 1H, J=15.0 Hz); MS(ESI$^+$) m/z 438.23 (M+H)$^+$.

Example 104

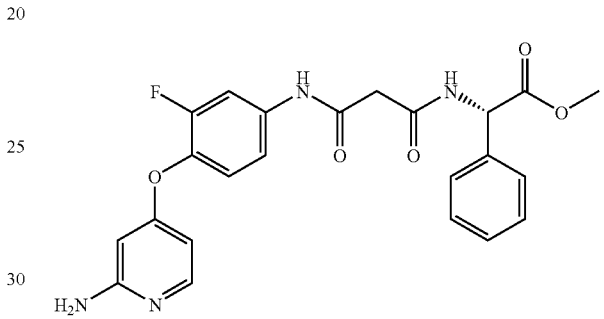

(S)-Methyl 2-(3-(4-(2-aminopyridin-4-yloxy)-3-fluorophenylamino)-3-oxopropanamido)-2-phenylacetate, hydrochloride salt 3-(4-(2-Aminopyridin-4-yloxy)-3-fluorophenylamino)-3-oxopropanoic acid (Compound C of Example 102, 30 mg, 0.10 mmol) was coupled with (S)-methyl 2-amino-2-phenylacetate hydrochloride (Aldrich, 30 mg, 0.10 mmol) in a manner similar to that which is described in Step C of Example 1 to give (S)-methyl 2-(3-(4-(2-aminopyridin-4-yloxy)-3-fluorophenylamino)-3-oxopropanamido)-2-phenylacetate, hydrochloride salt (21 mg, 43% yield). $^1$H NMR (DMSO-d$_6$) δ 10.58 (s, 1H), 9.04 (d, 1H, J=7.0 Hz), 7.97 (d, 1H, J=7.0 Hz), 7.75-7.88 (m, 3H), 7.42 (m, 7H), 6.72 (d, 1H, J=7.0 Hz), 6.12 (s, 1H), 5.45 (d, 1H, J=7.0 Hz), 3.63 (s, 3H), 3.43-3.38 (m, 2H); MS(ESI$^+$) m/z 453.26 (M+H)$^+$.

Example 105

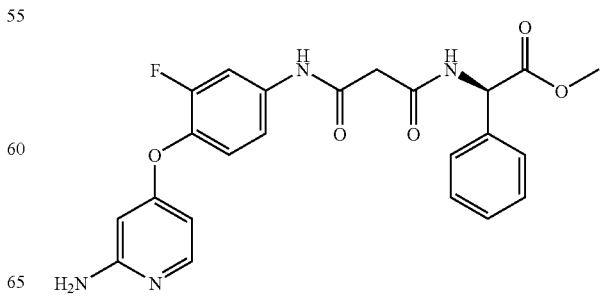

(R)-Methyl 2-(3-(4-(2-aminopyridin-4-yloxy)-3-fluorophenylamino)-3-oxopropanamido)-2-phenylacetate, hydrochloride salt 3-(4-(2-Aminopyridin-4-yloxy)-3-fluorophenylamino)-3-oxopropanoic acid (Compound C of Example 102, 30 mg, 0.10 mmol) was coupled with (R)-methyl 2-amino-2-phenylacetate, hydrochloride salt (Aldrich, 30 mg, 0.10 mmol) in a manner similar to that which is described in Step C of Example 1 to give (R)-methyl 2-(3-(4-(2-aminopyridin-4-yloxy)-3-fluorophenylamino)-3-oxopropanamido)-2-phenylacetate, hydrochloride salt (25 mg, 51% yield). $^1$H NMR (DMSO-$d_6$) δ 10.58 (s, 1H), 9.03 (d, 1H, J=7.0 Hz), 7.96 (d, 1H, J=7.0 Hz), 7.77-7.88 (m, 3H), 7.42 (m, 7H), 6.71 (d, 1H, J=7.5 Hz), 6.12 (s, 1H), 5.44 (d, 1H, J=7.0 Hz), 3.63 (s, 3H), 3.44-3.38 (m, 2H); MS(ESI$^+$) m/z 453.29 (M+H)$^+$.

Example 106

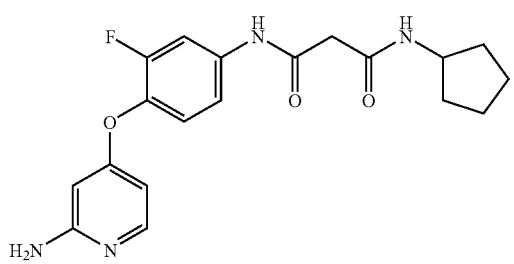

N$^1$-(4-(2-Aminopyridin-4-yloxy)-3-fluorophenyl)-N$^3$-cyclopentylmalonamide, hydrochloride salt 3-(4-(2-Aminopyridin-4-yloxy)-3-fluorophenylamino)-3-oxopropanoic acid (Compound C of Example 102, 30 mg, 0.10 mmol) was coupled with cyclopentanamine (Aldrich, 17 mg, 0.2 mmol) in a manner similar to that which is described in Step C of Example 1 to give N$^1$-(4-(2-aminopyridin-4-yloxy)-3-fluorophenyl)-N$^3$-cyclopentylmalonamide, hydrochloride salt (18 mg, 44% yield). $^1$H NMR (DMSO-$d_6$) δ 13.34 (s, 1H), 10.66 (s, 1H), 8.15 (d, 1H, J=7.0 Hz), 7.96 (d, 1H, J=7.0 Hz), 7.77-7.88 (m, 3H), 7.42 (m, 2H), 6.70 (d, 1H, J=7.5 Hz), 6.12 (s, 1H), 3.98 (m, 1H), 3.69 (s, 2H), 1.78 (m, 2H), 1.63 (m, 2H), 1.49 (m, 2H), 1.37 (m, 2H); MS(ESI$^+$) m/z 373.30 (M+H)$^+$.

Example 107

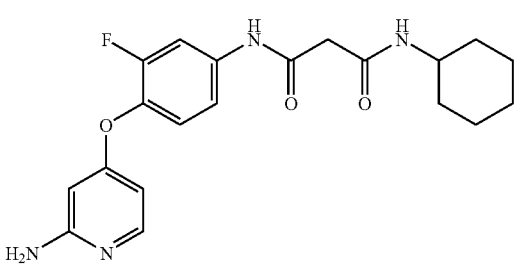

N$^1$-(4-(2-Aminopyridin-4-yloxy)-3-fluorophenyl)-N$^3$-cyclohexylmalonamide, hydrochloride salt 3-(4-(2-Aminopyridin-4-yloxy)-3-fluorophenylamino)-3-oxopropanoic acid (Compound C of Example 102, 30 mg, 0.10 mmol) was coupled with cyclohexanamine (Aldrich, 20 mg, 0.2 mmol) in a manner similar to that which is described in Step C of Example 1 to give N$^1$-(4-(2-aminopyridin-4-yloxy)-3-fluorophenyl)-N$^3$-cyclohexylmalonamide, hydrochloride salt (22 mg, 52% yield). $^1$H NMR (DMSO-$d_6$) δ 14.00 (s, 1H), 10.72 (s, 1H), 8.10 (d, 1H, J=7.0 Hz), 7.97 (d, 1H, J=7.0 Hz), 7.88 (m, 3H), 7.44 (m, 2H), 6.70 (m, 1H), 6.14 (d, 1H, J=2.0 Hz), 3.54 (m, 1H), 3.27 (s, 2H), 1.66-1.75 (m, 4H), 1.52 (m, 1H), 1.15-1.25 (m, 5H); MS(ESI$^+$) m/z 387.32 (M+H)$^+$.

Example 108

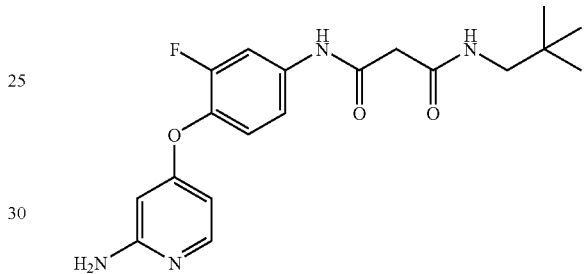

N$^1$-(4-(2-Aminopyridin-4-yloxy)-3-fluorophenyl)-N$^3$-neopentylmalonamide, hydrochloride salt 3-(4-(2-Aminopyridin-4-yloxy)-3-fluorophenylamino)-3-oxopropanoic acid (Compound C of Example 102, 30 mg, 0.10 mmol) was coupled with 2,2-dimethylpropan-1-amine (Aldrich, 12 mg, 0.2 mmol) in a manner similar to that which is described in Step C of Example 1 to give N$^1$-(4-(2-aminopyridin-4-yloxy)-3-fluorophenyl)-N$^3$-neopentylmalonamide, hydrochloride salt (13 mg, 32% yield). $^1$H NMR (DMSO-$d_6$) δ 13.34 (s, 1H), 10.69 (s, 1H), 8.08 (m, 1H), 7.96 (d, 1H, J=7.0 Hz), 7.87 (m, 3H), 7.44 (m, 2H), 6.70 (m, 1H), 6.13 (d, 1H, J=2.0 Hz), 3.34 (s, 2H), 2.91 (d, 2H, J=6.5 Hz), 0.84 (s, 9H); MS(ESI$^+$) m/z 375.32 (M+H)$^+$.

Example 109

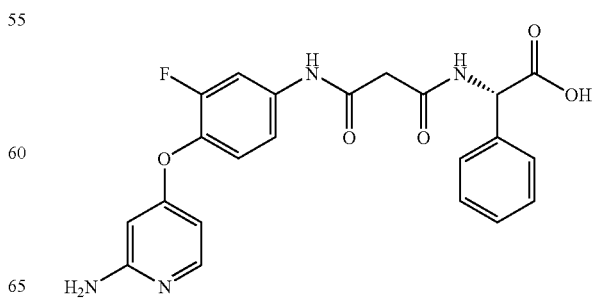

(S)-2-(3-(4-(2-Aminopyridin-4-yloxy)-3-fluorophenylamino)-3-oxopropanamido)-2-phenylacetic acid, hydrochloride salt Following a procedure similar to that which is described in Step C of Example 99, (S)-methyl 2-(3-(4-(2-aminopyridin-4-yloxy)-3-fluorophenylamino)-3oxopropanamido)-2-phenylacetate hydrochloride (Compound D of Example 102, 14 mg, 0.028 mmol) was hydrolyzed to give (S)-2-(3-(4-(2-aminopyridin-4-yloxy)-3-fluorophenylamino)-3-oxopropanamido)-2-phenylacetic acid, hydrochloride salt (13 mg, 97% yield). $^1$H NMR (DMSO-$d_6$) δ 13.20 (s, 1H), 10.57 (s, 1H), 8.92 (d, 1H, J=7.0 Hz), 7.95 (d, 1H, J=7.0 Hz), 7.87 (d, 1H, J=11.0 Hz), 7.70 (s, 2H), 7.41 (m, 8H), 6.69 (d, 1H, J=7.5 Hz), 6.12 (d, 1H, J=2.0 Hz), 5.35 (d, 1H, J=7.5 Hz), 3.42 (s, 2H); MS(ESI$^+$) m/z 439.27 (M+H)$^+$.

Example 110

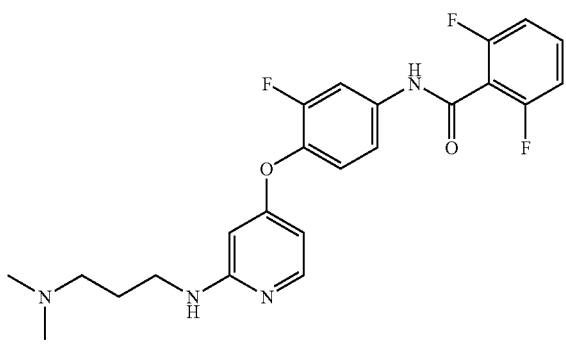

N-(4-(2-(3-(Dimethylamino)propylamino)pyridin-4-yloxy)-3-fluorophenyl)-2,6-difluorobenzamide, hydrochloride salt

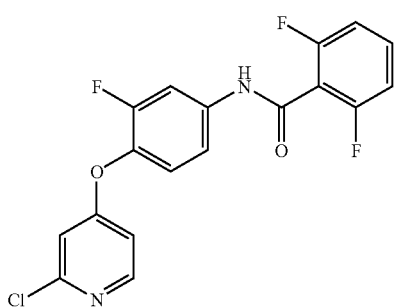

A) N-(4-(2-Chloropyridin-4-yloxy)-3-fluorophenyl)-2,6-difluorobenzamide

A solution 4-(2-chloropyridin-4-yloxy)-3-fluorobenzenamine (Compound B of Example 20, 64 mg, 0.27 mmol), THF (1 ml), Et$_3$N (100 μL) was treated dropwise with 2,6-difluorobenzoyl chloride (Aldrich, 33 μL, 0.27 mmol) and the mixture was stirred at rt for 30 min. The mixture was partitioned between EtOAc and saturated aq. NaHCO$_3$ and the EtOAc phase was separated, dried (MgSO$_4$) and concentrated in vacuo to give the title compound (102 mg, 100%) as white solid. MS(ESI$^+$): m/z 418.18 (M+H)$^+$.

B) N-(4-(2-(3-(Dimethylamino)propylamino)pyridin-4-yloxy)-3-fluorophenyl)-2,6-difluorobenzamide, hydrochloride salt A mixture of N-(4-(2-chloropyridin-4-yloxy)-3-fluorophenyl)-2,6-difluorobenzamide (70 mg, 0.19 mmol), 3-(dimethylamino)propylamine (44 mL, 0.35 mmol), Cs$_2$CO$_3$ (85 mg, 0.26 mmol) and CuCi (17 mg, 0.17 mmol) in a screw capped vial was purged with N$_2$. NMP and 2,2,6,6,-tetramethyl-3,5-heptanedione (31 mg, 0.17 mmol) were added to the mixture which was then heated at 120° C. for 4 h. The mixture was cooled, partitioned between EtOAc and saturated aq. NaHCO$_3$ solution and the EtOAc phase was separated, dried (MgSO$_4$) and concentrated in vacuo to give the crude product. Purification of the residue by preparative HPLC (Column C) and conversion to the hydrochloride salt was carried out in a similar manner as Step D of Example 33 to give the title compound (7 mg, 7%) as an off-white solid. MS(ESI$^+$): m/z 517.37 (M+H)$^+$.

Example 111

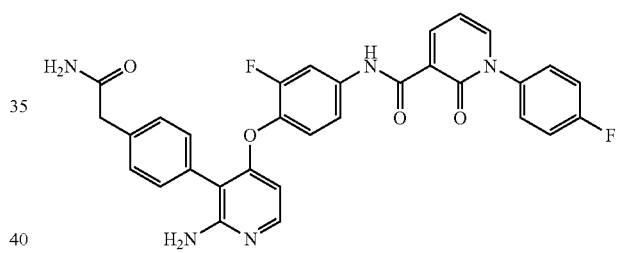

N-(4-(2-Amino-3-(4-(2-amino-2-oxoethyl)phenyl)pyridin-4-yloxy)-3-fluorophenyl)-1-(4-fluorophenyl)-2-oxo-1,2-dihydropyridine-3-carboxamide, hydrochloride salt A solution of 2-(4-(2-amino-4-(4-amino-2-fluorophenoxy)pyridin-3-yl)phenyl)acetamide (Compound C of Example 78, 18 mg, 0.05 mmol) in DMF (1.5 mL) was treated with 1-(4-fluorophenyl)-2-oxo-1,2-dihydropyridine-3-carboxylic acid (Compound B of Example 101, 11 mg, 0.05 mmol), DIPEA (10 μL, 0.06 mmol) and TBTU (19 mg, 0.06 nmol). The mixture was stirred at room temperature for 40 h. The mixture was concentrated under vacuum and the residue was purified by preparative HPLC (Column A) to give the title compound as a TFA salt. The TFA salt was dissolved in anhydrous MeOH and treated with 1 M HCl/Et$_2$O at 0° C. and stirred for 5 min. The mixture was then concentrated in vacuo to give the title compound (15 mg, 47%) as a yellow solid. $^1$H NMR (DMSO-$d_6$) δ 12.11 (s, 1H), 8.56 (dd, 1H, J=2.2, 7.1 Hz), 8.13 (dd, 1H, J=2.2, 6.7 Hz), 8.00 (dd, 1H, J=2.2, 12.6 Hz), 7.96 (d, 1H, J=7.7 Hz), 7.60-7.57 (m, 2H), 7.48-7.33 (m, 10H), 6.94 (s, 1H), 6.72 (dd, 1H, J=7.2, 7.2 Hz), 6.38 (d, 1H, J=7.2 Hz), 3.95 (s, 2H); MS(ESI$^+$): m/z 568.23 (M+H)$^+$.

Example 112

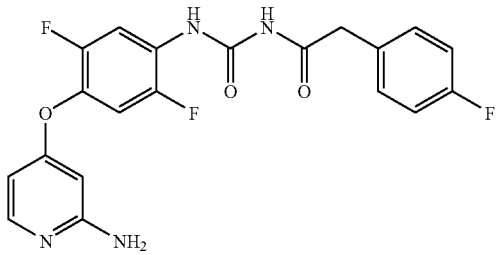

1-(4-(2-Aminopyridin-4-yloxy)-2,5-difluorophenyl)-3-(2-(4-fluorophenyl)-acetyl)urea, hydrochloric acid salt

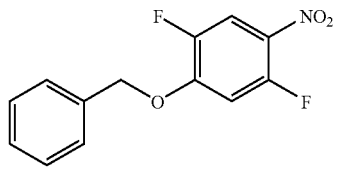

A) 1-((2,5-Difluoro-4-nitrophenoxy)methyl)benzene

A mixture of 2,4,5-trifluoronitrobenzene (5.4 g, 30.8 mmol), benzylalcohol (3.2 mL, 30.8 mmol) and potassium carbonate (6.4 g, 46.1 mmol), in DMF (20 mL), was stirred at ambient temperature for 72 h. Water (60 mL) was added and the mixture was cooled at 4° C. for 24 h. The resultant precipitate was filtered, rinsed with water and dried in vacuo to afford the product (7.5 g, 92%) as a pale yellow solid. $^1$H NMR (CDCl$_3$) δ 7.90-7.94 (m, 1H), 7.38-7.44 (m, 5H), 6.85-6.90 (m, 1H), 5.22 (s, 2H).

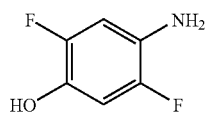

B) 4-Amino-2,5-difluorophenol

To a flask charged with 1-((2,5-difluoro-4-nitrophenoxy)methyl)benzene (4.1 g, 15.6 mmol), which was sequentially evacuated and then purged with nitrogen three times, was added 10% palladium on carbon (0.40 g). To the solids, under a nitrogen atmosphere, was added anhydrous methanol (100 mL). The mixture was then stirred under a hydrogen atmosphere for 16 h. Nitrogen was bubbled through the reaction mixture for thirty minutes, before the mixture was filtered through a pad of Celite®, which was then rinsed with methanol. The filtrate was concentrated in vacuo, then azeotroped with toluene to afford the title compound as a dark brown solid (2.2 g, 99%). $^1$H NMR (DMSO-d$_6$) δ 9.05 (br s, 1H), 6.53-6.65 (m, 2H), 4.68 (s, 2H); MS(ESI$^+$) m/z 146 (M+H)$^+$.

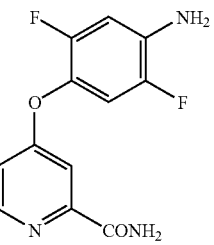

C) 4-(4-Amino-2,5-difluorophenoxy)picolinamide

To a mixture of potassium hydride (30-35% dispersion in mineral oil, 1.9 g, 13.9 mmol) in DMF (30 mL) was added 4-amino-2,5-difluorophenol (1.7 g, 11.6 mmol) as a solution in DMF (5 mL). After one hour of stirring at ambient temperature, 4-chloropicolinamide (1.8 g, 11.6 mmol) was added and the reaction mixture was heated to 100° C. for 135 h. The mixture was cooled to room temperature, quenched with 10% aqueous lithium chloride and then extracted three times with EtOAc. The combined organic layers were dried (MgSO$_4$), filtered and concentrated in vacuo. The resultant solid was partitioned between chloroform and water. The organic layer was washed with brine, dried (MgSO$_4$), filtered and concentrated in vacuo to a solid (3.0 g, 98%). $^1$H NMR (DMSO-d$_6$) δ 8.51-8.57 (m, 1H), 8.14 (br s, 1H), 7.74 (br s, 1H), 7.37-7.38 (m, 1H), 7.17-7.30 (m, 2H), 6.74-6.80 (m, 1H), 5.62 (s, 2H); MS(ESI$^+$) m/z 266 (M+H)$^+$.

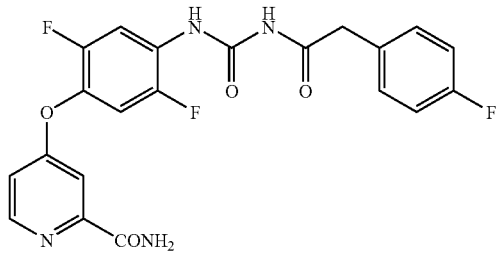

D) 1-(4-(2-Carbamoylpyridin-4-yloxy)-2,5-difluorophenyl)-3-(2-(4-fluorophenyl)acetyl)urea To a homogeneous mixture of 4-(4-amino-2,5-difluorophenoxy)picolinamide (0.15 g, 0.57 mmol) in THF (5 mL) was added diisopropylethylamine (0.10 mL, 0.57 mmol). The mixture was stirred for two minutes at ambient temperature before 2-(4-fluorophenyl)acetyl isocyanate (Compound D of Example 11, 0.36 M in toluene, 2.0 mL, 0.72 mmol) was added. After 3.5 hours, 2-(4-fluorophenyl)acetyl isocyanate (0.36 M in toluene, 2.0 mL, 0.72 mmol) was added to the reaction mixture. After an additional two hours, 2-(4-fluorophenyl)acetyl isocyanate (0.36 M in toluene, 2.0 mL, 0.72 mmol) was added to the reaction mixture. The mixture was then stirred for 16 hours before being concentrated in vacuo. The residue was treated with Et$_2$O and sonication and the resultant white solid was removed by filtration. The solid was treated with Et$_2$O and sonication two more times before vacuum filtration afforded a white solid (0.23 g, 91%). $^1$H NMR (DMSO-d$_6$) δ 11.29 (s, 1H), 10.92 (s, 1H), 8.56 (d, 1H, J=5.6 Hz), 8.21-8.26 (m, 1H), 8.16 (br s, 1H), 7.76 (br s, 1H), 7.66-7.71 (m, 1H), 7.12-7.44 (m, 6H), 3.77 (s, 2H); MS(ESI+) m/z 445 (M+H)+.

E) 1-(4-(2-Aminopyridin-4-yloxy)-2,5-difluorophenyl)-3-(2-(4-fluorophenyl)-acetyl)urea, hydrochloric acid salt Bis(trifluoroacetoxy)iodobenzene (Aldrich, 0.18 g, 0.42 mmol) was added to a solution of 1-(4-(2-carbamoylpyridin-4-yloxy)-2,5-difluorophenyl)-3-(2-(4-fluorophenyl)-acetyl)urea (0.13 g, 0.30 mmol), water (0.01 mL, 0.60 mmol) and pyridine (0.05 mL, 0.66 mmol) in DMF (2 mL) at room temperature. After ten minutes, additional DMF (2 mL) was added. The reaction mixture was then stirred for 16 hours before being concentrated in vacuo to approximately one half of its original volume. The resultant mixture was partitioned between 6 N HCl and Et₂O, the aqueous solution extracted with Et₂O and the combined organic layers discarded. The aqueous layer was neutralized with NaHCO₃(aq) and extracted with EtOAc. The combined organic layers were dried (Na₂SO₄), filtered and concentrated in vacuo. The residue was purified by silica gel chromatography (eluting with 0-5% MeOH in CHCl₃) and the appropriate fractions were concentrated in vacuo. The residue was dissolved in THF (1 mL), cooled to 0° C. and treated with HCl (4 N in dioxane, 0.5 mL, 2.0 mmol). The reaction mixture was allowed to warm to room temperature and stirred for one hour, before being lyophilized to afford the title compound (73 mg, 53%) as a white solid. ¹H NMR (DMSO-d₆) δ 13.54 (br s, 1H), 11.35 (s, 1H), 10.95 (s, 1H), 8.24-8.28 (m, 1H), 7.95-8.01 (m, 3H), 7.73-7.77 (m, 1H), 7.35-7.39 (m, 2H), 7.16-7.20 (m, 2H), 6.72-6.74 (m, 1H), 6.25 (s, 1H), 3.78 (s, 2H); HRMS(ESI+): 417.1175 (M+H)+ calcd., 417.1187 (M+H)+ found.

Example 113

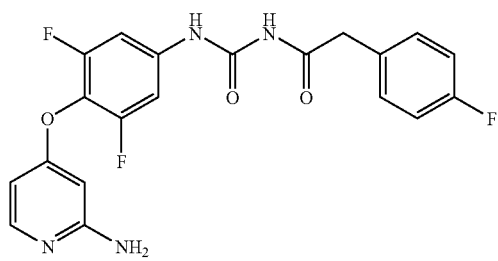

1-(4-(2-Aminopyridin-4-yloxy)-3,5-difluorophenyl)-3-(2-(4-fluorophenyl)-acetyl)urea, trifluoroacetic acid salt

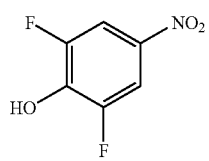

A) 2,6-Difluoro-4-nitrophenol 2,6-Difluorophenol (10.0 g, 76.9 mmol) was converted to the title compound (12.7 g, 94%) in a manner similar to the conditions described by Kirk et al. *J. Heterocyclic Chem.* 1976, 13, 1253. ¹H NMR (CDCl₃) δ 12.15 (br s, 1H), 8.01-8.10 (m, 2H).

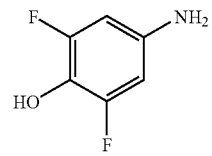

B) 4-Amino-2,6-difluorophenol 2,6-Difluoro-4-nitrophenol (2.1 g, 12.1 mmol) was converted to the title compound (1.7 g, 99%) in a manner similar to that described by Demopoulos et al. *J. Med. Chem.* 2004, 47, 2706. MS(ESI+) m/z 146 (M+H)+.

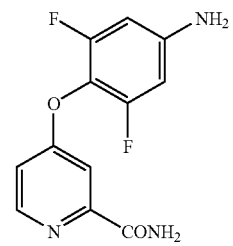

C) 4-(4-Amino-2,6-difluorophenoxy)picolinamide

4-Chloropicolinamide (0.47 g, 3.0 mmol) was converted to the title compound (0.23 g, 29%) in a manner similar to the preparation of Compound C of Example 112, except that 4-amino-2,6-difluorophenol (0.44 g, 3.0 mmol) was used instead of 4-amino-2,5-difluorophenol. ¹H NMR (DMSO-d₆) δ 8.60 (d, 1H, J=5.6 Hz), 8.22 (br s, 1H), 7.83 (br s, 1H), 7.45-7.46 (m, 1H), 7.30-7.32 (m, 1H), 6.43-6.49 (m, 2H), 5.94 (s, 2H); MS(ESI+) m/z 266 (M+H)+.

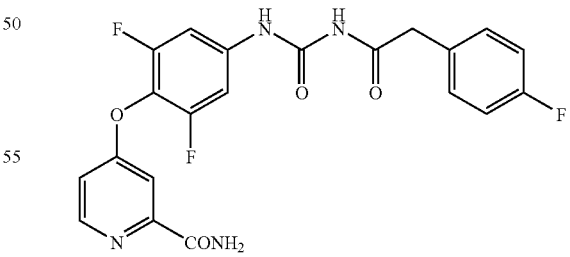

D) 1-(4-(2-Carbamoylpyridin-4-yloxy)-3,5-difluorophenyl)-3-(2-(4-fluorophenyl)acetyl)urea 4-(4-Amino-2,6-difluorophenoxy)picolinamide (104 mg, 0.39 mmol) was converted to the title compound (91 mg, 52%) in a manner similar to the preparation of Compound D of Example 112. ¹H NMR (DMSO-d₆) δ 11.07 (s, 1H), 10.62 (s, 1H), 8.50 (d, 1H, J=5.6 Hz), 8.11 (br s, 1H), 7.72 (br s, 1H), 7.61 (m, 2H), 7.36-7.37 (d, 1H, J=2.3 Hz), 7.23-7.31 (m, 3H), 7.11 (m, 2H), 3.69 (s, 2H); HRMS(ESI⁺), 445.1124 (M+H)⁺ calcd., 445.1117 (M+H)⁺ found.

E) 1-(4-(2-Aminopyridin-4-yloxy)-3,5-difluorophenyl)-3-(2-(4-fluorophenyl)-acetyl)urea, trifluoroacetic acid salt 1-(4-(2-Carbamoylpyridin-4-yloxy)-3,5-difluorophenyl)-3-(2-(4-fluorophenyl)acetyl)urea (87 mg, 0.20 mmol) was converted to the title compound in a manner similar to the preparation of Compound E of Example 112, except that the crude product was purified by preparative HPLC (YMC S10 ODS, 30×500 mm, 30 minute gradient from 58% to 90% aqueous methanol with 0.1% TFA). The appropriate fractions were combined and lyophilized to afford the title compound (23 mg, 22%) as a white solid. ¹H NMR (DMSO-d₆) δ 11.09 (s, 1H), 10.63 (s, 1H), 7.92 (d, 1H, J=7.2 Hz), 7.62-7.72 (m, 4H), 7.27-7.31 (m, 2H), 7.09-7.14 (m, 2H), 6.68-6.70 (m, 1H), 6.17-6.18 (m, 1H), 3.69 (s, 2H); MS(ESI⁺) m/z 417 (M+H)⁺.

Example 114

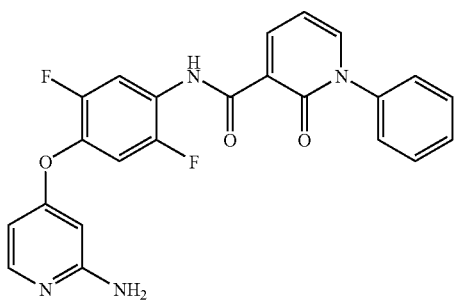

N-(4-(2-Aminopyridin-4-yloxy)-2,5-difluorophenyl)-2-oxo-1-phenyl-1,2-dihydropyridine-3-carboxamide, hydrochloric acid salt

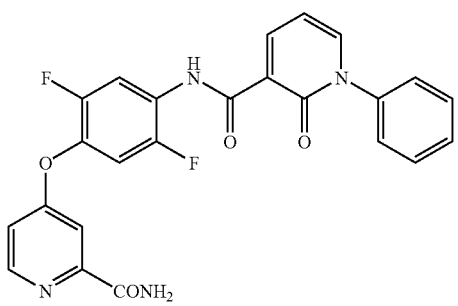

A) 4-(2,5-Difluoro-4-(2-oxo-1-phenyl-1,2-dihydropyridine-3-carboxamido)-phenoxy)picolinamide To a homogeneous mixture of 2-oxo-1-phenyl-1,2-dihydropyridine-3-carboxylic acid (Compound C of Example 57, 43 mg, 0.20 mmol) in DMF (4 mL) was added 1-hydroxybenzotriazole hydrate (22 mg, 0.16 mmol). The mixture was stirred until homogeneous before 1-(3-dimethylaminopropyl)-3-ethyl-carbodiimide hydrochloride (102 mg, 0.53 mmol) was added. After two minutes, 4-(4-amino-2,5-difluorophenoxy)picolinamide (Compound C of Example 112, 53 g, 0.20 mmol) was added and the reaction mixture stirred, at ambient temperature for 17 h. The reaction mixture was then warmed to 40° C. and stirred for an additional 143 h. After cooling to ambient temperature, the mixture was partitioned between EtOAc and 10% LiCl (aq). The organic layer was washed twice with 10% LiCl (aq), then concentrated in vacuo. The residue was purified by silica gel chromatography (eluting with 1:3 hexane/EtOAc) and the appropriate fractions were concentrated in vacuo to afford the title compound (45 mg, 49%). MS(ESI⁺) m/z 463 (M+H)⁺.

B) N-(4-(2-Aminopyridin-4-yloxy)-2,5-difluorophenyl)-2-oxo-1-phenyl-1,2-dihydropyridine-3-carboxamide, hydrochloric acid salt 4-(2,5-Difluoro-4-(2-oxo-1-phenyl-1,2-dihydropyridine-3-carboxamido)-phenoxy)picolinamide (45 mg, 0.10 mmol) was converted to the title compound (19 mg, 40%) in a manner similar to the preparation of Compound E of Example 112. ¹H NMR (DMSO-d₆) δ 13.40 (br s, 1H), 12.47 (s, 1H), 8.53-8.57 (m, 2H), 8.12-8.13 (m, 1H), 7.92-7.93 (m, 1H), 7.83 (s, 2H), 7.66-7.71 (m, 1H), 7.46-7.53 (m, 5H), 6.66-6.72 (m, 2H), 6.19 (s, 1H); HRMS(ESI⁺), 435.1269 (M+H)⁺ calcd., 435.1258 (M+H)⁺ found.

Example 115

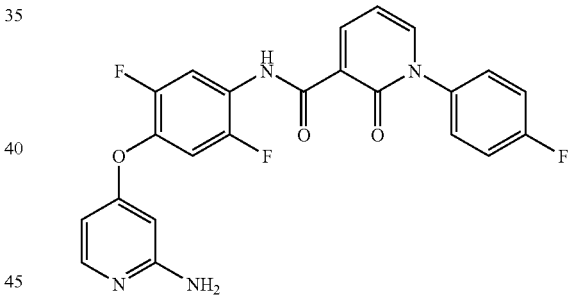

N-(4-(2-Aminopyridin-4-yloxy)-2,5-difluorophenyl)-1-(4-fluorophenyl)-2-oxo-1,2-dihydropyridine-3-carboxamide, hydrochloric acid salt

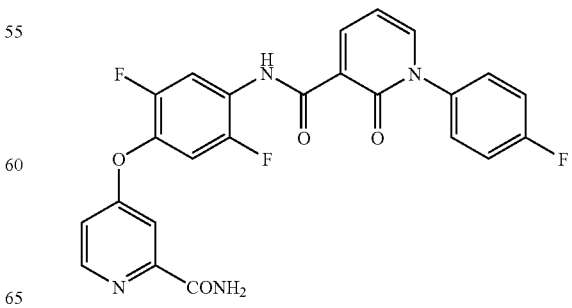

A) 4-(2,5-Difluoro-4-(1-(4-fluorophenyl)-2-oxo-1,2-dihydropyridine-3-carboxamido)phenoxy)picolinamide To a homogeneous mixture of 1-(4-fluorophenyl)-2-oxo-1,2-dihydropyridine-3-carboxylic acid (Compound B of Example 101, 50 mg, 0.21 mmol) and 4-(4-amino-2,5-difluorophenoxy)picolinamide (Compound C of Example 112, 69 mg, 0.26 mmol) in DMF (3 mL) was added DIPEA (0.05 mL, 0.26 mmol) and O-benzotriazol-1-yl-N,N,N',N'-bis(tetramethylene)-uranium hexafluorophosphate (TBTU) (83 mg, 0.26 mmol). The resulting solution was stirred for 18 hours before being quenched with 10% LiCl (aq). The mixture was partitioned between EtOAc and 10% LiCl (aq), the layers separated, and the aqueous layer extracted with EtOAc. The combined organic layers were washed twice with 10% LiCl (aq), then concentrated in vacuo. The residue was purified by silica gel chromatography (eluting with 1:3 hexane/EtOAc) and the appropriate fractions were concentrated in vacuo to afford the title compound (22 mg, 22%). MS(ESI$^+$) m/z 481 (M+H)$^+$.

B) N-(4-(2-Aminopyridin-4-yloxy)-2,5-difluorophenyl)-1-(4-fluorophenyl)-2-oxo-1,2-dihydropyridine-3-carboxamide, hydrochloric acid salt 4-(2,5-Difluoro-4-(1-(4-fluorophenyl)-2-oxo-1,2-dihydropyridine-3-carboxamido)phenoxy)picolinamide (22 mg, 0.04 mmol) was converted to the title compound (21 mg, 95%) in a manner similar to the preparation of Compound E of Example 112. $^1$H NMR (DMSO-d$_6$) δ 13.71 (br s, 1H), 12.43 (s, 1H), 8.48-8.57 (m, 2H), 8.10-8.13 (m, 1H), 7.93-7.95 (m, 3H), 7.61-7.70 (m, 1H), 7.53-7.56 (m, 2H), 7.29-7.39 (m, 2H), 6.64-6.72 (m, 2H), 6.10 (s, 1H); HRMS(ESI$^+$), 453.1175 (M+H)$^+$ calcd., 453.1168 (M+H)$^+$ found.

Example 116

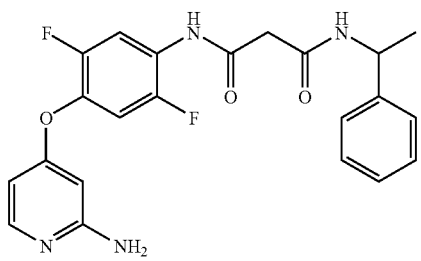

(±)-N$^1$-(4-(2-Aminopyridin-4-yloxy)-2,5-difluorophenyl)-N$^3$-(1-phenylethyl)malonamide, hydrochloric acid salt

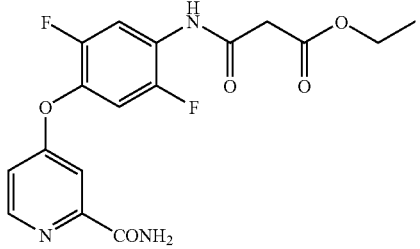

A) Ethyl 3-(4-(2-carbamoylpyridin-4-yloxy)-2,5-difluorophenylamino)-3-oxopropanoate 4-(4-Amino-2,5-difluorophenoxy)picolinamide (Compound C of Example 112, 1.0 g, 3.9 mmol) was converted to the title compound (320 mg, 22%) in a manner similar to the preparation of Compound A of Example 102. $^1$H NMR (DMSO-d$_6$) δ 10.32 (s, 1H), 8.54 (d, 1H, J=5.5 Hz), 8.14-8.17 (m, 2H), 7.75 (br s, 1H), 7.61-7.65 (m, 1H), 7.42-7.43 (m, 1H), 7.24-7.25 (m, 1H), 4.12 (q, 2H, J=7.2 Hz), 3.60 (s, 2H), 1.20 (t, 3H, J=7.2 Hz); MS(ESI$^+$) m/z 380 (M+H)$^+$.

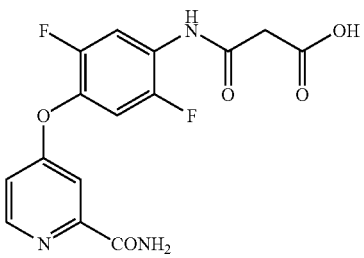

B) 3-(4-(2-Carbamoylpyridin-4-yloxy)-2,5-difluorophenylamino)-3-oxopropanoic acid To a heterogeneous mixture of ethyl 3-(4-(2-carbamoylpyridin-4-yloxy)-2,5-difluorophenylamino)-3-oxopropanoate (305 mg, 0.80 mmol) in MeOH (8 mL) was added aqueous 1 M NaOH (1.70 mL, 1.70 mmol). After one hour of stirring, the mixture was acidified with aqueous 1N HCl (5 mL). The reaction was extracted with EtOAc before the combined organic layers were dried (MgSO$_4$), filtered and concentrated in vacuo to afford the title compound (317 mg) which was used without further purification. HRMS(ESI$^+$), 352.0745 (M+H)$^+$ calcd., 352.0752 (M+H)$^+$ found.

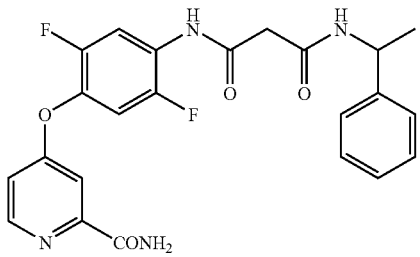

C) (±)-4-(2,5-Difluoro-4-(3-oxo-3-(1-phenylethylamino)propanamido)-phenoxy)picolinamide To a homogeneous mixture of 3-(4-(2-carbamoylpyridin-4-yloxy)-2,5-difluorophenylamino)-3-oxopropanoic acid (89 mg, 0.25 mmol) and (±)-1-phenyl-ethanamine (Aldrich, 0.05 mL, 0.38 mmol) in DMF (3 mL) was added DIPEA (0.07 mL, 0.38 mmol) and O-benzotriazol-1-yl-N,N,N',N'-bis(tetramethylene)uranium hexafluorophosphate (TBTU) (121 mg, 0.38 mmol). The resulting solution was stirred for 15 hours before being quenched with 10% LiCl (aq). The mixture was partitioned between EtOAc and 10% LiCl (aq), the layers separated, and the aqueous layer extracted with EtOAc. The combined organic layers were washed twice with 10% LiCl (aq), then concentrated in vacuo. The residue was purified by silica gel chromatography (eluting with 1:3 hexane/EtOAc) and the appropriate fractions were concentrated in vacuo to afford the title compound (42 mg, 37%). HRMS (ESI$^+$), 455.1532 (M+H)$^+$ calcd., 455.1528 (M+H)$^+$ found.

D) (±)-N$^1$-(4-(2-Aminopyridin-4-yloxy)-2,5-difluorophenyl)-N$^3$-(1-phenyl-ethyl)malonamide, hydrochloric acid salt (±)-4-(2,5-Difluoro-4-(3-oxo-3-(1-phenylethylamino)propanamido)phenoxy)-picolinamide (41 mg, 0.09 mmol) was converted to the title compound (26 mg, 62%) in a manner similar to the preparation of Compound E of Example 112. $^1$H NMR (DMSO-d$_6$) δ 10.46 (s, 1H), 8.70 (d, 1H, J=7.8 Hz), 8.21-8.26 (m, 1H), 8.00 (d, 1H, J=7.2 Hz), 7.89 (s, 2H), 7.67-7.72 (m, 1H), 7.22-7.36 (m, 5H), 6.73-6.76 (m, 1H), 6.21-6.22 (m, 1H), 4.93-4.96 (m, 1H), 3.57 (s, 2H), 1.35 (d, 3H, J=7.0 Hz); HRMS(ESI$^+$), 427.1582 (M+H)$^+$ calcd., 427.1574 (M+H)$^+$ found.

Example 117

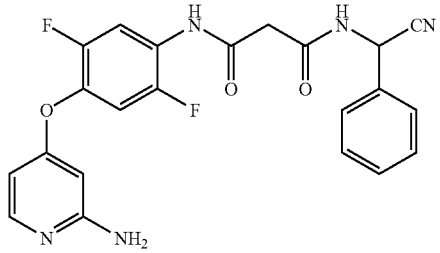

(±)-N$^1$-(4-(2-Aminopyridin-4-yloxy)-2,5-difluorophenyl)-N$^3$-(cyano(phenyl)-methyl)malonamide, trifluoroacetic acid salt

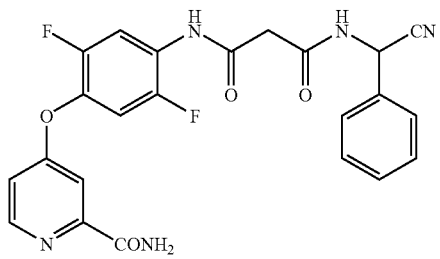

A) (±)-4-(4-(3-(Cyano(phenyl)methylamino)-3-oxopropanamido)-2,5-difluorophenoxy)picolinamide 3-(4-(2-Carbamoylpyridin-4-yloxy)-2,5-difluorophenylamino)-3-oxopropanoic acid (Compound B of Example 116, 70 mg, 0.20 mmol) was converted to the title compound (67 mg, 72%) in a manner similar to the preparation of Compound C of Example 116, except that (±)-2-amino-2-phenylacetonitrile hydrochloride (Aldrich, 47 mg, 0.28 mmol) was used instead of (±)-1-phenylethanamine. MS(ESI$^+$) m/z 466 (M+H)$^+$.

B) (±)-N-1-(4-(2-Aminopyridin-4-yloxy)-2,5-difluorophenyl)-N3-(cyano-(phenyl)methyl)malonamide, trifluoroacetic acid salt (±)-4-(4-(3-(Cyano(phenyl)methylamino)-3-oxopropanamido)-2,5-difluoro-phenoxy)picolinamide (65 g, 0.14 mmol) was converted to the title compound in a manner similar to the preparation of Compound E of Example 112, except that the crude product was purified by preparative HPLC (YMC S10 ODS, 30×500 mm, 30 minute gradient from 34% to 90% aqueous methanol with 0.1% TFA). The appropriate fractions were combined and lyophilized to afford the title compound (38 mg, 49%) as a white solid. $^1$H NMR (DMSO-d$_6$) δ 10.40 (s, 1H), 9.47 (d, 1H, J=7.63 Hz), 8.21-8.26 (m, 1H), 7.99 (d, 1H, J=7.2 Hz), 7.86 (br s, 2H), 7.68-7.73 (m, 1H), 7.43-7.54 (m, 5H), 6.74-6.77 (m, 1H), 6.20-6.22 (m, 2H), 3.55 (m, 2H); HRMS(ESI$^+$), 438.1378 (M+H)$^+$ calcd., 438.1374 (M+H)$^+$ found.

Example 118

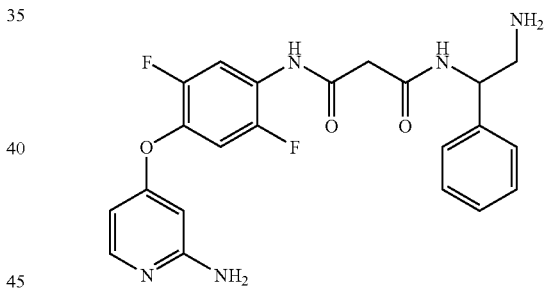

(±)-N$^1$-(2-Amino-1-phenylethyl)-N$^3$-(4-(2-aminopyridin-4-yloxy)-2,5-difluorophenyl)malonamide, bis-trifluoroacetic acid salt (±)-N$^1$-(4-(2-Aminopyridin-4-yloxy)-2,5-difluorophenyl)-N$^3$-(cyano(phenyl)-methyl)malonamide, trifluoroacetic acid salt (Compound B of Example 117, 21 mg, 0.04 mmol) was converted to the title compound in a manner similar to the conditions described by Campiani, et al. (*Tetrahedron* 2002, 58, 3689). The cobalt boride was purchased from Alfa Aesar. The crude product was purified by preparative HPLC (YMC S5 ODS, 10×250 mm, 30 minute gradient from 10% to 90% aqueous methanol with 0.1% TFA). Appropriate fractions were combined and lyophilized to afford the title compound (5 mg, 21%) as a white solid. $^1$H NMR (DMSO-d$_6$) δ 10.39 (s, 1H), 8.72 (d, 1H, J=8.5 Hz), 8.12-8.17 (m, 1H), 7.90-7.94 (m, 3H), 7.59-7.63 (m, 2H), 7.27-7.34 (m, 4H), 6.60-6.62 (m, 1H), 6.09-6.10 (m, 1H), 5.09-5.10 (m, 1H), 3.10-3-50 (m, 6H); HRMS(ESI$^+$), 442.1691 (M+H)$^+$ calcd., 442.1678 (M+H)$^+$ found.

Example 119

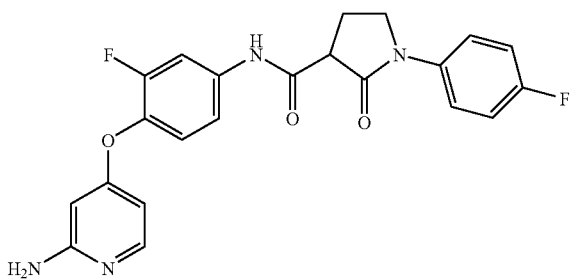

N-(4-(2-Aminopyridin-4-yloxy)-3-fluorophenyl)-1-(4-fluorophenyl)-2-oxopyrrolidine-3-carboxamide

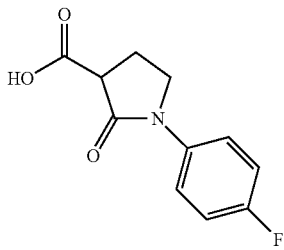

A)
1-(4-Fluorophenyl)-2-oxopyrrolidine-3-carboxylic acid

To a solution of 6,6-dimethyl-5,7-dioxaspiro[2.5]-octane-4,8-dione (Aldrich, 51 mg, 0.3 mmol) in DMF (0.5 mL) at room temperature was added 4-fluoroaniline (Aldrich, 33 mg, 0.3 mmol). The reaction mixture was heated at 90° C. for 2 h, cooled to room temperature, and used directly in the next step.

B) N-(4-(2-Aminopyridin-4-yloxy)-3-fluorophenyl)-1-(4-fluorophenyl)-2-oxopyrrolidine-3-carboxamide To a mixture of 1-(4-fluorophenyl)-2-oxopyrrolidine-3-carboxylic acid (0.3 mol), 4-(4-amino-2-fluorophenoxy)pyridin-2-amine (Compound B of Example 24, 21.9 mg, 0.1 mmol) in DMF (0.5 ml), was added HATU (76 mg, 0.2 mmol) and followed by diisopropylethylamine (0.1 mL, 0.57 mmol). The reaction mixture was stirred at room temperature overnight and was then quenched with 2 mL of methanol. The reaction mixture was purified by prep HPLC. The desired fractions were combined, neutralized with sat. aq. NaHCO$_3$ solution, and concentrated in vacuo to afford the title compound (18 mg, 43%) as a white solid. $^1$H NMR (DMSO-d$_6$) δ 10.76 (br s, 1H), 7.95 (d, 1H, J=7.2 Hz), 7.91 (m, 1H), 7.68 (m, 2H), 7.50 (m, 1H), 7.44 (t, 1H, J=10.0 Hz), 7.24 (m, 2H), 6.70 (m, 1H), 6.11 (d, 1H, J=2.8 Hz), 3.91 (m, 2H), 3.78 (t, 1H, J=5.0 Hz), 2.41 (m, 2H); MS(ESI$^+$) m/z 425.15 (M+H)$^+$.

Example 120

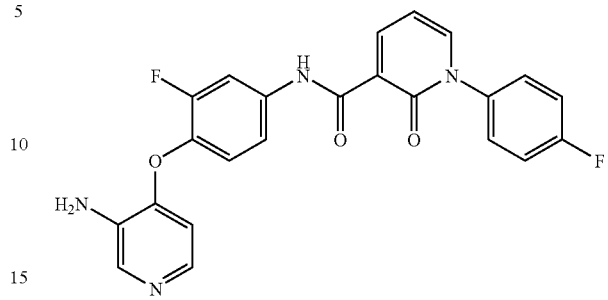

N-(4-(3-Aminopyridin-4-yloxy)-3-fluorophenyl)-1-(4-fluorophenyl)-2-oxo-1,2-dihydropyridine-3-carboxamide

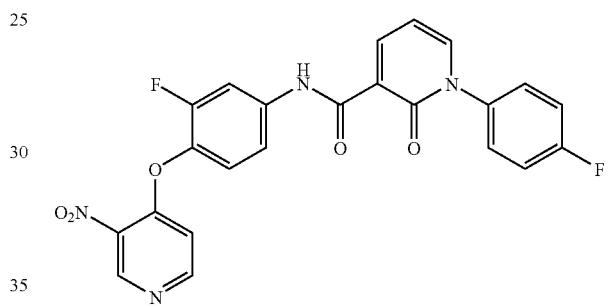

A) N-(3-Fluoro-4-(3-nitropyridin-4-yloxy)phenyl)-1-(4-fluorophenyl)-2-oxo-1,2-dihydropyridine-3-carboxamide Prepared from 3-fluoro-4-(3-nitropyridin-4-yloxy)benzenamine (Compound A of Example 72) in a manner similar to that of Example 62 to give the title compound (89%) as a tan solid. $^1$H NMR (CD$_3$OD) δ 9.13 (s, 1H), 8.72 (dd, 1H, J=8, 4 Hz), 8.60 (d, 1H, J=6 Hz), 8.07 (d, 1H, J=12 Hz), 8.01-7.99 (m, 1H), 7.58-7.55 (m, 2H), 7.45 (t, 1H, J=8 Hz), 7.40-7.32 (m, 3H), 6.99 (d, 1H, J=4 Hz), 6.76 (t, 1H, J=8 Hz); MS(ESI$^+$) m/z 465.18 (M+H)$^+$.

B) N-(4-(3-Aminopyridin-4-yloxy)-3-fluorophenyl)-1-(4-fluorophenyl)-2-oxo-1,2-dihydropyridine-3-carboxamide Prepared in a similar manner as Step C of Example 59. The crude product was purified by flash chromatography on silica gel (10% MeOH/EtOAc) to give the HCl salt of the title compound (58%) as an off-white solid. $^1$H NMR (DMSO-d$_6$) δ 12.07 (s, 1H), 8.59 (dd, 1H, J=7.6, 2.4 Hz), 8.14 (dd, 1H, J=6.4, 2 Hz), 8.04 (s, 1H), 7.99 (dd, 1H, J=13.2, 2.4 Hz), 7.66 (d, 1H, J=5.2 Hz), 7.63-7.60 (m, 2H), 7.46-7.41 (m, 3H), 7.22 (t, 1H, J=9.2 Hz), 6.74 (t, 1H, J=7.2 Hz), 6.46 (d, 1H, J=5.2 Hz), 5.26 (br s, 2H); MS(ESI$^+$): m/z 435.26 (M+H)$^+$.

Example 121

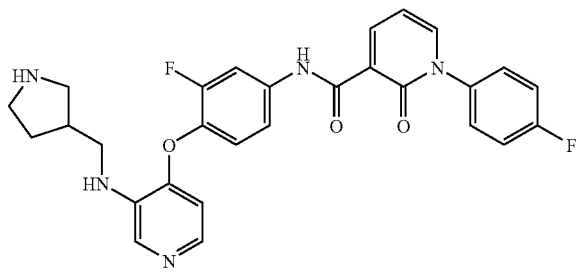

N-(3-Fluoro-4-(3-(pyrrolidin-3-ylmethylamino)pyridin-4-yloxy)phenyl)-1-(4-fluorophenyl)-2-oxo-1,2-dihydropyridine-3-carboxamide, hydrochloride salt To N-(4-(3-aminopyridin-4-yloxy)-3-fluorophenyl)-1-(4-fluorophenyl)-2-oxo-1,2-dihydropyridine-3-carboxamide (Example 120, 30 mg, 0.07 mmol) in DCE (1 mL) was added 3-formyl-pyrrolidine-1-carboxylic acid tert-butyl ester (CB Research and Development Inc., 28 mg, 0.14 mmol), acetic acid (5 uL, 0.084 mmol), then sodium triacetoxyborohydride (23 mg, 0.104 mmol). After stirring at rt for 6 h, a second portion (23 mg) of sodium triacetoxyborohydride was added. After stirring at rt for 2 h, the reaction mixture was charged with 4N HCl in dioxane (5 mL) and stirred an additional 1 h at rt. The reaction was diluted with 10% MeOH/EtOAc (10 mL) and washed with saturated sodium bicarbonate solution (10 mL). The aqueous phase was back-extracted with 10 mL of 10% MeOH/EtOAc and the combined organic layers were dried over anhydrous $Na_2SO_4$ and then concentrated in vacuo. The resulting crude product was purified by prep HPLC. The appropriate fractions were concentrated to remove methanol and then made basic with saturated aqueous sodium bicarbonate solution. The aqueous solution was extracted with 10% MeOH/EtOAc (3×20 mL) and the pooled organic extracts were dried over anhydrous $Na_2SO_4$ and then concentrated in vacuo. The residue was lyophilized from acetonitrile (1 mL)/water (3 mL)/1N aq HCl (0.2 mL) to give the HCl salt of the title compound (25 mg, 60%) as a white solid. $^1$H NMR (DMSO-$d_6$) δ 12.17 (s, 1H), 8.59 (dd, 1H, J=7.6, 2 Hz), 8.30 (s, 1H), 8.16 (dd, 1H, J=6.4, 2 Hz), 8.10 (dd, 1H, J=12.8, 2 Hz), 8.00 (d, 1H, J=6.4 Hz), 7.64-7.58 (m, 3H), 7.52 (t, 1H, J=9.2 Hz), 7.46-7.42 (m, 2H), 7.00 (d, 1H, J=6 Hz), 6.75 (t, 1H, J=7.2 Hz), 3.72-3.64 (m, 3H), 3.37-3.26 (m, 1H), 3.17-3.10 (m, 1H), 2.97-2.92 (m, 1H), 2.74-2.66 (m, 1H), 2.10-2.03 (m, 1H), 1.75-1.68 (m, 1H); MS(ESI$^+$) m/z 518.29 (M+H)$^+$.

Example 122

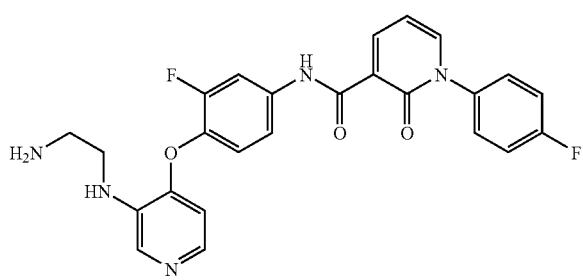

N-(4-(3-(2-Aminoethylamino)pyridin-4-yloxy)-3-fluorophenyl)-1-(4-fluorophenyl)-2-oxo-1,2-dihydropyridine-3-carboxamide, hydrochloride salt Prepared in a similar manner as Example 121 to give the HCl salt of the title compound (52%) as a white solid. $^1$H NMR (DMSO-$d_6$) δ 12.10 (s, 1H), 8.52 (dd, 1H, J=7.6, 2.4 Hz), 8.25 (s, 1H), 8.09 (dd, 1H, J=6.8, 2.4 Hz), 8.06-8.02 (m, 1H), 7.96 (d, 1H, J=6.4 Hz), 7.56-7.52 (m, 3H), 7.42-7.34 (m, 3H), 6.92 (d, 1H, J=6 Hz), 6.68 (t, 1H, J=6.8 Hz), 3.50-3.48 (m, 2H), 3.00-2.99 (m, 2H); MS(ESI$^+$) m/z 478.29 (M+H)$^+$.

Example 123

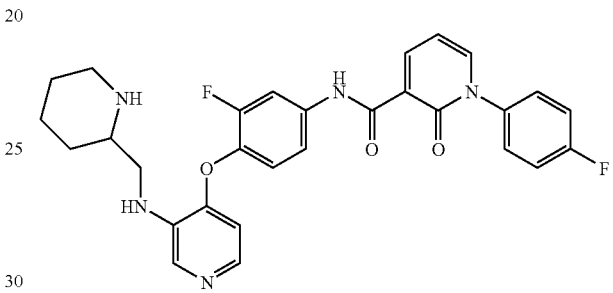

N-(3-Fluoro-4-(3-(piperidin-2-ylmethylamino)pyridin-4-yloxy)phenyl)-1-(4-fluorophenyl)-2-oxo-1,2-dihydropyridine-3-carboxamide, hydrochloride salt Prepared in a similar manner as Example 121 to give the HCl salt of the title compound (71%) as a yellow solid. $^1$H NMR (DMSO-$d_6$) δ 12.17 (s, 1H), 8.59 (dd, 1H, J=7.2, 2 Hz), 8.51 (s, 1H), 8.16 (dd, 1H, J=6.8, 2 Hz), 8.11 (dd, 1H, J=13.2, 2.4 Hz), 8.02 (d, 1H, J=6.4 Hz), 7.63-7.58 (m, 3H), 7.51 (t, 1H, J=8.8 Hz), 7.46-7.41 (m, 2H), 7.01 (d, 1H, J=6 Hz), 6.75 (t, 1H, J=6.8 Hz), 3.70-3.63 (m, 1H), 3.52-3.45 (m, 1H), 3.30-3.27 (m, 2H), 2.86-2.84 (m, 1H), 1.95-1.93 (m, 1H), 1.80-1.62 (m, 3H), 1.58-1.44 (m, 2H); MS(ESI$^+$) m/z 532.31 (M+H)$^+$.

Example 124

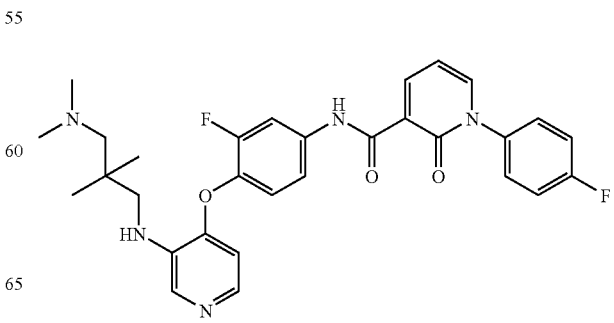

N-(4-(3-(3-(Dimethylamino)-2,2-dimethylpropylamino)pyridin-4-yloxy)-3-fluorophenyl)-1-(4-fluorophenyl)-2-oxo-1,2-dihydropyridine-3-carboxamide, hydrochloride salt Prepared in a similar manner as Example 121 to give the HCl salt of the title compound (58%) as a white solid. $^1$H NMR (DMSO-$d_6$) δ 12.10 (s, 1H), 8.57 (s, 1H), 8.52 (dd, 1H, J=7.6, 2 Hz), 8.09 (dd, 1H, J=6.8, 2.4 Hz), 8.03 (dd, 1H, J=13.2, 2.4 Hz), 7.90 (d, 1H, J=6.4 Hz), 7.56-7.51 (m, 3H), 7.44 (t, 1H, J=8.8 Hz), 7.39-7.35 (m, 2H), 6.92 (d, 1H, J=6.4 Hz), 6.68 (t, 1H, J=7.2 Hz), 3.33 (s, 2H), 3.10 (s, 2H), 2.77 (s, 3H), 2.76 (s, 3H), 1.07 (s, 6H); MS(ESI$^+$) m/z 548.34 (M+H)$^+$.

Example 125

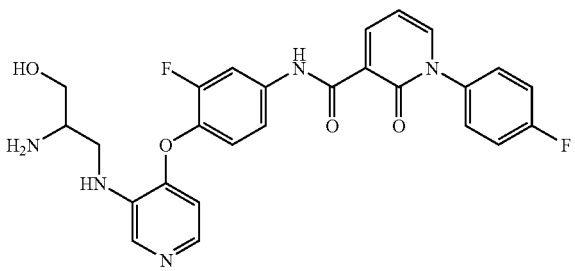

N-(4-(3-(2-Amino-3-hydroxypropylamino)pyridin-4-yloxy)-3-fluorophenyl)-1-(4-fluorophenyl)-2-oxo-1,2-dihydropyridine-3-carboxamide, hydrochloride salt Prepared in a similar manner as Example 121 to give the HCl salt of the title compound (65%) as a white solid. $^1$H NMR (DMSO-$d_6$) δ 12.10 (s, 1H), 8.52 (dd, 1H, J=7.2, 2 Hz), 8.30 (s, 1H), 8.09 (dd, 1H, J=6.8, 2.4 Hz), 8.03 (dd, 1H, J=12.8, 2 Hz), 7.96 (d, 1H, J=6.4 Hz), 7.56-7.52 (m, 3H), 7.43-7.35 (m, 3H), 6.93 (d, 1H, J=6 Hz), 6.68 (t, 1H, J=7.2 Hz), 3.65-3.56 (m, 2H), 3.48-3.45 (m, 3H); MS(ESI$^+$) m/z 508.27 (M+H)$^+$.

Example 126

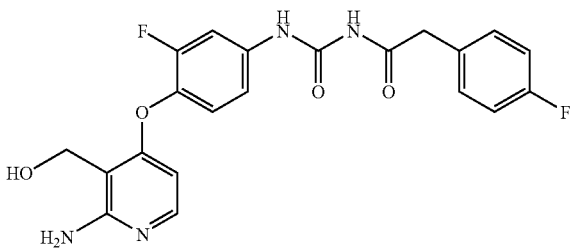

1-(4-(2-Amino-3-(hydroxymethyl)pyridin-4-yloxy)-3-fluorophenyl)-3-(2-(4-fluorophenyl)acetyl)urea, hydrochloride salt

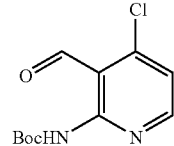

A) tert-Butyl 4-chloro-3-formylpyridin-2-ylcarbamate

To (4-chloro-pyridin-2-yl)-carbamic acid tert-butyl ester (CB Research and Development Inc., 2.0 g, 8.75 mmol) in THF (18 mL) under nitrogen at −78° C., was added n-BuLi (13.7 mL, 21.9 mmol, 1.6 M in hexanes) dropwise. After stirring at −78° C. for 45 min, a solution of DMF (1.93 mL) in THF (2 mL) was added dropwise. The reaction was stirred at −78° C. for 30 min and was then allowed to warm slowly to room temperature. The reaction was quenched with 1N aq HCl solution and then basified with saturated aqueous sodium bicarbonate solution (50 mL) and extracted with ethyl acetate (3×50 µL). The combined organic extracts were dried over anhydrous Na$_2$SO$_4$ and concentrated in vacuo. The crude product was purified by flash column chromatography on silica gel (EtOAc) to afford the title compound (0.95 g, 42%) as a white solid. $^1$H NMR (DMSO-$d_6$) δ 10.44 (s, 1H), 10.13 (s, 1H), 8.47 (d, 1H, J=5.2 Hz), 7.40 (d, 1H, J=5.6 Hz), 1.48 (s, 9H).

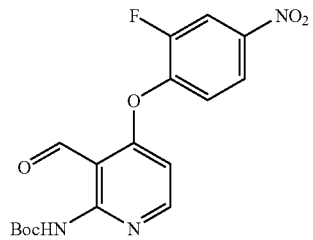

B) tert-Butyl 4-(2-fluoro-4-nitrophenoxy)-3-formylpyridin-2-ylcarbamate

To 2-fluoro-nitrophenol (Aldrich, 700 mg, 4.44 mmol) in DMF (5 mL) was added sodium hydride (60%, 180 mg, 4.44 mmol). After stirring at rt for 5 min, a solution of tert-butyl 4-chloro-3-formylpyridin-2-ylcarbamate (0.95 g, 3.7 mmol) in 5 mL of DMF was added to the mixture. The reaction mixture was stirred at 60° C. for 20 h. After cooling to rt, the reaction was diluted with EtOAc (50 mL), washed with 10% aqueous lithium chloride solution (2×40 mL) followed by saturated aqueous sodium bicarbonate solution (40 mL), dried over anhydrous Na$_2$SO$_4$, and concentrated in vacuo. The crude product was purified by flash chromatography on silica gel (50% EtOAc/hexanes) to give the title compound (1.0 g, 72%) as a yellow oil. $^1$H NMR (CD$_3$OD) δ 10.59 (s, 1H), 8.37-8.25 (m, 2H), 7.67 (t, 1H, J=7.6 Hz), 6.60 (d, 1H, J=6 Hz), 1.59 (s, 9H).

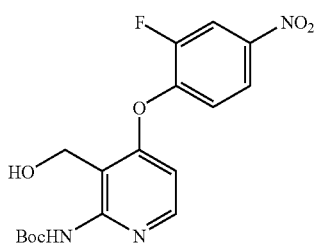

C) tert-Butyl 4-(2-fluoro-4-nitrophenoxy)-3-(hydroxymethyl)pyridin-2-ylcarbamate To tert-butyl 4-(2-fluoro-4-nitrophenoxy)-3-formylpyridin-2-ylcarbamate (75 mg, 0.2 mmol) in methanol (1 mL) at 0° C. was added sodium borohydride (7.6 mg, 0.20 mmol). After stirring at 0° C. for 30 min, the reaction was quenched with saturated aqueous ammonium chloride solution (1 mL). The reaction was diluted with EtOAc (5 mL) and the layers were separated. The organic layer was dried over anhydrous $Na_2SO_4$ and concentrated in vacuo to give the title compound (65 mg, 86%) as a white solid which was used without further purification. $^1$H NMR (CD$_3$OD) δ 8.28 (dd, 1H, J=10.4, 2.8 Hz), 8.22-8.18 (m, 2H), 7.45 (t, 1H, J=8.4 Hz), 6.68 (d, 1H, J=6 Hz), 4.81 (s, 2H), 1.57 (s, 9H); MS(ESI$^+$) m/z 380.27 (M+H)$^+$.

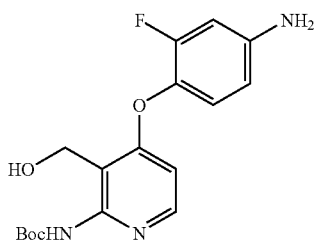

D) tert-Butyl 4-(4-amino-2-fluorophenoxy)-3-(hydroxymethyl)pyridin-2-ylcarbamate Prepared in a similar manner as Step C of Example 59 to give the title compound as a white solid. $^1$H NMR (CD$_3$OD) δ 8.14 (d, 1H, J=6 Hz), 6.97 (t, 1H, J=8.8 Hz), 6.62-6.54 (m, 2H), 6.46 (d, 1H, J=6.4 Hz), 4.64 (s, 2H), 1.55 (s, 9H); MS(ESI$^+$) m/z 350.11 (M+H)$^+$.

E) 1-(4-(2-Amino-3-(hydroxymethyl)pyridin-4-yloxy)-3-fluorophenyl)-3-(2-(4-fluorophenyl)acetyl) urea, hydrochloride salt Prepared in a similar manner as Step C of Example 59 to give the HCl salt of the title compound as a white solid. $^1$H NMR (DMSO-d$_6$) δ 10.99 (s, 1H), 10.56 (s, 1H), 7.82 (d, 1H, J=7.2 Hz), 7.74 (dd, 1H, J=13.6, 2.8 Hz), 7.31-26 (m, 3H), 7.19-7.02 (m, 3H), 6.16 (d, 1H, J=7.2 Hz), 4.57 (s, 2H), 3.69 (s, 2H); MS(ESI$^+$) m/z 429.16 (M+H)$^+$.

Example 127

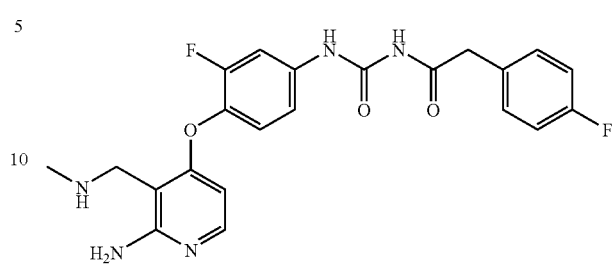

1-(4-(2-Amino-3-((methylamino)methyl)pyridin-4-yloxy)-3-fluorophenyl)-3-(2-(4-fluorophenyl)acetyl) urea, hydrochloride salt

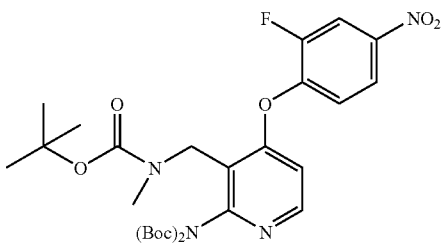

A) tert-Butyl(2-bis-BOC-amino-4-(2-fluoro-4-nitrophenoxy)pyridin-3-yl)methyl(methyl)carbamate To tert-butyl 4-(2-fluoro-4-nitrophenoxy)-3-formylpyridin-2-ylcarbamate (Compound B of Example 126, 75 mg, 0.2 mmol) in dichloroethane (1 mL) at 0° C. was added methylamine (240 μL, 0.24 mmol, 2M in THF), acetic acid (14 μL, 0.24 mmol), followed by sodium triacetoxyborohydride (400 mg, 1.89 mmol). After stirring at rt for 16 h, the reaction mixture was diluted with EtOAc (5 mL), washed with saturated aqueous sodium bicarbonate solution (5 mL), dried over anhydrous Na$_2$SO$_4$, and concentrated in vacuo. The crude product was purified by flash column chromatography on silica gel (20% MeOH/EtOAc) to give tert-butyl 4-(2-fluoro-4nitrophenoxy)-3-((methylamino)methyl)pyridin-2-ylcarbamate (37 mg, 47%) as a yellow oil.

To tert-butyl 4-(2-fluoro-4-nitrophenoxy)-3-((methylamino)methyl)pyridin-2-ylcarbamate (48 mg, 0.122 mmol) and DMAP (16 mg, 0.134 mmol) in dichloromethane (1 mL) was added di-tert-butyl dicarbonate (Aldrich, 32 mg, 0.15 mmol). After stirring at rt 30 min, a mixture of bis- and tris-BOC material (2:1) was observed. An additional portion of DMAP and di-tert-butyl dicarbonate was added. After stirring at rt for 30 min, the reaction was purified directly by flash column chromatography on silica gel (EtOAc) to give the title compound (44 mg, 61%) as a yellow oil. $^1$H NMR (CD$_3$OD) δ 8.50 (d, 1H, J=5.2 Hz), 8.15-7.97 (m, 2H), 7.43 (d, 1H, J=5.6 Hz), 7.07 (t, 1H, J=8.4 Hz), 4.64 (s, 2H), 2.83 (s, 3H), 1.44 (s, 27H); MS(ESI$^+$) m/z 593.34 (M+H)$^+$.

B) 1-(4-(2-Amino-3-((methylamino)methyl)pyridin-4-yloxy)-3-fluorophenyl)-3-(2-(4-fluorophenyl)acetyl)urea, hydrochloride salt Prepared in a similar manner as Step C of Example 59 to give the HCl salt of the title compound (60%) as a white solid. $^1$H NMR (DMSO-d$_6$) δ 10.88 (s, 1H), 10.35 (s, 1H), 7.45-7.42 (m, 1H), 7.30 (m, 3H), 7.11-7.07 (m, 4H), 6.52 (d, 1H, J=7.2 Hz), 4.02 (s, 2H), 3.66 (s, 2H), 2.54 (s, 3H); MS(ESI$^+$) m/z 442.30 (M+H)$^+$.

Example 128

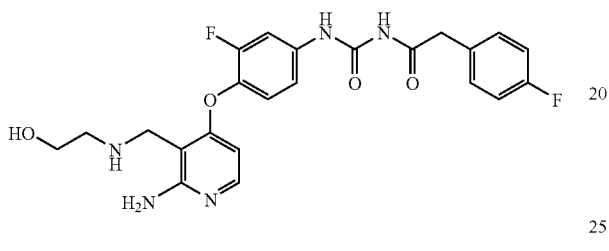

1-(4-(2-Amino-3-((2-hydroxyethylamino)methyl)pyridin-4-yloxy)-3-fluorophenyl)-3-(2-(4-fluorophenyl)acetyl)urea, trifluoroacetic acid salt

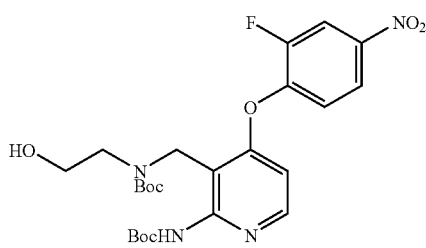

A) tert-Butyl(2-BOC-amino-4-(2-fluoro-4-nitrophenoxy)pyridin-3-yl)methyl(2-hydroxyethyl)carbamate Prepared in a similar manner as Step A of Example 127 to give the title compound (14%) as a yellow oil. $^1$H NMR (CD$_3$OD) δ 8.30 (dd, 1H, J=10.4, 2.8 Hz), 8.23-8.20 (m, 2H), 7.52 (t, 1H, J=8.4 Hz), 6.64 (d, 1H, J=7.2 Hz), 4.71 (s, 2H), 3.65 (t, 2H, J=6 Hz), 3.40 (m, 2H), 1.57 (s, 18H); MS(ESI$^+$) m/z 523.32 (M+H)$^+$.

B) 1-(4-(2-Amino-3-((2-hydroxyethylamino)methyl)pyridin-4-yloxy)-3-fluorophenyl)-3-(2-(4-fluorophenyl)acetyl)urea, trifluoroacetic acid salt Prepared in a similar manner as Step C of Example 59 to give the TFA salt of the title compound (45%) as a white solid. $^1$H NMR (DMSO-d$_6$) δ 11.12 (s, 1H), 10.69 (s, 1H), 8.01 (d, 1H, J=6.8 Hz), 7.87 (dd, 1H, J=12.8, 2.4 Hz), 7.53-7.40 (m, 4H), 7.26-7.20 (m, 2H), 6.68 (d, 1H, J=7.2 Hz), 4.34 (s, 2H), 3.81 (s, 2H), 3.75 (t, 2H, J=7.2 Hz), 3.18 (m, 2H); MS(ESI$^+$) m/z 472.24 (M+H)$^+$.

Example 129

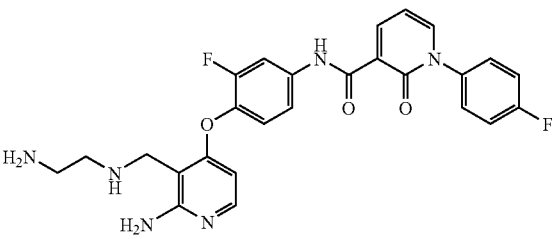

N-(4-(2-Amino-3-((2-aminoethylamino)methyl)pyridin-4-yloxy)-3-fluorophenyl)-1-(4-fluorophenyl)-2-oxo-1,2-dihydropyridine-3-carboxamide, trifluoroacetic acid salt

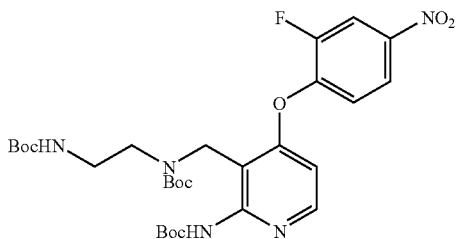

A) tert-Butyl(2-BOC-amino-4-(2-fluoro-4-nitrophenoxy)pyridin-3-yl)methyl(2-BOC-aminoethyl)carbamate Prepared in a similar manner as Step A of Example 127 to give the title compound (19%) as a yellow oil. $^1$H NMR (CD$_3$OD) δ 8.30 (dd, 1H, J=10, 2.4 Hz), 8.23-8.20 (m, 2H), 7.52 (t, 1H, J=8.4 Hz), 6.61 (d, 1H, J=7.2 Hz), 4.65 (s, 2H), 3.39 (m, 2H), 3.25 (m, 2H), 1.61 (s, 27H); MS(ESI$^+$) m/z 622.47 (M+H)$^+$.

B) N-(4-(2-Amino-3-((2-aminoethylamino)methyl)pyridin-4-yloxy)-3-fluorophenyl)-1-(4-fluorophenyl)-2-oxo-1,2-dihydropyridine-3-carboxamide, trifluoroacetic acid salt The nitro group was reduced in a similar manner as Step C of Example 59 and then the amide was formed in a manner similar to Example 62 to give the TFA salt of the title compound (28%) as a white solid. $^1$H NMR (DMSO-d$_6$) δ 12.09 (s, 1H), 8.52 (dd, 1H, J=7.2, 2 Hz), 8.09 (dd, 1H, J=6.4, 2 Hz), 7.99 (dd, 1H, J=12.8, 2.4 Hz), 7.89 (d, 1H, J=6.4 Hz), 7.56-7.52 (m, 2H), 7.49-7.47 (m, 1H), 7.39-7.33 (m, 3H), 6.68 (t, 1H, J=7.2 Hz), 6.07 (d, 1H, J=7.2 Hz), 4.25 (s, 2H), 3.20 (m, 2H), 3.08 (m, 2H); MS(ESI$^+$) m/z 507.23 (M+H)$^+$.

Example 130

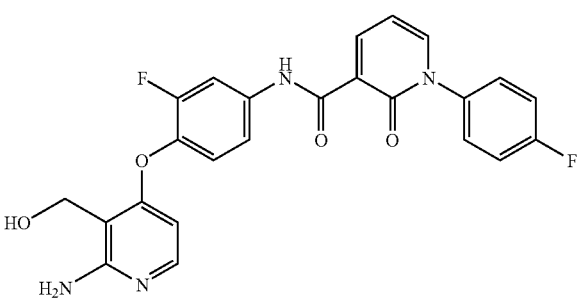

N-(4-(2-Amino-3-(hydroxymethyl)pyridin-4-yloxy)-3-fluorophenyl)-1-(4-fluorophenyl)-2-oxo-1,2-dihydropyridine-3-carboxamide, trifluoroacetic acid salt

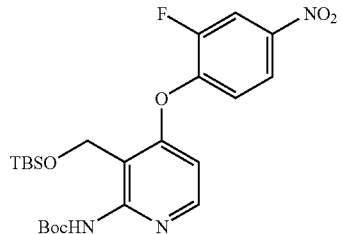

A) tert-Butyl 3-((tert-butyldimethylsilyloxy)methyl)-4-(2-fluoro-4-nitrophenoxy)pyridin-2-ylcarbamate To tert-butyl 4-(2-fluoro-4-nitrophenoxy)-3-(hydroxymethyl)pyridin-2-ylcarbamate (Compound C of Example 126, 100 mg, 0.26 mmol) in dichloromethane (3 mL) was added imidazole (21 mg, 0.31 mmol) followed by tert-butyldimethylsilyl chloride (40 mg, 0.26 mmol). After stirring at rt for 1 h, a second equivalent of tert-butyldimethylsilyl chloride (40 mg, 0.26 mmol) was added. The reaction was stirred at rt for 3 h and was then diluted with dichloromethane (10 mL), washed with water (10 mL), dried over anhydrous $Na_2SO_4$, and concentrated in vacuo. The crude product was purified by flash column chromatography on silica gel (50% EtOAc/hexanes) to give the title compound (102 mg, 79%) as a white solid. $^1$H NMR (CD$_3$OD) δ 8.16 (dd, 1H, J=10.4, 2.8 Hz), 8.09-8.05 (m, 2H), 7.29 (t, 1H, J=8.4 Hz), 6.53 (d, 1H, J=5.6 Hz), 4.84 (s, 2H), 1.43 (s, 9H), 0.84 (s, 9H), 0.00 (s, 6H); MS(ESI$^+$) m/z 494.29 (M+H)$^+$.

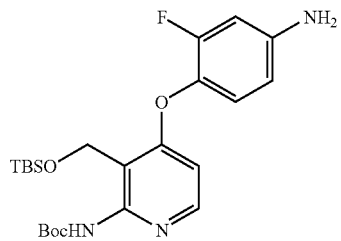

B) tert-Butyl 4-(4-amino-2-fluorophenoxy)-3-((tert-butyldimethylsilyloxy)-methyl)pyridin-2-ylcarbamate Prepared in a similar manner as Step C of Example 59 give the title compound (95 mg, 98%) as a yellow oil. $^1$H NMR (CD$_3$OD) δ 7.90 (d, 1H, J=6 Hz), 6.76 (t, 1H, J=8.8 Hz), 6.43 (dd, 1H, J=12.8, 2.8 Hz), 6.39-6.37 (m, 1H), 6.21 (d, 1H, J=5.6 Hz), 4.85 (s, 2H), 1.39 (s, 9H), 0.81 (s, 9H), 0.01 (s, 6H); MS(ESI$^+$) m/z 464.34 (M+H)$^+$.

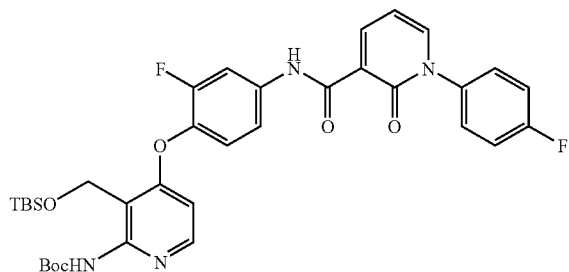

C) tert-Butyl 3-((tert-butyldimethylsilyloxy)methyl)-4-(2-fluoro-4-(1-(4-fluorophenyl)-2-oxo-1,2-dihydropyridine-3-carboxamido)phenoxy)pyridin-2-ylcarbamate Prepared in a manner similar to that of Example 62 to give the title compound (86%) as a colorless oil. $^1$H NMR (CD$_3$OD) δ 8.51 (dd, 1H, J=7.6, 2.4 Hz), 7.93 (d, 1H, J=6 Hz), 7.84-7.80 (m, 2H), 7.40-7.37 (m, 2H), 7.21-7.15 (m, 3H), 7.06 (t, 1H, J=8.8 Hz), 6.57 (t, 1H, J=6.8 Hz), 6.26 (d, 1H, J=5.6 Hz), 4.86 (s, 2H), 1.40 (s, 9H), 0.82 (s, 9H), 0.00 (s, 6H); MS(ESI$^+$) m/z 679.34 (M+H)$^+$.

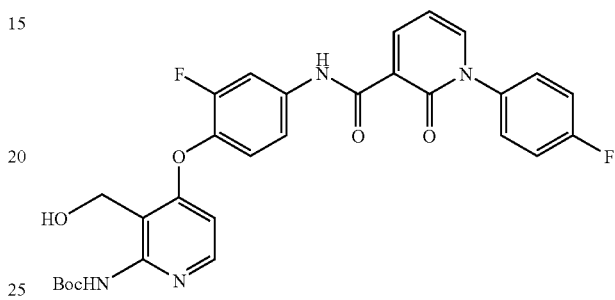

D) tert-Butyl 4-(2-fluoro-4-(1-(4-fluorophenyl)-2-oxo-1,2-dihydropyridine-3-carboxamido)phenoxy)-3-(hydroxymethyl)pyridin-2-ylcarbamate To tert-Butyl 3-((tert-butyldimethylsilyloxy)methyl)-4-(2-fluoro-4-(1-(4-fluorophenyl)-2-oxo-1,2-dihydropyridine-3-carboxamido)phenoxy)pyridin-2-ylcarbamate (119 mg, 0.176 mmol) in THF (2 mL) at rt was added tetrabutylammonium flouride (260 μL, 0.264 mmol, 1 M in THF). After stirring at rt for 30 min, the reaction was diluted with ethyl acetate (20 mL), washed with water followed by brine (10 mL each), dried over anhydrous MgSO$_4$, and concentrated in vacuo. The crude product was purified by flash column chromatography on silica gel (5% MeOH/EtOAc) to give the title compound (66 mg, 66%) as a yellow oil. $^1$H NMR (CD$_3$OD) δ 8.62 (dd, 1H, J=7.2, 2 Hz), 8.04 (d, 1H, J=6 Hz), 7.94-7.90 (m, 2H), 7.50-7.46 (m, 2H), 7.33-7.25 (m, 3H), 7.20 (t, 1H, J=8.8 Hz), 6.67 (t, 1H, J=6.8 Hz), 6.40 (d, 1H, J=5.2 Hz), 4.78 (s, 2H), 1.49 (s, 9H); MS(ESI$^+$) m/z 565.17 (M+H)$^+$.

E) N-(4-(2-Amino-3-(hydroxymethyl)pyridin-4-yloxy)-3-fluorophenyl)-1-(4-fluorophenyl)-2-oxo-1,2-dihydropyridine-3-carboxamide, trifluoroacetic acid salt To tert-butyl 4-(2-fluoro-4-(1-(4-fluorophenyl)-2-oxo-1,2-dihydropyridine-3-carboxamido)phenoxy)-3-(hydroxymethyl)pyridin-2-ylcarbamate (33 mg 0.058 mmol) in THF (2 mL) at rt was added 4N HCl in dioxane (10 mL). After stirring at rt for 8 h, the reaction was concentrated in vacuo. The resulting crude product was purified by prep HPLC. The appropriate fractions were concentrated and toluene was added (2×3 mL) and the resulting mixture was concentrated again. The residue was lyophilized from acetonitrile (1 mL)/water (3 mL) to give the TFA salt of the title compound (14 mg, 42%) as a white solid. $^1$H NMR (DMSO-d$_6$) δ 12.08 (s, 1H), 8.52 (dd, 1H, J=7.2, 2 Hz), 8.09 (dd, 1H, J=6.8, 2 Hz), 7.99 (dd, 1H, J=12.8, 2.4 Hz), 7.81 (d, 1H, J=7.2 Hz), 7.56-7.52 (m, 2H), 7.48-7.46 (m, 1H), 7.39-7.34 (m, 2H), 7.30 (t, 1H, J=9.2 Hz), 6.67 (t, 1H, J=7.2 Hz), 6.21 (d, 1H, J=7.2 Hz), 4.58 (s, 2H); MS(ESI$^+$) m/z 465.17 (M+H)$^+$.

Example 131

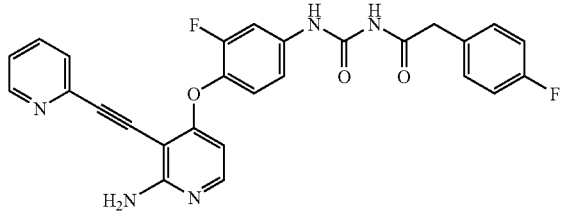

1-(4-(2-Amino-3-(2-(pyridin-2-yl)ethynyl)pyridin-4-yloxy)-3-fluoro phenyl)-3-(2-(4-fluorophenyl)acetyl)urea, dihydrochloride salt

A) 4-(2-Fluoro-4-nitrophenoxy)-3-(2-(pyridin-2-yl)ethynyl)pyridin-2-amine

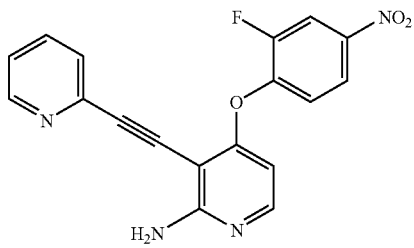

A solution of 4-(2-fluoro-4-nitrophenoxy)-3-iodopyridin-2-amine (Compound C of Example 34, 100 mg, 0.27 mmol), 2-ethynylpyridine (Aldrich, 56 µL, 0.54 mmol), Et₃N (2 mL), and THF (2 mL) was degassed by vacuum/argon purge and then treated with CuI (6 mg, 0.032 mmol) and (Ph₃P)₄Pd (20 mg, 0.017 mmol). The reaction mixture was heated at 60° C. for 45 min, cooled to RT and diluted with EtOAc. The mixture was washed with saturated aqueous NaHCO₃ solution, brine, dried (MgSO₄) and concentrated in vacuo. The crude product was purified by flash chromatography on SiO₂ using 0-1.5% MeOH/CH₂Cl₂ to give the title compound (55 mg, 57%) as an olive green solid. $^1$H NMR (DMSO-d$_6$) δ 8.53 (d, 1H, J=5.1 Hz), 8.42-8.37 (m, 1H), 8.19-8.12 (m, 1H), 7.96 (d, 1H, J=5.6 Hz), 7.85-7.78 (m, 1H), 7.71 (d, 1H, J=7.6 Hz), 7.52 (t, 1H, J=8.6 Hz), 7.36 (ddd, 1H, J=7.6, 5.1, 1.0 Hz), 6.71 (s, 2H), 6.21 (d, 1H, J=5.6 Hz); MS(ESI⁺): m/z 351.25 (M+H)⁺.

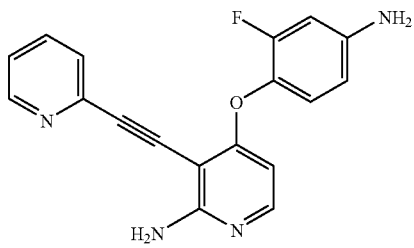

B) 4-(4-Amino-2-fluorophenoxy)-3-(2-(pyridin-2-yl)ethynyl)pyridin-2-amine

The title compound was prepared from the reduction of 4-(2-fluoro-4-nitrophenoxy)-3-(2-(pyridin-2-yl)ethynyl)pyridin-2-amine (35 mg, 0.10 mmol) using zinc dust (65 mg, 1.0 mmol) and NH₄Cl (53 mg, 1.0 mmol) in the same manner as Step C of Example 11. This gave the title compound (25 mg, 78%) as brown oil. MS(ESI⁺): m/z 321.25 (M+H)⁺.

C) 1-(4-(2-Amino-3-(2-(pyridin-2-yl)ethynyl)pyridin-4-yloxy)-3-fluorophenyl)-3-(2-(4-fluorophenyl)acetyl)urea, dihydrochloride salt The title compound was prepared from 4-(4-amino-2-fluorophenoxy)-3-(2-(pyridin-2-yl)ethynyl)pyridin-2-amine (25 mg, 0.078 mmol) and a 0.3 M solution of 2-(4-fluorophenyl)acetyl isocyanate in toluene (Compound D of Example 11, 0.26 mL, 0.078 mmol) in the same manner as Step E of Example 11. The crude product was prepared by preparative HPLC (Column B). The TFA salt was converted to the hydrochloride in the same manner as in Step E of Example 36 to give the title compound (18 mg, 40%) as a brown solid. $^1$H NMR (DMSO-d$_6$) δ 11.06 (s, 1H), 10.63 (s, 1H), 8.62 (d, 1H, J=4.6 Hz), 8.23 (s, 1H), 7.99 (d, 1H, J=7.1 Hz), 7.94-7.84 (m, 3H), 7.87-7.76 (m, 1H), 7.51-7.42 (m, 3H), 7.39-7.32 (m, 2H), 7.21-7.13 (m, 2H), 6.30 (d, 1H, J=7.1 Hz), 3.74 (s, 2H) MS(ESI⁺): m/z 498.11 (M+H)⁺.

Example 132

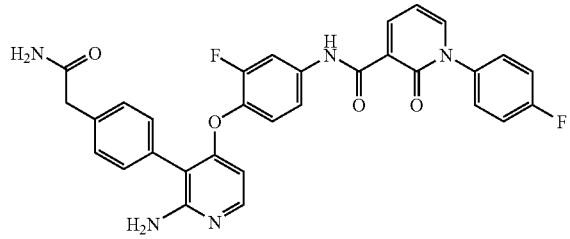

N-(4-(2-Amino-3-(4-(2-amino-2-oxoethyl)phenyl)pyridin-4-yloxy)-3-fluorophenyl)-1-(4-fluorophenyl)-2-oxo-1,2-dihydropyridine-3-carboxamide, hydrochloride salt The title compound was prepared from 2-(4-(2-amino-4-(4-amino-2-fluorophenoxy)pyridin-3-yl)phenyl)acetamide (Compound C of Example 78, 18 mg, 0.05 mmol) and 1-(4-fluorophenyl)-2-oxo-1,2-dihydropyridine-3-carboxylic acid (Compound B of Example 101, 11 mg, 0.05 mmol) in the same manner as Example 62. The crude product was prepared by preparative HPLC (Column B) followed by conversion of the TFA salt to the hydrochloride salt (15 mg, 50%). $^1$H NMR (DMSO-d$_6$) δ 12.11 (s, 1H), 8.58-8.54 (m, 1H), 8.13 (dd, 1H, J=6.6, 2.2 Hz), 8.00 (dd, 1H, J=12.6, 2.2 Hz), 7.96 (d, 1H, J=7.7 Hz), 7.59 (dd, 2H, J=8.8, 4.9 Hz), 7.47-7.41 (m, 6H), 7.40-7.35 (m, 3H), 6.94 (s, 1H), 6.72 (t, 1H, J=7.1 Hz), 6.38 (d, 1H, J=7.1 Hz), 3.44 (s, 2H); MS(ESI⁺): m/z 568.23 (M+H)⁺.

Example 133

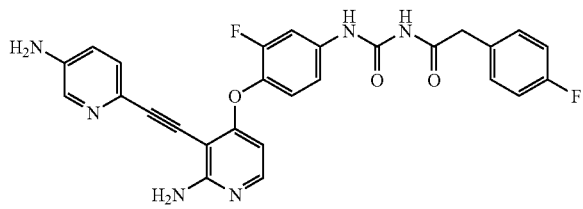

1-(4-(2-Amino-3-(2-(5-aminopyridin-2-yl)ethynyl)
pyridin-4-yloxy)-3-fluorophenyl)-3-(2-(4-fluorophenyl)acetyl)urea, dihydrochloride salt

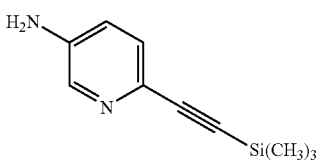

A) 6-(2-(Trimethylsilyl)ethynyl)pyridin-3-amine

A mixture of 3-amino-6-bromopyridine (Alfa Aesar, 1.0 g, 5.8 mmol), ethynyl trimethylsilane (1.7 mL, 17.3 mmol), CH$_3$CN (3 mL), DMF (2 mL) and Et$_3$N (2 mL) was treated with CuI (60 mg, 0.32 mmol) and (Ph$_3$P)$_4$Pd (114 mg, 0.10 mmol) and the mixture stirred at 45° C. for 1.5 h. More ethynyltrimethylsilane (1.7 mL, 17.3 mmol) was added to the reaction and the mixture was stirred for 2 h. The mixture was concentrated in vacuo and the residue partitioned between EtOAc and saturated aqueous NaHCO$_3$ solution. The EtOAc phase was washed with brine, dried (MgSO$_4$) and concentrated in vacuo. The crude product was purified by flash chromatography on SiO$_2$ using 0-6% EtOAc/hexanes to give the title compound (0.75 g, 68%) as a brown solid. $^1$H NMR (DMSO-d$_6$) δ 7.85 (s, 1H), 7.15 (d, 1H, J=8.1 Hz), 6.81 (d, 1H, J=8.1 Hz), 5.76 (s, 2H), 0.19 (s, 9H); MS(ESI$^+$): m/z 191.20 (M+H)$^+$.

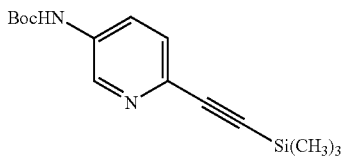

B) tert-Butyl
6-(2-(trimethylsilyl)ethynyl)pyridin-3-ylcarbamate

A solution 6-(2-(trimethylsilyl)ethynyl)pyridin-3-amine (0.5 g, 2.6 mmol) in THF was cooled to −50° C. and treated dropwise with 1.0 M NaHMDS in THF (5.3 mL, 5.5 mmol). The mixture was warmed to −20° C., treated with BOC anhydride in one portion and allowed to warm to RT over 25 min. The mixture was partitioned between EtOAc and saturated aqueous NaHCO$_3$ solution and the EtOAc phase was separated and washed with brine. The EtOAc solution was dried (MgSO$_4$) and concentrated in vacuo. The crude product was purified by flash chromatography on SiO$_2$ using 0-25% EtOAc/hexanes to give the product (0.5 g, 67%) as a white solid. $^1$H NMR (DMSO-d$_6$) δ 9.80 (s, 1H), 8.58 (d, 1H, J=2.0 Hz), 7.86 (dd, J=8.6, 2.5 Hz, 1H), 7.44 (d, 1H, J=8.6 Hz), 1.47 (s, 9H), 0.22 (s, 9H); MS(ESI$^+$): m/z 291.34 (M+H)$^+$.

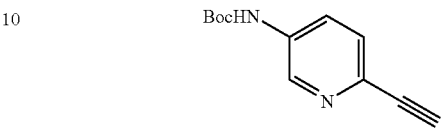

C) tert-Butyl 6-ethynylpyridin-3-ylcarbamate

A solution of tert-butyl 6-(2-(trimethylsilyl)ethynyl)pyridin-3-ylcarbamate (62 mg, 0.21 mmol) in THF (5 mL) was cooled to −15° C. and treated with 1.0 M tetrabutylammonium fluoride (Aldrich, 0.25 mL, 0.25 mmol) and stirred for 40 min. The mixture was concentrated in vacuo and partitioned between EtOAc and saturated aqueous NaHCO$_3$ solution. The EtOAc phase was washed with brine, dried (MgSO$_4$) and concentrated in vacuo to give the title compound (45 mg, 100%) as an off-white solid. $^1$H NMR (DMSO-d$_6$) δ 9.78 (s, 1H), 8.58 (d, 1H, J=2.5 Hz), 7.92-7.84 (m, 1H), 7.46 (d, 1H, J=8.6 Hz), 4.17 (s, 1H), 1.47 (s, 9H); MS(ESI$^+$): m/z 219.20 (M+H)$^+$.

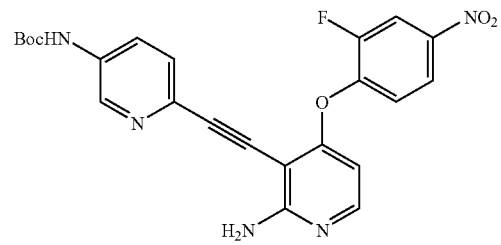

D) tert-Butyl 6-(2-(2-amino-4-(2-fluoro-4-nitrophenoxy)pyridin-3-yl)ethynyl)pyridin-3-ylcarbamate The title compound was prepared from tert-butyl 6-ethynylpyridin-3-ylcarbamate and 4-(2-fluoro-4-nitrophenoxy)-3-iodopyridin-2-amine (Compound C of Example 34) in the same manner as Step A of Example 46 in 44% yield. $^1$H NMR (DMSO-d$_6$) δ 9.77 (s, 1H), 8.56 (s, 1H), 8.40-8.36 (m, 1H), 8.14 (d, 1H, J=8.8 Hz), 7.94 (d, 1H, J=5.5 Hz), 7.89 (d, 1H, J=8.2 Hz), 7.59 (d, 1H, J=8.8 Hz), 7.53-7.47 (m, 1H), 6.63 (br s, 2H), 6.21 (d, 1H, J=6.0 Hz), 1.47 (s, 9H); MS(ESI$^+$): m/z 466.22 (M+H)$^+$.

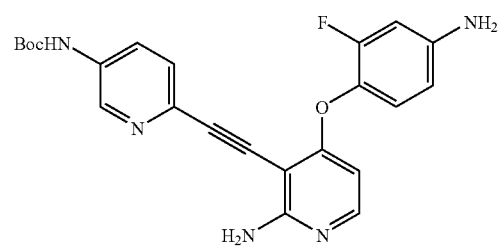

E) tert-Butyl 6-(2-(2-amino-4-(4-amino-2-fluorophenoxy)pyridin-3-yl)ethynyl)pyridin-3-ylcarbamate The title compound was prepared from tert-butyl 6-(2-(2-amino-4-(2-fluoro-4-nitrophenoxy)pyridin-3-yl)ethynyl)pyridin-3-ylcarbamate in the same manner as Step C of Example 11 in quantitative yield. MS(ESI$^+$): m/z 436.29 (M+H)$^+$.

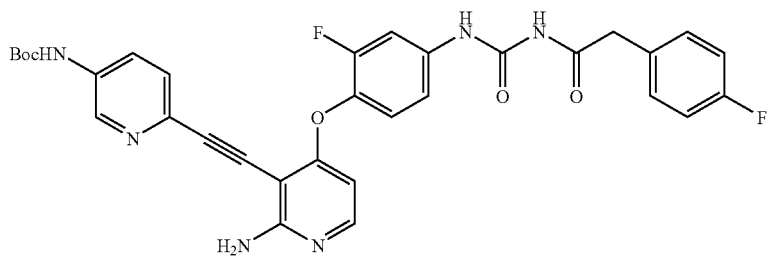

F) tert-Butyl 6-(2-(2-amino-4-(2-fluoro-4-(3-(2-(4-fluorophenyl)acetyl)ureido)phenoxy)pyridin-3-yl)ethynyl)pyridin-3-ylcarbamate The title compound was prepared from tert-butyl 6-(2-(2-amino-4-(2-fluoro-4-nitrophenoxy)pyridin-3-yl)ethynyl)pyridin-3-ylcarbamate in the same manner as Step E of Example 11 in 80% yield. $^1$H NMR (DMSO-d$_6$) δ 11.02 (s, 1H), 10.56 (s, 1H), 9.78 (s, 1H), 8.59 (d, 1H, J=2.5 Hz), 7.91 (dd, 1H, J=8.6, 2.5 Hz), 7.81 (d, 1H, J=5.6 Hz), 7.75 (dd, 1H, J=12.7, 2.5 Hz), 7.68 (d, 1H, J=8.6 Hz), 7.44-7.27 (m, 5H), 7.19-7.13 (m, 2H), 6.47 (s, 2H), 5.86-5.81 (m, 1H), 1.48 (s, 9H); MS(ESI$^+$): m/z 615.34 (M+H)$^+$.

G) 1-(4-(2-Amino-3-(2-(5-aminopyridin-2-yl)ethynyl)pyridin-4-yloxy)-3-fluorophenyl)-3-(2-(4-fluorophenyl)acetyl)urea, dihydrochloride salt A solution of tert-butyl 6-(2-(2-amino-4-(2-fluoro-4-(3-(2-(4-fluorophenyl)acetyl)ureido)phenoxy)pyridin-3-yl)ethynyl)pyridin-3-ylcarbamate (23 mg, 0.037 mmol) in CH$_2$Cl$_2$ (2 mL) and treated with TFA (0.5 mL) and stirred at RT for 1 h. The mixture was concentrated in vacuo and the crude product purified by preparative HPLC (Column B) and converted to its hydrochloride salt (11 mg, 52%) in the same manner as Step E of Example 36. $^1$H NMR (DMSO-d$_6$) δ 11.05 (s, 1H), 10.62 (s, 1H), 8.05 (s, 1H), 7.97 (d, 1H, J=2.7 Hz), 7.94 (d, 1H, J=7.1 Hz), 7.82 (d, 1H, J=12.1 Hz), 7.66 (d, 1H, J=8.8 Hz), 7.45-7.45 (m, 2H), 7.35 (dd, 2H, J=8.2, 5.5 Hz), 7.20 (d, 1H, J=6.6 Hz), 7.16 (t, 2H, J=8.8 Hz), 6.24 (d, 1H, J=6.6 Hz), 3.74 (s, 2H); MS(ESI$^+$): m/z 515.19 (M+H)$^+$.

Example 134

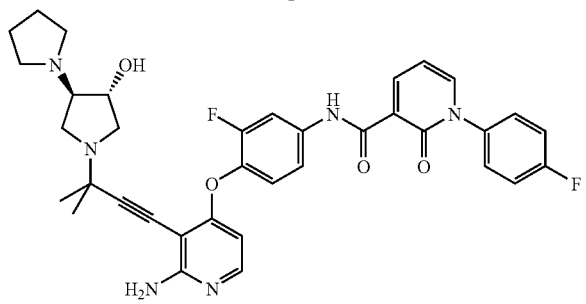

N-(4-(2-Amino-3-(3-(((3R,4R)-3-hydroxy-4-(pyrrolidin-1-yl)pyrrolidin-1-yl)-3-methylbut-1-ynyl)pyridin-4-yloxy)-3-fluorophenyl)-α-(4-fluorophenyl)-2-oxo-1,2-dihydropyridine-3-carboxamide, trihydrochloride salt

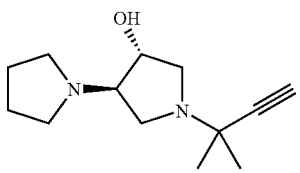

A) (3R,4R)-1-(2-Methylbut-3-yn-2-yl)-4-(pyrrolidin-1-yl)pyrrolidin-3-ol

A mixture of (3R,4R)-4-(pyrrolidin-1-yl)pyrrolidin-3-ol (Lexicon Pharma, 1.56 g, 10.0 mmol) and 3-chloro-3-methyl-1-butyne (GFS Chmeical, Inc., 1.36 g, 13.2 mmol), THF (15 mL) and Et$_3$N (13.3 mmol) was treated with CuI (77 mg, 0.78 mmol). An exothermic reaction ensued with concomitant formation of a precipitate. After stirring at RT for 15 h, the mixture was concentrated in vacuo and partitioned between EtOAc and saturated aqueous NaHCO$_3$ solution. The aqueous phase was extracted twice with EtOAc and the combined EtOAc phases were dried (MgSO$_4$) and concentrated to give a light brown solid (1.0 g, 45%). $^1$H NMR (CDCl$_3$) δ 4.20 (br s, 1H), 3.13-3.04 (m, 1H), 2.95 (dd, 1H, J=10.1, 6.6 Hz), 2.77 (dd, 1H, J=10.1, 2.6 Hz), 2.64 (m, 3H), 2.61 (m, 2H), 2.55-2.46 (m, 1H), 2.26 (s, 1H), 1.85-1.74 (m, 4H), 1.38 (s, 3H), 1.36 (s, 3H); MS(ESI$^+$): m/z 223.29 (M+H)$^+$.

217

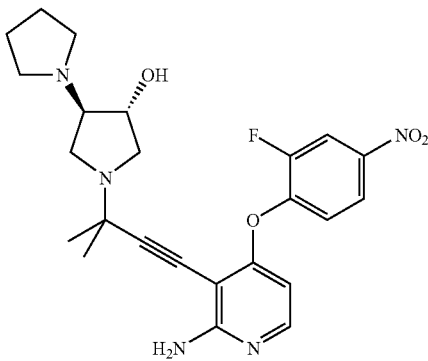

B) (3R,4R)-1-(4-(2-Amino-4-(2-fluoro-4-nitrophenoxy)pyridin-3-yl)-2-methylbut-3-yn-2-yl)-4-(pyrrolidin-1-yl)pyrrolidin-3-ol The title compound was prepared from (3R,4R)-1-(2-methylbut-3-yn-2-yl)-4-(pyrrolidin-1-yl)pyrrolidin-3-ol and 4-(2-fluoro-4-nitrophenoxy)-3-iodopyridin-2-amine (Compound C of Example 34) in the same manner as Step D of Example 35 in 57% yield. $^1$H NMR (CDCl$_3$) δ 8.10 (dd, 1H, J=10.2, 2.5 Hz), 8.03 (d, 1H, J=9.2 Hz), 7.99 (d, 1H, J=5.6 Hz), 7.13-7.06 (m, 1H), 6.26 (d, 1H, J=6.1 Hz), 5.18 (br s, 2H), 4.21 (m, 1H), 3.10-2.99 (m, 1H), 2.96 (s, 1H), 2.70 (dd, 2H, J=9.7, 3.1 Hz), 2.66-1.15 (m, 2H), 1.87-1.76 (m, 5H), 133-1.32 (m, 2H), 1.32 (m, 3H); 1.34 (m, 3H); MS(ESI$^+$): m/z 470.20 (M+H)$^+$.

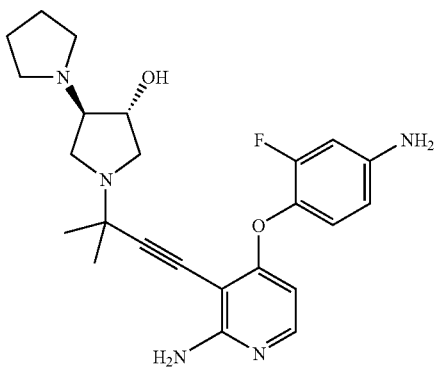

C) (3R,4R)-1-(4-(2-Amino-4-(4-amino-2-fluorophenoxy)pyridin-3-yl)-2-methylbut-3-yn-2-yl)-4-(pyrrolidin-1-yl)pyrrolidin-3-ol The title compound was prepared from (3R,4R)-1-(4-(2-amino-4-(2-fluoro-4-nitrophenoxy)pyridin-3-yl)-2-methylbut-3-yn-2-yl)-4-(pyrrolidin-1-yl)pyrrolidin-3-ol in the same manner as Step C of Example 11 in 95% yield. MS(ESI$^+$): m/z 440.37 (M+H)$^+$.

D) N-(4-(2-Amino-3-(3-((3R,4R)-3-hydroxy-4-(pyrrolidin-1-yl)pyrrolidin-1-yl)-3-methylbut-1-ynyl)pyridin-4-yloxy)-3-fluorophenyl)-1-(4-fluorophenyl)-2-oxo-1,2-dihydropyridine-3-carboxamide, trihydrochloride salt The title compound was prepared from (3R,4R)-1-(4-(2-amino-4-(4-amino-2-fluorophenoxy)pyridin-3-yl)-2-methylbut-3-yn-2-yl)-4-(pyrrolidin-1-yl)pyrrolidin-3-ol and 1-(4-fluorophenyl)-2-oxo-1,2-dihydropyridine-3-carboxylic acid (Compound B of Example 101) in the same manner as Example 62 in 50% yield. $^1$H NMR (DMSO-d$_6$) δ 12.14 (s, 1H), 8.62-8.54 (m, 1H), 8.14 (dd, 3H, J=6.6, 2.0 Hz), 8.05 (d, 1H, J=13.2 Hz), 7.99 (d, 1H, J=7.1 Hz), 7.62-7.51 (m, 5H), 7.42 (t, 2H, J=8.6 Hz), 6.78-6.70 (m, 1H), 6.32 (d, 1H, J=7.1 Hz), 4.65 (br s, 1H), 3.94-3.84 (m, 1H), 3.71 (d, 2H, J=16.8 Hz), 3.60 (m, 2H), 3.52 (m, 1H), 3.22-3.08 (m, 2H), 2.00-1.91 (m, 2H), 1.88-1.78 (m, 2H), 1.70 (s, 6H); MS(ESI$^+$): m/z 655.40 (M+H)$^+$.

Example 135

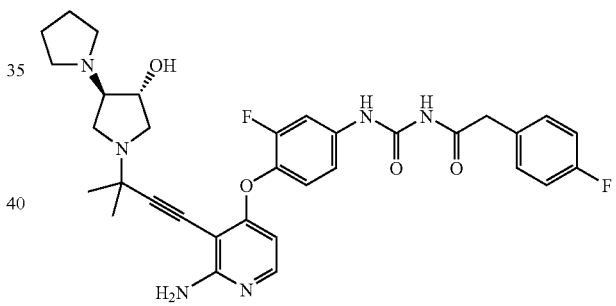

1-(4-(2-Amino-3-(3-((3R,4R)-3-hydroxy-4-(pyrrolidin-1-yl)pyrrolidin-1-yl)-3-methylbut-1-ynyl)pyridin-4-yloxy)-3-fluorophenyl)-3-(2-(4-fluorophenyl)acetyl)urea, trihydrochloride salt The title compound was prepared form (3R,4R)-1-(4-(2-amino-4-(4-amino-2-fluorophenoxy)pyridin-3-yl)-2-methylbut-3-yn-2-yl)-4-(pyrrolidin-1-yl)pyrrolidin-3-ol in 40% yield in the same manner as Step E of Example 11. $^1$H NMR (DMSO-d$_6$) δ 11.06 (s, 1H), 10.62 (s, 1H), 7.97 (d, 2H, J=6.6 Hz), 7.80 (d, 1H, J=11.7 Hz), 7.51-7.40 (m, 2H), 7.38-7.32 (m, 2H), 7.16 (t, 2H, J=8.6 Hz), 6.25 (d, 1H, J=6.6 Hz), 4.63-4.53 (m, 1H), 3.79-3.68 (m, 1H), 3.74 (s, 2H), 3.68-3.56 (m, 2H), 3.51-3.43 (m, 2H), 3.08-2.99 (m, 4H), 1.98-1.92 (m, 2H), 1.89-1.77 (m, 2H), 1.64 (s, 6H); MS(ESI$^+$): m/z 619.41 (M+H)$^+$.

Example 136

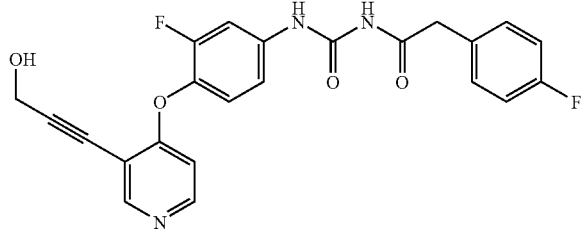

1-(3-Fluoro-4-(3-(3-hydroxyprop-1-ynyl)pyridin-4-yloxy)phenyl)-3-(2-(4-fluorophenyl)acetyl)urea, hydrochloride salt

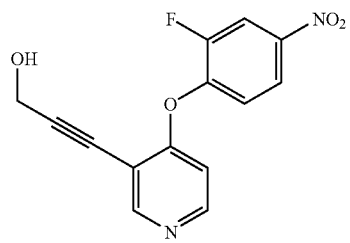

A) 3-(4-(2-Fluoro-4-nitrophenoxy)pyridin-3-yl)prop-2-yn-1-ol

The title compound was prepared from 4-(2-fluoro-4-nitrophenoxy)-3-iodopyridine (Compound A of Example 33) and propargyl alcohol (Aldrich) in 77% yield in the same manner as Step A of Example 36. $^1$H NMR (DMSO-$d_6$) δ 8.69 (s, 1H), 8.49 (d, 1H, J=5.6 Hz), 8.43 (dd, 1H, J=10.7, 2.5 Hz), 8.17 (d, 1H, J=9.2 Hz), 7.57 (t, 1H, J=8.6 Hz), 7.04 (d, 1H, J=5.6 Hz), 5.40 (t, 1H, J=6.1 Hz), 4.28 (d, 2H, J=6.1 Hz); MS(ESI$^+$): m/z 289.15 (M+H)$^+$.

B) 3-(4-(4-Amino-2-fluorophenoxy)pyridin-3-yl)prop-2-yn-1-ol

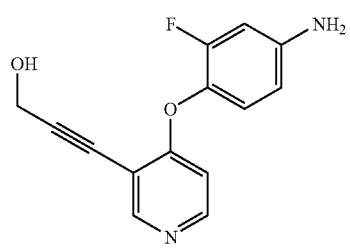

The title compound was prepared in form 3-(4-(2-fluoro-4-nitrophenoxy)pyridin-3-yl)prop-2-yn-1-ol in 95% yield in the same manner as Step C of Example 11. MS(ESI$^+$): m/z 259.21 (M+H)$^+$.

C) 1-(3-Fluoro-4-(3-(3-hydroxyprop-1-ynyl)pyridin-4-yloxy)phenyl)-3-(2-(4-fluorophenyl)acetyl)urea, hydrochloride salt The title compound was prepared from 3-(4-(4-amino-2-fluorophenoxy)pyridin-3-yl)prop-2-yn-1-ol in 36% yield in the same manner as Step E of Example 11. $^1$H NMR (DMSO-$d_6$) δ 11.06 (s, 1H), 10.63 (s, 1H), 8.79 (s, 1H), 8.49 (d, 1H, J=6.1 Hz), 7.82 (d, 1H, J=12.2 Hz), 7.45-7.40 (m, 2H), 7.38-7.33 (m, 2H), 7.23-7.13 (m, 2H), 6.89 (d, 1H, J=6.1 Hz), 4.37 (s, 2H), 3.74 (s, 2H); MS(ESI$^+$): m/z 438.23 (M+H)$^+$.

Example 137

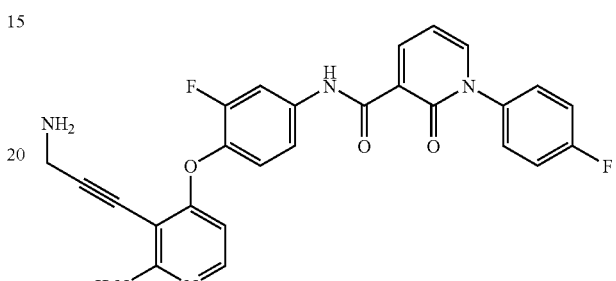

N-(4-(2-Amino-3-(3-aminoprop-1-ynyl)pyridin-4-yloxy)-3-fluorophenyl)-1-(4-fluorophenyl)-2-oxo-1,2-dihydropyridine-3-carboxamide, dihydrochloride salt

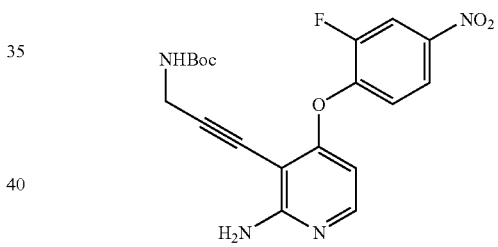

A) tert-Butyl 3-(2-amino-4-(2-fluoro-4-nitrophenoxy)pyridin-3-yl)prop-2-ynylcarbamate The title compound was prepared from N-Boc propargylamine (Compound A of Example 42) and 4-(2-fluoro-4-nitrophenoxy)-3-iodopyridin-2-amine (Compound C of Example 34) in the same manner as Step A of Example 42 in 59% yield. $^1$H NMR (DMSO-$d_6$) δ 8.35 (dd, 1H, J=10.7, 2.5 Hz), 8.12 (d, 1H, J=9.2 Hz), 7.88 (d, 1H, J=5.6 Hz), 7.39 (t, 1H, J=8.6 Hz), 7.31 (t, 1H, J=5.1 Hz), 6.53 (s, 2H), 6.15 (d, 1H, J=5.6 Hz), 3.92 (d, 2H, J=5.6 Hz), 1.36 (s, 9H); MS(ESI$^+$): m/z 403.34 (M+H)$^+$.

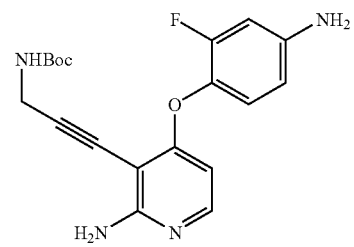

B) tert-Butyl 3-(2-amino-4-(4-amino-2-fluorophenoxy)pyridin-3-yl)prop-2-ynylcarbamate The title compound was prepared from tert-butyl 3-(2-amino-4-(2-fluoro-4-nitrophenoxy)pyridin-3-yl)prop-2-ynylcarbamate in quantitative yield in the same manner as Step C of Example 11. MS(ESI⁺): m/z 373.35 (M+H)⁺.

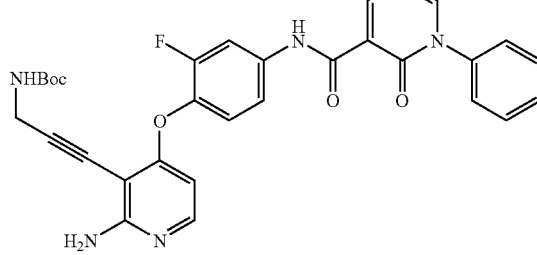

C) tert-Butyl 3-(2-amino-4-(2-fluoro-4-(1-(4-fluorophenyl)-2-oxo-1,2-dihydropyridine-3-carboxamido)phenoxy)pyridin-3-yl)prop-2-ynylcarbamate The title compound was prepared from tert-butyl 3-(2-amino-4-(4-amino-2-fluorophenoxy)pyridin-3-yl)prop-2-ynylcarbamate and 1-(4-fluorophenyl)-2-oxo-1,2-dihydropyridine-3-carboxylic acid (Compound B of Example 101) in the same manner as Example 62 in 48% yield. ¹H NMR (DMSO-d₆) δ 12.07 (s, 1H), 8.57 (dd, 1H, J=7.1, 2.0 Hz), 8.12 (dd, 1H, J=6.6, 2.0 Hz), 8.00-7.93 (m, 1H), 7.75 (d, 1H, J=5.1 Hz), 7.61 (d, 2H, J=5.1 Hz), 7.59 (d, 1H, J=4.6 Hz), 7.48-7.37 (m, 4H), 7.30-7.25 (m, 1H), 6.72 (t, 1H, J=7.1 Hz), 6.37 (br s, 1H), 5.80 (d, 1H, J=6.1 Hz), 4.00 (d, 2H, J=5.1 Hz), 1.38 (s, 9H); MS(ESI⁺): m/z 588.26 (M+H)⁺.

D) N-(4-(2-Amino-3-(3-aminoprop-1-ynyl)pyridin-4-yloxy)-3-fluorophenyl)-1-(4-fluorophenyl)-2-oxo-1,2-dihydropyridine-3-carboxamide, dihydrochloride salt The title compound was prepared from tert-butyl 3-(2-amino-4-(2-fluoro-4-(1-(4-fluorophenyl)-2-oxo-1,2-dihydropyridine-3-carboxamido)phenoxy)pyridin-3-yl)prop-2-ynylcarbamate in 80% yield in the same manner as Step E of Example 36. ¹H NMR (DMSO-d₆) δ 12.13 (s, 1H), 8.57 (dd, 1H, J=7.1, 2.0 Hz), 8.51 (s, 2H), 8.14 (dd, 1H, J=6.6, 2.0 Hz), 8.11-8.02 (m, 1H), 7.98-7.90 (m, 1H), 7.60 (dd, 2H, J=9.2, 5.1 Hz), 7.53 (d, 1H, J=9.2 Hz), 7.46-7.37 (m, 3H), 6.76-6.71 (m, 1H), 6.20 (d, 1H, J=6.6 Hz), 4.11-4.04 (m, 2H); MS(ESI⁺): m/z 488.16 (M+H)⁺.

Example 138

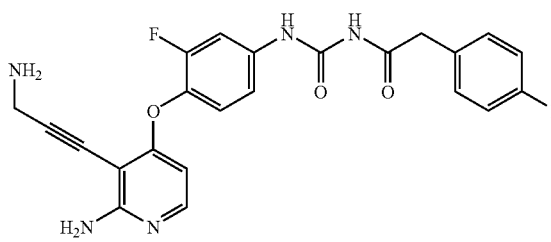

1-(4-(2-Amino-3-(3-aminoprop-1-ynyl)pyridin-4-yloxy)-3-fluorophenyl)-3-(2-(4-fluorophenyl)acetyl) urea, dihydrochloride salt

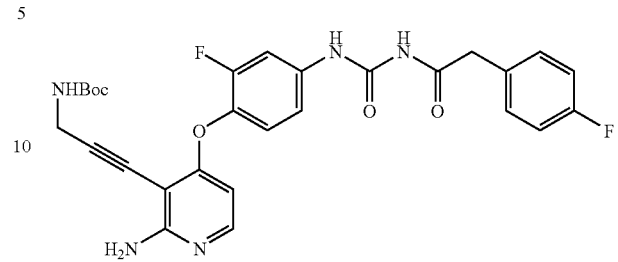

A) tert-Butyl 3-(2-amino-4-(2-fluoro-4-(3-(2-(4-fluorophenyl)acetyl)ureido)phenoxy)pyridin-3-yl)prop-2-ynylcarbamate The title compound was prepared from tert-butyl 3-(2-amino-4-(4-amino-2-fluorophenoxy)pyridin-3-yl)prop-2-ynylcarbamate in 38% yield in the same manner as Step E of Example 11. ¹H NMR (DMSO-d₆) δ 11.02 (s, 1H), 10.55 (s, 1H), 7.80-7.73-7.69 (m, 2H), 7.38-7.29 (m, 3H), 7.33 (d, 1H, J=5.1 Hz), 7.30-7.21 (m, 1H), 7.21-7.13 (m, 2H), 6.37 (br s, 1H), 5.76 (d, 1H, J=6.1 Hz), 4.00 (s, 2H), 3.73 (s, 2H), 1.38 (s, 9H); MS(ESI⁺): m/z 552.24 (M+H)⁺.

B) 1-(4-(2-Amino-3-(3-aminoprop-1-ynyl)pyridin-4-yloxy)-3-fluorophenyl)-3-(2-(4-fluorophenyl)acetyl) urea, dihydrochloride salt The title compound was prepared from tert-butyl 3-(2-amino-4-(2-fluoro-4-(3-(2-(4-fluorophenyl)acetyl)ureido)phenoxy)pyridin-3-yl)prop-2-ynylcarbamate in 65% yield in the same manner as Step E of Example 11. ¹H NMR (DMSO-d₆) δ 11.05 (s, 1H), 10.61 (s, 1H), 8.48 (br s, 3H), 7.90 (d, 1H, J=6.6 Hz), 7.84-7.76 (m, 2H), 7.45-7.39 (m, 1H), 7.39-7.32 (m, 3H), 7.20-7.13 (m, 2H), 6.11 (d, 1H, J=6.1 Hz), 4.09-4.03 (m, 2H), 3.74 (s, 2H); MS(ESI⁺): m/z 452.12 (M+H)⁺.

Example 139

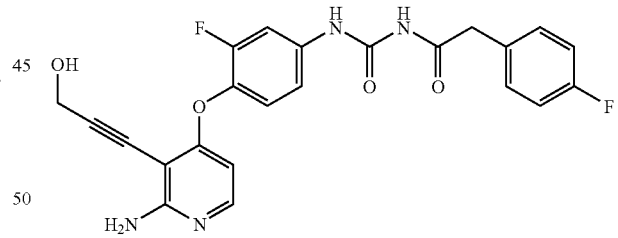

1-(4-(2-Amino-3-(3-hydroxyprop-1-ynyl)pyridin-4-yloxy)-3-fluorophenyl)-3-(2-(4-fluorophenyl)acetyl) urea, hydrochloride salt

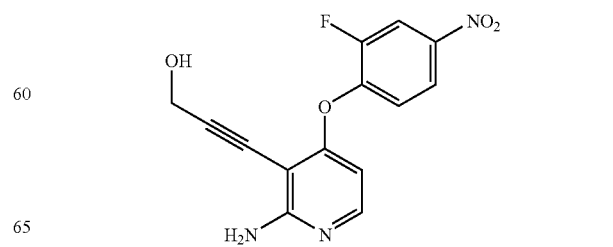

A) 3-(2-Amino-4-(2-fluoro-4-nitrophenoxy)pyridin-3-yl)prop-2-yn-1-ol

The title compound was prepared from propargyl alcohol (Aldrich) and 4-(2-fluoro-4-nitrophenoxy)-3-iodopyridin-2-amine (Compound C of Example 34) in 46% in the same manner as Step A of Example 36. $^1$H NMR (DMSO-$d_6$) δ 8.40-8.34 (m, 1H), 8.13 (d, 1H, J=8.6 Hz), 7.88 (d, 1H, J=5.6 Hz), 7.42 (t, 1H, J=8.6 Hz), 6.49 (s, 2H), 6.14 (d, 1H, J=6.1 Hz), 5.26-5.20 (m, 1H), 4.26 (d, 2H, J=6.1 Hz); MS(ESI$^+$): m/z 304.23 (M+H)$^+$.

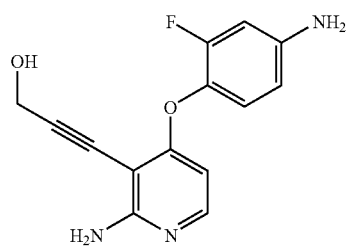

B) 3-(2-Amino-4-(4-amino-2-fluorophenoxy)pyridin-3-yl)prop-2-yn-1-ol

The title compound was prepared form 3-(2-amino-4-(2-fluoro-4-nitrophenoxy)pyridin-3-yl)prop-2-yn-1-ol in 65% yield. MS(ESI$^+$): m/z 274.21 (M+H)$^+$.

C) 1-(4-(2-Amino-3-(3-hydroxyprop-1-ynyl)pyridin-4-yloxy)-3-fluorophenyl)-3-(2-(4-fluorophenyl)acetyl)urea, hydrochloride salt The title compound was prepared from 3-(2-amino-4-(4-amino-2-fluorophenoxy)pyridin-3-yl)prop-2-yn-1-ol in 48% yield. $^1$H NMR (DMSO-$d_6$) δ 11.05 (s, 1H), 10.60 (s, 1H), 7.86 (d, 1H, J=7.1 Hz), 7.83-7.77 (m, 1H), 7.44-7.37 (m, 2H), 7.37-7.32 (m, 3H), 7.20-7.13 (m, 2H), 6.14 (d, J=6.6 Hz, 1H), 4.37 (s, 2H), 3.74 (s, 2H); MS(ESI$^+$): m/z 453.28 (M+H)$^+$.

Example 140

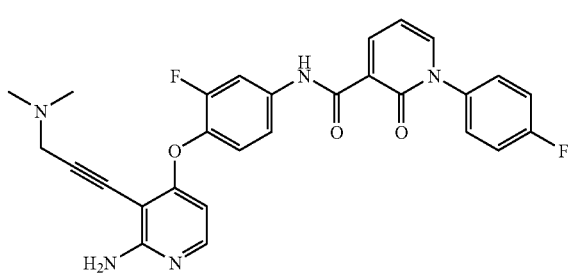

N-(4-(2-Amino-3-(3-(dimethylamino)prop-1-ynyl)pyridin-4-yloxy)-3-fluorophenyl)-1-(4-fluorophenyl)-2-oxo-1,2-dihydropyridine-3-carboxamide, dihydrochloride salt

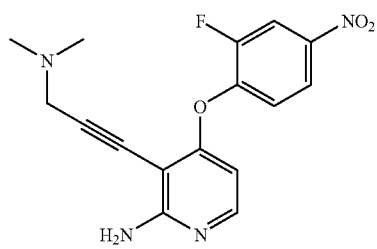

A) 3-(3-(Dimethylamino)prop-1-ynyl)-4-(2-fluoro-4-nitrophenoxy)pyridin-2-amine The title compound was prepared from 1-dimethylamin-2-propyne (Aldrich) and 4-(2-fluoro-4-nitrophenoxy)-3-iodopyridin-2-amine (Compound C of Example 34) in 64% yield in the same manner as Step A of Example 42. $^1$H NMR (DMSO-$d_6$) δ 8.36 (dd, 1H, J=10.7, 2.5 Hz), 8.11 (d, 1H, J=8.6 Hz), 7.93 (d, 1H, J=5.6 Hz), 7.30 (t, 1H, J=8.6 Hz), 6.43 (br s, 2H), 6.28 (d, 1H, J=6.1 Hz), 3.41 (s, 2H), 2.05 (s, 6H); MS(ESI$^+$): m/z 331.28 (M+H)$^+$.

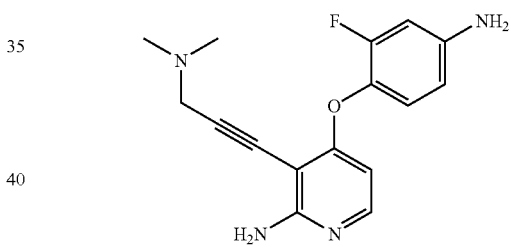

B) 4-(4-Amino-2-fluorophenoxy)-3-(3-(dimethylamino)prop-1-ynyl)pyridin-2-amine The title compound was prepared from 3-(3-(dimethylamino)prop-1-ynyl)-4-(2-fluoro-4-nitrophenoxy)pyridin-2-amine in 77% yield in the same manner as Step C of Example 11. MS(ESI$^+$): m/z 301.30 (M+H)$^+$.

C) N-(4-(2-Amino-3-(3-(dimethylamino)prop-1-ynyl)pyridin-4-yloxy)-3-fluorophenyl)-1-(4-fluorophenyl)-2-oxo-1,2-dihydropyridine-3-carboxamide, dihydrochloride salt The title compound was prepared from 4-(4-amino-2-fluorophenoxy)-3-(3-(dimethylamino)prop-1-ynyl)pyridin-2-amine and 1-(4-fluorophenyl)-2-oxo-1,2-dihydropyridine-3-carboxylic acid (Compound B of Example 101) in the same manner as Example 62 in 71% yield. $^1$H NMR (DMSO-$d_6$) δ12.14 (s, 1H), 11.39 (s, 1H), 8.60-8.53 (m, 1H), 8.33 (s, 1H), 8.14 (dd, 1H, J=6.6, 2.2 Hz), 8.05 (dd, 1H, J=12.7, 2.2 Hz), 7.98 (d, 1H, J=7.0 Hz), 7.61 (d, 1H, J=5.3 Hz), 7.58 (d, 1H, J=4.8 Hz), 7.56-7.50 (m, 1H), 7.37-7.47 (m, 3H), 6.76-6.69 (m, 1H), 6.30 (d, 1H, J=7.0 Hz), 4.39 (s, 2H), 2.84 (s, 6H); MS(ESI⁺): m/z 480.28 (M+H)⁺.

Example 141

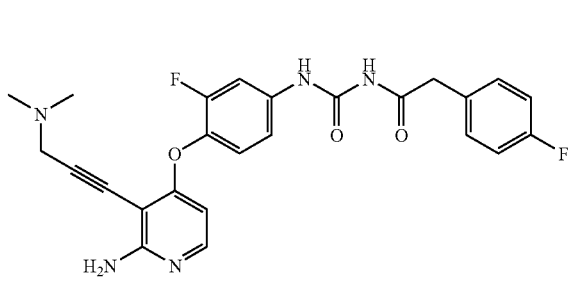

1-(4-(2-Amino-3-(3-(dimethylamino)prop-1-ynyl)pyridin-4-yloxy)-3-fluorophenyl)-3-(2-(4-fluorophenyl)acetyl)urea, dihydrochloride salt The title compound was prepared from 4-(4-amino-2-fluorophenoxy)-3-(3-(dimethylamino)prop-1-ynyl)pyridin-2-amine in a similar manner as Step E of Example 11 in 70% yield. ¹H NMR (DMSO-d₆) δ 11.46 (br s, 1H), 11.07 (s, 1H), 10.64 (s, 1H), 8.37 br (s, 1H), 7.98 (t, 1H, J=7.5 Hz), 7.81 (d, 1H, J=13.6 Hz), 7.43-7.32 (m, 4H), 7.20-7.09 (m, 2H), 6.27 (d, 1H, J=7.0 Hz), 4.38 (s, 2H), 3.75 (s, 2H), 2.84 (s, 6H); MS(ESI⁺): m/z 516.31 (M+H)⁺.

Example 142

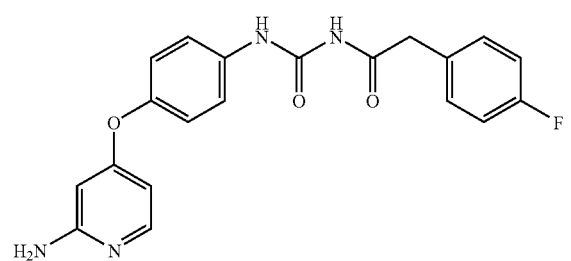

1-(4-(2-Aminopyridin-4-yloxy)phenyl)-3-(2-(4-fluorophenyl)acetyl)urea, hydrochloride salt

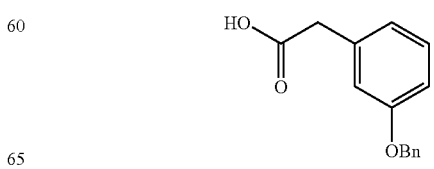

A) 4-(4-Aminophenoxy)picolinamide

The title compound was prepared in a similar manner described in Step B' of Example 24, starting from 4-aminophenol. Yield: 85%. MS(ESI⁺) m/z 230 (M+H)⁺.

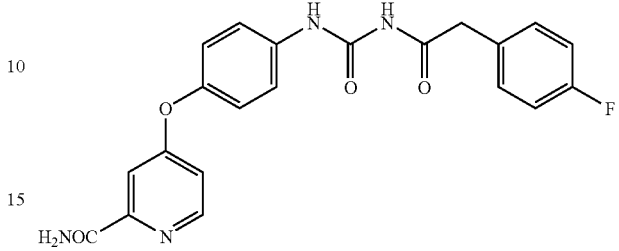

B) 1-(4-(2-Carbamoylpyridin-4-yloxy)phenyl)-3-(2-(4-fluorophenyl)acetyl)urea

The title compound was prepared in a similar manner described in Step C' of Example 24. Yield: 95%. MS(ESI⁺) m/z 409 (M+H)⁺.

C) 1-(4-(2-Aminopyridin-4-yloxy)phenyl)-3-(2-(4-fluorophenyl)acetyl)urea, hydrochloride salt The title compound was prepared in a similar manner described in Step D' of Example 24. Yield: 58%. ¹H NMR (DMSO-d₆) δ 12.86 (s, 1H), 10.97 (s, 1H), 10.51 (s, 1H), 7.91 (d, 1H, J=6.0 Hz), 7.67 (d, 3H, J=9.0 Hz), 7.34 (dd, 2H, J=9.0, 5.0 Hz), 7.21 (d, 2H, J=9.0 Hz), 7.16 (t, 2H, J=9.0 Hz), 6.63 (dd, 1H, J=9.5, 2.0 Hz), 6.05 (d, 1H, J=2.0 Hz), 3.73 (s, 2H); MS(ESI⁺) m/z 381 (M+H)⁺.

Example 143

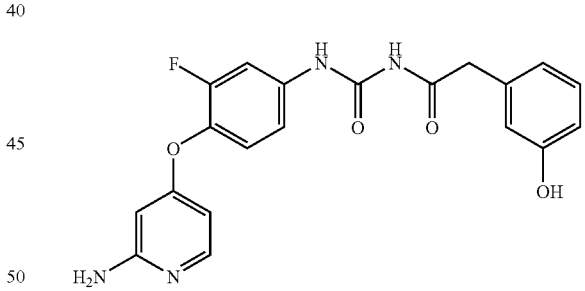

1-(4-(2-Aminopyridin-4-yloxy)-3-fluorophenyl)-3-(2-(3-hydroxyphenyl)acetyl)urea

A) 2-(3-(Benzyloxy)phenyl)acetic acid

To a solution of 3-hydroxyphenylacetic acid (Acros, 3.04 g, 20 mmol) in 20 mL of DMF were added $K_2CO_3$ (6.90 g, 50 mmol) and benzyl bromide (4.75 mL, 40 mmol) at room temperature. The reaction mixture was stirred for 24 h. The suspension was filtered and washed with diethyl ether. The filtrate was then washed with brine and dried over $MgSO_4$. Filtration, followed by concentration, provided the crude benzyl 2-(3-(benzyloxy)phenyl)acetate which was used in the next step. MS (ESI$^+$) m/z 355 (M+Na)$^+$.

The crude benzyl 2-(3-(benzyloxy)phenyl)acetate was dissolved in a mixture of MeOH (20 mL) and THF (50 mL). To this solution was added 40 mL of 1N NaOH (40 mmol). The reaction mixture was stirred at room temperature for 2 h. The organic solvent was removed in vacuo. The remaining aqueous solution was extracted with diethyl ether (2×50 mL). The aqueous solution was then acidified with 1N HCl (50 mL) and the title compound precipitated. The solid was collected by filtration (4.35 g, 90% two steps). MS(ESI$^+$) m/z 265 (M+Na)$^+$.

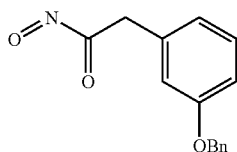

B) 2-(3-(Benzyloxy)phenyl)acetyl isocyanate

To a solution of 2-(3-(benzyloxy)phenyl)acetic acid (484 mg, 2.0 mmol) in DCM (10 mL) at room temperature was added 1 drop of DMF and thionyl chloride (0.30 mL, 4 mmol). The reaction mixture was stirred at room temperature for 1 h and then at 50° C. for 0.5 h. The mixture was cooled and the solvent was removed in vacuo. The residue was dissolved in 5 mL of toluene and AgOCN (600 mg, 4.0 mmol) was added. The suspension was stirred for 0.5 h and it was filtered to provide a solution of 2-(3-(benzyloxy)phenyl) acetyl isocyanate in toluene (0.40 M).

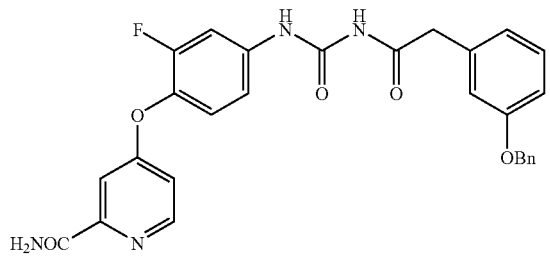

C) 1-(2-(3-(Benzyloxy)phenyl)acetyl)-3-(4-(2-carbamoylpyridin-4-yloxy)-3-fluorophenyl)urea The title compound was prepared in a similar manner described in Step C' of Example 24, using the solution of Step B of this Example. Yield: 63%. MS(ESI$^+$) m/z 515 (M+H)$^+$.

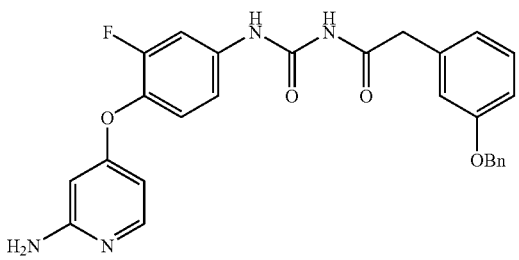

D) 1-(4-(2-Aminopyridin-4-yloxy)-3-fluorophenyl)-3-(2-(3-(benzyloxy)phenyl)acetyl)urea The title compound was prepared in a similar manner described in Step D' of Example 24. Yield: 61%. MS(ESI$^+$) m/z 487 (M+H)$^+$.

E) 1-(4-(2-Aminopyridin-4-yloxy)-3-fluorophenyl)-3-(2-(3-hydroxyphenyl)acetyl)urea To a solution of 1-(4-(2-aminopyridin-4-yloxy)-3-fluorophenyl)-3-(2-(3-(benzyloxy)phenyl)acetyl)urea (150 mg, 0.31 mmol) in a mixture of 5 mL of EtOAc and 3 mL of MeOH was added 10% Pd/C (200 mg). The suspension was stirred under $H_2$ atmosphere for 1 h. Filtration, followed by concentration, provided the title compound (77 mg, 63%). $^1$H NMR (DMSO-d$_6$) δ 10.95 (s, 1H), 10.54 (s, 1H), 9.35 (s, 1H), 7.74 (d, 1H, J=6.0 Hz), 7.68 (dd, 1H, J=13.0, 2.0 Hz), 7.30 (dd, 1H, J=9.0, 1.1 Hz), 7.23 (t, 1H, J=9.0 Hz), 7.07 (t, 1H, J=8.0 Hz), 6.69 (s, 1H), 6.68 (d, 1H, J=7.0 Hz), 6.62 (dd, 1H, J=7.0, 2.0 Hz), 6.10 (dd, 1H, J=6.0, 2.0 Hz), 5.90 (s, 2H), 5.73 (d, 1H, J=2.0 Hz), 3.27 (s, 2H); MS(ESI$^+$) m/z 397 (M+H)$^+$.

Example 144

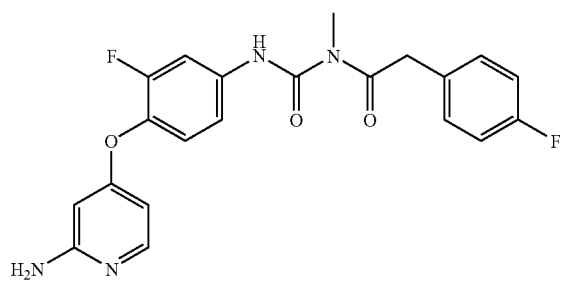

3-(4-(2-Aminopyridin-4-yloxy)-3-fluorophenyl)-1-(2-(4-fluorophenyl)acetyl)-1-methylurea, hydrochloride salt

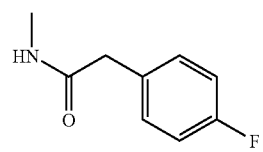

A) 2-(4-Fluorophenyl)-N-methylacetamide

To a solution of methylamine in THF (2.0 M, 5 mL, 10 mmol) was added 4-fluorophenylacetyl chloride (518 mg, 3.0 mmol) at −78° C. The reaction mixture was stirred from −78° C. to room temperature for 1 h. The solution was diluted with H₂O and extracted with EtOAc. The organic layer was washed with brine and dried over MgSO₄. Filtration, followed by concentration, provided the title compound (490 mg, 98%). MS(ESI⁺) m/z 168 (M+H)⁺.

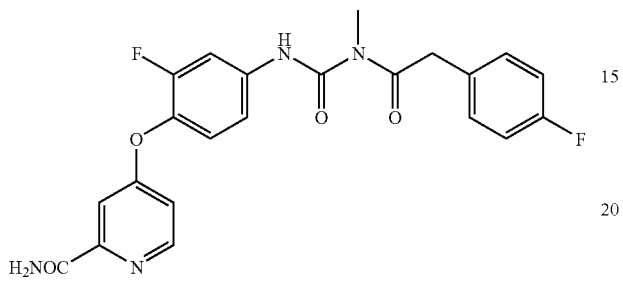

B) 3-(4-(2-Carbamoylpyridin-4-yloxy)-3-fluorophenyl)-1-(2-(4-fluorophenyl)acetyl)-1-methylurea To a solution of 2-(4-fluorophenyl)-N-methylacetamide (89 mg, 0.53 mmol) in 2 mL of THF at −78° C. was added MeLi in Et₂O (1.6 M, 0.34 mL, 0.55 mmol). The solution was stirred at −78° C. for 5 min and then 20% phosgene in toluene (1.9 M, 0.29 mL, 0.55 mmol) was introduced quickly. After 2 min, 4-(4-amino-2-fluorophenoxy)picolinamide (Compound B' of Example 24, 100 mg, 0.40 mmol) was added, followed by the addition of DMF (2 mL) and DIEA (0.4 mL). The reaction mixture was stirred at room temperature for 1 h and quenched with H₂O. The solution was then extracted with EtOAc and the organic layer was washed with brine, dried over MgSO₄. After filtration and concentration, the residue was purified by silica gel chromatography to give the title compound (77 mg, 33%). MS(ESI⁺) m/z 441 (M+H)⁺.

C) 3-(4-(2-Aminopyridin-4-yloxy)-3-fluorophenyl)-1-(2-(4-fluorophenyl)acetyl)-1-methylurea, hydrochloride salt The title compound was prepared in a similar manner described in Step D' of Example 24. Yield: 24%. ¹H NMR (DMSO-d₆) δ 13.20 (s, 1H), 11.17 (s, 1H), 7.90 (d, 1H, J=7.0 Hz), 7.78-7.74 (m, 3H), 7.39-7.34 (m, 2H), 7.23-7.21 (m, 2H), 7.10-7.05 (m, 2H), 6.63 (dd, 1H, J=7.0, 2.0 Hz), 6.08 (d, 1H, J=2.0 Hz), 4.00 (s, 2H), 3.24 (s, 3H); MS(ESI⁺) m/z 413 (M+H)⁺.

Example 145

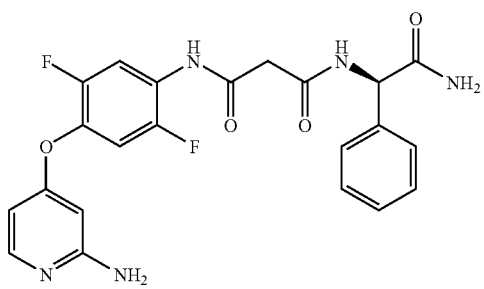

(R)-N¹-(2-Amino-2-oxo-1-phenylethyl)-N³-(4-(2-aminopyridin-4-yloxy)-2,5-difluorophenyl)malonamide, trifluoroacetic acid salt

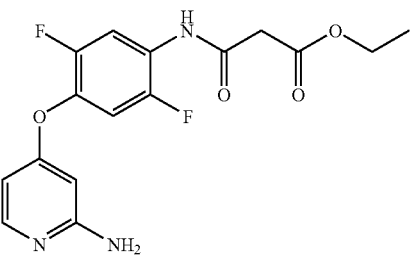

A) Ethyl 3-(4-(2-aminopyridin-4-yloxy)-2,5-difluorophenylamino)-3-oxopropanoate Ethyl 3-(4-(2-carbamoylpyridin-4-yloxy)-2,5-difluorophenylamino)-3-oxopropanoate (Compound A of Example 116, 0.73 g, 1.9 mmol) was converted to the title compound (0.24 g, 35%) in a manner similar to the preparation of Compound E of Example 112. MS(ESI⁺) m/z 352 (M+H)⁺.

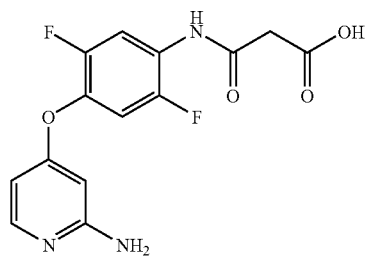

B) 3-(4-(2-Aminopyridin-4-yloxy)-2,5-difluorophenylamino)-3-oxopropanoic acid Ethyl 3-(4-(2-aminopyridin-4-yloxy)-2,5-difluorophenylamino)-3-oxopropanoate (0.24 g, 0.68 mmol) was converted to the title compound (0.039 mg, 18%) in a manner similar to the preparation of Compound B of Example 116. HRMS (ESI⁺), Calcd.: 324.0796 (M+H)⁺, found: 324.0795 (M+H)⁺.

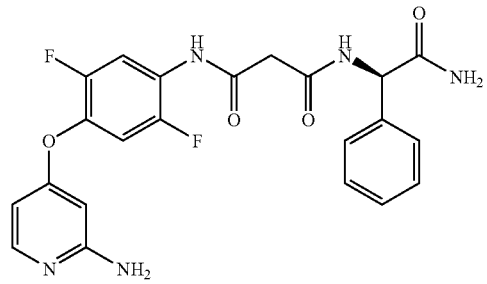

C) (R)-N¹-(2-Amino-2-oxo-1-phenylethyl)-N³-(4-(2-aminopyridin-4-yloxy)-2,5-difluorophenyl)malonamide trifluoroacetic acid salt 3-(4-(2-Aminopyridin-4-yloxy)-2,5-difluorophenylamino)-3-oxopropanoic acid (0.039 g, 0.12 mmol) was coupled with (R)-2-amino-2-phenylacetamide hydrochloride (Bachem, 0.023 g, 0.12 mmol), in a manner similar to the preparation of Example 103, to afford the title compound (0.0048 g, 7%). ¹H NMR (DMSO-d$_6$) δ 10.33 (s, 1H), 8.77 (d, 1H, J=7.8 Hz), 8.10-8.19 (m, 1H), 7.90 (d, 1H, J=7.2 Hz), 7.60-7.75 (m, 4H), 7.17-7.39 (m, 6H), 6.66-6.69 (m, 1H), 6.11 (s, 1H), 5.35 (d, 1H, J=7.8 Hz); HRMS(ESI$^+$), Calcd.: 456.1483 (M+H)$^+$, found: 456.1487 (M+H)$^+$.

Example 146

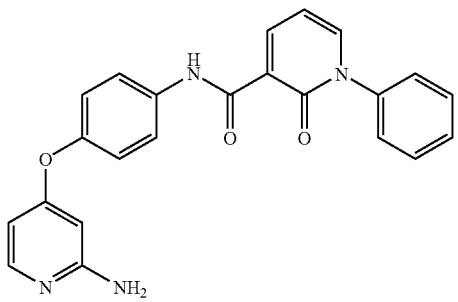

N-(4-(2-Aminopyridin-4-yloxy)phenyl)-2-oxo-1-phenyl-1,2-dihydropyridine-3-carboxamide, hydrochloride salt

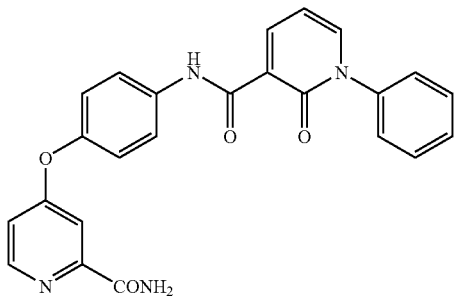

A) 4-(4-(2-Oxo-1-phenyl-1,2-dihydropyridine-3-carboxamido)phenoxy) picolinamide 4-(4-Aminophenoxy)picolinamide (Compound A of Example 142, 0.030 g, 0.13 mmol) was coupled with Compound C of Example 57 (0.028 g, 0.13 mmol), in a manner similar to the preparation of Compound A of Example 115, to afford the title compound (0.057 g, 100%) which was used without further purification. MS(ESI$^+$) m/z 427 (M+H)$^+$.

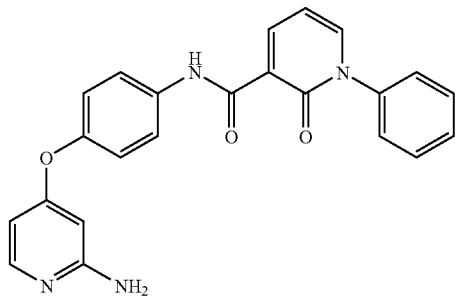

B) N-(4-(2-Aminopyridin-4-yloxy)phenyl)-2-oxo-1-phenyl-1,2-dihydropyridine-3-carboxamide, hydrochloride salt 4-(4-(2-Oxo-1-phenyl-1,2-dihydropyridine-3-carboxamido)phenoxy) picolinamide (0.055, 0.13 mmol) was converted to the title compound (0.0093 g, 16%) in a manner similar to the preparation of Compound E of Example 112. ¹H NMR (CD$_3$OD) δ 12.10 (s, 1H), 8.59-8.61 (m, 1H), 7.88-7.90 (m, 1H), 7.69-7.76 (m, 3H), 7.39-7.53 (m, 5H), 7.10-7.13 (m, 2H), 6.66 (t, 1H, J=6.9 Hz), 6.53-6.55 (m, 1H), 6.07-6.08 (m, 1H), 4.75 (br s, 2H); HRMS(ESI$^+$), Calcd.: 399.1457 (M+H)$^+$, found: 399.1453 (M+H)$^+$.

Example 147

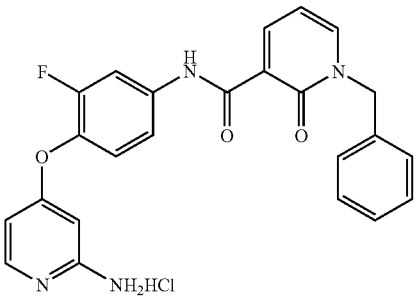

N-(4-(2-Aminopyridin-4-yloxy)-3-fluorophenyl)-1-benzyl-2-oxo-1,2-dihydropyridine-3-carboxamide, hydrochloride salt

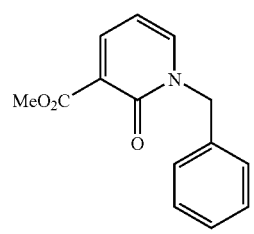

A) Methyl 1-benzyl-2-oxo-1,2-dihydropyridine-3-carboxylate

A heterogeneous mixture of methyl 2-oxo-2H-pyran-3-carboxylate (Aldrich, 2.0 g, 13 mmol, 1.0 eq) and 4-fluorobenzylamine (1.5 mL, 13 mmol, 1.0 eq) in DMF (10 ml) were stirred at room temperature for 3 h. The reaction mixture was treated with EDCI (3.4 g, 18 mmol, 1.4 eq) and DMAP (0.11 g, 9.91 mmol, 0.07 eq) at room temperature and the resulting solution was stirred for 12 h. The reaction mixture was quenched with 1N aqueous HCl and the solution was extracted with ethyl acetate (4×50 mL). The combined organic extracts were washed with 10% aqueous LiCl (3×70 mL), dried ($Na_2SO_4$), filtered and the filtrate concentrated in vacuo to afford the product (2.5 g, 73%) as a solid, that was used without further purification. $^1$H NMR (DMSO-$d_6$) δ 8.17-8.20 (m, 1H), 8.03-8.05 (m, 1H), 7.38-7.46 (m, 2H), 7.16-7.22 (m, 2H), 6.37 (dd, 1H, J=6.94 Hz), 5.13 (s, 2H), 3.73 (s, 3H); HRMS(ESI$^+$), Calcd.: 262.0879, found: 262.0885.

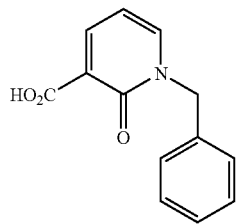

B) 1-Benzyl-2-oxo-1,2-dihydropyridine-3-carboxylic acid

A solution of methyl 1-benzyl-2-oxo-1,2-dihydropyridine-3-carboxylate (2.4 g, 9.2 mmol, 1.0 eq) in MeOH (25 mL) was treated with 5N aqueous sodium hydroxide (4.6 mL, 24 mmol, 2.6 eq) at room temperature and the reaction mixture was stirred for 15 h. The reaction mixture was then concentrated in vacuo, diluted with water and the solution was extracted with ethyl acetate, discarding the organic fraction. The aqueous fraction was cooled to 0° C. and was acidified with concentrated HCl. The resulting solid was filtered, washed with water and the solid dried in vacuo to afford the product (1.6 g, 70%), which was used without further purification. $^1$H NMR (DMSO-$d_6$) δ 8.39-8.44 (m, 2H), 7.42-7.46 (m, 2H), 7.18-7.24 (m, 2H), 6.78 (dd, 1H, J=6.98 Hz), 5.31 (s, 2H); HRMS(ESI$^+$), Calcd.: 248.0723, found: 248.0718.

C) 4-(4-(1-Benzyl-2-oxo-1,2-dihydropyridine-3-carboxamido)-2-fluorophenoxy)picolinamide A homogeneous solution of 1-benzyl-2-oxo-1,2-dihydropyridine-3-carboxylic acid (0.10 g, 0.41 mmol, 1.0 eq), 4-(4-amino-2-fluorophenoxy)picolinamide (0.10 g, 0.41 mmol, 1.0 eq) and TBTU (0.17 g, 0.45 mmol, 1.1 eq) in DMF (2 mL) was treated with DIPEA (0.18 mL, 1.0 mmol, 2.5 eq) at room temperature and the reaction mixture was stirred for 12 h. The reaction mixture was quenched with 10% aqueous LiCl (15 mL) and the resulting solution was extracted with ethyl acetate (4×40 mL). The combined organic extracts were washed with 10% aqueous LiCl (4×50 mL), dried ($Na_2SO_4$), filtered and the filtrate concentrated in vacuo. The residue was purified by flash column chromatography (SiO$_2$, eluting with ethyl acetate) to afford the product (0.13 g, 67%) as a solid. $^1$H NMR (DMSO-$d_6$) δ 12.26 (s, 1H), 8.49-8.56 (m, 2H), 8.33-8.36 (m, 1H), 8.15 (br m, 1H), 8.03-8.07 (m, 1H), 7.74-7.75 (m, 1H), 7.51-7.54 (m, 1H), 7.41-7.46 (m, 4H), 7.20-7.24 (m, 3H), 6.71 (dd, 1H, J=6.89 Hz), 5.32 (s, 2H)HRMS(ESI$^+$), Calcd.: 477.1374, found: 477.1378.

D) N-(4-(2-aminopyridin-4-yloxy)-3-fluorophenyl)-1-benzyl-2-oxo-1,2-dihydropyridine-3-carboxamide, hydrochloride salt Bis(trifluoroacetoxy)iodobenzene (0.12 g, 0.28 mmol, 1.1 eq) was added to a solution of 4-(4-(1-benzyl-2-oxo-1,2-dihydropyridine-3-carboxamido)-2-fluorophenoxy)picolinamide (0.12 g, 0.26 mmol, 1.0 eq), and water (0.01 mL, 0.51 mmol, 20 eq) in DMF (1 mL) at room temperature. Pyridine (0.065 mL, 0.77 mmol, 3.0 eq) was added to the homogeneous mixture and the reaction mixture was stirred at room temperature for 12 h. The reaction mixture was quenched with 1N aqueous HCl (1 mL) and the resulting solution was extracted with diethyl ether (3×5 mL), discarding the organic layer. The aqueous fraction was neutralized with 1N aqueous NaOH and the resulting solution was extracted with 9/1 CHCl$_3$/MeOH (4×10 mL). The combined organic extracts were dried ($Na_2SO_4$), filtered and the filtrate was concentrated in vacuo. The residue was purified by flash chromatography (SiO$_2$, eluting 0-3% MeOH in CHCl$_3$) and the appropriate fractions were concentrated in vacuo. The free base was dissolved in THF, cooled to 0° C. and the homogeneous solution treated with anhydrous 4N HCl in dioxane. The reaction mixture was warmed to room temperature, concentrated in vacuo and the residue triturated with diethyl ether, discarding the filtrate. The solid was dried in vacuo to afford the title compound (0.082 g, 66%) as a HCl salt. $^1$H NMR (DMSO-$d_6$) δ 13.66 (br s, 1H), 8.49-8.51 (m, 1H), 8.39-8.49 (m, 1H), 8.37-8.39 (m, 1H), 8.00-8.09 (m, 3H), 7.54-7.56 (m, 1H), 7.43-7.48 (m, 3H), 7.19-7.24 (m, 2H), 6.69-6.72 (m, 2H), 6.21-6.22 (m, 1H), 5.32 (s, 2H); HRMS(ESI$^+$), Calcd.: 449.1425, found: 449.1406.

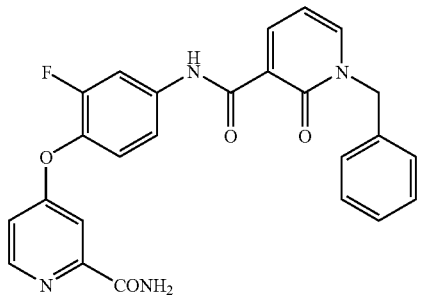

Example 148

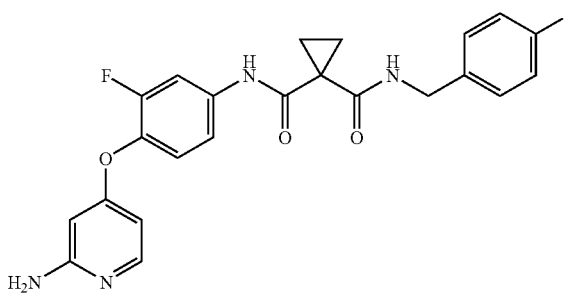

N-(4-Fluoro benzyl)-N-(4-(2-aminopyridin-4-yloxy)-3-fluorophenyl)cyclopropane-1,1-dicarboxamide

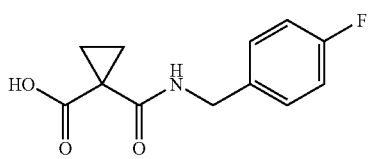

A) 1-((4-Fluorobenzyl)carbamoyl)cyclopropanecarboxylic acid

To a solution of 1,1-cyclopropanecarboxylic acid (Aldrich, 390 mg, 3.0 mmol) in THF (5 mL) at 0° C. was added triethylamine (0.42 mL, 3.0 mmol). After stirring for 30 min at 0° C., thionyl chloride (0.219 mL, 3.0 mmol) was added to the reaction mixture. The mixture was stirred at 0° C. for an additional 30 min and a solution of 4-fluorobenzylamine (Aldrich, 375 mg, 3.0 mmol) in THF (2 mL) was added. The reaction mixture was stirred at 0° C. for 2 h, diluted with ethyl acetate (100 mL) and extracted with 1 N NaOH (10 mL). The aqueous phase was acidified with 1 N HCl to pH 1-2. The solid which formed was collected by filtration (343 mg, 48%). MS(ESI$^+$) m/z 238.24 (M+H)$^+$.

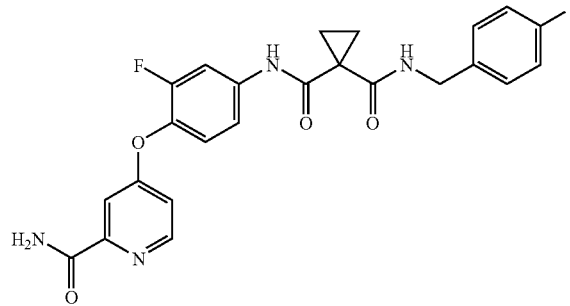

B) N-(4-Fluorobenzyl)-N-(4-(2-carbamoylpyridin-4-yloxy)-3-fluorophenyl)cyclopropane-1,1-dicarboxamide To a solution of 4-(4-amino-2-fluorophenoxy)picolinamide (Compound B' of Example 24, 49 mg, 0.2 mmol) in DMF (2 mL) at room temperature was added 1-((4-fluorobenzyl)carbamoyl)cyclopropanecarboxylic acid (47 mg, 0.2 mmol), HATU (Perseptive Biosystem, 114 mg, 0.3 mmol), and DIEA (0.2 mL, 1.1 mmol). The reaction mixture was stirred at rt for 2 h, and then quenched by adding 4 mL of methanol. The reaction mixture was purified by prep. HPLC. The desired fractions were combined, neutralized with aq. K$_2$HPO$_4$, and concentrated in vacuo. The solid which formed was collected by filtration (29 mg, 31%). $^1$H NMR (DMSO-d$_6$) δ 10.78 (br s, 1H), 8.53 (d, 1H, J=5.5 Hz), 8.47 (t, 1H, J=5.5 Hz), 8.11 (s, 1H), 7.88 (dd, 1H, J=13.2, 2.3 Hz), 7.70 (s, 1H), 7.47 (d, 1H, J=9.2 Hz), 7.38 (t, 1H, J=9.2 Hz), 7.34-7.29 (m, 3H), 7.22 (dd, 1H, J=5.5, 2.8 Hz), 7.13 (t, 2H, J=8.8 Hz), 4.30 (d, 2H, J=5.5 Hz), 1.37 (d, 4H, J=10.6 Hz); MS(ESI$^+$) m/z 467.12 (M+H)$^+$.

C) N-(4-Fluorobenzyl)-N-(4-(2-aminopyridin-4-yloxy)-3-fluorophenyl)cyclopropane-1,1-dicarboxamide To a solution of N-(4-fluorobenzyl)-N-(4-(2-carbamoylpyridin-4-yloxy)-3-fluorophenyl)cyclopropane-1,1-dicarboxamide (25 mg, 0.05 mmol) in DMF (1 mL) at room temperature was added pyridine (0.2 mL), water (0.1 mL), and [bis(trifluoroacetoxyl)-iodo]benzene (Aldrich, 34 mg, 0.08 mmol). The reaction mixture was stirred at rt for 2 h, and then quenched by adding 2 mL of methanol. The reaction mixture was purified by prep. HPLC. The desired fractions were combined, neutralized with aq. K$_2$HPO$_4$, concentrated and extracted with ethyl acetate. The organic extracts were dried over MgSO$_4$ and concentrated in vacuo. The residue was dissolved in a small amount of CH$_3$CN/H$_2$O and lyophillized to dryness to give the title comopound (21 mg, 90%) as a white solid. $^1$H NMR (DMSO-d$_6$) δ 10.87 (br s, 1H), 8.44 (t, 1H, J=6.0 Hz), 7.91 (d, 1H, J=6.6 Hz), 7.88 (d, 1H, J=13.2 Hz), 7.37-7.29 (m, 6H), 7.13 (t, 2H, J=8.8 Hz), 4.29 (d, 2H, J=6.1 Hz), 1.38 (d, 4H, J=2.2 Hz); MS(ESI$^+$) m/z 439.14 (M+H)$^+$.

We claim:
1. A compound having Formula II:

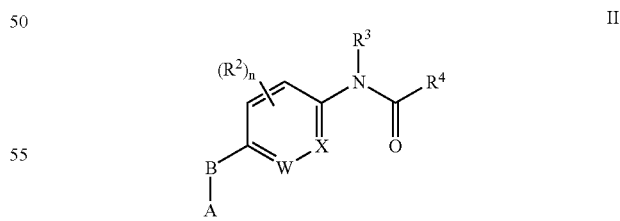

or an enantiomer, diastereomer, or pharmaceutically acceptable salt thereof wherein:
each R$^2$ is independently H, halogen, OR$^5$, NR$^6$R$^7$, alkyl, and/or haloalkyl;
B is O, S, SO, or SO$_2$;
W is C;
X is C;
n is zero to 4;

$R^3$, $R^5$, $R^6$, and $R^7$ are independently H and/or alkyl;
$R^4$ is a monocyclic 5- to 6-membered nitrogen containing heteroaryl, optionally substituted with one or more substituents selected from alkyl, hydroxy, alkoxy, halogen, phenyl, fluorophenyl, =O, and benzyl, provided that
(a) if $R^4$ is monocyclic ring pyridyl, $R^4$ is monocyclic ring not substituted with both hydroxy and methoxy; and
(b) if $R^4$ is monocyclic ring pyrimidinyl, it is not substituted with =O;

A is 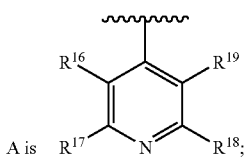

$R^{16}$, $R^{17}$, $R^{18}$, and $R^{19}$ are H, halogen, $NR^{30}R^{31}$, $OR^{32}$, alkyl, hydroxyalkyl, pyridyl, alkenyl, alkynyl, and/or alkynyl substituted with —OH, —NH$_2$, —N(alkyl)$_2$, or pyridyl, phenyl, phenyl substituted with aminoalkyl;
$R^{30}$ and $R^{31}$ are independently selected from H, alkyl, aminoalkyl, benzyl, methoxybenzyl, phenyl, fluorophenyl, and pyridyl; and
$R^{32}$ is H or alkyl.

2. The compound according to claim 1 or an enantiomer, diastereomer, or pharmaceutically acceptable salt thereof, wherein $R^4$ is pyrazolyl, pyridinonyl, or pyridyl-N-oxide, optionally substituted with one or more substituents selected from alkyl, hydroxy, alkoxy, halogen, phenyl, fluorophenyl, and benzyl.

3. The compound according to claim 1 or an enantiomer, diastereomer, or pharmaceutically acceptable salt thereof, wherein $R^2$ is H, $C_1$ to $C_4$ alkyl, halogen, or haloalkyl.

4. The compound according to claim 1 or an enantiomer, diastereomer, or pharmaceutically acceptable salt thereof, wherein B is S, SO, or SO$_2$.

5. The compound according to claim 1 or an enantiomer, diastereomer, or pharmaceutically acceptable salt thereof wherein B is O.

6. The compound according to claim 1 or an enantiomer, diastereomer, or pharmaceutically acceptable salt thereof, wherein $R^4$ is pyridyl optionally substituted with one or more substituents selected from alkyl, hydroxy, alkoxy, halogen, phenyl, fluorophenyl, and benzyl.

7. The compound according to claim 6 or an enantiomer, diastereomer, or pharmaceutically acceptable salt thereof, wherein:
$R^4$ is substituted with phenyl, fluorophenyl, benzyl, $C_1$ to $C_4$ alkyl, alkoxy, and/or halogen; and
$R^{18}$ and $R^{19}$ are each H.

8. The compound according to claim 5 or an enantiomer, diastereomer, or pharmaceutically acceptable salt thereof, wherein $R^4$ is pyridinonyl optionally substituted with one or more substituents selected from alkyl, hydroxy, alkoxy, halogen, phenyl, fluorophenyl, and benzyl.

9. The compound according to claim 8 or an enantiomer, diastereomer, or pharmaceutically acceptable salt thereof, wherein:
$R^4$ is substituted with phenyl, fluorophenyl, benzyl, $C_1$ to $C_4$ alkyl, alkoxy, and/or halogen; and
$R^{18}$ and $R^{19}$ are each H.

10. The compound according to claim 5 or an enantiomer, diastereomer, or pharmaceutically acceptable salt thereof, wherein $R^4$ is optionally substituted pyridyl-N-oxide optionally substituted with one or more substituents selected from alkyl, hydroxy, alkoxy, halogen, phenyl, fluorophenyl, and benzyl.

11. The compound according to claim 10 or an enantiomer, diastereomer, or pharmaceutically acceptable salt thereof, wherein:
$R^4$ is substituted with phenyl, fluorophenyl, benzyl, $C_1$ to $C_4$ alkyl, alkoxy, and/or halogen; and
$R^{18}$ and $R^{19}$ are each H.

12. The compound according to claim 5 or an enantiomer, diastereomer, or pharmaceutically acceptable salt thereof, wherein $R^4$ is optionally substituted pyrazolyl optionally substituted with one or more substituents selected from alkyl, hydroxy, alkoxy, halogen, phenyl, fluorophenyl, and benzyl.

13. The compound according to claim 12 or an enantiomer, diastereomer, or pharmaceutically acceptable salt thereof, wherein:
$R^4$ is substituted with phenyl, fluorophenyl, benzyl, $C_1$ to $C_4$ alkyl, alkoxy, and/or halogen; and
$R^{18}$ and $R^{19}$ are each H.

14. A compound selected from: N-(4-(2-Aminopyridin-4-yloxy)-3-fluorophenyl)-2-bromoisonicotinamide, trifluoroacetic acid salt (48); N-(4-(2-Aminopyridin-4-yloxy)-3-fluorophenyl)-2-(4-fluorophenylamino) isonicotinamide, bis-trifluoroacetic acid salt (49); N-(4-(2-Aminopyridin-4-yloxy)-3-fluorophenyl)-6-oxo-1,6-dihydropyridine-2-carboxamide, trifluoroacetic acid salt (50); N-(4-(2-aminopyridin-4-yloxy)-3-fluorophenyl)-2-oxo-1,2-dihydropyridine-3-carboxamide, trifluoroacetic acid salt (51); N-(4-(2-Aminopyridin-4-yloxy)-3-fluorophenyl)-6-methyl-2-oxo-1,2-dihydropyridine-3-carboxamide, trifluroacetic acid salt (52); N-(4-(2-Aminopyridin-4-yloxy)-3-fluorophenyl)-5-chloro-2-oxo-1,2-dihydropyridine-3-carboxamide, trifluoroacetic acid salt (53); N-(4-(2-Aminopyridin-4-yloxy)-3-fluorophenyl)-5-bromo-2-oxo-1,2-dihydropyridine-3-carboxamide, trifluoroacetic acid salt (54); N-(4-(2-Aminopyridin-4-yloxy)-3-fluorophenyl)-6-methyl-4-oxo-1,4-dihydropyridine-3-carboxamide, trifluoroacetic acid salt (55); N-(4-(2-Aminopyridin-4-yloxy)-3-fluorophenyl)-5-benzyl-4-oxo-1,4-dihydropyridine-3-carboxamide, trifluoroacetic acid salt (56); N-(4-(2-Aminopyridin-4-yloxy)-3-fluorophenyl)-2-oxo-1-phenyl-1,2-dihydropyridine-3-carboxamide, trifluoroacetic acid salt (57); N-(4-(2-Aminopyridin-4-yloxy)-3-fluorophenyl)-6-(4-fluorophenyl)pyridyl-N-oxide-amide, trifluoroacetic acid salt (58); N-(3-Fluoro-4-(3-(6-(piperazin-1-yl)pyridin-3-yl)pyridin-4-yloxy)phenyl)-2-oxo-1-phenyl-1,2-dihydropyridine-3-carboxamide, hydrochloride salt (62); N-(3-Fluoro-4-(3-(4-(piperazin-1-yl)phenyl)pyridin-4-yloxy)phenyl)-2-oxo-1-phenyl-1,2-dihydropyridine-3-carboxamide, trihydrochloride salt (66); N-(3-Fluoro-4-(3-(4-(2-hydroxyethyl)phenyl)pyridin-4-yloxy)phenyl)-2-oxo-1-phenyl-1,2-dihydropyridine-3-carboxamide (67); N-(4-(3-(4-(2-Aminoethyl)phenyl)pyridin-4-yloxy)-3-fluorophenyl)-2-oxo-1-phenyl-1,2-dihydropyridine-3-carboxamide, dihydrochloride salt (68); N-(4-(3-(4-((2-(Methylamino)ethyl)carbamoyl)phenyl)pyridin-4-yloxy)-3-fluorophenyl)-1-(4-fluorophenyl)-2-oxo-1,2-dihydropyridine-3-carboxamide, dihydrochloride salt (69); N-(4-(3-(4-(2-Aminoethyl)carbamoyl)phenyl)pyridin-4-yloxy)-3-fluorophenyl)-1-(4-fluorophenyl)-2-oxo-1,2-dihydropyridine-3-carboxamide, dihydrochloride salt (70); N-(4-(3-(4-((2-(Dimethylamino)ethyl)carbamoyl)phenyl)pyridin-4-yloxy)-3-fluorophenyl)-1-(4-fluorophenyl)-2-oxo-1,2-dihydropyridine-3-carboxamide, dihydrochloride salt (71); N-(4-(2-Aminopyridin-4-yloxy)-3-fluorophenyl)-1-benzyl-5-methyl-1H-pyrazole-3-carboxamide, hydrochloride salt (98); N-(4-(2-

Aminopyridin-4-yloxy)-3-fluorophenyl)-1-(4-fluorophenyl)-2-oxo-1,2-dihydropyridine-3-carboxamide, hydrochloride salt (101); N-(4-(2-Amino-3-(4-(2-amino-2-oxoethyl)phenyl)pyridin-4-yloxy)-3-fluorophenyl)-1-(4-fluorophenyl)-2-oxo-1,2-dihydropyridine-3-carboxamide, hydrochloride salt (111); N-(4-(2-Aminopyridin-4-yloxy)-2,5-difluorophenyl)-2-oxo-1-phenyl-1,2-dihydropyridine-3-carboxamide, hydrochloric acid salt (114); N-(4-(2-Aminopyridin-4-yloxy)-2,5-difluorophenyl)-1-(4-fluorophenyl)-2-oxo-1,2-dihydropyridine-3-carboxamide, hydrochloric acid salt (115); N-(4-(3-Aminopyridin-4-yloxy)-3-fluorophenyl)-1-(4-fluorophenyl)-2-oxo-1,2-dihydropyridine-3-carboxamide (120); N-(3-Fluoro-4-(3-(pyrrolidin-3-ylmethylamino)pyridin-4-yloxy)phenyl)-1-(4-fluorophenyl)-2-oxo-1,2-dihydropyridine-3-carboxamide, hydrochloride salt (121); N-(4-(3-(2-Aminoethylamino)pyridin-4-yloxy)-3-fluorophenyl)-1-(4-fluorophenyl)-2-oxo-1,2-dihydropyridine-3-carboxamide, hydrochloride salt (122); N-(3-Fluoro-4-(3-(piperidin-2-ylmethylamino)pyridin-4-yloxy)phenyl)-1-(4-fluorophenyl)-2-oxo-1,2-dihydropyridine-3-carboxamide, hydrochloride salt (123); N-(4-(3-(3-(Dimethylamino)-2,2-dimethylpropylamino) pyridin-4-yloxy)-3-fluorophenyl)-1-(4-fluorophenyl)-2-oxo-1,2-dihydropyridine-3-carboxamide, hydrochloride salt (124); N-(4-(3-(2-Amino-3-hydroxypropylamino)pyridin-4-yloxy)-3-fluorophenyl)-1-(4-fluorophenyl)-2-oxo-1,2-dihydropyridine-3-carboxamide, hydrochloride salt (125); N-(4-(2-Amino-3-((2-aminoethylamino)methyl)pyridin-4-yloxy)-3-fluorophenyl)-1-(4-fluorophenyl)-2-oxo-1,2-dihydropyridine-3-carboxamide, trifluoroacetic acid salt (129); N-(4-(2-Amino-3-(hydroxymethyl)pyridin-4-yloxy)-3-fluorophenyl)-1-(4-fluorophenyl)-2-oxo-1,2-dihydropyridine-3-carboxamide, trifluoroacetic acid salt (130); N-(4-(2-Amino-3-(4-(2-amino-2-oxoethyl)phenyl)pyridin-4-yloxy)-3-fluorophenyl)-1-(4-fluorophenyl)-2-oxo-1,2-dihydropyridine-3-carboxamide, hydrochloride salt (132); N-(4-(2-Amino-3-(3-((3R,4R)-3-hydroxy-4-(pyrrolidin-1-yl)pyrrolidin-1-yl)-3-methylbut-1-ynyl)pyridin-4-yloxy)-3-fluorophenyl) -1-(4-fluorophenyl)-2-oxo-1,2-dihydropyridine-3-carboxamide, trihydrochloride salt (134); N-(4-(2-Amino-3-(3-aminoprop-1-ynyl)pyridin-4-yloxy)-3-fluorophenyl)-1-(4-fluorophenyl)-2-oxo-1,2-dihydropyridine-3-carboxamide, dihydrochloride salt (137); N-(4-(2-Amino-3-(3-(dimethylamino)prop-1-ynyl)pyridin-4-yloxy)-3-fluorophenyl)-1-(4-fluorophenyl)-2-oxo-1,2-dihydropyridine-3-carboxamide, dihydrochloride salt (140); N-(4-(2-Aminopyridin-4-yloxy)phenyl)-2-oxo-1-phenyl-1,2-dihydropyridine-3-carboxamide, hydrochloride salt (146); and N-(4-(2-Aminopyridin-4-yloxy)-3-fluorophenyl)-1-benzyl-2-oxo-1,2-dihydropyridine-3-carboxamide, hydrochloride salt (147).

15. A compound according to claim 1 or an enantiomer, diastereomer, or pharmaceutically acceptable salt thereof, having an $IC_{50}$ value of less than about 1.0 μM, as measured by Met kinase assay.

16. A pharmaceutical composition comprising a therapeutically effective amount of a compound according to claim 1 or an enantiomer, diastereomer, or pharmaceutically acceptable salt thereof, and a pharmaceutically acceptable carrier.

17. The compound according to claim 1 or an enantiomer, diastereomer, or pharmaceutically acceptable salt thereof, wherein:

$R^2$ is H or halogen;
$R^3$ is H; and
$R^4$ is pyrazolyl, pyridyl, pyridinonyl, or pyridyl-N-oxide, optionally substituted with one or more substituents selected from alkyl, hydroxy, alkoxy, halogen, phenyl, fluorophenyl, =O, and benzyl.

* * * * *

UNITED STATES PATENT AND TRADEMARK OFFICE
CERTIFICATE OF CORRECTION

PATENT NO. : 7,459,562 B2
APPLICATION NO. : 11/111144
DATED : December 2, 2008
INVENTOR(S) : Borzilleri et al.

It is certified that error appears in the above-identified patent and that said Letters Patent is hereby corrected as shown below:

Column 237, lines 6-9
"(a) if $R^4$ is monocyclic ring pyridyl, $R^4$ is monocyclic ring not substituted with both hydroxy and methoxy; and
(b) if $R^4$ is monocyclic ring pyrimidinyl, it is not substituted with =O;" should read:

-- (a) if $R^4$ is pyridyl, $R^4$ is not substituted with both hydroxy and methoxy; and
(b) if $R^4$ is pyrimidinyl, it is not substituted with =O; --

Signed and Sealed this

Twenty-fourth Day of March, 2009

JOHN DOLL
*Acting Director of the United States Patent and Trademark Office*